(12) United States Patent
Fang et al.

(10) Patent No.: US 7,615,572 B2
(45) Date of Patent: Nov. 10, 2009

(54) PYRROLE AND PYRAZOLE DAAO INHIBITORS

(75) Inventors: Q. Kevin Fang, Wellesley, MA (US); Seth Hopkins, Clinton, MA (US); Michele Heffernan, Worcester, MA (US); Milan Chytil, Clinton, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 12/335,250

(22) Filed: Dec. 15, 2008

(65) Prior Publication Data
US 2009/0170916 A1    Jul. 2, 2009

Related U.S. Application Data

(62) Division of application No. 11/023,924, filed on Dec. 28, 2004, now Pat. No. 7,488,747.

(60) Provisional application No. 60/532,979, filed on Dec. 29, 2003.

(51) Int. Cl.
A61K 31/416 (2006.01)

(52) U.S. Cl. .................... 514/419; 514/423; 548/361.1; 548/374.1; 548/530

(58) Field of Classification Search ........................ None
See application file for complete search history.

(56) References Cited

U.S. PATENT DOCUMENTS 5,859,042 A    1/1999    Lee et al.

FOREIGN PATENT DOCUMENTS

WO    WO 03/039540    5/2003

OTHER PUBLICATIONS van Herk et al., Pyrazole Derivatives as Partial Agonists for the Nicotinic Acid Receptor, Journal of Medicinal Chemistry, 46(18):3945-51 (2003).
Ashton et al., Nonpeptide Angiotensin II Antagonists Derived from 1H-Pyrazole-5-carboxylates and 4-Aryl-1-H-imidazole-5-carboxylates; Journal of Medicinal Chemistry, 36, pp. 3595-3605 (1993).

Primary Examiner—Kamal A Saeed
(74) Attorney, Agent, or Firm—Heslin Rothenberg Farley & Mesiti P.C.

(57) ABSTRACT

Methods for increasing D-Serine concentration and reducing concentration of the toxic products of D-Serine oxidation, for enhancing learning, memory and/or cognition, or for treating schizophrenia, Alzheimer's disease, ataxia or neuropathic pain, or preventing loss in neuronal function characteristic of neurodegenerative diseases involve administering to a subject in need of treatment a therapeutically effective amount of a compound of formula I, or a pharmaceutically acceptable salt or solvate thereof:

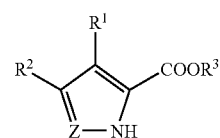

wherein
  $R^1$ and $R^2$ are independently selected from hydrogen, halo, nitro, alkyl, acyl, alkylaryl, and $XYR^5$; or $R^1$ and $R^2$, taken together, form a 5, 6, 7 or 8-membered substituted or unsubstituted carbocyclic or heterocyclic group;
  X and Y are independently selected from O, S, NH, and $(CR^6R^7)_n$;
  $R^3$ is hydrogen, alkyl or $M^+$;
  M is aluminum, calcium, lithium, magnesium, potassium, sodium, zinc ion or a mixture thereof;
  Z is N or $CR^4$;
  $R^4$ is from selected from hydrogen, halo, nitro, alkyl, alkylaryl, and $XYR^5$;
  $R^5$ is selected from aryl, substituted aryl, heteroaryl and substituted heteroaryl;
  $R^6$ and $R^7$ are independently selected from hydrogen and alkyl;
  n is an integer from 1 to 6;
  at least one of $R^1$, $R^2$ and $R^4$ is other than hydrogen; and
  at least one of X and Y is $(CR^6R^7)_n$.
D-serine or cycloserine may be coadministered along with the compound of formula I.

8 Claims, No Drawings

PYRROLE AND PYRAZOLE DAAO INHIBITORS

CROSS-REFERENCE TO RELATED APPLICATIONS

This Application is a divisional of U.S. application Ser. No. 11/023,924, filed Dec. 28, 2004, now U.S. Pat. No. 7,488,747 which is non-provisional of and claims the benefit of U.S. Provisional Application No. 60/532,979, filed Dec. 29, 2003. The entire disclosures of the prior Applications are incorporated herein by reference.

BACKGROUND OF THE INVENTION

The enzyme D-amino acid oxidase (DAAO) metabolizes D-amino acids, and in particular, metabolizes D-serine in vitro at physiological pH. DAAO is expressed in the mammalian brain and periphery. D-Serine's role as a neurotransmitter is important in the activation of the N-methyl-D-aspartate (NMDA) selective subtype of the glutamate receptor, an ion channel expressed in neurons, here denoted as NMDA receptor. Small organic molecules, which inhibit the enzymatic cycle of DAAO, may control the levels of D-serine, and thus influence the activity of the NMDA receptor in the brain. NMDA receptor activity is important in a variety of disease states, such as schizophrenia, psychosis, ataxias, ischemia, several forms of pain including neuropathic pain, and deficits in memory and cognition. Small organic molecules that inhibit the enzymatic cycle of DAAO may also control production of toxic metabolites of D-serine oxidation, such as hydrogen peroxide and ammonia. Thus, these molecules may influence the progression of cell loss in neurodegenerative disorders. Neurodegenerative diseases are diseases in which CNS neurons and/or peripheral neurons undergo a progressive loss of function, usually accompanied by (and perhaps caused by) a physical deterioration of the structure of either the neuron itself or its interface with other neurons. Such conditions include Parkinson's disease, Alzheimer's disease, Huntington's disease and neuropathic pain. N-methyl-D-aspartate (NMDA)-glutamate receptors are expressed at excitatory synapses throughout the central nervous system (CNS). These receptors mediate a wide range of brain processes, including synaptic plasticity, that are associated with certain types of memory formation and learning. NMDA-glutamate receptors require binding of two agonists to effect neurotransmission. One of these agonists is the excitatory amino acid L-glutamate, while the second agonist, at the so-called "strychnine-insensitive glycine site", is now thought to be D-serine. In animals, D-serine is synthesized from L-serine by serine racemase and degraded to its corresponding ketoacid by DAAO. Together, serine racemase and DAAO are thought to play a crucial role in modulating NMDA neurotransmission by regulating CNS concentrations of D-serine.

Alzheimer's disease is manifested as a form of dementia that typically involves mental deterioration, reflected in memory loss, confusion, and disorientation. In the context of the present invention, dementia is defined as a syndrome of progressive decline in multiple domains of cognitive function, eventually leading to an inability to maintain normal social and/or occupational performance. Early symptoms include memory lapses and mild but progressive deterioration of specific cognitive functions, such as language (aphasia), motor skills (apraxia) and perception (agnosia). The earliest manifestation of Alzheimer's disease is often memory impairment, which is required for a diagnosis of dementia in both the National Institute of Neurological and Communicative Disorders and Stroke—Alzheimer's Disease—and the Alzheimer's Disease and Related Disorders Association (NINCDS-ADRDA) criteria (McKhann et al., 1984, Neurology 34:939-944), which are specific for Alzheimer's disease, and the American Psychiatric Association's Diagnostic and Statistical Manual of Mental Disorders, Fourth Edition (DSM-IV) criteria, which are applicable for all forms of dementia. The cognitive function of a patient may also be assessed by the Alzheimer's disease Assessment Scale-cognitive subscale (ADAS-cog; Rosen et al., 1984, Am. J. Psychiatry 141:1356-1364). Alzheimer's disease is typically treated by acetylcholine esterase inhibitors such as tacrine hydrochloride or donepezil. Unfortunately, the few forms of treatment for memory loss and impaired learning available at present are not considered effective enough to make any significant difference to a patient, and there is currently a lack of a standard nootropic drug for use in such treatment.

Neuropsychiatric disorders include schizophrenia, autism, and attention deficit disorder. Clinicians recognize a distinction among such disorders, and there are many schemes for categorizing them. The Diagnostic and *Statistical Manual of Mental Disorders, Revised*, Fourth Ed., (DSM-IV-R), published by the American Psychiatric Association, provides a standard diagnostic system upon which persons of skill rely, and is incorporated herein by reference. According to the framework of the DSM-IV, the mental disorders of Axis I include: disorders diagnosed in childhood (such as Attention Deficit Disorder (ADD) and Attention Deficit-Hyperactivity Disorder (ADHD)) and disorders diagnosed in adulthood. The disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

ADD and ADHD are disorders that are most prevalent in children and are associated with increased motor activity and a decreased attention span. These disorders are commonly treated by administration of psychostimulants such as methylphenidate and dextroamphetamine sulfate.

Schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates. So-called negative symptoms of schizophrenia include affect blunting, anergia, alogia and social withdrawal, which can be measured using SANS (Andreasen, 1983, Scales for the Assessment of Negative Symptoms (SANS), Iowa City, Iowa). Positive symptoms of schizophrenia include delusion and hallucination, which can be measured using PANSS (Positive and Negative Syndrome Scale) (Kay et al., 1987, Schizophrenia Bulletin 13:261-276). Cognitive symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, J. Nerv. Ment. Dis. 182:631-638) or with cognitive tasks such as the Wisconsin Card Sorting Test. Conventional antipsychotic drugs, which act on the dopamine $D_2$ receptor, can be used to treat the positive symptoms of schizophrenia, such as delusion and hallucination. In general, conventional antipsychotic drugs and atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

Other conditions that are manifested as deficits in memory and learning include benign forgetfulness and closed head injury. Benign forgetfulness refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale. Closed head injury refers to a clinical condition after head injury or trauma. Such a condition, which is characterized by cognitive and memory impairment, can be diagnosed as "amnestic disorder due to a general medical condition" according to DSM-IV.

Known inhibitors of DAAO include benzoic acid, pyrrole-2-carboxylic acids, and indole-2-carboxylic acids, as described by Frisell, et al., *J. Biol. Chem.*, 223:75-83 (1956) and Parikh et al., *JACS*, 80:953 (1958). Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. Several examples of traumatic events that may result in neurotoxic injury are given, including hypoxia, anoxia, and ischemia, associated with perinatal asphyxia, cardiac arrest or stroke. Neurodegeneration is associated with CNS disorders such as convulsions and epilepsy. U.S. Pat. Nos. 5,373,018; 5,374,649; 5,686,461; 5,962,496 and 6,100,289, to Cugola, disclose treatment of neurotoxic injury and neurodegenerative disease using indole derivatives. None of the above references mention improvement or enhancement of learning, memory or cognition.

WO 03/039540 discloses enhancement of learning, memory and cognition and treatment of neurodegenerative disorders using DAAO inhibitors, including indole-2-carboxylic acids. However, there remains a need for new drugs that are clinically effective in treating memory defects, impaired learning and loss of cognition, and other symptoms related to NMDA receptor activity, or lack thereof.

Certain pyrazole-3-carboxylic acids are described as partial agonists for the nicotinic acid receptor by van Herk, et al. (J. Med. Chem., 46(18):3945-51 (2003)). A synthetic route for preparation of the compounds is shown, and inhibition of binding of nicotinic acid by the compounds was determined. There is no mention of activity at the NMDA receptor, or inhibition of DAAO.

SUMMARY OF THE INVENTION

It has been unexpectedly discovered that certain pyrrole and pyrazole derivatives exhibit more potent inhibition of DAAO activity than known inhibitors. Dramatically low concentrations of these compounds have been observed to inhibit DAAO in vitro, particularly relative to known DAAO inhibitors such as benzoic acid, pyrrole-2-carboxylic acid, and indole-2-carboxylic acid. Because of this ability to inhibit DAAO activity, the certain pyrrole and pyrazole derivatives are useful in treating a variety of diseases and/or conditions wherein modulation of D-Serine levels, and/or its oxidative products, is effective in ameliorating symptoms, along with a reduction in undesirable side effects. In particular, the compounds may be useful for increasing D-Serine levels and reducing levels of toxic products of D-Serine oxidation; thus, the compounds are useful for enhancing learning, memory and/or cognition, or for treating schizophrenia, for treating or preventing loss of memory and/or cognition associated with Alzheimer's disease, for treating ataxia, or for preventing loss of neuronal function characteristic of neurodegenerative diseases.

Accordingly, in one aspect, the invention relates to methods for increasing D-Serine and reducing the toxic products of D-Serine oxidation, for enhancing learning, memory and/ or cognition, or for treating schizophrenia, for treating or preventing loss of memory and/or cognition associated with Alzheimer's disease, for treating ataxia, for treating neuropathic pain, or for preventing loss of neuronal function characteristic of neurodegenerative diseases.

The methods involve administering to a subject a therapeutic amount of a compound of formula I, or a pharmaceutically acceptable salt or solvate thereof:

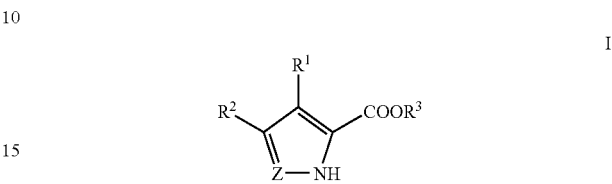

wherein
- $R^1$ and $R^2$ are independently selected from hydrogen, halo, nitro, alkyl, acyl, alkylaryl, and $XYR^5$; or $R^1$ and $R^2$, taken together, form a 5, 6, 7 or 8-membered substituted or unsubstituted carbocyclic or heterocyclic group;
- X and Y are independently selected from O, S, NH, and $(CR^6R^7)_n$;
- $R^3$ is hydrogen, alkyl or $M^+$;
- M is aluminum, calcium, lithium, magnesium, potassium, sodium, zinc or a mixture thereof;
- $R^6$ and $R^7$ are independently selected from hydrogen and alkyl;
- Z is N or $CR^4$;
- $R^4$ is from selected from hydrogen, halo, nitro, alkyl, alkylaryl, and $XYR^5$;
- $R^5$ is selected from aryl, substituted aryl, heteroaryl and substituted heteroaryl;
- n is an integer from 1 to 6;
- at least one of $R^1$, $R^2$ and $R^4$ is other than hydrogen; and
- at least one of X and Y is $(CR^6R^7)_n$.

In a second aspect the invention relates to methods for treating autism, schizophrenia, Alzheimer's disease, ataxia, neuropathic pain or neurodegenerative diseases, comprising administering a therapeutically effective amount of the above D-amino acid oxidase (DAAO) inhibitor of formula I to a subject in need of treatment for one or more of these conditions.

In preferred embodiments, the compounds of formula I are substituted pyrrole-2-carboxylic acids or pyrazole-3-carboxylic acids, for example:

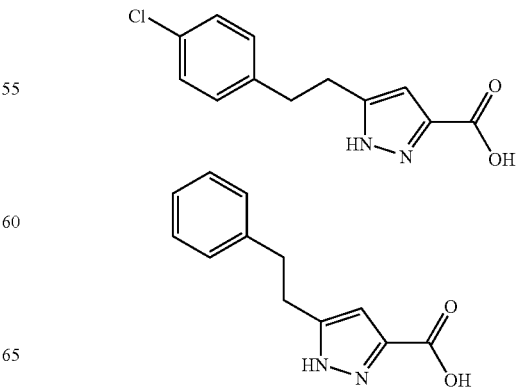

-continued

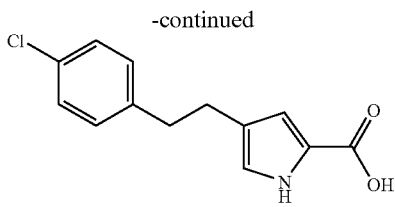

DETAILED DESCRIPTION OF THE INVENTION

The present invention relates to methods for increasing D-serine and reducing the toxic products of D-serine oxidation, for enhancing learning, memory and/or cognition, or for treating schizophrenia, for treating or preventing loss of memory and/or cognition associated with Alzheimer's disease, for treating ataxia, or for preventing loss of neuronal function characteristic of neurodegenerative diseases. The methods include administering to a subject a therapeutic amount of a compound of formula I:

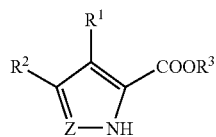

I or a pharmaceutically acceptable salt or solvate thereof, wherein
$R^1$ and $R^2$ are independently selected from hydrogen, halo, nitro, alkyl, acyl, alkylaryl, and $XYR^5$; or $R^1$ and $R^2$, taken together, form a 5, 6, 7 or 8-membered substituted or unsubstituted carbocyclic or heterocyclic group;
X and Y are independently selected from O, S, NH, and $(CR^6R^7)_n$;
$R^3$ is hydrogen, alkyl or $M^+$;
M is aluminum, calcium, lithium, magnesium, potassium, sodium, zinc or a mixture thereof;
$R^6$ and $R^7$ are independently selected from hydrogen and alkyl;
Z is N or $CR^4$;
$R^4$ is from selected from hydrogen, halo, nitro, alkyl, alkylaryl, and $XYR^5$;
$R^5$ is selected from aryl, substituted aryl, heteroaryl and substituted heteroaryl;
n is an integer from 1 to 6;
at least one of $R^1$, $R^2$ and $R^4$ is other than hydrogen; and
at least one of X and Y is $(CR^6R^7)_n$.

Therapeutic treatment with a compound of formula I improves and/or enhances memory, learning and cognition, particularly in individuals suffering from neurodegenerative diseases such as Alzheimer's, Huntington's or Parkinson's diseases. The compounds also ameliorate cognitive dysfunctions associated with aging and improve catatonic schizophrenia.

Compounds of formula I possess unique pharmacological characteristics with respect to inhibition of DAAO, and influence the activity of the NMDA receptor in the brain, particularly by controlling the levels of D-serine. Therefore, these compounds are effective in treating conditions and disorders, especially CNS-related disorders, modulated by DAAO, D-serine and/or NMDA receptor activity, with diminished side effects compared to administration of the current standards of treatment. These conditions and disorders include, but are not limited to, neuropsychiatric disorders, such as schizophrenia, autism, attention deficit disorder (ADD and ADHD) and childhood learning disorders, and neurodegenerative diseases and disorders, such as MLS (cerebellar ataxia), Alzheimer's disease, Parkinson's disease, Huntington's disease, amyotrophic lateral sclerosis, Down syndrome, neuropathic pain, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury. Compounds of formula I may also be useful for the treatment of neurotoxic injury that follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

Accordingly, the present invention relates to methods for increasing the concentration of D-serine and/or decreasing the concentration of toxic products of D-serine oxidation by DAAO in a mammal, for treating schizophrenia, for treating or preventing loss of memory and/or cognition associated with Alzheimer's disease, for treating ataxia, or for preventing loss of neuronal function characteristic of neurodegenerative diseases, for enhancing learning, memory and/or cognition, or for treating neuropathic pain. Each of the methods comprises administering to a subject in need thereof a therapeutically effective amount of a compound of formula I or a pharmaceutically acceptable salt or solvate thereof:

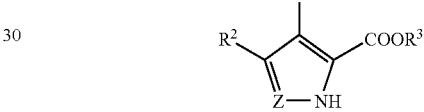

I wherein
$R^1$ and $R^2$ are independently selected from hydrogen, halo, nitro, alkyl, acyl, alkylaryl, arylalkyl, and $XYR^5$; or $R^1$ and $R^2$, taken together, form a 5, 6, 7 or 8-membered substituted or unsubstituted carbocyclic or heterocyclic group;
X and Y are independently selected from O, S, NH, and $(CR^6R^7)_n$;
$R^3$ is hydrogen, alkyl or $M^+$;
M is aluminum, calcium, lithium, magnesium, potassium, sodium, zinc or a mixture thereof;
Z is N or $CR^4$;
$R^4$ is from selected from hydrogen, halo, nitro, alkyl, alkylaryl, arylalkyl and $XYR^5$;
$R^5$ is selected from aryl, substituted aryl, heteroaryl and substituted heteroaryl;
$R^6$ and $R^7$ are independently selected from hydrogen and alkyl;
n is an integer from 1 to 6;
at least one of $R^1$, $R^2$ and $R^4$ is other than hydrogen; and
at least one of X and Y is $(CR^6R^7)_n$.

In some embodiments, D-serine or cycloserine may be coadministered along with the compound(s) of formula I.

Compounds of formula I are typically more selective than known DAAO inhibitors, including indole-2-carboxylates, and demonstrate higher selectivity for DAAO inhibition relative to binding at the NMDA receptor's D-serine binding site. The compounds also exhibit an advantageous profile of activity including good bioavailability. Accordingly, they offer advantages over many art-known methods for treating disorders modulated by DAAO, D-serine or NMDA receptor activity. For example, unlike many conventional antipsychotic therapeutics, DAAO inhibitors can produce a desirable reduction in the cognitive symptoms of schizophrenia. Conventional antipsychotics often produce undesirable side effects, including tardive dyskinesia (irreversible involuntary movement disorder), extra pyramidal symptoms, and akathesia, and these may be reduced or eliminated by administering compounds of formula I.

In another aspect, the present invention also relates to compounds of formula IA, or pharmaceutically acceptable salts or solvates thereof, and pharmaceutical compositions containing them:

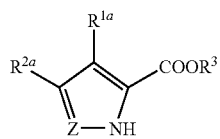

IA wherein $R^{1a}$, $R^{2a}$ and $R^4$ are independently selected from hydrogen, halo, nitro, alkyl, arylalkyl, alkylaryl, and $XYR^5$;

X and Y are independently selected from O, S, NH, and $(CR^6R^7)_n$;

$R^3$ is hydrogen, alkyl or $M^+$;

M is aluminum, calcium, lithium, magnesium, potassium, sodium, zinc or a mixture thereof;

$R^5$ is selected from aryl, substituted aryl, heteroaryl and substituted heteroaryl;

$R^6$ and $R^7$ are independently selected from hydrogen and alkyl;

Z is N or $CR^4$;

n is an integer from 1 to 6;

at least one of $R^{1a}$ and $R^{2a}$ is $XYR^5$; and at least one of X and Y is $(CR^6R^7)_n$;

with the proviso that formula 1A does not include 5-phenethyl-1H-pyrazole-3-carboxylic acid, that is, when $R^{1a}$ is hydrogen, $R^{2a}$ is $XYR^5$; X and Y are $(CR^6R^7)_n$; $R^3$ is hydrogen, $R^6$ and $R^7$ are hydrogen; Z is N; n is 2, $R^5$ may not be phenyl.

Compounds of formula IA form a subset of the compounds of formula I, and may therefore be used in the methods of the present invention without limitation.

In preferred embodiments, the compounds of formula I and IA are pyrrole-2-carboxylic acids, substituted at the 4-position, or pyrazole-3-carboxylic acids, substituted at the 5-position. Preferred substituents for compounds of formula I and IA, 4-substituted pyrrole-2-carboxylic acids and 5-substituted pyrazole-3-carboxylic acids are arylalkyl, substituted arylalkyl, and higher alkyl ($C_6C_{20}$). Preferred arylalkyl substituents are arylethyl groups, particularly phenethyl, in such embodiments, the compounds of formula I and IA are pyrrole-2-carboxylic acids, substituted at the 4-position with a substituted or unsubstituted aryl group joined to the 4-position of the pyrrole through a two-atom tether, or a pyrazole-3-carboxylic acid, substituted at the 5-position with a substituted or unsubstituted aryl group joined to the 5-position of the pyrrole through a two-atom tether. In other preferred embodiments of the compounds of formula I and IA, pyrrole-2-carboxylic acids and pyrazole-3-carboxylic acids, $R^1$ and $R^2$, taken together, form a 5, 6, 7 or 8-membered substituted or unsubstituted carbocyclic or heterocyclic group.

Particularly preferred pyrrole and pyrazole D-amino acid oxidase inhibitors include:

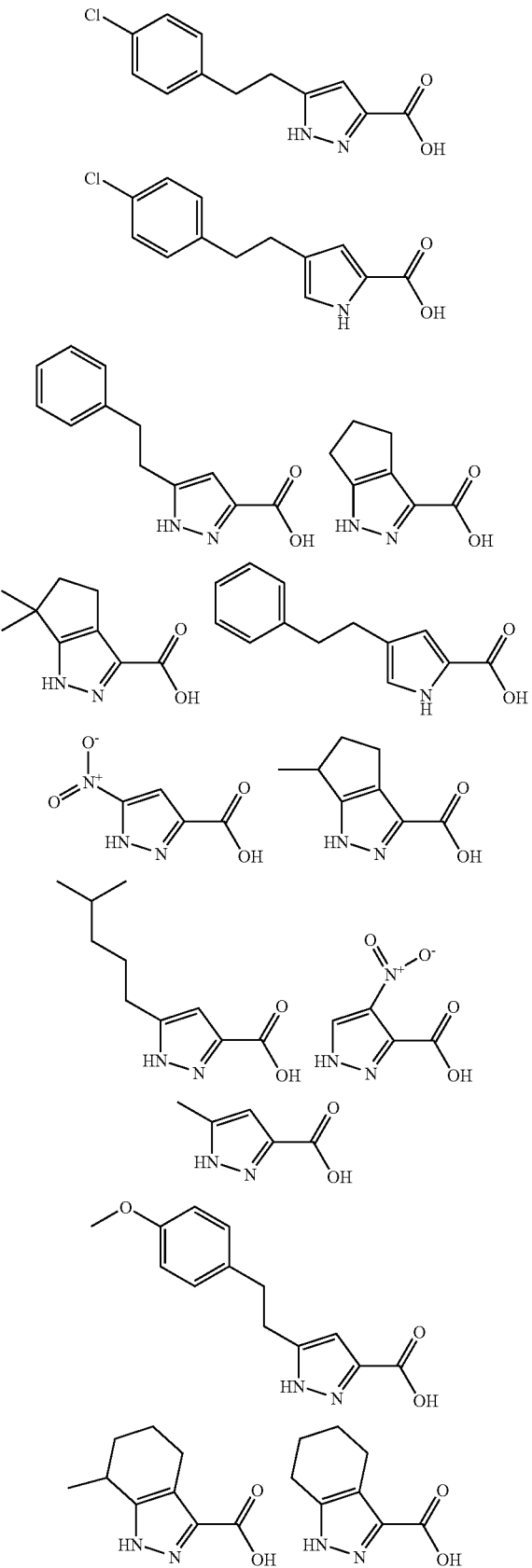

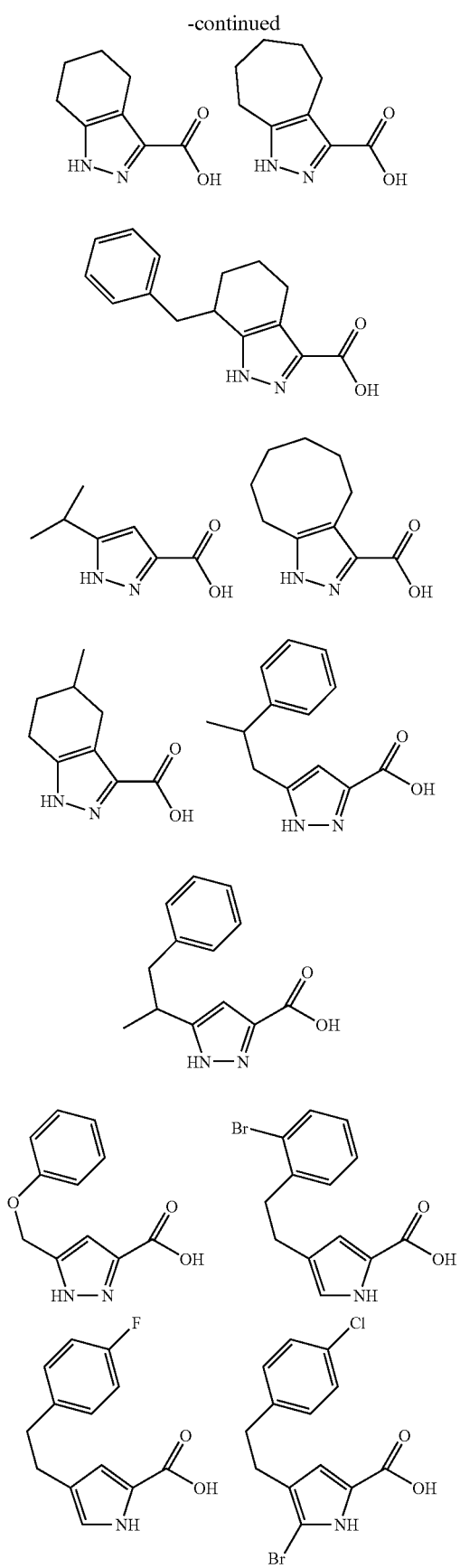
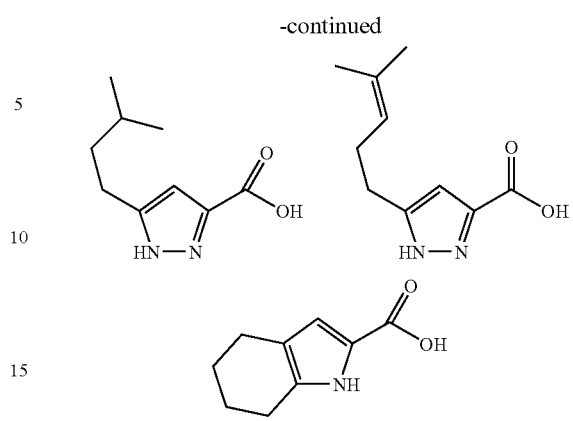

The invention includes compounds of formula I and IA, as well as pharmaceutically acceptable salts and solvates of these compounds. The terminology "compound or a pharmaceutically acceptable salt or solvate of a compound" intends the inclusive meaning of "or", in that a material that is both a salt and a solvate is encompassed. Pharmaceutically acceptable salts include, but are not limited to, inorganic salts of aluminum, calcium, lithium, magnesium, potassium, sodium and zinc, and organic salts of lysine, N,N'-dibenzylethylenediamine, chloroprocaine, choline, diethanolamine, ethylenediamine, meglumine (N-methylglucamine), procaine and tromethamine.

The compounds of formula I and IA may be prepared by known methods, by the procedures illustrated in the Examples, or by the methods shown in Schemes 1-5.

SCHEME 1
Method for the synthesis of 3-substituted-1H-pyrrole-2-carboxylic acid ester starting materials

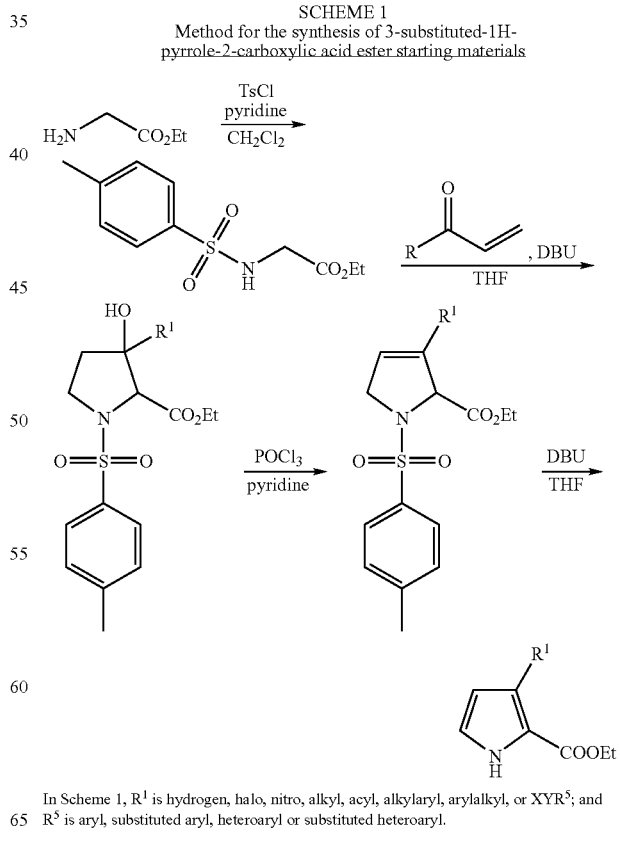

In Scheme 1, $R^1$ is hydrogen, halo, nitro, alkyl, acyl, alkylaryl, arylalkyl, or $XYR^5$; and $R^5$ is aryl, substituted aryl, heteroaryl or substituted heteroaryl.

SCHEME 2
Method for the synthesis of 5-substituted-1H-pyrrole-2-carboxylic acid ester starting materials

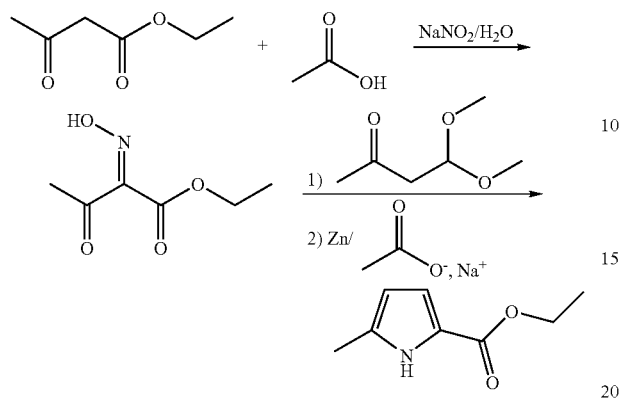

SCHEME 3
Method for the synthesis of 4-substituted-, 3,4-disubstituted-, 4,5-disubstituted-, or 3,4,5-trisubstituted 1H-pyrrole-2-carboxylic acids

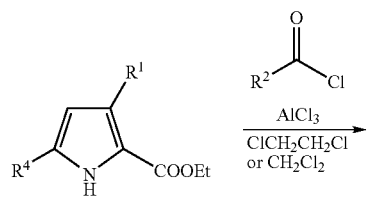

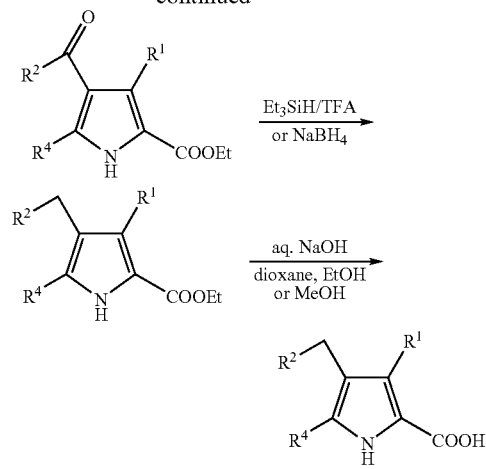

Note: All acid chloride starting materials used were either commercially available, or were synthesized from the requisite commercially available carboxylic acid using thionyl chloride or oxalyl chloride. The following are typical experimental conditions: A solution of the requisite acid in thionyl chloride (or in toluene with 10 equivalents of thionyl chloride) was heated at 60° C. for 1 to 4 hours to obtain the corresponding acyl chloride, then the solvent was evaporated under vacuum. The acid chlorides were used in the acylation reactions without further purification.

SCHEME 4
Method for the synthesis of amine-substituted 1H-pyrrole-2-carboxylic acids using reductive amination:

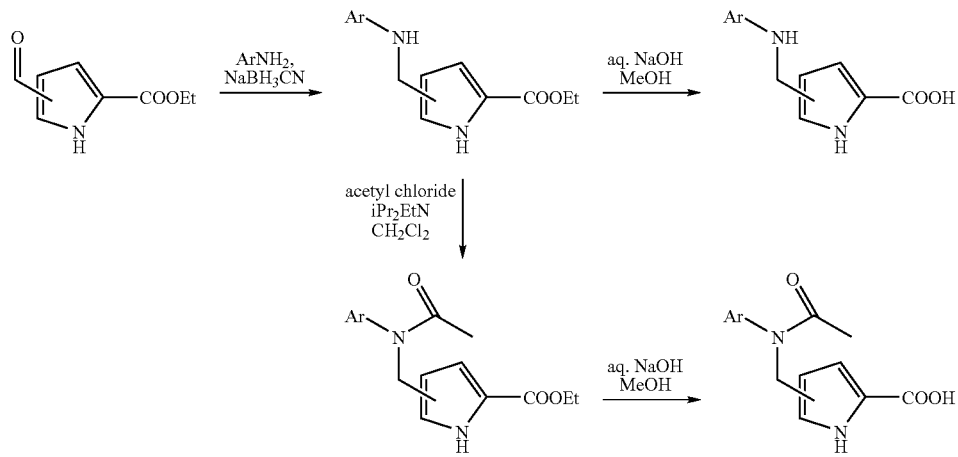

Note:
In this scheme, Ar is an aromatic group such as phenyl or a substituted aromatic group such as 4-chlorophenyl, or heteroaryl or substituted heteroaryl
Also, other acid chlorides such as propionyl chloride, for example, may be used in place of acetyl chloride.

SCHEME 5
Barton-Zard Method for the synthesis of
3,4-disubstituted 1H-pyrrole-2-carboxylic acids

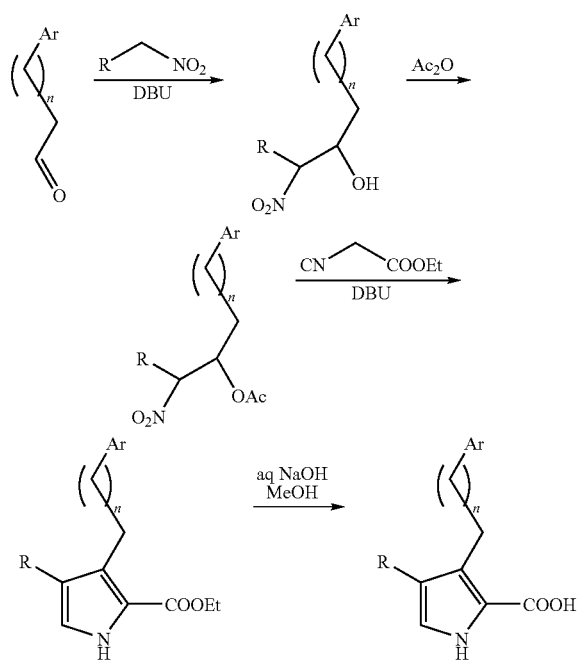

In this Scheme, Ar is an aromatic group such as phenyl or a substituted aromatic such as 4-chlorophenyl, n = 0, 1 or 2, or heteroaryl or substituted heteroaryl and R = hydrogen, halo, nitro, alkyl, or acyl.

Subjects for treatment according to the present invention include humans (patients) and other mammals in need of therapy for the stated condition. Patients having a need for therapy for improving or enhancing learning and memory are those exhibiting symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause. Dementia is characterized by multiple clinically significant deficits in cognition that represent a significant change from a previous level of functioning, including memory impairment involving inability to learn new material or forgetting of previously learned material. Memory can be formally tested by measuring the ability to register, retain, recall and recognize information. A diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

Compounds of formula I and IA may also be used in conjunction with therapy involving administration of D-serine or an analog thereof, such as a salt of D-serine, an ester of D-serine, alkylated D-serine, or a precursor of D-serine, or can be used in conjunction with therapy involving administration of antipsychotics, antidepressants, psychostimulants, and/or Alzheimer's disease therapeutics.

In animals, several established models of learning and memory are available to examine the beneficial cognitive enhancing effects and potential related side effects of treatment. Descriptions of tests that may be employed to assess changes in cognition in non-human species are given in Sarter, Martin, *Intern. J. Neuroscience*, 32:765-774 (1987). The tests include the Morris water maze (Stewart and Morris, *Behavioral Neuroscience*, R. Saghal, Ed., p. 107 (1993)), delayed non-match to sample and social discrimination models.

The Morris water maze is one of the best-validated models of learning and memory, and it is sensitive to the cognitive enhancing effects of a variety of pharmacological agents. The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia. In addition, this animal paradigm accurately models the increasing degree of impairment with advancing age and the increased vulnerability of the memory trace to pre-test delay or interference which is characteristic of amnesiac patients. The test is a simple spatial learning task in which the animal is placed in a tank of tepid water, which is opaque due to the addition of powdered milk. The animals learn the location of the platform relative to visual cues located within the maze and the testing room; this learning is referred to as place learning. Groups of animals receive control solution or a dosage of the therapeutic agent, at the desired time interval prior to training or after training. Control animals typically reach the platform within five to ten seconds after three days of training. The measure of the memory modulator effects of a therapeutic agent is a shift of this time period. In the second or probe phase of the test, animals which have previously learned the position of the platform are placed in the tank from which the platform has been removed. Animals that remember the position of the platform will spend more time in the quadrant that had contained the platform and will make more crossings over the position previously occupied by the platform. Increases in memory or cognitive ability are manifested by animals spending more time in the correct quadrant or making more crossing over the position previously occupied by the platform as compared with control animals. Decreases in memory or cognitive ability are manifested by animals spending less time in the correct quadrant or making less crossings of the platform position than control animals.

In the delayed non-match to sample test an animal is presented with a stimulus (for example lever A). After a period of time the animal is presented with two choices (example lever A and lever B). Selection of the choice that does not match the original stimulus (lever B) results in a reward. Greater than chance selection of the proper choice indicates that the original stimulus was remembered. As the time between stimulus and choice response is increased, performance decreases and approaches pure chance. The number of correct choices at a given time is related to cognitive ability. Deficits in cognition or memory may be induced physically, biochemically or by the use of aged animals.

In the social interaction test a foreign animal (animal B) is introduced into the home cage of the test animal (animal A). Animal A will recognize the introduced animal as foreign and investigate it. If animal B is removed and reintroduced at a later time, the test animal (animal A) will spend less time investigating the new cage mate as it remembers it from the previous introduction. As time between introductions increases, more time is spent investigating the new animal the second time as it is less well remembered. The time spent investigating the new cage mate during the second introduction is inversely related to cognitive ability. Deficits in cognition or memory may be introduced physically, biochemically or by the use of aged animals.

In humans, methods for improving learning and memory may be measured by such tests as the Wechsler Memory Scale and the Minimental test. A standard clinical test for determining if a patient has impaired learning and memory is the Minimental Test for Learning and Memory (Folstein et al., J. Psychiatric Res. 12:185, 1975), especially for those suffering from head trauma, Korsakoffs disease or stroke. The test result serves as an index of short-term, working memory of the kind that deteriorates rapidly in the early stages of dementing or amnesiac disorders. Ten pairs of unrelated words (e.g., army-table) are read to the subject. Subjects are then asked to recall the second word when given the first word of each pair. The measure of memory impairment is a reduced number of paired-associate words recalled relative to a matched control group. Improvement in learning and memory constitutes either (a) a statistically significant difference between the performance of treated patients as compared to members of a placebo group; or (b) a statistically significant change in performance in the direction of normality on measures pertinent to the disease model. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task. Another potential application for therapeutic interventions against memory impairment is suggested by age-related deficits in performance which are effectively modeled by the longitudinal study of recent memory in aging mice.

The Wechsler Memory Scale is a widely used pencil-and-paper test of cognitive function and memory capacity. In the normal population, the standardized test yields a mean of 100 and a standard deviation of 15, so that a mild amnesia can be detected with a 10-15 point reduction in the score, a more severe amnesia with a 20-30 point reduction, and so forth. During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory within the context of the present invention occurs when there is a statistically significant difference in the direction of normality in the paired-associate test, for example, between the performance of therapeutic agent treated patients as compared to members of the placebo group or between subsequent tests given to the same patient.

The prepulse inhibition test may be used to identify compounds that are effective in treating schizophrenia. The test is based upon the observations that animals or humans that are exposed to a loud sound will display a startle reflex and that animals or humans exposed to a series of lower intensity sounds prior to the higher intensity test sound will no longer display as intense of a startle reflex. This is termed prepulse inhibition. Patients diagnosed with schizophrenia display defects in prepulse inhibition, that is, the lower intensity prepulses no longer inhibit the startle reflex to the intense test sound. Similar defects in prepulse inhibition can be induced in animals via drug treatments (scopolamine, ketamine, PCP or MK801) or by rearing offspring in isolation. These defects in prepulse inhibition in animals can be partially reversed by drugs known to be efficacious in schizophrenia patients. It is felt that animal prepulse inhibition models have face value for predicting efficacy of compounds in treating schizophrenia patients.

If desired, compounds of formula I and IA may also be used in conjunction with therapy involving administration of D-serine or an analog thereof, such as a salt of D-serine, an ester of D-serine, alkylated D-serine, or a precursor of D-serine. The compounds may also be used in conjunction with therapy involving administration of antipsychotics (for treating schizophrenia and other psychotic conditions), psychostimulants (for treating attention deficit disorder, depression, or learning disorders), antidepressants, nootropics (for example, piracetam, oxiracetam or aniracetam), acetylcholinesterase inhibitors (for example, the physostigmine related compounds, tacrine or donepezil) and/or Alzheimer's disease therapeutics (for treating Alzheimer's disease). Such methods for conjoint therapies are included within the invention.

The phrase "therapeutically effective amount" as used herein means that amount of a compound, material, or composition comprising a compound of the present invention which is effective for producing some desired therapeutic effect by inhibition of DAAO in at least a sub-population of cells in an animal and thereby blocking the biological consequences of that pathway in the treated cells, at a reasonable benefit/risk ratio applicable to any medical treatment.

The term "pharmaceutically acceptable salt" refers to salts prepared from pharmaceutically acceptable non-toxic bases including inorganic bases and organic bases. Suitable pharmaceutically acceptable base addition salts for the compounds of the present invention include metallic salts made from aluminum, calcium, lithium, magnesium, potassium, sodium and zinc or organic salts made from lysine, N,N'-dibenzylethylene diamine, chloroprocaine, choline, diethanolamine, ethylenediamine, meglumine (N-methylglucamine), procaine and tromethamine.

In general, the compounds of the present invention are commercially available or may be prepared by methods well known to persons of skill in the art. In addition, methods described below, or modifications thereof, using readily available starting materials, reagents and conventional synthesis procedures may be employed. In these reactions, it is also possible to make use of variants that are in themselves known, but are not mentioned here.

In the context of the present invention, alkyl is intended to include linear, branched, or cyclic hydrocarbon structures and combinations thereof, including lower alkyl and higher alkyl.

Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes, for example, n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, pyrrole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 20 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle or heterocyclic means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, substituted alkynyl, haloalkyl, alkoxy, carbonyl, carboxy, carboxalkoxy, carboxamido, acyloxy, amidino, nitro, halogen, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.\

Oxaalkyl refers to an alkyl residue in which one or more carbons have been replaced by oxygen. It is attached to the parent structure through an alkyl residue. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

In the context of the present invention, compounds that are considered to possess activity as DAAO inhibitors are those displaying 50% inhibition of the enzymatic cycle of DAAO ($IC_{50}$) a concentration of about $\leq 100$ μM, preferably, about $\leq 10$ μM and more preferably about $\leq 1$ μM.

Many of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

While it may be possible for compounds of formula I and IA to be administered as the raw chemical, it is preferable to present them as a pharmaceutical composition. According to a further aspect, the present invention provides a pharmaceutical composition comprising a compound of formula I or IA or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations, are well known to those skilled in the art, and general methods for preparing them are found in any standard pharmacy school textbook, for example, *Remington: The Science and Practice* of Pharmacy., A. R. Gennaro, ed. (1995), the entire disclosure of which is incorporated herein by reference.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in *Remington: The Science and Practice of Pharmacy*, pages 1660-1675 (1995).

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

Pharmaceutical compositions containing compounds of formula I or IA may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 1 mg per day to about 7000 mg per day, preferably about 1 mg per day to about 100 mg per day, and more preferably about 25 mg per day to about 50 mg per day, in single or divided doses. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage be titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

It should be understood that in addition to the ingredients particularly mentioned above, the formulations of this invention may include other agents conventional in the art having regard to the type of formulation in question, for example those suitable for oral administration may include flavoring agents.

EXAMPLES

Procedures for the Preparation of Pyrazoles

Example 1

Synthesis of 6,6-Dimethyl-1,4,5,6-tetrahydrocyclopentapyrazole-3-carboxylic acid (3)

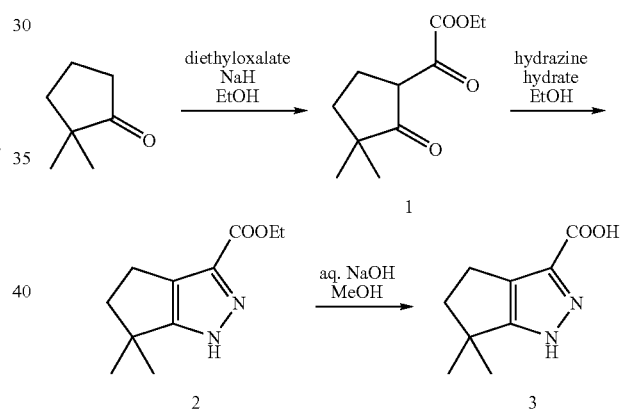

Synthesis of
(3,3-Dimethyl-2-oxocyclopentyl)-oxoacetic acid
ethyl ester (1)

Sodium hydride (0.428 g, 17.8 mmol) was added slowly to a NaCl ice bath containing EtOH (5.4 mL, 3.3 M) stirring under $N_2$. 2,2-dimethylcyclopentanone (2.00 g, 17.83 mmol) and diethyloxalate (2.42 mL, 17.8 mmol) were mixed together, and then added to the chilled NaOEt solution. After stirring for 15 minutes, the reaction was warmed to room temperature and stirred for 6 hours, at which point the reaction was judged complete by TLC. The reaction was quenched at 0° C. with 1N HCl and extracted 2× with $CH_2Cl_2$. The combined organics were washed with $H_2O$, dried with $Na_2SO_4$, filtered, and concentrated to yield 3.4084 g (90.0%) of crude 2 that was sufficiently pure by NMR to go on to the next step without further purification. Note: NaOEt purchased from Aldrich may be substituted for the NaOEt synthesized in situ. $^1$H (CDCl$_3$, 400 MHz): δ 4.29 (2H, q, J=7.3 Hz), 2.82 (2H, t, J=7.3 Hz), 1.76 (2H, t, J=7.3 Hz), 1.32 (3H, t, J=7.3 Hz), 1.07 (6H, s) ppm. $^{13}$C (CDCl$_3$, 100 MHz): δ 218, 162.89, 153.15, 115.98, 62.12, 46.16, 36.39, 23.98, 23.87, 14.22 ppm.

Synthesis of 6,6-dimethyl-1,4,5,6-tetrahydrocyclopentavyrazole-3-carboxylic acid ethyl ester (2)

Hydrazine hydrate (0.229 mL, 4.71 mmol) was added to a stirring room temperature solution of 1 (0.9961 g, 4.71 mmol) in EtOH (4.7 mL, 1 M) under N$_2$. The reaction was then heated to reflux until judged complete by TLC (2 h). The reaction was concentrated and purified by silica gel chromatography (Combiflash column, 70:30:2 Hexanes:CH$_2$Cl$_2$:2N NH$_3$ in EtOH). Only pure fractions were combined and concentrated to obtain 0.6955 g (71.2%) of 2. $^1$H (CDCl$_3$, 400 MHz): δ 11.04 (1H, broad s), 4.33 (2H, q, J=7.3 Hz), 2.76 (2H, t, J=6.8 Hz), 2.26 (2H, t, J=6.8 Hz), 1.33 (3H, t, J=7.3 Hz), 1.31 (6H, s) ppm. $^{13}$C (CDCl$_3$, 100 MHz): δ 168.08, 160.61, 128.73, 127.27, 61.15, 47.22, 38.64, 27.57, 22.00, 14.48 ppm.

Synthesis of 6,6-Dimethyl-1,4,5,6-tetrahydrocyclopentapyrazole-3-carboxylic acid (3)

Freshly prepared aq. NaOH (10 M in H$_2$O, 15.1 mmol) was added to a stirring, room temperature solution of 2 (0.6289 g, 3.02 mmol) in MeOH (7.6 mL, 0.4 M) under N$_2$. The reaction was then heated to reflux until the reaction was judged complete by TLC (2.5 h). The reaction was concentrated, redissolved in EtOAc and H$_2$O, and extracted with EtOAc. 10% aq. HCl was added dropwise until the pH=4, then the organic was removed, and the aqueous layer was extracted with EtOAc again. The combined organics were dried with Na$_2$SO$_4$, filtered, and concentrated. A small amount of CH$_2$Cl$_2$ and hexanes were added to the colored solid product, and the colored impurity was pipetted off. The remaining solid was dried to obtain 0.2371 g (43.6%) of 3 as an off-white solid. Note: The precipitation method used below appears to be the preferred protocol. $^1$H (CD$_3$OD, 400 MHz): δ 2.75 (2H, t, J=6.8 Hz), 2.29 (2H, t, J=6.8 Hz), 1.29 (6H, s) ppm. $^{13}$C (CD$_3$OD, 100 MHz): δ 166.15, 162.23, 130.46, 126.93, 47.10, 38.22, 26.62, 21.52 ppm. DEPT (CD$_3$OD, 100 MHz): CH$_3$ carbons: 26.62; CH$_2$ carbons: 47.10, 21.52 ppm: LCMS: 181.4 (M+1); 163.6 ((M+1)−18). HPLC: 7.538 min.

Example 2

Synthesis of 3-methyl-1,4,5,6-tetrahydrocyclopentapyrazole-3-carboxylic acid (6)

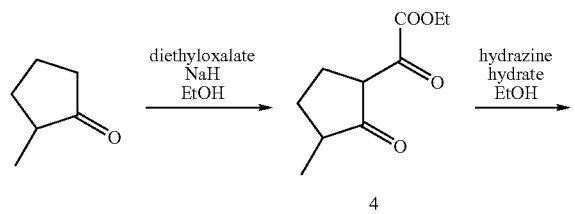

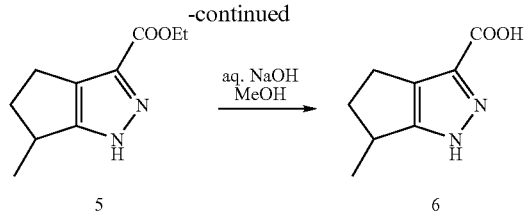

Synthesis of (3-methyl-2-oxocyclopentyl)-oxoacetic acid ethyl ester (4)

2-methylcyclopentanone (1.0058 g, 10.2 mmol) and diethyloxalate (1.38 mL, 10.2 mmol) were mixed together, and then added to a solution of NaOEt (~3 M, 3.4 mL) stirring in an ice bath under N$_2$. After stirring for 15 minutes, the reaction was warmed to room temperature and stirred overnight. The reaction was quenched at 0° C. with 1N HCl and extracted 2x with CH$_2$Cl$_2$. The combined organics were washed with H$_2$O, dried with Na$_2$SO$_4$, filtered, and concentrated to yield crude 4. The crude material was purified with 98:2 to 96:4 Hexanes:EtOAc to obtain 0.5635 g (27.7%) of 4. $^1$H (CDCl$_3$, 400 MHz): δ 4.29 (2H, q, J=7.1 Hz), 2.96 (1H, ddd, J=17.6, 8.1, 1.5 Hz), 2.69 (1H, ddd, J=17.6, 9.5, 8.1 Hz), 2.57-2.47 (1H, m), 2.24 (1H, dtd, J=12.5, 8.3, 2.4 Hz), 1.49 (1H, dtd, J=12.5, 10.3, 8.4 Hz), 1.34 (3H, t, J=7.1 Hz), 1.13 (3H, d, J=7.0 Hz) ppm. $^{13}$C (CDCl$_3$, 100 MHz): δ 164.09, 153.19, 117.67, 62.92, 44.76, 30.60, 30.36, 26.55, 14.63, 14.37 ppm.

Synthesis 6-methyl-1,4,5,6-tetrahydrocyclopentpyrazole-3-carboxylic acid ethyl ester (5)

Hydrazine hydrate (0.101 mL, 2.05 mmol) was added to a stirring room temperature solution of 4 (0.4055 g, 2.05 mmol) in EtOH (2.0 mL, 1 M) under N$_2$. The reaction was then heated to reflux until judged complete by TLC. The reaction was concentrated and purified by silica gel chromatography (Combiflash column, 96:4 Hexanes:2N NH$_3$ in EtOH): Only pure fractions were combined and concentrated to obtain 0.2003 g (50.4%) of 5. $^1$H (CDCl$_3$, 400 MHz): δ 9.55 (1H, broad s), 4.35 (2H, q, J=7.1 Hz), 3.26-3.16 (1H, m), 2.89-2.63 (3H, m), 2.09-1.98 (1H, m), 1.37 (3H, t, J=7.2 Hz), 1.30 (3H, d, J=6.9 Hz) ppm. Partial $^{13}$C (CDCl$_3$, 100 MHz): δ 128.67, 61.32, 39.73, 32.64, 22.94, 19.62, 14.52 ppm. HPLC: 8.901 min.

Synthesis of 6-methyl-1,4,5,6-tetrahydrocyclopentapyrazole-3-carboxylic acid (6)

Freshly prepared aq. NaOH (10 M in H$_2$O, 5.02 mmol) was added to a stirring, room temperature solution of 5 (0.1949 g, 1.00 mmol) in MeOH (12.5 mL, 0.4 M) under N$_2$. The reaction was then heated to reflux until the reaction was judged complete by TLC (0.5 h). The reaction was concentrated and then dissolved in 2 mL H$_2$O. 10% aq. HCl was added dropwise until the pH=2. The white solid that precipitated from the reaction was filtered off and washed with cold H$_2$O. The solid was dried under vacuum overnight to obtain 0.1223 g (73.3%) of 6. $^1$H (CD$_3$OD, 400 MHz): δ 3.18-3.07 (1H, m), 2.84-2.62 (3H, m), 2.08-1.96 (1H, m), 1.25 (3H, d, J=6.8 Hz) ppm. $^{13}$C (CD$_3$OD, 100 MHz): δ 164.49, 163.43, 131.67, 129.41, 40.87, 33.40, 23.61, 19.73 ppm. DEPT (CD$_3$OD, 100 MHz): CH$_3$ carbons: 19.73; CH$_2$ carbons: 40.87, 23.61; CH carbons: 33.40 ppm. HPLC: 7.006 min.

Example 3

Synthesis of 4-methyl-1,4,5,6-tetrahydrocyclopentapyrazole-3-carboxylic acid (11) and 5-methyl-1,4,5,6-tetrahydrocyclopentapyrazole-3-carboxylic acid (12)

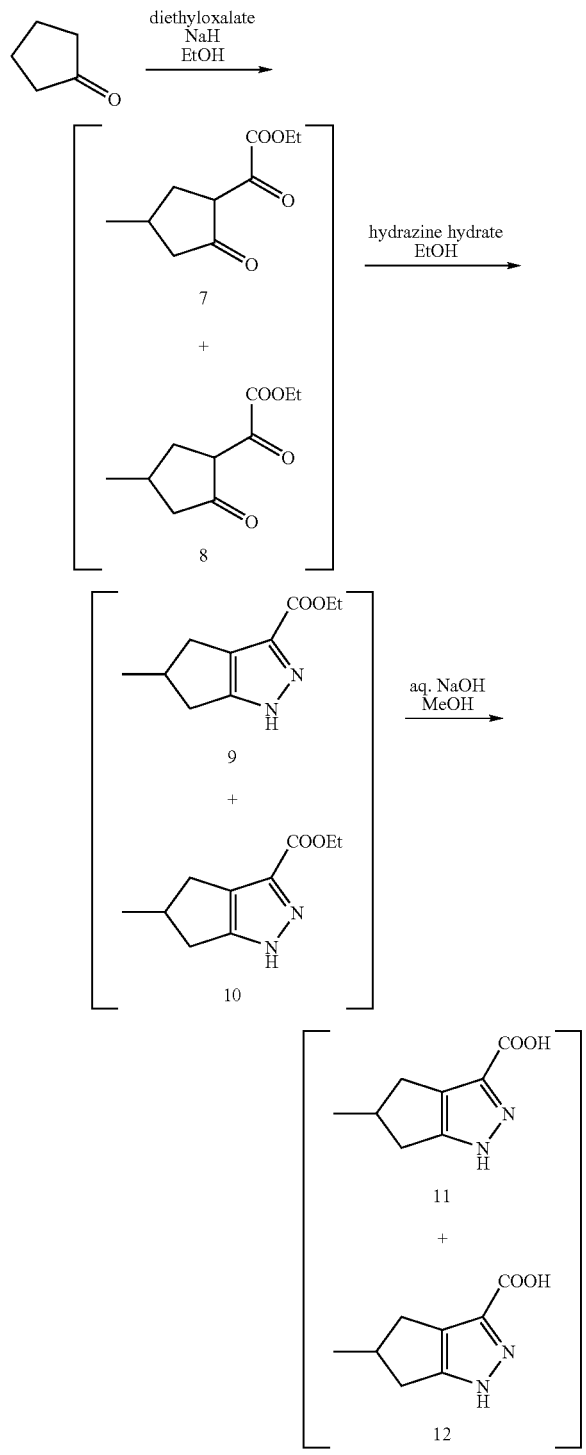

Synthesis of (2-methyl-5-oxocyclopentyl)-oxoacetic acid ethyl ester (7) and (4-methyl-2-oxocyclopentyl)-oxoacetic acid ethyl ester (8)

Sodium hydride (0.122 g, 5.09 mmol) was added slowly to a NaCl ice bath containing EtOH (1.54 mL, 3.3 M) stirring under $N_2$. 3-methylcyclopentanone (0.500 g, 5.09 mmol) and diethyloxalate (0.69 mL, 5.09 mmol) were mixed together, and then added to the chilled NaOEt solution. After stirring for 15 minutes, the reaction was warmed to room temperature and stirred for 6 hours, at which point the reaction was judged complete by TLC. The reaction was quenched at 0° C. with 1N HCl and extracted 2× with $CH_2Cl_2$. The combined organics were washed with $H_2O$, dried with $Na_2SO_4$, filtered, and concentrated to yield 0.5591 g (55.4%) of crude 7 and 8 as an approximately 1:1.1 mixture. Although conditions to separate the isomers were not found, the mixture was sufficiently pure by NMR to go on to the next step without further purification. Note: NaOEt purchased from Aldrich may be substituted for the NaOEt synthesized in situ. $^1H$ ($CDCl_3$, 400 MHz): δ 4.33 & 4.31 (2H, q, J=7.3 Hz, 3.54-3.45, 3.20-3.08, 2.64-2.30, 2.15-2.04, 1.74-1.66, 1.35 & 1.34 (3H, t, J=7.3 Hz, 1.16 & 1.10 (3H, d, J=7.3 & 6.4 Hz) ppm. $^{13}C$ ($CDCl_3$, 100 MHz): δ 214.05, 162.98, 152.36, 117.34, 62.23, 46.44, 35.92 & 35.76, 29.45 & 28.65, 21.00 & 20.91, 14.25 & 14.17 ppm.

Synthesis of 4-methyl-1,4,5,6-tetrahydrocyclopentapyrazole-3-carboxylic acid (9) and 5-methyl-1,4,5,6-tetrahydrocyclopentavyrazole-3-carboxylic acid ethyl ester (10)

Hydrazine hydrate (0.127 mL, 2.62 mmol) was added to a stirring room temperature solution of 7 and 8 (0.5064 g, 2.62 mmol) in EtOH (2.6 mL, 1 M) under $N_2$. The reaction was then heated to reflux until judged complete by TLC (2.3 h). The reaction was concentrated and purified by silica gel chromatography (Combiflash column, 70:30:2 Hexanes:$CH_2Cl_2$:2N $NH_3$ in EtOH). Only pure fractions were combined and concentrated to obtain 0.3132 g (63.1%) of 9 and 10. Conditions to separate the isomers were not found. $^1H$ ($CDCl_3$, 400 MHz): δ 11.26 & 11.18 (1H, broad s), 4.35 & 4.34 (2H, q, J=7.3 Hz), 3.28-3.18 (0.48H, m), 3.02-2.90 (1.5H, m), 2.86-2.76 (0.52H, m), 2.74-2.61 (1H, m), 2.09-1.88 (1H, m), 2.15-1.80 (0.52H, m), 1.36 & 1.35 (3H, t, J=7.3 Hz), 1.28 & 1.19 (3H, d, J=6.3 Hz for 1.28 & 4.4 Hz for 1.19) ppm. Partial $^{13}C$ ($CDCl_3$, 100 MHz): δ 133.67, 128.61, 61.12, 40.25 & 39.35, 33.24 & 32.46, 32.30 & 23.91, 21.69 & 20.55, 14.48 & 14.46 ppm. DEPT ($CDCl_3$, 100 MHz): $CH_3$ carbons: 21.69 & 20.55, 14.48 & 14.46; $CH_2$ carbons: 61.12, 39.35, 33.24 & 32.46, 23.91; CH carbons: 40.25, 32.30 ppm. HPLC: 8.974 min.

Synthesis of 4-methyl-1,4,5,6-tetrahydrocyclopentavyrazole-3-carboxylic acid (11) and 5-methyl-1,4,5,6-tetrahydrocyclopentapyrazole-3-carboxylic acid (12)

Freshly prepared aq. NaOH (10 M in $H_2O$, 8.07 mmol) was added to a stirring, room temperature solution of 9 and 10 (0.3132 g, 1.61 mmol) in MeOH (4.0 mL, 0.4 M) under $N_2$. The reaction was then heated to reflux until the reaction was judged complete by TLC. The reaction was concentrated and then dissolved in 3 mL $H_2O$. 10% aq. HCl was added dropwise until the pH=2. The white solid that precipitated from the reaction was filtered off and washed with cold $H_2O$. The solid was dried under vacuum overnight to obtain 0.1781 g (66.4%) of a mixture of 11 and 12. $^1H$ ($CD_3OD$, 400 MHz): δ

3.34-3.16, 3.02-2.84, 2.80-2.58, 2.40-2.26, 2.10-1.98, 1.28 & 1.20 (3H, d, J=7.0 & 6.3 Hz) ppm. $^{13}$C (CD$_3$OD, 100 MHz): δ 162.36 & 162.19, 158.43 & 158.43, 133.52, 128.16, 40.37 & 39.18, 32.39 & 32.06, 32.03 & 22.91, 20.61 & 19.68 ppm. DEPT (CD$_3$OD, 100 MHz): CH$_3$ carbons: 20.61 & 19.68; CH$_2$ carbons: 39.18, 32.39 & 32.06, 22.91; CH carbons: 40.37, 32.03 ppm. LCMS: 167.4 (M+1); 149.4 ((M+1)−18): HPLC: 6.984 min.

Example 4

Synthesis of 1,4,5,6,7,8-Hexahydrocycloheptapyrazole-3-carboxylic acid (15)

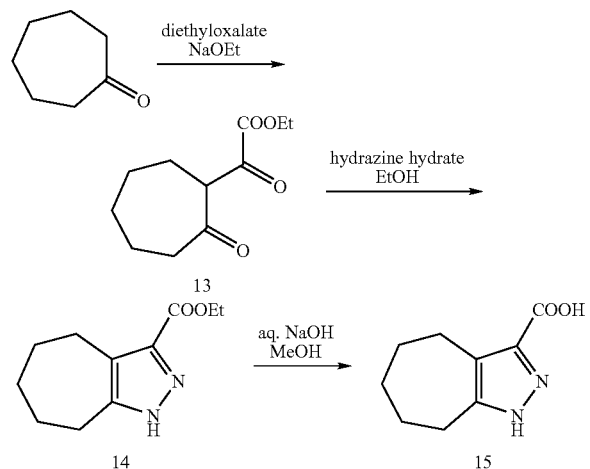

Synthesis oxo-(2-oxocycloheptyl)-acetic acid ethyl ester (13)

Cycloheptanone (1.9998 g, 17.8 mmol) and diethyloxalate (2.42 mL, 17.8 mmol) were mixed together, and then added to a solution of NaOEt (~3 M, 5.94 mL) stirring in an ice bath under N$_2$. After stirring for 15 minutes, the reaction was warmed to room temperature and stirred overnight. The reaction was quenched at 0° C. with 1N HCl and extracted 2× with CH$_2$Cl$_2$. The combined organics were washed with H$_2$O, dried with Na$_2$SO$_4$, filtered, and concentrated to yield crude 13. The crude material was purified with 1:1 Hexanes: CH$_2$Cl$_2$ to obtain 1.9775 g (52.3%) of 13. Note: The product was still not completely pure at this point, but was carried on to the next step. $^1$H (CDCl$_3$, 400 MHz): δ 4.31 (2H, q, J=7.3 Hz), 2.66-2.58 (2H, m), 2.48-2.43 (2H, m), 1.77-1.59 (6H, m), 1.34 (3H, t, J=7.3H) ppm.

Synthesis of 1,4,5,6,7,8-Hexahydrocycloheptavyrazole-3-carboxylic acid ethyl ester (14)

Hydrazine hydrate (0.142 mL, 2.94 mmol) was added to a stirring room temperature solution of 13 (0.6229 g, 2.94 mmol) in EtOH (2.9 mL, 1 M) under N$_2$. The reaction was then heated to reflux until judged complete by TLC (4.5 h): The reaction was concentrated and purified by silica gel chromatography (Combiflash column, 70:30:2 Hexanes:CH$_2$Cl$_2$: 2N NH$_3$ in EtOH): Only pure fractions were combined and concentrated to obtain 0.4428 g (72.3%) of 14. $^1$H (CDCl$_3$, 400 MHz): δ 8.56 (1H, broad s), 4.30 (2H, q, J=7.1 Hz), 2.92-2.86 (2H, m), 2.73-2.78 (2H, m), 1.84-1.76 (2H, m), 1.65-1.57 (4H, m), 1.30 (3H, t, J=7.1 Hz) ppm. $^{13}$C (CDCl$_3$, 100 MHz): δ 162.11, 150.70, 134.97, 124.58, 60.85, 32.33, 28.63, 28.32, 27.39, 24.42, 14.47 ppm. DEPT (CD$_3$OD, 100 MHz): CH$_3$ carbons: 14.47; CH$_2$ carbons: 60.85, 32.33, 28.63, 28.32, 27.39, 24.42; ppm. HPLC: 9.19 min.

Synthesis of 1,4,5,6,7,8-Hexahydrocycloheptaoyrazole-3-carboxylic acid (15)

Freshly prepared aq. NaOH (10 M in H$_2$O, 9.66 mmol) was added to a stirring, room temperature solution of 14 (0.4029 g, 1.93 mmol) in MeOH (4.8 mL, 0.4 M) under N$_2$. The reaction was then heated to reflux until the reaction was judged complete by TLC (0.5 h): The reaction was concentrated and then dissolved in 3.8 mL H$_2$O. 10% aq. HCl was added dropwise until the pH=2. The white solid that precipitated from the reaction was filtered off and washed with cold H$_2$O. The solid was dried under vacuum overnight to obtain 15. Note: An undesired impurity that does not crash out of solution upon HCl addition has a retention time of 8.708 min by HPLC. $^1$H (CD$_3$OD, 400 MHz): δ 2.98-2.90 (2H, m), 2.80-2.72 (2H, m), 1.92-1.82 (2H, m), 1.70-1.58 (4H, m) ppm. $^{13}$C (CD$_3$OD, 100 MHz): δ 164.81, 151.31, 136.87, 125.13, 33.36, 29.73, 28.78, 28.49, 25.17 ppm. DEPT (CD$_3$OD, 100 MHz): CH$_2$ carbons: 33.36, 29.73, 28.78, 28.49, 25.17 ppm. HPLC: 7.545 min.

Example 5

Synthesis of 5-(4-methylpentyl)-1H-pyrazole-3-carboxylic acid (18)

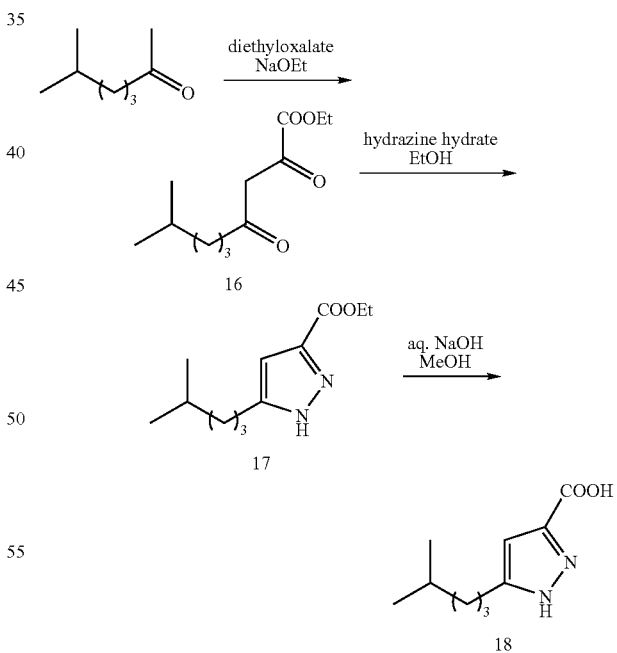

Synthesis of 8-methyl-2,4-dioxononanoic acid ethyl ester (16)

6-Methyl-2-heptanone (0.9981 g, 7.80 mmol) and diethyloxalate (1.06 mL, 7.80 mmol) were mixed together, and then added to a solution of NaOEt (~3 M, 2.6 mL) stirring in an ice bath under $N_2$. After stirring for 15 minutes, the reaction was warmed to room temperature and stirred overnight. The reaction was quenched at 0° C. with 1N HCl and extracted 2× with $CH_2Cl_2$. The combined organics were washed with $H_2O$, dried with $Na_2SO_4$, filtered, and concentrated to yield crude 16. The crude material was purified with 1:1 Hexanes:$CH_2Cl_2$ to obtain 0.8342 g (46.9%) of 16. $^1H$ ($CD_3OD$, 400 MHz): δ 6.36 (1H, s), 4.30 (2H, q, J=7.1 Hz), 2.50 (2H, t, J=7.3 Hz), 1.68-1.59 (2H, m), 1.61-1.50 (1H, m), 1.33 (3H, t, J=7.1 Hz), 1.25-1.17 (2H, m), 0.89 (6H, d, J=7.0 Hz) ppm. $^{13}C$ ($CD_3OD$, 100 MHz): δ 204.41, 166.93, 163.28, 102.66, 63.29, 41.89, 39.41, 28.92, 23.65, 22.89, 14.33 ppm.

Synthesis of 5-(4-methylpentyl)-1H-pyrazole-3-carboxylic acid ethyl ester (17)

Hydrazine hydrate (0.943 mL, 1.91 mmol) was added to a stirring room temperature solution of 16 (0.4354 g, 1.91 mmol) in EtOH (1.9 mL, 1 M) under $N_2$. The reaction was then heated to reflux until judged complete by TLC. The reaction was concentrated and purified by silica gel chromatography (Combiflash column, 96:4 Hexanes:2N $NH_3$ in EtOH): Only pure fractions were combined and concentrated to obtain 0.3132 g (63.1%) of 17. $^1H$ ($CDCl_3$, 400 MHz): δ 9.60 (1H, broad s), 6.58 (1H, s), 4.34 (2H, q, J=7.2 Hz), 2.66 (2H, t, J=7.7 Hz), 1.67-1.57 (2H, m), 1.58 (1H, m), 1.36 (3H, t, J=7.2 Hz), 1.24-1.15 (2H, m), 0.85 (6H, d, J=6.5 Hz) ppm. Partial $^{13}C$ ($CDCl_3$, 100 MHz): δ 162.22, 106.59, 61.17, 38.58, 27.99, 27.20, 26.57, 22.72, 14.48 ppm. DEPT ($CDCl_3$, 100 MHz): $CH_3$ carbons: 22.72, 14.48; $CH_2$ carbons: 61.17, 38.58, 27.20, 26.57; CH carbons: 106.59, 27.99 ppm. HPLC: 10.072 min.

Synthesis of 5-(4-methylpentyl)-1H-pyrazole-3-carboxylic acid (18)

Freshly prepared aq. NaOH (10 M in $H_2O$, 4.97 mmol) was added to a stirring, room temperature solution of 17 (0.2229 g, 0.994 mmol) in MeOH (12.4 mL, 0.4 M) under $N_2$. The reaction was then heated to reflux until the reaction was judged complete by HPLC (20 min): The reaction was concentrated and then dissolved in 2.0 mL $H_2O$. 10% aq. HCl was added dropwise until the pH=2. The white solid that precipitated from the reaction was filtered off and washed with cold $H_2O$. The solid was dried under vacuum overnight to obtain 0.1565 g (80.2%) of 18. $^1H$ ($CD_3OD$, 400 MHz): 66.56 (1H, s), 2.68 (2H, t, J=7.6 Hz), 1.67 (2H, quint, J=7.8 Hz), 1.63-1.51 (1H, m), 1.23 (2H, dt, J=8.8, 7.1 Hz), 0.89 (6H, d, J=6.4 Hz) ppm. $^{13}C$ ($CD_3OD$, 100 MHz): δ 163.79, 149.69, 142.80, 107.65, 39.46, 28.92, 28.11, 26.90, 22.91 ppm. DEPT ($CD_3OD$, 100 MHz): $CH_3$ carbons: 22.91; $CH_2$ carbons: 39.46, 28.11, 26.90; CH carbons: 107.65, 28.92 ppm. HPLC: 8.579 min.

Example 6

Synthesis of 5-phenethyl-1H-pyrazole-3-carboxylic acid (21)

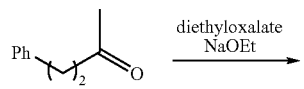

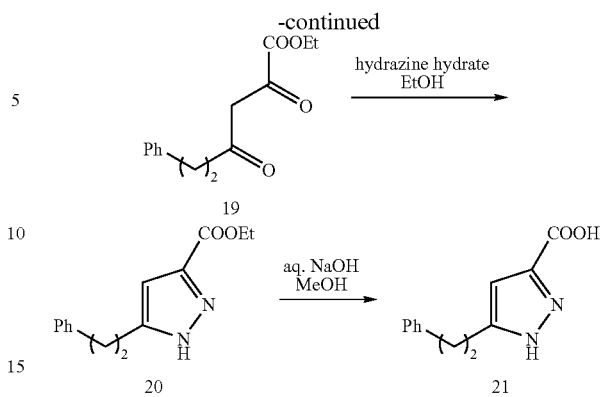

Synthesis of 2,4-dioxo-6-phenylhexanoic acid ethyl ester (19)

Benzylacetone (1.0 g, 6.75 mmol) and diethyloxalate (0.92 mL, 6.75 mmol) were mixed together, and then added to a solution of NaOEt (~3 M, 2.3 mL) stirring in an ice bath under $N_2$. After stirring for 15 minutes, the reaction was warmed to room temperature and stirred overnight. The reaction was quenched at 0° C. with 1N HCl and extracted 2× with $CH_2Cl_2$. The combined organics were washed with $H_2O$, dried with $Na_2SO_4$, filtered, and concentrated to yield crude 19. The crude material was purified with 1:1 Hexanes:$CH_2Cl_2$ to obtain 0.7348 g (43.9%) of 19. $^1H$ ($CD_3OD$, 400 MHz): δ 7.27-7.12 (5H, m), 4.26 (2H, q, J=7.2 Hz), 2.89 (2H, t, J=7.3 Hz), 2.81 (2H, t, J=7.3 Hz), 1.30 (3H, t, J=7.1 Hz) ppm. Partial $^{13}C$ ($CD_3OD$, 100 MHz): δ 163.32, 141.74, 129.43, 129.29, 127.16, 126.95, 103.06, 63.34, 43.46, 31.34, 14.24 ppm. DEPT ($CD_3OD$, 100 MHz): $CH_3$ carbons: 14.24; $CH_2$ carbons: 63.34, 43.46, 31.34; CH carbons: 129.43, 129.29, 127.16, 103.06 ppm. HPLC: 10.279 min.

Synthesis of 5-phenethyl-1H-pyrazole-3-carboxylic acid ethyl ester (20)

Hydrazine hydrate (0.109 mL, 2.24 mmol) was added to a stirring room temperature solution of 19 (0.5570 g, 2.24 mmol) in EtOH (2.2 mL, 1 M) under $N_2$. The reaction was then heated to reflux until judged complete by HPLC. The reaction was concentrated and purified by silica gel chromatography (Combiflash column, 70:30:2 Hexanes:$CH_2Cl_2$:2N $NH_3$ in EtOH). Only pure fractions were combined and concentrated to obtain 0.2983 g (54.4%) of 20. $^1H$ ($CDCl_3$, 400 MHz): δ 11.7 (1H, broad s), 7.30-7.11 (5H, m), 6.60 (1H, s), 4.32 (2H, q, J=7.1 Hz), 3.07-2.92 (4H, m), 1.31 (3H, t, J=7.1 Hz) ppm. Partial $^{13}C$ ($CDCl_3$, 100 MHz): δ 162.13, 147.42, 140.97, 128.72, 128.59, 126.48, 106.79, 61.16, 35.63, 28.18, 14.47 ppm. DEPT ($CDCl_3$, 100 MHz): $CH_3$ carbons: 14.47; $CH_2$ carbons: 61.16, 35.63, 28.18; CH carbons: 128.72, 128.59, 126.48, 106.79 ppm. HPLC: 9.299 min.

Synthesis of 5-phenethyl-1H-pyrazole-3-carboxylic acid (21)

Freshly prepared aq. NaOH (10 M in $H_2O$, 5.06 mmol) was added to a stirring, room temperature solution of 17 (0.2477 g, 1.01 mmol) in MeOH (2.5 mL, 0.4 M) under $N_2$. The reaction was then heated to reflux until the reaction was judged complete by HPLC (30 min). The reaction was concentrated and then dissolved in 2.0 mL $H_2O$. 10% aq. HCl was added dropwise until the pH=2. The white solid that precipitated from the reaction was filtered off and washed with cold H₂O. The solid was dried under vacuum overnight to obtain 21. Note. An undesired impurity that does not crash out of solution upon HCl addition has a retention time of 8.919 min by HPLC. $^1$H (CD₃OD, 400 MHz): δ 7.28-7.20 (2H, m), 7.20-6.92 (3H, m), 6.66 (1H, s), 3.02-2.92 (4H, m) ppm. $^{13}$C (CD₃OD, 100 MHz): δ 164.79, 148.33, 142.96, 142.11, 129.45, 129.43, 127.21, 107.51, 36.56, 28.97 ppm. DEPT (CD₃OD, 100 MHz): CH₂ carbons: 36.50, 28.91; CH carbons: 129.45, 129.43, 127.24, 107.60 ppm. HPLC: 8.050 min.

Example 7

Synthesis of 5-[2-(4-Methoxyphenyl)-ethyl]-1H-pyrazole-3-carboxylic acid (24)

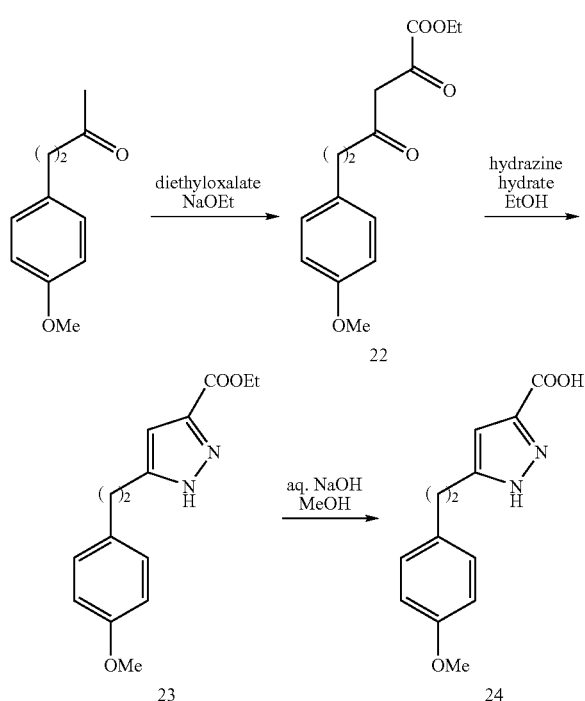

Synthesis of 6-(4-methoxyphenyl)-2,4-dioxohexanoic acid ethyl ester (22)

4-(4-methoxyphenyl)-2-butanone (14.9908 g, 84.2 mmol) and diethyloxalate (12.3434 g, 84.2 mmol) were mixed together, and then added to a solution of NaOEt (~3 M, 28.1 mL) stirring in an ice bath under N₂. After stirring for 15 minutes, the reaction was warmed to room temperature and stirred. After 10 min, the reaction completely solidified. An additional 100 mL EtOH was added, the reaction was placed on mechanical shaker overnight. The reaction was quenched at 0° C. with 1N HCl and extracted 2× with CH₂Cl₂. The combined organics were washed with H₂O, dried with Na₂SO₄, filtered, and concentrated to yield crude 22. The crude material was purified with 1:1 Hexanes:CH₂Cl₂ to obtain 22. $^1$H (CDCl₃, 400 MHz): δ 14.39 (1H, broad s), 7.10 (2H, d, J=7.1 Hz), 6.82 (2H, d, J=6.3 Hz), 6.34 (1H, s), 4.33 (2H, q, J=7.1 Hz), 3.77 (3H, s), 2.91 (2H, t, J=7.3 Hz), 2.78 (2H, t, J=7.3 Hz), 1.36 (3H, t, J=7.1 Hz) ppm. $^{13}$C (CDCl₃, 100 MHz): δ 202.53, 166.46, 162.29, 158.36, 132.36, 129.44, 114.20, 102.11, 62.75, 55.47, 43.02, 29.94, 14.27 ppm. DEPT (CDCl₃, 100 MHz): CH₃ carbons: 55.47, 14.27; CH₂ carbons: 62.75, 43.02, 29.94; CH carbons: 129.44, 114.20, 102.11 ppm. HPLC: 10.12 min. (Starting material: HPLC: 9.10 min.)

Synthesis of 5-[2-(4-Methoxyphenyl)-ethyl]-1H-pyrazole-3-carboxylic acid ethyl ester (23)

Hydrazine hydrate (0.513 mL, 10.6 mmol) was added to a stirring room temperature solution of 22 (2.9241 g, 10.5 mmol) in EtOH (10.6 mL, 1 M) under N₂. The reaction was then heated to reflux until judged complete by HPLC (45 min): The reaction was concentrated and crystallized from EtOH to obtain 23. $^1$H (CDCl₃, 400 MHz): δ 11.67 (1H, broad s), 7.06 (2H, d, J=8.3 Hz), 6.78 (2H, d, J=8.3 Hz), 6.57 (1H, s), 4.30 (2H, q, J=7.0 Hz), 3.76 (3H, s), 2.98 (2H, t, J=7.7 Hz), 2.88 (2H, t, J=7.7 Hz), 1.30 (3H, t, J=7.1 Hz) ppm. $^{13}$C (CDCl₃, 100 MHz): δ 162.20, 158.13, 147.05, 141.79, 132.94, 129.42, 113.98, 106.61, 61.02, 55.36, 34.65, 28.23, 14.37 ppm. DEPT (CDCl₃, 100 MHz): CH₃ carbons: 55.36, 14.37; CH₂ carbons: 61.02, 34.65, 28.23; CH carbons: 129.42, 113.98, 106.61 ppm. HPLC: 9.200 min.

Synthesis of 5-[2-(4-Methoxyphenyl)-ethyl]-1H-pyrazole-3-carboxylic acid (24)

Freshly prepared aq. NaOH (10 M in H₂O, 25.4 mmol) was added to a stirring, room temperature solution of 23 (1.391 g, 5.07 mmol) in MeOH (12.7 mL, 0.4 M) under N₂. The reaction was then heated to reflux until the reaction was judged complete by HPLC (30 min): The reaction was concentrated and then dissolved in 10 mL H₂O. The reaction was extracted with a small amount of EtOAc, then the aqueous layer was made acidic (pH=2) with the dropwise addition of 10% aq. HCl. The white solid that precipitated from the reaction was filtered off and washed with cold H₂O. The solid was dried under vacuum overnight to obtain 0.3771 g of relatively pure 24. 24 was further purified by recrystallization from warm MeOH to obtain 0.1317 g of pure 24. No attempts were made to recover remaining 24 from the mother liquor. $^1$H (CD₃OD, 400 MHz): δ 7.07 (2H, d, J=8.2 Hz), 6.84 (2H, d, J=8.6 Hz), 6.53 (1H, s), 3.73 (3H, s), 2.97-2.84 (4H, m) ppm. $^{13}$C (CD₃OD, 100 MHz): δ 164.86, 159.60, 148.26, 143.15, 134.01, 130.36, 114.81, 107.50, 55.60, 35.67, 29.10 ppm.

Example 8

Synthesis of 4-Benzyl-1H-pyrrole-2-carboxylic acid methyl ester (26)

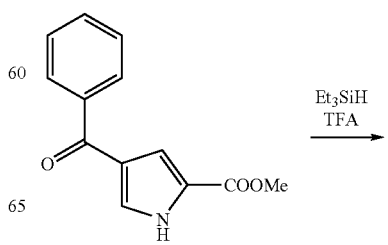

-continued

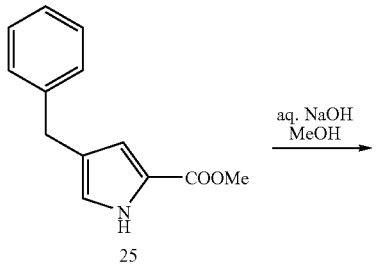

Synthesis of 4-Benzyl-1H-pyrrole-2-carboxylic acid methyl ester (25)

Triethylsilane (0.215 mL, 1.35 mmol) was added to a stirring, room temperature solution of methyl-4-benzoyl-1H-pyrrole-2-carboxylate (0.1118 g, 0.488 mmol) in trifluoroacetic acid (TFA) (1.04 mL, 0.47 M) under $N_2$. After stirring overnight, the reaction was complete by HPLC. The TFA was removed under vacuum, and the crude product was taken up in EtOAc, washed with brine, dried with $Na_2SO_4$, filtered, concentrated, and purified by silica gel chromatography (Combiflash column, 95:5 Hexanes:EtOAc) to obtain pure 25 (0.0604 g, 57.5%): $^1H$ ($CDCl_3$, 400 MHz): δ 9.44 (1H, broad s), 7.34-7.21 (5H, m), 6.78 (1H, s), 6.75 (1H, s), 3.853 (2H, s), 3.846 (3H, s) ppm. $^{13}C$ ($CDCl_3$, 100 MHz): δ 162.09, 141.68, 128.85, 128.70, 126.25, 125.55, 122.67, 121.86, 115.74, 51.70, 33.41 ppm. HPLC: 9.693 min. (Starting material: 8.611 min.)

Synthesis of 4-Benzyl-1H-pyrrole-2-carboxylic acid methyl ester (26)

Freshly prepared aq. NaOH (10 M in $H_2O$, 1.40 mmol) was added to a stirring, room temperature solution of 25 (0.0602 g, 0.280 mmol) in MeOH (0.70 mL, 0.4 M) under $N_2$. Another 0.7 mL of MeOH was added due to precipitation of the starting material, and the reaction was heated to reflux until the reaction was judged complete by HPLC. The reaction was concentrated and then dissolved in 0.55 mL $H_2O$. 10% aq. HCl was added dropwise until the pH=2. The white solid that precipitated from the reaction was filtered off and washed with cold $H_2O$. The solid was dried under vacuum overnight to obtain 0.0495 g (94.5%) of 26. $^1H$ ($CD_3OD$, 400 MHz): δ 10.83 (1H, broad s), 7.27-7.11 (5H, m), 6.71 (1H, s), 6.66 (1H, s), 3.78 (2H, s) ppm. $^{13}C$ ($CD_3OD$, 100 MHz): δ 164.45, 143.25, 129.58, 129.31, 126.81, 126.18, 123.70, 122.96, 116.68, 34.03 ppm. DEPT ($CD_3OD$, 100 MHz): $CH_2$ carbons: 34.03; CH carbons: 129.58, 129.31, 126.81, 122.96, 116.68 ppm. HPLC: 8.647 min.

Example 9

Synthesis of 4-Phenethyl-1H-pyrrole-2-carboxylic acid (28)

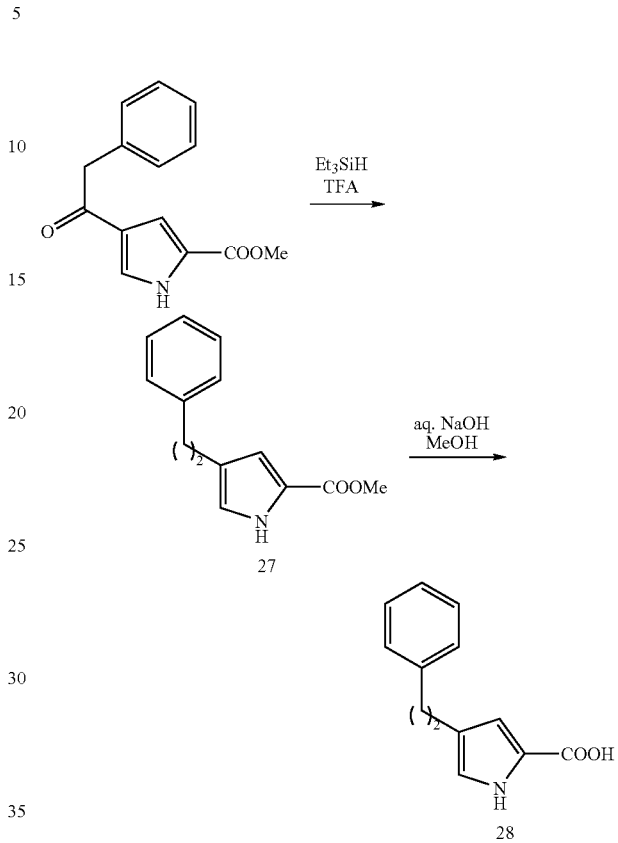

Synthesis of 4-Phenethyl-1H-pyrrole-2-carboxylic acid methyl ester (27)

Triethylsilane (0.323 mL, 2.03 mmol) was added to a stirring, room temperature solution of methyl-4-phenylacetyl-1H-pyrrole-2-carboxylate (0.1593 g, 0.655 mmol) in trifluoroacetic acid (TFA) (1.47 mL, 0.45 M) under $N_2$. After stirring overnight, the reaction was complete by HPLC. The TFA was removed under vacuum, and the crude product was taken up in EtOAc, washed with brine, dried with $Na_2SO_4$, filtered, concentrated, and purified by silica gel chromatography (Combiflash column, 95:5 Hexanes:EtOAc) to obtain pure 27 (0.0755 g, 50.3%): $^1H$ ($CDCl_3$, 400 MHz): δ 9.17 (1H, broad s), 7.32-7.25 (2H, m), 7.23-7.17 (3H, m), 6.80 (1H, s), 6.69 (1H, s), 3.85 (3H, s), 2.93-2.85 (2H, m), 2.84-2.75 (2H, m) ppm. $^{13}C$ ($CDCl_3$, 100 MHz): δ 161.97, 142.15, 128.70, 128.55, 126.13, 125.96, 122.40, 121.26, 115.28, 51.67, 37.57, 28.92 ppm. DEPT ($CDCl_3$, 100 MHz): $CH_3$ carbons: 51.67; $CH_2$ carbons: 37.57, 28.92; CH carbons: 128.70, 128.55, 126.13, 121.26, 115.28 ppm. HPLC: 10.033 min. (Starting material: 8.751 min.)

Synthesis of 4-Phenethyl-1H-pyrrole-2-carboxylic acid (28)

Freshly prepared aq. NaOH (10 M in $H_2O$, 1.65 mmol) was added to a stirring, room temperature solution of 27 (0.0755 g, 0.329 mmol) in MeOH (0.82 mL, 0.4 M) under $N_2$. Another 0.7 mL of MeOH was added due to precipitation of the starting material, and the reaction was heated to reflux until the reaction was judged complete by HPLC (2 h): The reaction was concentrated and then dissolved in 0.55 mL $H_2O$. 10% aq. HCl was added dropwise until the pH=2. The white solid that precipitated from the reaction was filtered off and washed with cold $H_2O$. The solid was dried under vacuum overnight to obtain pure 28. $^1H$ ($CDCl_3$, 400 MHz): δ 10.87 (1H, broad s), 7.25-7.18 (2H, m), 7.17-7.69 (3H, m), 6.70 (1H, s), 6.67 (1H, s), 2.83 (2H, t, J=7.6 Hz), 2.74 (2H, t, J=7.6 Hz) ppm. $^{13}C$ ($CDCl_3$, 100 MHz): δ 164.53, 143.39, 129.50, 129.21, 126.76, 126.38, 123.49, 122.85, 116.48, 38.68, 29.94 ppm. DEPT ($CDCl_3$, 100 MHz): $CH_2$ carbons: 38.68, 29.94; CH carbons: 129.50, 129.21, 126.76, 122.85, 116.48 ppm. HPLC: 8.579 min.

Example 10

Synthesis of 5-benzyl-1H-pyrrole-2-carboxylic acid (32)

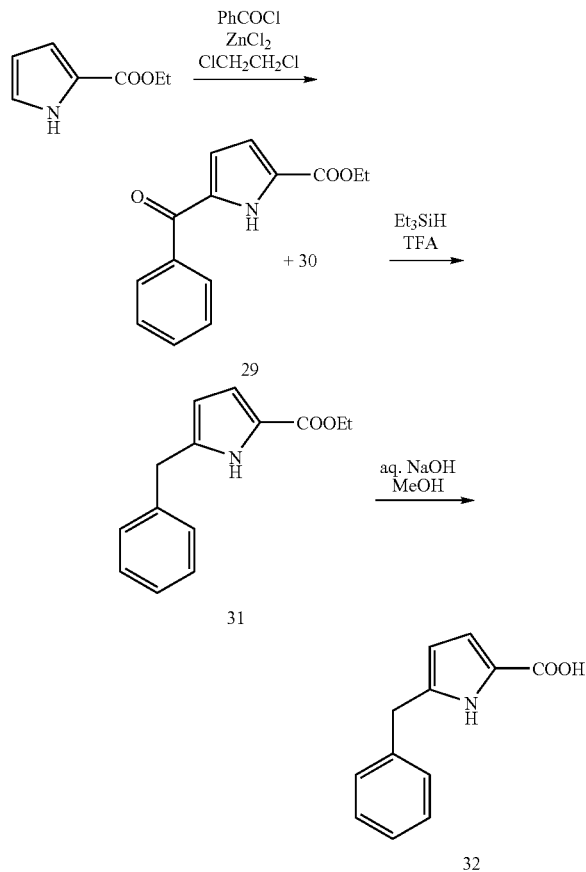

Synthesis of 5-benzoyl-1H-pyrrole-2-carboxylic acid ethyl ester (29) and 4-benzoyl-1H-pyrrole-2-carboxylic acid ethyl ester (30)

Ethylpyrrole-2-carboxylate (1.0013 g, 7.20 mmol) in a minimal amount (2.5 mL) of dichloroethane was added to an ice cooled stirring mixture of zinc chloride (1.96 g, 14.4 mmol) and benzoyl chloride (1.67 mL, 14.4 mmol) in dichloroethane (10.9 mL, 0.66 M) under $N_2$. After stirring 10 min, the ice bath was removed, and the reaction was heated to 50° C. until it was judged complete by TLC (35 min, 9:1 Hexanes:EtOAc): The reaction was the cooled, and carefully poured onto ice water. The reaction was extracted into $CH_2Cl_2$ with 3 portions of solvent. The combined organics were washed with $H_2O$, dilute HCl, and brine, then dried with $Na_2SO_4$, filtered, concentrated, and purified by silica gel chromatography (Combiflash column, 95:5 to 50:50 Hexanes:EtOAc) to obtain 29 (higher Rf) and pure 30 (lower Rf, 0.5646 g, 32.3%): 29 was further purified by silica gel chromatography (Combiflash column, 100% $CH_2Cl_2$) to achieve 0.6168 g (35.2%) of 29.

Spectral data for 29: $^1H$ ($CDCl_3$, 400 MHz): δ 10.19 (1H, broad s), 7.90 (2H, d, J=7.6 Hz), 7.59 (1H, t, J=7.3 Hz), 7.49 (2H, t, J=7.3 Hz), 6.94 (1H, dd, J=3.9, 2.4 Hz), 6.83 (1H, dd, J=3.9, 2.4 Hz), 4.38 (2H, q, J=7.0 Hz), 1.38 (3H, t, J=7.1 Hz) ppm. $^{13}C$ ($CDCl_3$, 100 MHz): δ 185.37, 160.56, 137.69, 133.30, 132.72, 129.27, 128.69, 127.97, 118.75, 115.72, 61.39, 14.55 ppm. DEPT ($CDCl_3$, 100 MHz): $CH_3$ carbons: 14.55; $CH_2$ carbons: 61.39; CH carbons: 132.72, 129.27, 128.69, 118.75, 115.72 ppm. HPLC: 9.792 min. (Starting material: 8.36 min.)

Spectral data for 30: $^1H$ ($CDCl_3$, 400 MHz): δ 10.29 (1H, broad s), 7.84 (2H, dd, J=8.0, 1.2 Hz), 7.59-7.53 (2H, m), 7.48 (2H, t, J=7.6 Hz), 7.36 (1H, dd, J=2.4, 1.5 Hz), 4.38 (2H, t, J=7.3 Hz), 1.35 (3H, t, J=7.3 Hz) ppm. $^{13}C$ ($CDCl_3$, 100 MHz): δ 190.93, 161.47, 139.21, 132.23, 129.22, 128.77, 128.61, 124.35, 116.91, 112.82, 61.30, 14.55 ppm. DEPT ($CDCl_3$, 100 MHz): $CH_3$ carbons: 14.55; $CH_2$ carbons: 61.30; CH carbons: 132.23, 129.22, 128.77, 128.61, 116.91 ppm. HPLC: 9.048 min.

Synthesis of 5-benzyl-1H-pyrrole-2-carboxylic acid ethyl ester (31)

Triethylsilane (0.323 mL, 2.03 mmol) was added to a stirring, room temperature solution of 5-benzoyl-1H-pyrrole-2-carboxylic acid ethyl ester (29) (0.4180 g, 1.72 mmol) in trifluoroacetic acid (TFA) (4.1 mL, 0.42 M) under $N_2$. After stirring overnight, the reaction did not appear to be complete by HPLC. Addition of addition quantities of triethylsilane did not result in any further changes by HPLC, so the reaction was worked up. The TFA was removed under vacuum, and the crude product was taken up in EtOAc, washed with brine, dried with $Na_2SO_4$, filtered, concentrated, and purified by silica gel chromatography (Combiflash column, 98:2 to 95:5 Hexanes:EtOAc) to obtain pure 31 (0.2190 g, 55.6%). $^1H$ ($CDCl_3$, 400 MHz): δ 9.05 (1H, broad s), 7.35-7.28 (2H, m), 7.28-7.23 (1H, m), 7.23-7.18 (2H, m), 6.85 (1H, t, J=3.2 Hz), 6.0 (1H, t, J=3.2 Hz), 4.27 (2H, q, J=7.1 Hz), 4.00 (2H, s), 1.32 (3H, t, J=7.3 Hz) ppm. Partial $^{13}C$ ($CDCl_3$, 100 MHz): δ 138.51, 136.86, 128.99, 128.88, 126.98, 122.26, 116.08, 109.41, 60.39, 34.37, 14.70 ppm. DEPT ($CDCl_3$, 100 MHz): $CH_3$ carbons: 14.70; $CH_2$ carbons: 60.39, 34.37; CH carbons: 128.99, 128.88, 126.98, 116.08, 109.41 ppm. HPLC: 10.014 min.

Synthesis of 5-benzyl-1H-pyrrole-2-carboxylic acid (32)

Freshly prepared aq. NaOH (10 M in $H_2O$, 4.78 mmol) was added to a stirring, room temperature solution of 31 (0.2190 g, 0.955 mmol) in MeOH (2.4 mL, 0.4 M) under $N_2$. The reaction was heated to reflux until the reaction was judged complete by HPLC (40 min). The product was concentrated and then dissolved in 1.9 mL $H_2O$. 10% aq. HCl was added dropwise until the pH=2. The white solid that precipitated from the reaction was filtered off and washed with cold H₂O. The solid was dried under vacuum overnight to obtain 32 as a pale pink, impure solid (0.0845 g). 32 was further purified by adding CHCl₃, stirring, and filtering off pure white 32 (0.0445 g). Note. The undesired impurity has a retention time of 9.643 min by HPLC. Also, the ¹³C NMR of 32 at room temperature showed doublets for the peaks corresponding to the pyrrole carbons, benzyl carbon, and acid carbon. When the NMR probe was heated to 28° C., all doubled peaks collapsed into single peaks as reported below. ¹H (CD₃OD, 400 MHz): δ 11.04 (1H, broad s), 7.27-7.13 (5H, m), 6.80 (1H, d, J=3.4 Hz), 5.87 (1H, d, J=3.4 Hz) 3.93 (2H, s) ppm. ¹³C (CD₃OD, 100 MHz): δ 164.52, 140.71, 139.04, 129.56, 129.42, 127.27, 122.77, 117.59, 109.66, 34.65 ppm. DEPT (CD₃OD, 100 MHz): CH₂ carbons: 34.65; CH carbons: 129.56, 129.42, 127.27, 117.59, 109.66 ppm. HPLC: 8.698 min.

Example 11

Synthesis of 5-phenethyl-1H-pyrrole-2-carboxylic acid (36)

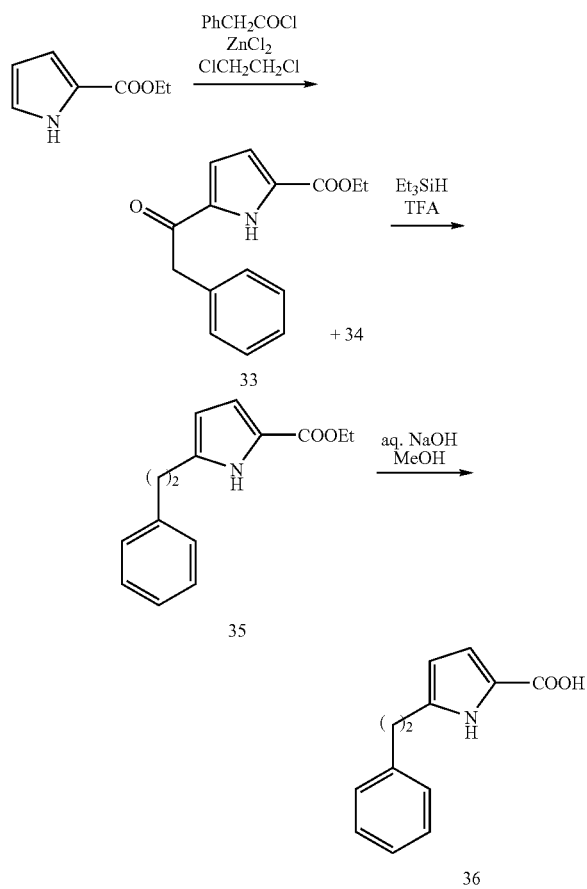

Synthesis of 5-phenylacetyl-1H-pyrrole-2-carboxylic acid ethyl ester (33) and 4-phenylacetyl-1H-pyrrole-2-carboxylic acid ethyl ester (34)

Ethylpyrrole-2-carboxylate (2.5182 g, 18.1 mmol) in a minimal amount of dichloroethane was added to an ice cooled stirring mixture of zinc chloride (4.9891 g, 36.6 mmol) and phenylacetyl chloride (4.76 mL, 35.9 mmol) in dichloroethane (25 mL, 0.72 M) under N₂. After stirring 10 min, the ice bath was removed, and the reaction was heated to 50° C. until it was judged complete by TLC (30 min., 9:1 Hexanes:EtOAc): The reaction was the cooled, and carefully poured onto ice water. The reaction was extracted into CH₂Cl₂ with 3 portions of solvent. The combined organics were washed with H₂O, dilute HCl, and brine, then dried with Na₂SO₄, filtered, concentrated, and purified by silica gel chromatography (Combiflash column, 90:10 to 60:40 Hexanes:EtOAc) to obtain 33 (lower Rf) and 34 (higher Rf): 33 was found to contain a colored impurity that was easily removed by adding hexanes and removing the colored solution. Following treatment with hexanes, 33 (0.7239 g, 15.5%) was sufficiently pure to continue to the next step.

Spectral data for 33: ¹H (CDCl₃, 400 MHz): δ 9.87 (1H, broad s), 7.35-7.23 (5H, m), 6.92-6.87 (2H, m), 4.34 (2H, q, J=7.1 Hz), 4.09 (2H, s), 1.36 (3H, t, J=7.1 Hz) ppm. ¹³C (CDCl₃, 100 MHz): δ 188.72, 160.49, 134.40, 133.63, 129.57, 128.96, 127.82, 127.32, 116.60, 115.73, 61.39, 45.59, 14.54 ppm. DEPT (CDCl₃, 100 MHz): CH₃ carbons: 14.54; CH₂ carbons: 61.39, 45.59; CH carbons: 129.57, 128.96, 127.32, 116.60, 115.73 ppm. HPLC: 9.714 min. (Starting material: 8.36 min.)

Spectral data for 34: ¹H (CDCl₃, 400 MHz): δ 10.16 (1H, broad s), 7.74 (1H, s), 7.72 (1H, s), 7.44-7.23 (5H, m), 4.33 (2H, q, J=7.1 Hz), 4.18 (2H, s), 1.34 (3H, t, J=7.1 Hz) ppm. Partial ¹³C (CDCl₃, 100 MHz): δ 193.45, 160.64, 61.43, 47.97, 14.49 ppm. HPLC: 10.7 min.

Synthesis of 5-phenethyl-1H-pyrrole-2-carboxylic acid ethyl ester (35)

Triethylsilane (0.46 mL, 2.88 mmol) was added to a stirring, room temperature solution of 5-phenylacetyl-1H-pyrrole-2-carboxylic acid ethyl ester (33) (0.240 g, 0.929 mmol) in trifluoroacetic acid (TFA) (2.2 mL, 0.42 M) under N₂. The reaction was judged complete by HPLC after 3.5 h. The TFA was removed under vacuum, and the crude product was taken up in EtOAc, washed with brine, dried with Na₂SO₄, filtered, concentrated, and purified by silica gel chromatography (Combiflash column, 60:40 Hexanes:CH₂Cl₂ to obtain 35, which appeared pure by TLC, but impure by HPLC. Pure 35 was obtained by preparative reverse phase HPLC with the following conditions: 0 to 10 min, 35:65 H₂O:CH₃CN. 10-11 min, 35:65 to 0:100 H₂O:CH₃CN; 20 mL/min.; λ=254 nM; 50.8 mg/mL, 0.8 mL/injection. ¹H (CDCl₃, 400 MHz): δ 9.46 (1H, broad s), 7.33-7.16 (5H, m), 6.85 (1H, t, J=2.9 Hz), 5.99 (1H, t, J=2.9 Hz), 4.29 (2H, q, J=7.1 Hz), 2.97 (4H, s), 1.33 (3H, t, J=7.1 Hz) ppm. ¹³C (CDCl₃, 100 MHz): δ 161.76, 141.16, 138.18, 128.69, 128.52, 126.46, 121.52, 116.06, 108.46, 60.36, 35.89, 29.83, 14.67 ppm. DEPT (CDCl₃, 100 MHz): CH₃ carbons: 14.67; CH₂ carbons: 60.36, 35.89, 29.83; CH carbons: 128.69, 128.52, 126.46, 116.06, 108.46 ppm. HPLC: 10.392 min.

Synthesis of 5-phenethyl-1H-pyrrole-2-carboxylic acid (36)

Freshly prepared aq. NaOH (10 M in H₂O, 1.67 mmol) was added to a stirring, room temperature solution of 35 (0.0814 g, 0.333 mmol) in MeOH (0.83 mL, 0.4 M) under N₂. 0.4 mL of iPrOH was added to solubilize 35. The reaction was heated to reflux until the reaction was judged complete by HPLC. The product was concentrated and then dissolved in 1.9 mL H₂O. 10% aq. HCl was added dropwise until the pH=2. The white solid that precipitated from the reaction was filtered off and washed with cold H$_2$O. The solid was dried under vacuum overnight to obtain 36 as a pale pink solid (Note: An undesired impurity has a retention time of 12.055 min by HPLC. Also, the $^{13}$C NMR of 36 at room temperature showed doublets for the peaks corresponding to the pyrrole carbons, benzyl carbon, and acid carbon. When the NMR probe was heated to 28° C., all doubled peaks collapsed into single peaks as reported below. $^1$H (CD$_3$OD, 400 MHz): δ 10.97 (1H, broad s), 7.25-7.20 (2H, m), 7.18-7.11 (3H, m), 6.76 (1H, d, J=3.4 Hz), 5.90 (1H, d, J=3.4 Hz), 2.94-2.84 (4H, m) ppm. $^{13}$C (CD$_3$OD, 100 MHz): δ 164.51, 142.68, 139.79, 129.40, 129.30, 126.98, 122.36, 117.47, 108.90, 37.00, 30.67 ppm. DEPT (CDCl$_3$, 100 MHz): CH$_2$ carbons: 37.00, 30.67; CH carbons: 129.40, 129.30, 126.98, 117.47, 108.90 ppm. HPLC: 11.239 min.

Example 12

Synthesis of 4-[2-(4-chlorophenyl)-ethyl]-1H-pyrrole-2-carboxylic acid (39)

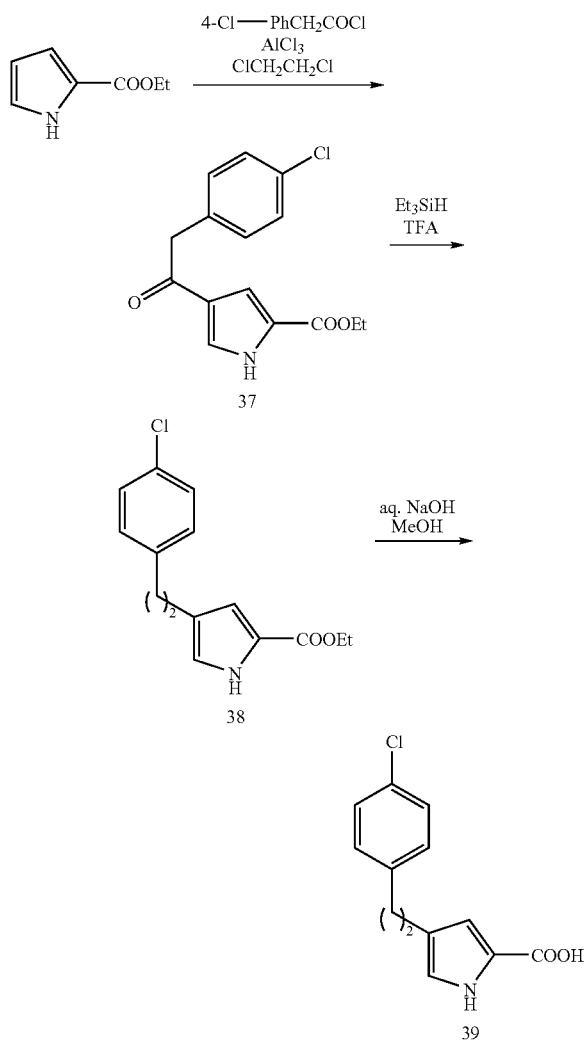

Synthesis of 4-[2-(4-chlorophenyl)-acetyl]-1H-pyrrole-2-carboxylic acid ethyl ester (37)

Ethylpyrrole-2-carboxylate (1.0195 g, 7.33 mmol) in a minimal amount of dichloroethane was added to an ice cooled stirring mixture of aluminum chloride (1.934 g, 14.5 mmol) and 4-chlorobenzeneacetyl chloride (2.7841 g, 14.73 mmol) in dichloroethane (10.9 mL, 0.67 M) under N$_2$. After stirring 10 min, the ice bath was removed, and the reaction was stirred at room temperature for 60 minutes, with little change by TLC (9:1 Hexanes:EtOAc): After heating to 60° C. for an additional hour, only a small quantity of starting material was left by TLC. The reaction was cooled to room temperature, PS-Trisamine™ resin (6.3954 g, 24.30 mmol) and dichloroethane (10 mL) were added, and the reaction was stirred for 3 hours. The reaction was then filtered through a glass-fritted funnel directly into ice water. The resin was rinsed with CH$_2$Cl$_2$, then the organic layers were removed, dried with Na$_2$SO$_4$, filtered, concentrated, and purified by silica gel chromatography (Combiflash column, 95:5 to 50:50 Hexanes:EtOAc) to obtain 1.0345 g (48.4%) 37 as a pale orange solid. Note. A small amount of CH$_2$Cl$_2$ was required to solubilize the crude product before placement on the silica column. $^1$H (CDCl$_3$, 400 MHz): δ 10.07 (1H, broad s), 7.55-7.52 (1H, m), 7.33-7.30 (1H, m), 7.27 (2H, d, J=8.3 Hz), 7.14 (2H, d, J=8.3 Hz), 4.35 (2H, q, J=7.0 Hz), 4.04 (2H, s), 1.37 (3H, t, J=7.1 Hz) ppm. $^{13}$C (CDCl$_3$, 100 MHz): δ 192.55, 160.97, 133.10, 132.75, 130.76, 128.69, 126.80, 126.25, 124.30, 114.95, 61.06, 45.79, 14.31 ppm. DEPT (CDCl$_3$, 100 MHz): CH$_3$ carbons: 14.31; CH$_2$ carbons: 61.06, 45.79; CH carbons: 130.76, 128.69, 126.80, 114.96 ppm. HPLC: 10.049 min.

Synthesis of 4-[2-(4-chlorophenyl)-ethyl]-1H-pyrrole-2-carboxylic acid ethyl ester (38)

Triethylsilane (1.13 mL, 7.08 mmol) was added to a stirring, room temperature solution of 4-[2-(4-chlorophenyl)-acetyl]-1H-pyrrole-2-carboxylic acid ethyl ester (37) (0.6662 g, 2.28 mmol) in trifluoroacetic acid (TFA) (5.54 mL, 0.42 M) under N$_2$. After stirring at room temperature for 4 hours, the TFA was removed under vacuum, and the crude product was taken up in EtOAc, washed with brine, dried with Na$_2$SO$_4$, filtered, concentrated, and purified by preparative reverse phase HPLC with the following conditions: 0 to 12 min, 35:65 H$_2$O:CH$_3$CN. 12-13 min, 35:65 to 0:100 H$_2$O:CH$_3$CN; 20 mL/min.; λ=254 nM; 137 mg/mL; 1.0 mL/injection. 0.2704 g (42.6%) of 38 was obtained as a fluffy white solid. (Note: An undesired impurity has a retention time of 12.055 min by HPLC.) $^1$H (CDCl$_3$, 400 MHz): δ 8.99 (1H, broad s), 7.23 (2H, d, J=8.3 Hz), 7.09 (2H, d, J=8.3 Hz), 6.76 (1H, s), 6.64 (1H, s), 4.30 (2H, q, J=7.0 Hz), 2.84 (2H, t, J=7.6 Hz), 2.75 (2H, t, J=7.6 Hz), 1.35 (3H, t, J=7.1 Hz) ppm. $^{13}$C (CDCl$_3$, 100 MHz): δ 161.14, 140.25, 131.52, 129.80, 128.32, 125.17, 122.62, 120.66, 114.73, 60.25, 36.62, 28.53, 14.43 ppm. DEPT (CDCl$_3$, 100 MHz): CH$_3$ carbons: 14.43; CH$_2$ carbons: 60.25, 36.62, 28.53; CH carbons: 129.80, 128.32, 120.66, 114.73 ppm. HPLC: 11.049 min.

Synthesis of 4-[2-(4-chlorophenyl)-ethyl]-1H-pyrrole-2-carboxylic acid (39)

Freshly prepared aq. NaOH (10 M in H$_2$O, 4.84 mmol) was added to a stirring, room temperature solution of 38 (0.2689 g, 0.968 mmol) in MeOH (2.42 mL, 0.4 M) under N$_2$. The reaction was heated to reflux until the reaction was judged complete by HPLC (30 min): The product was concentrated and then dissolved in 5 mL H$_2$O. The product was extracted with EtOAc, then the aqueous layer was made acidic (pH=2) with the dropwise addition of 10% aq. HCl. The white solid that precipitated from the reaction was filtered off and washed with cold H₂O. The solid was dried under vacuum overnight to obtain 39 as a pale pink solid (Note: An undesired impurity has a retention time of 10.956 min by HPLC. $^1$H (CD$_3$OD, 400 MHz): δ 10.89 (1H, broad s), 7.22 (2H, d, J=8.3 Hz), 7.13 (2H, d, J=8.3 Hz), 6.69 (1H, s), 6.66 (1H, s), 2.82 (2H, t, J=7.1 Hz), 2.73 (2H, t, J=7.1 Hz) ppm. $^{13}$C (CD$_3$OD, 100 MHz): δ 164.48, 142.15, 132.49, 131.15, 129.21, 125.97, 123.60, 122.88, 116.44, 37.92, 29.70 ppm. DEPT (CDCl$_3$, 100 MHz): CH$_2$ carbons: 37.92, 29.70; CH carbons: 131.15, 129.21, 122.88, 116.44 ppm. HPLC: 9.996 min.

Example 13

Synthesis of 5-phenoxymethyl-1H-pyrazole-3-carboxylic acid (42)

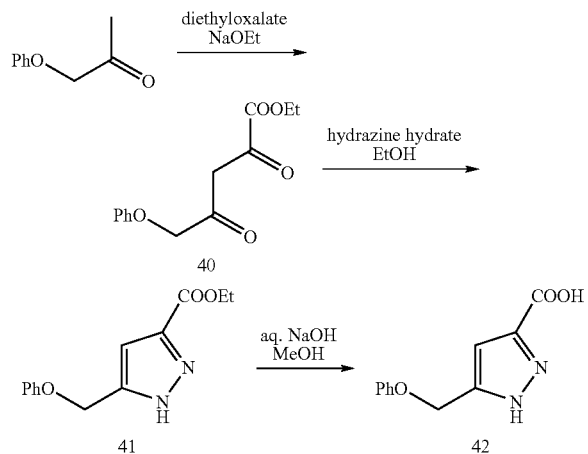

Synthesis of 2,4-dioxo-5-phenoxypentanoic acid ethyl ester (40)

Phenoxyacetone (5.0240 g, 33.46 mmol) and diethyloxalate (4.52 mL, 33.29 mmol) were mixed together, and then added to a solution of NaOEt (~3 M, 11.1 mL) stirring in an ice bath under N$_2$. After stirring for 15 minutes, the reaction was warmed to room temperature and stirred overnight. The reaction was quenched at 0° C. with 1N HCl and extracted 2× with CH$_2$Cl$_2$. The combined organics were washed with H$_2$O, dried with Na$_2$SO$_4$, filtered, and concentrated to yield crude 40. The crude material was purified with 1:1 Hexanes: CH$_2$Cl$_2$ to obtain 1.3490 g (15.4%) of 40. $^1$H (CDCl$_3$, 400 MHz): δ 7.31 (2H, t, J=7.5 Hz), 7.01 (1H, t, J=7.3 Hz), 6.91 (2H, d, J=8.8 Hz), 6.76 (1H, s), 4.67 (2H, s), 4.35 (2H, q, J=7.1 Hz), 1.38 (3H, t, J=7.1 Hz) ppm. $^{13}$C (CDCl$_3$, 100 MHz): δ 199.61, 166.38, 161.55, 157.37, 129.63, 121.89, 114.48, 98.97, 70.13, 62.60, 13.90 ppm. DEPT (CDCl$_3$, 100 MHz): CH$_3$ carbons: 13.90; CH$_2$ carbons: 70.13, 62.60; CH carbons: 129.63, 121.89, 114.48, 98.97 ppm. HPLC: 10.180 min. (Starting material: 9.053 min)

Synthesis of 5-phenoxymethyl-1H-pyrazole-3-carboxylic acid ethyl ester (41)

Hydrazine hydrate (0.197 mL, 4.06 mmol) was added to a stirring room temperature solution of 40 (1.0163 g, 4.06 mmol) in EtOH (4.1 mL, 1 M) under N$_2$. The reaction was then heated to reflux until judged complete by HPLC. The reaction was concentrated and purified by silica gel chromatography (Combiflash column, 92:4:4 Hexanes:CH$_2$Cl$_2$: 2N NH$_3$ in EtOH): Only pure fractions were combined and concentrated to obtain 0.5474 g (54.7%) of 41. $^1$H (CDCl$_3$, 400 MHz): δ 12.12 (1H, broad s), 7.28 (2H, t, J=7.8 Hz), 7.01-6.94 (3H, m), 6.91 (1H, s), 5.17 (2H, s), 4.36 (2H, q, J=7.0 Hz), 1.36 (3H, t, J=7.1 Hz) ppm. Partial $^{13}$C (CDCl$_3$, 100 MHz): δ 158.11, 129.48, 121.26, 114.71, 107.83, 62.61, 61.31, 14.17 ppm. HPLC: 9.505 min.

Synthesis of 5-phenoxymethyl-1H-pyrazole-3-carboxylic acid (42)

Freshly prepared aq. NaOH (10 M in H$_2$O, 10.49 mmol) was added to a stirring, room temperature solution of 41 (0.5164 g, 2.10 mmol) in MeOH (5.2 mL, 0.4 M) under N$_2$. The reaction was then heated to reflux until the reaction was judged complete by HPLC (20 min): The reaction was concentrated and then dissolved in 4.2 mL H$_2$O. 10% aq. HCl was added dropwise until the pH=2. The white solid that precipitated from the reaction was filtered off and washed with cold H$_2$O. The solid was dried under vacuum overnight to obtain 0.4044 g (88.4%) of 42 as a white solid. Note. An undesired impurity that does not crash out of solution upon HCl addition has a retention time of 9.127 min by $^1$H (CDCl$_3$, 400 MHz): δ 7.26 (2H, t, J=8.0 Hz), 6.99 (2H, d, J=8.3 Hz), 6.94 (1H, t, J=7.3 Hz), 6.85 (1H, s), 5.10 (2H, s) ppm. $^{13}$C (CDCl$_3$, 100 MHz): δ 163.68, 159.73, 146.60, 141.13, 130.51, 122.27, 115.83, 108.88, 63.06 ppm. DEPT (CDCl$_3$, 100 MHz): CH$_2$ carbons: 63.06; CH carbons: 130.51, 122.27, 115.83, 108.88 ppm. HPLC: 8.272 min.

Example 14

Synthesis of 4-(3-phenylpropyl)-1H-pyrrole-2-carboxylic acid (45)

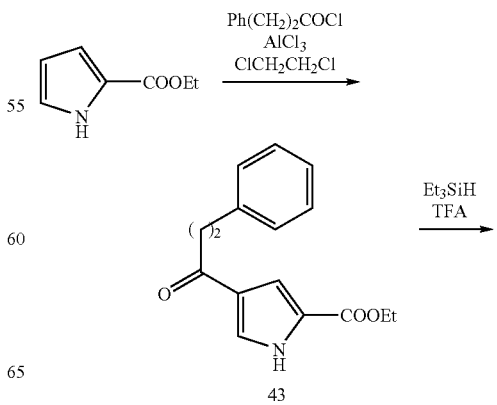

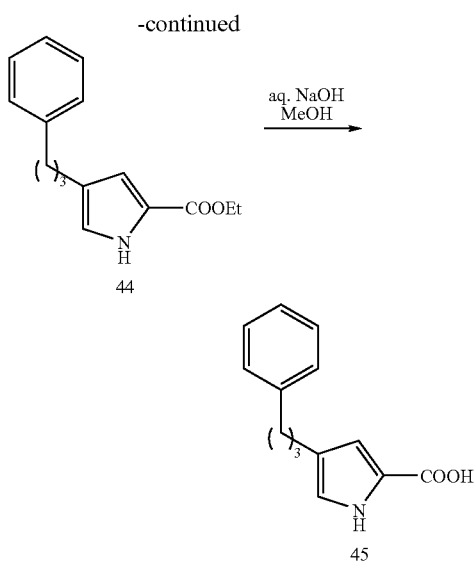

Synthesis of 4-(3-phenylpropionyl)-1H-pyrrole-2-carboxylic acid ethyl ester (43)

Ethylpyrrole-2-carboxylate (1.6236 g, 11.67 mmol) in a minimal amount of dichloroethane was added to an ice cooled stirring mixture of aluminum chloride (3.1085 g, 23.30 mmol) and hydrocinnanomyl chloride (3.9058 g, 23.16 mmol) in dichloroethane (17.7 mL, 0.67 M) under $N_2$. After stirring 10 min, the ice bath was removed, and the reaction was stirred at room temperature for 60 minutes, with little change by TLC (9:1 Hexanes:EtOAc): After heating to 60° C. for an additional hour, only a small quantity of starting material was left by TLC. The reaction was cooled to room temperature, Polyamine resin HL (2.60 mmol/g, 16.41 g, 42.67 mmol) and dichloroethane (10 mL) were added, and the reaction was stirred for 3 hours. The reaction was then filtered through a glass-fritted funnel directly into ice water. The resin was rinsed with $CH_2Cl_2$, then the organic layers were removed, dried with $Na_2SO_4$, filtered, concentrated, and purified by silica gel chromatography (Combiflash column, 92:8:4 Hexanes:$CH_2Cl_2$:2N $NH_3$ in EtOH) to obtain 0.5501 g (14.1%) of 43 as a pale orange solid. $^1H$ (CDCl$_3$, 400 MHz): δ 10.70 (1H, broad s), 7.56 (1H, s), 7.36-7.17 (6H, m), 4.35 (2H, q, J=7.0 Hz), 3.18-3.10 (2H, m), 3.10-3.01 (2H, m), 1.37 (3H, t, J=7.1 Hz) ppm. $^{13}C$ (CDCl$_3$, 100 MHz): δ 194.98, 161.18, 141.13, 128.31, 128.20, 126.64, 126.42, 125.92, 123.96, 114.72, 60.84, 41.19, 30.04, 14.16 ppm. DEPT (CDCl$_3$, 100 MHz): CH$_3$ carbons: 14.16; CH$_2$ carbons: 60.84, 41.19, 30.04; CH carbons: 128.31, 128.20, 126.64, 125.92, 114.72 ppm. HPLC: 9.975 min.

Synthesis of 4-(3-phenylpropyl)1H-pyrrole-2-carboxylic acid ethyl ester (44)

Triethylsilane (0.776 mL, 4.87 mmol) was added to a stirring, room temperature solution of 43 (0.5266 g, 1.57 mmol) in trifluoroacetic acid (TFA) (3.74 mL, 0.42 M) under $N_2$. After stirring at room temperature for 4 hours, the TFA was removed under vacuum, and the crude product was taken up in EtOAc, washed with brine, dried with $Na_2SO_4$, filtered, concentrated, and purified by preparative reverse phase HPLC with the following conditions: 0 to 11 min, 35:65 H$_2$O:CH$_3$CN. 11.5-20 min, 35:65 to 0:100 H$_2$O:CH$_3$CN; 20 mL/min.; λ=254 nM; 200 mg/mL, 0.7 mL/injection. 0.2455 g (48.7%) of 44 was obtained as a fluffy white solid. (Note: An undesired impurity has a retention time of 12.062 min by HPLC.) $^1H$ (CDCl$_3$, 400 MHz): δ 9.27 (1H, broad s), 7.34-7.26 (2H, m), 7.24-7.17 (3H, m), 6.81 (1H, s), 6.75 (1H, s), 4.33 (2H, q, J=7.1 Hz), 2.67 (2H, t, J=7.8 Hz), 2.53 (2H, t, J=7.8 Hz), 1.93 (2H, quint, J=7.8 Hz), 1.37 (3H, t, J=7.1 Hz) ppm. $^{13}C$ (CDCl$_3$, 100 MHz): δ 161.34, 142.31, 128.40, 128.22, 125.99, 125.64, 122.47, 120.73, 114.82, 60.17, 35.33, 32.47, 26.17, 14.41 ppm. DEPT (CDCl$_3$, 100 MHz): CH$_3$ carbons: 14.41; CH$_2$ carbons: 60.17, 35.33, 32.47, 26.17; CH carbons: 128.40, 128.22, 125.64, 120.73, 114.82 ppm. HPLC: 11.140 min.

Synthesis of 4-(3-phenylpropyl)1H-pyrrole-2-carboxylic acid (45)

Freshly prepared aq. NaOH (10 M in H$_2$O, 3.82 mmol) was added to a stirring, room temperature solution of 44 (0.2455 g, 0.7644 mmol) in MeOH (1.9 mL, 0.4 M) under $N_2$. The reaction was heated to reflux until the reaction was judged complete by HPLC (25 min): The product was concentrated and then dissolved in 1.5 mL H$_2$O. The product was extracted with EtOAc, then the aqueous layer was made acidic (pH=2) with the dropwise addition of 10% aq. HCl. EtOAc was added, and the product was extracted into the organic layer. The organic layer was dried with Na$_2$SO$_4$, filtered, and concentrated to obtain 56.1 mg of product that contained a few minor impurities by HPLC. The product was taken up into a minimal amount of CHCl$_3$ with heating, and then a small amount of hexanes was added to precipitate the product. The product was filtered, and dried to obtain 16.0 mg of 45. (Note: An undesired impurity has a retention time of 10.843 min by HPLC. $^1H$ (CD$_3$OD, 400 MHz): δ 7.24 (2H, t, J=7.3 Hz), 7.16 (2H, d, J=7.3 Hz), 7.13 (1H, t, J=7.3 Hz), 6.75 (1H, s), 6.71 (1H, s), 2.61 (2H, t, J=7.8 Hz), 2.46 (2H, t, J=7.8 Hz), 1.86 (2H, quint, J=7.8 Hz) ppm. $^{13}C$ (CD$_3$OD, 100 MHz): δ 164.54, 143.73, 129.47, 129.27, 126.73, 126.66, 123.49, 122.56, 116.34, 36.41, 34.23, 27.21 ppm. DEPT (CDCl$_3$, 100 MHz): CH$_2$ carbons: 36.41, 34.23, 27.21; CH carbons: 129.47, 129.27, 126.66, 122.56, 116.34 ppm. HPLC: 9.845 min.

Example 15

Synthesis of 5-(3-methylbutyl)-1H-pyrazole-3-carboxylic acid (48)

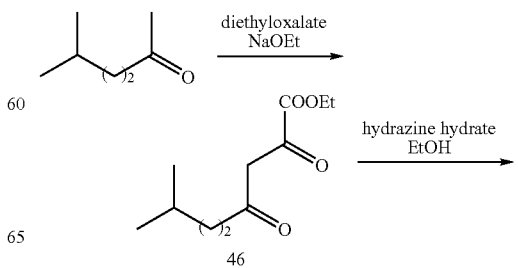

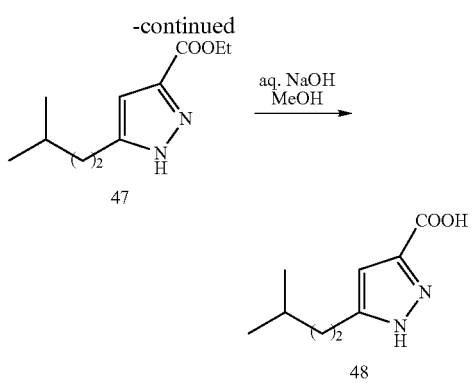

Synthesis of 7-methyl-2,4-Dioxooctanoic acid ethyl ester (46)

5-methyl-2-hexanone (5.0084 g, 43.9 mmol) and diethyloxalate (5.95 mL, 43.8 mmol) were mixed together, and then added to a solution of NaOEt (3 M, 14.6 mL) stirring in an ice bath under $N_2$. After stirring for 15 minutes, the reaction was warmed to room temperature and stirred overnight. The reaction was quenched at 0° C. with 1N HCl and extracted 2× with $CH_2Cl_2$. The combined organics were washed with $H_2O$, dried with $Na_2SO_4$, filtered, and concentrated to yield crude 46. The crude material was purified with 1:1 Hexanes: $CH_2Cl_2$ to obtain 6.6035 g (70.3%) of 46. $^1$H (CDCl$_3$, 400 MHz): δ 6.28 (1H, s), 4.25 (2H, q, J=7.0 Hz), 2.40 (2H, t, 7.6 Hz), 1.54-1.41 (3H, m), 1.27 (3H, t, J=7.3 Hz), 0.82 (6H, d, J=6.3 Hz) ppm. $^{13}$C (CDCl$_3$, 100 MHz): δ 203.40, 166.27, 161.85, 101.37, 62.15, 38.74, 33.39, 27.46, 21.99, 13.77 ppm. DEPT (CDCl$_3$, 100 MHz): CH$_3$ carbons: 21.99, 13.77; CH$_2$ carbons: 62.15, 38.74, 33.39; CH carbons: 101.37, 27.46 ppm. HPLC: 11.038 min.

Synthesis of 5-(3-methylbutyl)-1H-pyrazole-3-carboxylic acid ethyl ester (47)

Hydrazine hydrate (1.43 mL, 2.95 mmol) was added to a stirring room temperature solution of 46 (6.3112 g, 2.95 mmol) in EtOH (29.5 mL, 1 M) under $N_2$. The reaction was then stirred at room temperature until judged complete by HPLC (35 min): The reaction was concentrated and purified by silica gel chromatography (Combiflash column, 96:4 Hexanes:2N NH$_3$ in EtOH): Only pure fractions were combined and concentrated to obtain 4.3911 g (70.9%) of 47. $^1$H (CDCl$_3$, 400 MHz): δ 13.01 (1H, broad s), 6.52 (1H, s), 4.29 (2H, q, J=7.1 Hz), 2.64 (2H, t, J=7.8 Hz), 1.57-1.41 (3H, m), 1.26 (3H, t, J=7.1 Hz), 5.85 (6H, d, J=5.9 Hz) ppm. $^{13}$C (CDCl$_3$, 100 MHz): δ 162.37, 146.26, 143.1, 105.73, 60.53, 37.88, 27.35, 23.42, 22.11, 14.06 ppm. HPLC: 10.006 min.

Synthesis of 5-(3-methylbutyl)-1H-pyrazole-3-carboxylic acid (48)

Freshly prepared aq. NaOH (10 M in H$_2$O, 80.85 mmol) was added to a stirring, room temperature solution of 47 (3.40 g, 16.17 mmol) in MeOH (40.4 mL, 0.4 M) under $N_2$. The reaction was then heated to reflux until the reaction was judged complete by HPLC (6 min): The reaction was concentrated and then dissolved in 14 mL H$_2$O. 10% aq. HCl was added dropwise until the pH=2. The white solid that precipitated from the reaction was filtered off and washed with cold H$_2$O. The solid was dried under vacuum overnight to obtain 2.8753 g (97.6%) of 48. (Note: An undesired impurity has a retention time of 9.522 min by HPLC.) $^1$H (CDCl$_3$, 400 MHz): δ 6.61 (1H, s), 2.70 (2H, t, J=7.8 Hz), 1.63-1.51 (3H, m), 0.94 (6H, d, J=6.3 Hz) ppm. $^{13}$C (CDCl$_3$, 100 MHz): δ 164.35, 149.48, 143.00, 107.34, 39.35, 28.71, 24.69, 22.65 ppm. DEPT (CDCl$_3$, 100 MHz): CH$_3$ carbons: 22.65; CH$_2$ carbons: 39.35, 24.69; CH carbons: 107.34, 28.71 ppm. HPLC: 9.522 min.

Example 16

Synthesis of 5-(4-Methylpent-3-enyl)-1H-pyrazole-3-carboxylic acid (51)

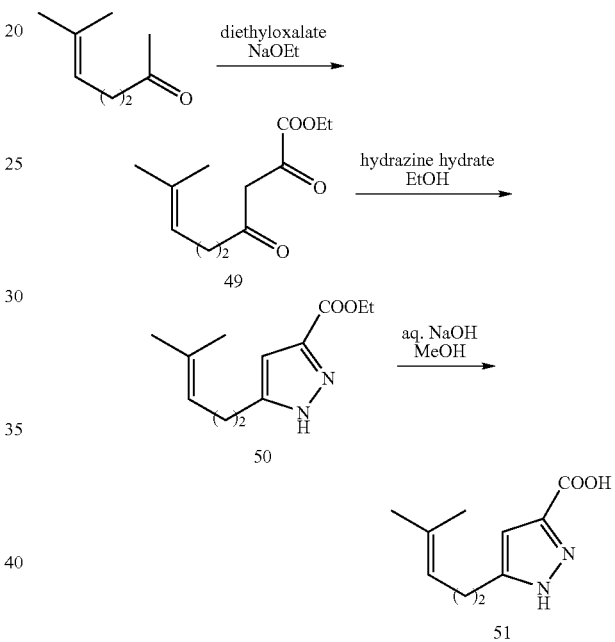

Synthesis of 8-Methyl-2,4-dioxonon-7-enoic acid ethyl ester (49)

Sodium hydride (0.465 g, 19.4 mmol) was added slowly to a NaCl ice bath containing EtOH (5.88 mL, 3.3 M) stirring under $N_2$. 6-Methylhept-5-en-2-one (2.4412 g, 19.3 mmol) and diethyloxalate (2.63 mL, 19.4 mmol) were mixed together, and then added to the chilled NaOEt solution. After stirring for 15 minutes, the reaction was warmed to room temperature and stirred for 6 hours, at which point the reaction was judged complete by TLC. The reaction was quenched at 0° C. with 1N HCl and extracted 2× with CH$_2$Cl$_2$. The combined organics were washed with H$_2$O, dried with Na$_2$SO$_4$, filtered, and concentrated, and purified by silica gel chromatography (Combiflash column, 70:30:3 Hexanes:CH$_2$Cl$_2$:2N NH$_3$ in EtOH): Only pure fractions were combined and concentrated to obtain 1.9190 g (43.8%) of 49. $^1$H (CDCl$_3$, 400 MHz): δ 14.44 (1H, broad s), 6.34 (1H, s), 5.06 (1H, t, J=7.3 Hz), 4.33 (2H, q, J=7.1 Hz), 2.49 (2H, t, J=7.3 Hz), 2.31 (2H, q, J=7.3 Hz), 1.66 (3H, s), 1.60 (3H, s), 1.35 (3H, t, J=7.1 Hz) ppm. $^{13}$C (CDCl$_3$, 100 MHz): δ 202.83, 166.39, 162.08, 133.42, 121.90, 101.64, 62.40, 40.92, 25.59, 23.34, 17.61, 13.96 ppm. DEPT (CDCl$_3$, 100 MHz): CH$_3$ carbons: 25.59, 17.62, 13.97; CH$_2$ carbons: 62.40, 40.92, 23.34; CH carbons: 121.90, 101.64 ppm. HPLC: 11.007 min.

Synthesis of 5-(4-Methylpent-3-enyl)-1H-pyrazole-3-carboxylic acid ethyl ester (50)

Hydrazine hydrate (0.41 mL, 8.48 mmol) was added to a stirring room temperature solution of 49 (0.1.9190 g, 8.48 mmol) in EtOH (8.5 mL, 1 M) under N$_2$. The reaction was then heated to reflux until judged complete by HPLC (1/2 h): The reaction was concentrated and purified by silica gel chromatography (Combiflash column, 96:4 Hexanes:2N NH$_3$ in EtOH): $^1$H (CDCl$_3$, 400 MHz): δ 12.73 (1H, broad s), 6.57 (1H, s), 5.09 (1H, t, J=6.8 Hz), 4.32 (2H, q, J=7.1 Hz), 2.70 (2H, t, J=7.5 Hz), 2.29 (2H, q, J=7.5 Hz), 1.63 (3H, s), 1.52 (3H, s), 1.30 (3H, t, J=7.1 Hz) ppm. Partial $^{13}$C (CDCl$_3$, 100 MHz): δ 162.27, 106.11, 60.65, 31.49, 27.53, 25.52, 17.51, 13.10 ppm. HPLC: 9.986 min.

Synthesis of 5-(4-Methylpent-3-enyl)-1H-pyrazole-3-carboxylic acid (51)

Freshly prepared aq. NaOH (10 M in H$_2$O, 11.85 mmol) was added to a stirring, room temperature solution of 50 (0.0.5269 g, 2.37 mmol) in MeOH (5.9 mL, 0.4 M) under N$_2$. The reaction was then heated to reflux until the reaction was judged complete by HPLC (5 min): The reaction was concentrated, redissolved in H$_2$O, and extracted with EtOAc. 10% aq. HCl was added dropwise to the aqueous layer until the pH=2. The white solid that precipitated from the reaction was filtered off and washed with cold H$_2$O. The solid was dried under vacuum overnight to obtain 0.4034 g (87.6%) of 51. $^1$H (CD$_3$OD, 400 MHz): δ 6.56 (1H, s), 5.14 (1H, t), 2.68 (2H, t, J=7.3 Hz), 2.33 (2H, q, J=7.3 Hz), 1.67 (3H, s), 1.56 (3H, s) ppm. $^{13}$C (CD$_3$OD, 100 MHz): δ 164.94, 148.55, 143.23, 123.94, 107.32, 28.89, 27.04, 25.85, 17.69 ppm. DEPT (CD$_3$OD, 100 MHz): CH$_3$ carbons: 25.85, 17.69; CH$_2$ carbons: 28.89, 27.04; CH carbons: 123.94, 107.32 ppm: HPLC: 8.475 min.

Example 17

Synthesis of 5-[2-(2,2,6-trimethylcyclohexyl)-ethyl]-1H-pyrazole-3-carboxylic acid (54)

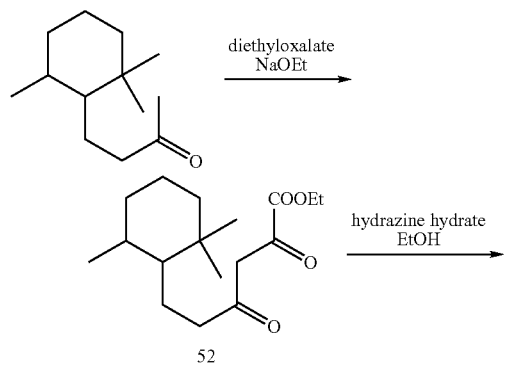

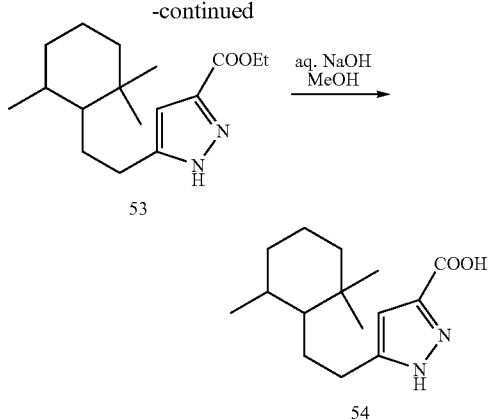

Synthesis of 2,4-dioxo-6-(2,2,6-trimethylcyclohexyl)-hexanoic acid ethyl ester (52)

Sodium hydride (0.6447 g, 25.52 mmol) was added slowly to a NaCl ice bath containing EtOH (10 mL, 2.6 M) stirring under N$_2$. 4-(2,2,6-trimethylcyclohexyl)-butan-2-one (5.0072 g, 25.50 mmol) and diethyloxalate (3.7241 g, 25.48 mmol) were mixed together, and then added to the chilled NaOEt solution. After stirring for 5 minutes, the reaction was warmed to room temperature. The reaction quickly solidified. An additional 10 mL EtOH was added, and the reaction was allowed to stand for another 3 h. The reaction was quenched at 0° C. with 1N HCl and extracted 2× with CH$_2$Cl$_2$. The combined organics were washed with H$_2$O, dried with Na$_2$SO$_4$, filtered, concentrated, and purified by silica gel chromatography (Combiflash column, 1:1 Hexanes: CH$_2$Cl$_2$): Only pure fractions were combined and concentrated to obtain 52. $^1$H (CDCl$_3$, 400 MHz): δ 14.51 (1H, broad s), 6.34 (1H, s), 4.34 (2H, q, J=7.1 Hz), 2.44 (2H, t, J=8.3 Hz), 1.96-1.84 (1H, m), 1.68-1.22 (m), 1.36 (3H, t, J=7.1 Hz), 1.18-0.98 (m), 0.94 (3H, s), 0.87 (3H, s), 0.85 (3H, d, J=7.3 Hz) ppm. Partial $^{13}$C (CDCl$_3$, 100 MHz): δ 203.45, 167.17, 162.40, 101.80, 62.71, 49.28, 42.60, 30.46, 20.86, 14.27 ppm. Partial DEPT (CDCl$_3$, 100 MHz): CH$_3$ carbons: 14.27; CH$_2$ carbons: 62.71; CH carbons: 101.80 ppm. HPLC: 12.576 min.

Synthesis of 5-[2-(2,2,6-trimethylcyclohexyl)-ethyl]-1H-pyrazole-3-carboxylic acid ethyl ester (53)

Hydrazine hydrate (0.867 mL, 17.9 mmol) was added to a stirring room temperature solution of 52 (5.2981 g, 17.9 mmol) in EtOH (17.9 mL, 1 M) under N$_2$. The reaction was then heated to reflux until judged complete by HPLC. The reaction was concentrated and purified by silica gel chromatography (Combiflash column, 97:3 Hexanes:2N NH$_3$ in EtOH) to obtain 1.6604 g (31.8%) of 53. Partial $^1$H (CDCl$_3$, 400 MHz): δ 12.45 (1H, broad s), 6.58 (1H, s), 4.32 (2H, q, J=7.1 Hz), 2.63 (2H, t, J=8.3 Hz), 1.31 (3H, t, J=7.1 Hz), 0.90 (3H, s), 0.83 (3H, s), 0.78 (3H, d, J=6.8 Hz) ppm. Partial $^{13}$C (CDCl$_3$, 100 MHz): δ 106.04, 60.66, 48.99, 34.03, 30.10, 24.89, 14.17 ppm. HPLC: 12.000 min.

Synthesis of 5-[2-(2,2,6-trimethylcyclohexyl)-ethyl]-1H-pyrazole-3-carboxylic acid (54)

Freshly prepared aq. NaOH (10 M in H$_2$O, 2.73 mmol) was added to a stirring, room temperature solution of 53 (0.1594 g, 0.5451 mmol) in MeOH (1.36 mL, 0.4 M) under N$_2$. The reaction was then heated to reflux until the reaction was judged complete by HPLC (5 min). The reaction was concentrated, redissolved in H$_2$O, and extracted with EtOAc. 10% aq. HCl was added dropwise to the aqueous layer until the pH=2. The white solid that precipitated from the reaction was filtered off and washed with cold H$_2$O. The solid was dried under vacuum overnight to obtain 0.0119 g (8.2%) of 54. An additional 0.0590 g (40.9%) of 54 was obtained, although slightly impure, from the EtOAc layer. $^1$H (CD$_3$OD, 400 MHz): δ 6.56 (1H, s), 2.64 (2H, t, J=7.8 Hz), 2.03-1.89 (1H, m), 1.69-1.53 (2H, m), 1.55-1.41 (2H, m), 1.39-1.27 (2H, m), 1.20-1.06 (3H, m), 0.97 (3H, s), 0.91 (3H, s), 0.86 (3H, d, J=6.8 Hz) ppm. $^{13}$C (CD$_3$OD, 100 MHz): δ 165.07, 149.02, 143.33, 107.26, 50.24, 37.04, 35.11, 31.58, 31.33, 29.00, 28.87, 28.37, 26.30, 22.13, 18.90 ppm. DEPT (CD$_3$OD, 100 MHz): CH$_3$ carbons: 29.00, 28.87, 18.90; CH$_2$ carbons: 37.04, 31.33, 28.37, 26.30, 22.13; CH carbons: 107.26, 50.24, 31.58 ppm. HPLC: 10.497 min.

Example 18

Synthesis of 5-(2-Phenylpropyl)-1H-pyrazole-3-carboxylic acid (58)

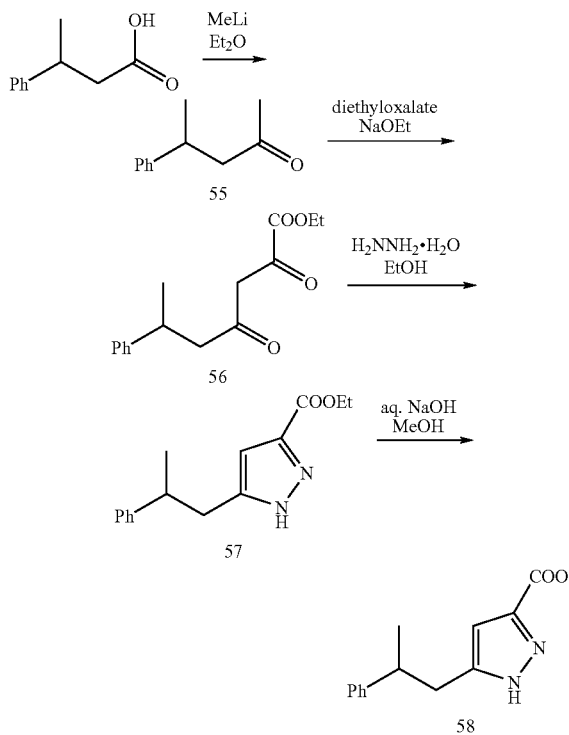

Synthesis of 4-Phenylpentan-2-one (55)

1.6 M Methyl lithium (22.8 mL, 36.5 mmol) was added over 1 hour to a stirring 0° C. solution of 3-Phenylbutyric acid (1.8298 g, 11.14 mmol) in dry Et$_2$O (56 mL, 0.2 M): The ice bath was removed, and the reaction was allowed to stir at room temperature for 2⅔ additional hours. Another 0.8 mL MeLi (1.12 mmol, 0.10 equiv) was added, and the reaction was stirred for another 30 minutes. The reaction was then poured into rapidly stirring ice water containing aq. HCl. The organic layer was removed, washed with NaHCO$_3$ and brine, then dried with Na$_2$SO$_4$, filtered and concentrated to achieve pure 55 (1.2324 g, 68.2%): $^1$H (CDCl$_3$, 400 MHz): δ 7.30 (2H, t, J=7.3 Hz), 7.22 (2H, d, J=7.3 Hz), 7.20 (2H, t, J=7.3 Hz), 3.37-3.27 (1H, m), 2.76 (1H, dd, J=16.1, 6.3 Hz), 2.66 (1H, dd, J=16.1, 7.8 Hz), 2.05 (3H, s), 1.28 (3H, d, J=7.3 Hz) ppm. $^{13}$C (CDCl$_3$, 100 MHz): δ 208.01, 146.42, 128.80, 127.03, 126.57, 52.16, 35.67, 30.77, 22.28 ppm. DEPT (CDCl$_3$, 100 MHz): CH$_3$ carbons: 30.77, 22.28; CH$_2$ carbons: 52.16; CH carbons: 128.80, 127.03, 126.57, 35.67 ppm. HPLC: 10.017 min. (Note: SM has HPLC retention time of 9.041 min.)

Synthesis of 2,4-dioxo-6-phenylheptanoic acid ethyl ester (56)

Sodium hydride (0.1702 g, 7.09 mmol) was added slowly to a NaCl ice bath containing EtOH (2.6 mL, 2.7 M) stirring under N$_2$. 4-Phenylpentan-2-one (55) (1.0493 g, 6.47 mmol) and diethyloxalate (0.88 mL, 6.47 mmol) were mixed together, and then added to the chilled NaOEt solution. After stirring for 5 minutes, the reaction was warmed to room temperature. After 90 min, the reaction was quenched at 0° C. with 1N HCl and extracted 2× with CH$_2$Cl$_2$. The combined organics were washed with H$_2$O, dried with Na$_2$SO$_4$, filtered, concentrated to provide 56 (0.7230 g, 42.6%) which was used without further purification in the next step. $^1$H (CDCl$_3$, 400 MHz): δ 7.34-7.16 (5H, m), 6.30 (1H, s), 4.33 (2H, q, J=7.0 Hz), 3.39-3.26 (1H, m), 2.82 (1H, dd, J=15.1, 6.8 Hz), 2.72 (1H, dd, J=15.1, 7.8 Hz), 1.36 (3H, t, J=7.0 Hz), 1.32 (3H, d, J=6.8 Hz) ppm. HPLC: 10.934 min.

Synthesis of 5-(2-phenylpropyl)-1H-pyrazole-3-carboxylic acid ethyl ester (57)

Hydrazine hydrate (0.134 mL, 2.76 mmol) was added to a stirring room temperature solution of 56 0.7230 g, 2.76 mmol) in EtOH (2.8 mL, 1 M) under N$_2$. The reaction was then heated to reflux until judged complete by HPLC (50 min): The reaction was concentrated and purified by preparative reverse phase HPLC with the following conditions: 0 to 24 min, 55:45 H$_2$O:CH$_3$CN; 24-25 min, 55:45 to 0:100 H$_2$O:CH$_3$CN; 20 mL/min.; λ=214 nM; 100 mg/mL, 0.2 mL/injection. 0.0489 g of 57 was obtained. $^1$H (CDCl$_3$, 300 MHz): δ 10.77 (1H, broad s), 7.36-7.14 (5H, m), 6.49 (1H, s), 4.33 (2H, q, J=7.0 Hz), 3.16-2.86 (3H, m), 1.33 (3H, t, J=7.0 Hz), 1.27 (3H, d, J=5.9 Hz) ppm. $^{13}$C (CDCl$_3$, 75 MHz): δ 162.01, 145.94, 145.75, 141.50, 128.43, 126.76, 126.32, 106.98, 60.87, 39.94, 34.64, 21.34, 14.12 ppm. DEPT (CDCl$_3$, 75 MHz): CH$_3$ carbons: 21.34, 14.12; CH$_2$ carbons: 60.87, 34.64; CH carbons: 128.43, 126.77, 126.32, 106.98, 39.94 ppm. HPLC: 10.052 min.

Synthesis of 5-(2-phenylpropyl)-1H-pyrazole-3-carboxylic acid (58)

Freshly prepared aq. NaOH (10 M in H$_2$O, 0.947 mmol) was added to a stirring, room temperature solution of 57 (0.0489 g, 0.1893 mmol) in MeOH (0.47 mL, 0.4 M) under N$_2$. The reaction was then heated to reflux until the reaction was judged complete by HPLC (8 min): The reaction was concentrated, redissolved in H$_2$O, and extracted with EtOAc (1 mL): 10% aq. HCl was added dropwise to the aqueous layer until the pH=2. The white solid that precipitated from the reaction was filtered off and washed with cold H$_2$O. The solid was dried under vacuum overnight to obtain 0.0298 g (68.3%) of 58. $^1$H (CD$_3$OD, 400 MHz): δ 7.24 (2H, t, J=7.3 Hz), 7.18 (2H, d, J=7.3 Hz), 7.14 (1H, t, J=7.3 Hz), 6.42 (1H, s), 3.11-3.01 (1H, m), 2.95 (1H, dd, J=14.1, 7.3 Hz), 2.89 (1H, dd, J=14.1, 7.8 Hz), 1.26 (3H, d, J=6.8 Hz) ppm. $^{13}$C (CD$_3$OD, 100 MHz): δ 164.83, 147.35, 147.13, 143.02, 129.45, 127.92, 127.35, 108.07, 41.46, 35.58, 22.05 ppm. DEPT (CD$_3$OD, 100 MHz): CH$_3$ carbons: 22.05; CH$_2$ carbons: 35.58; CH carbons: 129.45, 127.92, 127.35, 108.07, 41.46 ppm. HPLC: 8.764 min.

Example 19

Synthesis of 5-(1-methyl-2-phenylethyl)-1H-pyrazole-3-carboxylic acid (62)

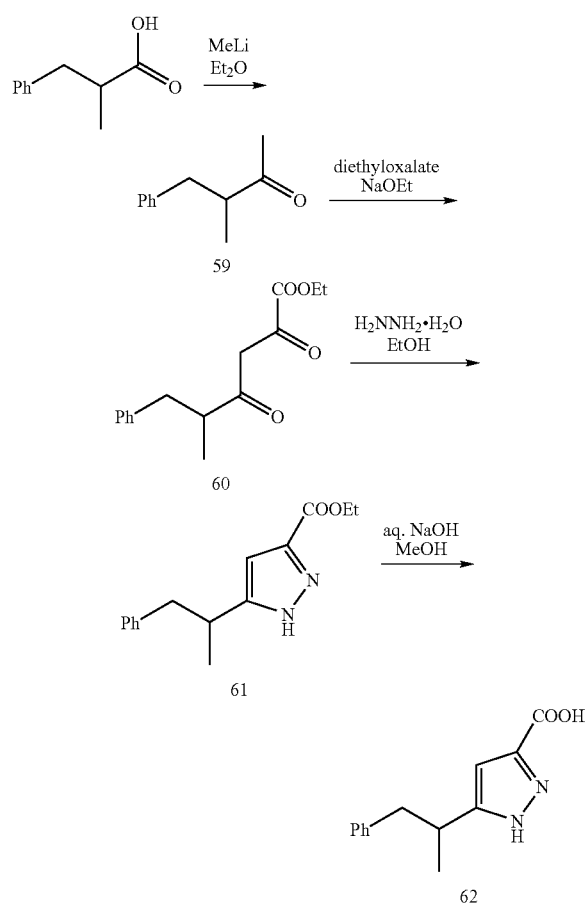

Synthesis of 3-Methyl-4-phenylbutan-2-one (59)

1.4 M Methyl lithium (34.8 mL, 48.72 mmol) was added over 70 min to a stirring 0° C. solution of α-methylhydrocinnamic acid (4.0019 g, 24.36 mmol) in dry Et$_2$O (122 mL, 0.2 M): The ice bath was removed, and the reaction was allowed to stir at room temperature for 2 additional hours. The reaction was the poured into rapidly stirring ice water containing aq. HCl. The organic layer was removed, washed with NaHCO$_3$ and brine, then dried with Na$_2$SO$_4$, filtered, concentrated, and purified by silica gel chromatography (Combiflash column, 95:5 Hexanes:EtOAc) to achieve pure 59 (2.3038 g, 58.3%): $^1$H (CDCl$_3$, 400 MHz): δ 7.28 (2H, t, J=7.3 Hz), 7.20 (1H, t, J=7.3 Hz), 7.16 (2H, d, J=7.3 Hz), 3.00 (1H, dd, J=13.7, 6.8 Hz), 2.83 (1H, app sex, 7.0 Hz), 2.56 (1H, dd, J=13.7, 7.8 Hz), 2.08 (3H, s), 1.09 (3H, d, J=6.8 Hz) ppm. $^{13}$C (CDCl$_3$, 100 MHz): δ 211.99, 139.53, 128.79, 128.28, 126.10, 48.65, 38.75, 28.74, 16.10 ppm. DEPT (CDCl$_3$, 100 MHz): CH$_3$ carbons: 28.74, 16.10; CH$_2$ carbons: 38.75; CH carbons: 128.79, 128.28, 126.10, 48.65 ppm. HPLC: 10.229 min. (Note: SM has HPLC retention time of 9.225 min.)

Synthesis of 5-methyl-2,4-dioxo-6-phenylhexanoic acid ethyl ester (60)

Sodium hydride (0.3965 g, 16.52 mmol) was added slowly to a NaCl ice bath containing EtOH (5.6 mL, 2.6 M) stirring under N$_2$. 59 (2.2727 g, 14.01 mmol) and diethyloxalate (2.0649 g, 14.13 mmol) were mixed together, and then added to the chilled NaOEt solution. After stirring for 5 minutes, the reaction was warmed to room temperature. After stirring for 5 h, the reaction was quenched at 0° C. with 1N HCl and extracted 2× with CH$_2$Cl$_2$. The combined organics were washed with H$_2$O, dried with Na$_2$SO$_4$, filtered, concentrated, and purified by silica gel chromatography (Combiflash column, 67:30:3 Hexanes:CH$_2$Cl$_2$:2N NH$_3$ in EtOH): Only pure fractions were combined and concentrated to obtain 60. $^1$H (CDCl$_3$, 400 MHz): δ 14.55 (1H, broad s), 7.32-7.12 (5H, m), 6.36 (1H, s), 4.33 (2H, q, J=7.0 Hz), 3.05 (1H, dd, J=13.5, 6.8 Hz), 2.84 (1H, app sex, J=7.0 Hz), 2.67 (1H, dd, J=13.5, 7.8 Hz), 1.36 (3H, t, J=7.1 Hz), 2.33 (3H, d, J=7.0 Hz) ppm. $^{13}$C (CDCl$_3$, 100 MHz): δ 205.78, 166.96, 161.88, 138.75, 128.80, 128.30, 126.29, 100.75, 62.32, 46.35, 39.10, 16.51, 13.88 ppm. DEPT (CDCl$_3$, 100 MHz): CH$_3$ carbons: 16.51, 13.88; CH$_2$ carbons: 62.32, 39.10; CH carbons: 128.80, 128.30, 126.29, 100.75, 46.35 ppm. HPLC: 11.084 min.

Synthesis of 5-(2-phenylpropyl)-1H-pyrazole-3-carboxylic acid ethyl ester (61)

Hydrazine hydrate (0.1564 mL, 3.23 mmol) was added to a stirring room temperature solution of 60 (0.8460 g, 3.223 mmol) in EtOH (3.2 mL, 1 M) under N$_2$. The reaction was then heated to reflux until judged complete by HPLC. The reaction was concentrated and purified by silica gel chromatography (Combiflash column, 87:7:4 Hexanes:CH$_2$Cl$_2$:2N NH$_3$ in EtOH) to obtain 0.6423 g (77.1%) of 61. $^1$H (CDCl$_3$, 300 MHz): δ 7.26-7.14 (3H, m), 7.08 (2H, d, J=7.0 Hz), 6.61 (1H, s), 4.34 (2H, q, J=7.2 Hz), 3.23 (1H, app sex, J=7.1 Hz), 3.00 (1H, dd, J=13.5, 6.7 Hz), 2.77 (1H, dd, J=13.5, 8.0 Hz), 1.34 (3H, t, J=7.1 Hz), 1.26 (3H, d, J=7.3 Hz) ppm. Partial $^{13}$C (CDCl$_3$, 75 MHz): δ 161.86, 139.47, 128.99, 128.20, 126.14, 104.99, 60.80, 43.37, 33.39, 19.60, 14.18 ppm. DEPT (CDCl$_3$, 75 MHz): CH$_3$ carbons: 19.60, 14.18; CH$_2$ carbons: 60.80, 43.37; CH carbons: 128.99, 128.20, 126.14, 104.99, 33.39 ppm. HPLC: 10.129 min.

Synthesis of 5-(2-phenylpropyl)-1H-pyrazole-3-carboxlic acid (62)

Freshly prepared aq. NaOH (10 M in H$_2$O, 1.01 mmol) was added to a stirring, room temperature solution of 61 (0.0523 g, 0.2024 mmol) in MeOH (0.51 mL, 0.4 M) under $N_2$. The reaction was then heated to reflux until the reaction was judged complete by HPLC (9 min): The reaction was concentrated, redissolved in $H_2O$, and extracted with EtOAc. 10% aq. HCl was added dropwise to the aqueous layer until the pH=2. When a white solid did not precipitate as expected, EtOAc was added, and the organic layer was removed, dried with $Na_2SO_4$, filtered, and concentrated to provide pure 62. $^1H$ ($CD_3OD$, 400 MHz): δ 7.24-7.18 (2H, m), 7.17-7.05 (3H, m), 6.56 (1H, s), 3.17 (1H, app sex, J=7.3 Hz), 2.96 (1H, dd, J=13.6, 7.3 Hz), 2.80 (1H, dd, J=13.7, 7.8 Hz), 1.25 (3H, d, J=6.8 Hz) ppm. $^{13}C$ ($CD_3OD$, 100 MHz): 6164.88, 153.40, 142.91, 140.97, 130.09, 129.25, 127.21, 106.11, 44.41, 34.96, 20.35 ppm. DEPT ($CD_3OD$, 100 MHz): $CH_3$ carbon: 20.35; $CH_2$ carbon: 44.41; CH carbons: 130.09, 129.25, 127.21, 106.11, 34.96 ppm. HPLC: 8.849 min.

Example 20

Synthesis of 4-[2-(2-bromophenyl)-ethyl]-1H-pyrrole-2-carboxylic acid (65)

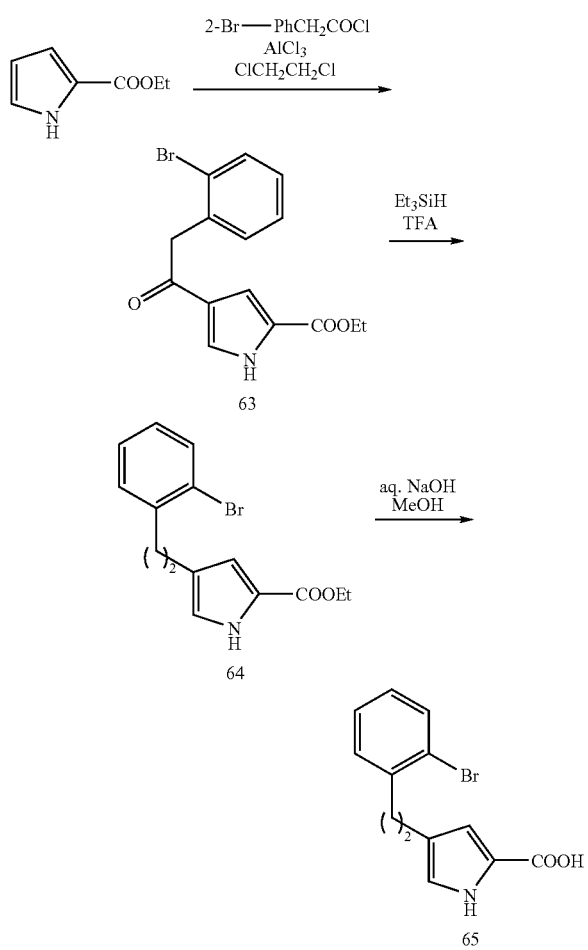

Synthesis of 4-[2-(2-bromophenyl)-acetyl]-1H-pyrrole-2-carboxylic acid ethyl ester (63)

Ethylpyrrole-2-carboxylate (1.9428 g, 13.96 mmol) in a minimal amount (5 mL) of dichloroethane was added to an ice cooled stirring mixture of aluminum chloride (4.0458 g, 30.34 mmol) and 2-bromophenylacetyl chloride (6.7116 g, 28.74 mmol) in dichloroethane (44 mL, 0.66 M) under $N_2$. The ice bath was removed, and the reaction was stirred at room temperature for 2 h. 19.2977 g (2.6 mMol/g) Polyamine resin HL (200-400 mesh) and dichloroethane (20 mL) were added, and the reaction was stirred for ~100 min. The reaction was then filtered through a glass-fritted funnel directly into ice water. The resin was rinsed with $CH_2Cl_2$, then the organic layers were removed, dried with $Na_2SO_4$, filtered, concentrated, and purified by silica gel chromatography (Combiflash column, 80:20 to 60:40 Hexanes:EtOAc) to obtain 2.5751 g (54.9%) 63 as a white solid. Note: A small amount of $CH_2Cl_2$ was required to solubilize the crude product before placement on the silica column. $^1H$ ($CDCl_3$, 400 MHz): δ 10.32 (1H, broad s), 7.57-7.53 (2H, m), 7.38-7.37 (1H, m), 7.29-7.21 (2H, m), 7.13-7.07 (1H, m), 4.35 (2H, q, J=7.2 Hz), 4.25 (2H, s), 1.36 (3H, t, J=7.2 Hz) ppm. $^{13}C$ ($CDCl_3$, 100 MHz): δ 191.78, 161.04, 134.91, 132.62, 131.66, 128.59, 127.40, 126.95, 126.25, 124.98, 124.17, 114.88, 60.92, 46.56, 14.26 ppm. DEPT ($CDCl_3$, 100 MHz): $CH_3$ carbons: 14.26; $CH_2$ carbons: 60.92, 46.56; CH carbons: 132.62, 131.66, 128.59, 127.40, 126.95, 114.88 ppm. HPLC: 10.078 min.

Synthesis of 4-[2-(2-bromophenyl)-ethyl]-1H-pyrrole-2-carboxylic acid ethyl ester (64)

Triethylsilane (2.25 mL, 14.1 mmol) was added to a stirring, room temperature solution of 63 (1.5291 g, 4.55 mmol) in trifluoroacetic acid (TFA) (10.8 mL, 0.42 M) under $N_2$. After stirring at room temperature for 3 hours, the reaction was heated to 35° C. for 35 min, then the TFA was removed under vacuum, and the crude product was taken up in EtOAc, washed with brine, dried with $Na_2SO_4$, filtered, concentrated, and purified by preparative reverse phase HPLC with the following conditions: 0 to 12 min, 35:65 $H_2O:CH_3CN$; 14-15 min, 35:65 to 0:100 $H_2O:CH_3CN$; 20 mL/min.; λ=254 nM; 3.67 g/mL, 0.2 mL/injection. 0.8402 g (57.3%) of 64 was obtained as a fluffy white solid. (Note: An undesired impurity has a retention time of 12.281 min by HPLC.) $^1H$ ($CDCl_3$, 400 MHz): δ 9.07 (1H, broad s), 7.55 (1H, dd, J=8.0, 1.3 Hz), 7.21 (1H, td, J=7.3, 1.3 Hz), 7.17 (1H, dd, J=7.6, 2.4 Hz), 7.06 (1H, ddd, J=7.9, 7.0, 2.3 Hz), 6.82 (1H, s), 6.72 (1H, s), 4.32 (2H, t, J=7.2 Hz), 2.99 (2H, t, J=8.0 Hz), 2.78 (2H, t, J=7.9 Hz), 1.36 (3H, t, J=7.2 Hz) ppm. $^{13}C$ ($CDCl_3$, 100 MHz): δ 161.21, 141.03, 132.75, 130.41, 127.63, 127.32, 125.31, 124.43, 122.66, 120.68, 114.83, 60.22, 37.78, 27.03, 14.48 ppm. DEPT ($CDCl_3$, 100 MHz): $CH_3$ carbons: 14.48; $CH_2$ carbons: 60.22, 37.78, 27.03; CH carbons: 132.75, 130.41, 127.63, 127.32, 120.68, 114.83 ppm. HPLC: 11.355 min.

Synthesis of 4-[2-(2-bromophenyl)-ethyl]-1H-pyrrole-2-carboxylic acid (65)

Freshly prepared aq. NaOH (10 M in $H_2O$, 13.04 mmol) was added to a stirring, room temperature solution of 64 (0.8402 g, 2.608 mmol) in MeOH (6.5 mL, 0.4 M) under $N_2$. The reaction was heated to reflux until the reaction was judged complete by HPLC (10 min): The product was concentrated and then dissolved in 10 mL $H_2O$. The product was extracted with EtOAc until the organic layer no longer turned yellow, then the aqueous layer was made acidic (pH=2) with the dropwise addition of 10% aq. HCl. The product oiled out of solution, so EtOAc was added, and the organic layer was removed, dried with $Na_2SO_4$, filter, concentrated to obtain 65 (0.3934 g, 51.3%) as a white solid (Note: An undesired impurity has a retention time of 11.066 min by HPLC): $^1H$ (CD$_3$OD, 400 MHz): δ 7.51 (1H, d, J=7.8 Hz), 7.24-7.16 (2H, m), 7.05 (1H, ddd, J=8.2, 6.3, 2.9 Hz), 6.72 (1H, s), 6.71 (1H, s), 2.96 (2H, t, J=8.0 Hz), 2.73 (2H, t, J=7.8 Hz)) ppm. $^{13}$C (CD$_3$OD, 100 MHz): δ 164.48, 142.42, 133.71, 131.80, 128.79, 128.53, 125.89, 125.20, 123.54, 122.61, 116.38, 38.99, 28.20 ppm. DEPT (CDCl$_3$, 100 MHz): CH$_2$ carbons: 38.99, 28.20; CH carbons: 133.71, 131.80, 128.53, 122.61, 116.38 ppm. HPLC: 10.035 min.

Example 21

Synthesis of 5-[2-(4-Chlorophenyl)-ethyl]-1H-pyrazole-3-carboxylic acid (69)

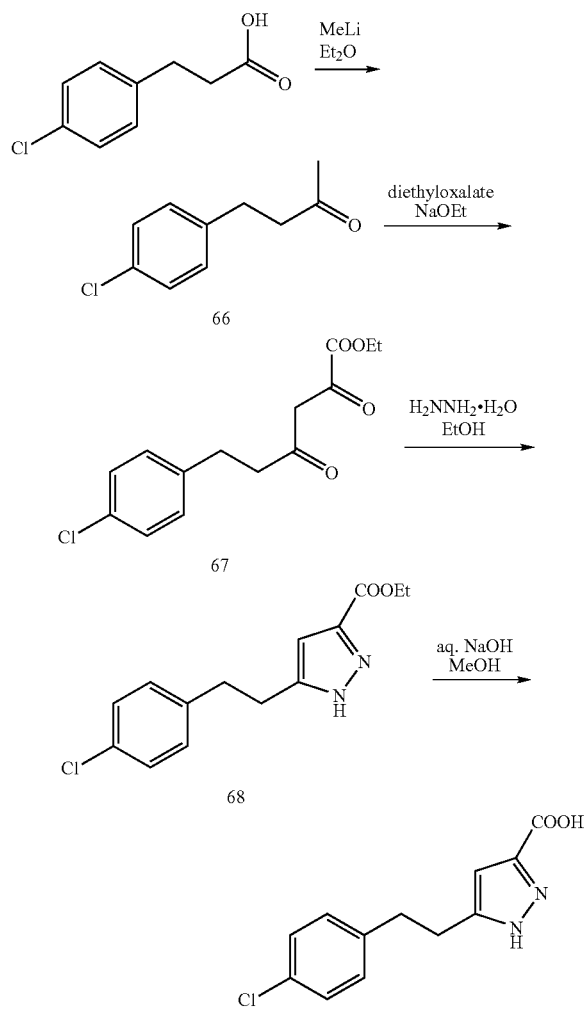

Synthesis of 4-(4-chlorophenyl)-butan-2-one (66)

1.6 M Methyl lithium (33.9 mL, 54.17 mmol) was added over 70 min to a stirring 0° C. solution of 3-(4-chlorophenyl)-propionic acid (5.0072 g, 27.08 mmol) in dry Et$_2$O (135 mL, 0.2 M): The ice bath was removed, and the reaction was allowed to stir at room temperature overnight. The reaction was the poured into rapidly stirring ice water containing aq. HCl. The organic layer was removed, washed with NaHCO$_3$ and brine, then dried with Na$_2$SO$_4$, filtered, concentrated, and purified by silica gel chromatography (Combiflash column, 98:2 to 95:5 Hexanes:EtOAc) to achieve pure 66 (2.4253 g, 49.0%): $^1$H (CDCl$_3$, 400 MHz): δ 7.14 (2H, d, J=8.3 Hz), 7.03 (2H, d, J=8.3 Hz), 2.77 (2H, t, J=7.5 Hz), 2.64 (2H, t, J=7.5 Hz), 2.04 (3H, s) ppm. $^{13}$C (CDCl$_3$, 100 MHz): δ 207.12, 139.38, 131.59, 129.55, 128.35, 44.62, 29.82, 28.78 ppm. DEPT (CDCl$_3$, 100 MHz): CH$_3$ carbons: 29.82; CH$_2$ carbons: 44.62, 28.78; CH carbons: 129.55, 128.35 ppm. HPLC: 10.361 min. (Note: SM has HPLC retention time of 9.409 min.)

Synthesis of 6-(4-chlorophenyl)-2,4-dioxohexanoic acid ethyl ester (67)

Sodium hydride (0.4163 g, 17.35 mmol) was added slowly to a NaCl ice bath containing EtOH (5.3 mL, 2.5 M) stirring under N$_2$. 66 (2.4253 g, 13.28 mmol) and diethyloxalate (1.803 g, 13.28 mmol) were mixed together, and then added to the chilled NaOEt solution. After stirring for 5 minutes, the reaction was warmed to room temperature. After 10 minutes, the reaction solidified and an additional 10 mL EtOH was added. After stirring for ~5 h, the reaction was quenched at 0° C. with 1N HCl and extracted 2× with CH$_2$Cl$_2$. The combined organics were washed with H$_2$O, dried with Na$_2$SO$_4$, filtered, concentrated, and purified by silica gel chromatography (Combiflash column, 1:1 Hexanes:CH$_2$Cl$_2$): Only pure fractions were combined and concentrated to obtain 67 (1.7561 g, 46.8%): $^1$H (CDCl$_3$, 400 MHz): δ 14.27 (1H, broad s), 7.22 (2H, d, J=8.3 Hz), 7.10 (2H, d, J=8.3 Hz), 6.32 (1H, s), 4.31 (2H, q, J=7.2 Hz), 2.92 (2H, t, J=7.8 Hz), 2.78 (2H, t, J=7.8 Hz), 1.34 (3H, t, J=7.2 Hz) ppm. $^{13}$C (CDCl$_3$, 100 MHz): δ 201.59, 166.07, 161.79, 138.51, 132.00, 128.53, 128.54, 101.72, 62.38, 42.08, 29.60, 13.88 ppm. DEPT (CDCl$_3$, 100 MHz): CH$_3$ carbons: 13.88; CH$_2$ carbons: 62.38, 42.08, 29.60; CH carbons: 129.53, 128.54, 101.72 ppm. HPLC: 11.103 min.

Synthesis of 5-[2-(4-Chlorophenyl)-ethyl]-1H-pyrazole-3-carboxylic acid ethyl ester (68)

Hydrazine hydrate (0.300 mL, 6.18 mmol) was added to a stirring room temperature solution of 67 (0.1.7484 g, 6.18 mmol) in EtOH (6.2 mL, 1 M) under N$_2$. The reaction was then heated to reflux until judged complete by HPLC (40 min): Upon cooling, a white crystalline solid precipitated from the reaction. The solid was separated by filtration, washed with EtOH, and dried to obtain pure 68 (0.9092 g, 52.7%): $^1$H (CDCl$_3$, 300 MHz): δ 12.44 (1H, broad s), 7.21 (2H, d, J=8.3 Hz), 7.08 (2H, d, J=8.1 Hz), 6.58 (1H, s), 4.33 (2H, q, J=7.0 Hz), 3.00 (2H, t, J=7.0 Hz), 2.93 (2H, t, J=7.0 Hz), 1.33 (3H, t, J=7.0 Hz) ppm. Partial $^{13}$C (CDCl$_3$, 75 MHz): δ 139.12, 131.93, 129.67, 128.50, 106.49, 60.94, 34.72, 14.20 ppm. HPLC: 10.269 min.

Synthesis of 5-[2-(4-Chlorophenyl)-ethyl]-1H-pyrazole-3-carboxylic acid (69)

Freshly prepared aq. NaOH (10 M in H$_2$O, 16.31 mmol) was added to a stirring, room temperature solution of 68 (0.9092 g, 3.26 mmol) in MeOH (8.2 mL, 0.4 M) under N$_2$. The reaction was then heated to reflux until the reaction was judged complete by HPLC (7 min). The reaction was concentrated, redissolved in H$_2$O (5 mL), and extracted with EtOAc (2 mL). 10% aq. HCl was added dropwise to the aqueous layer until the pH=2. The white solid that precipitated was filtered off and washed with cold H$_2$O. The solid was dried under vacuum overnight to obtain 0.7543 g (92.2%) of 69.

Since 69 still contained a very small amount of an impurity, it was dissolved in 38 mL of toluene with 10 mL of EtOAc and 14 mL of EtOH while heating to reflux. Pure white solid precipitated from the reaction after sitting overnight (0.4052 g). solid (Note: An undesired impurity has a retention time of 9.904 min by HPLC). $^1$H (CD$_3$OD, 400 MHz): δ 7.24 (2H, d, J=8.3 Hz), 7.15 (2H, d, J=8.3 Hz), 6.54 (1H, s), 2.95 (4H, s) ppm. $^{13}$C (CD$_3$OD, 100 MHz): δ 164.68, 148.23, 142.84, 140.91, 133.00, 131.08, 129.46, 107.59, 35.83, 28.78 ppm. DEPT (CD$_3$OD, 100 MHz): CH$_2$ carbons: 35.83, 28.78; CH carbons: 131.08, 129.46, 107.59 ppm. HPLC: 9.026 min.

Example 22

Synthesis of 5-bromo-4-[2-(4-chlorophenyl)-ethyl]-1H-pyrrole-2-carboxylic acid (70)

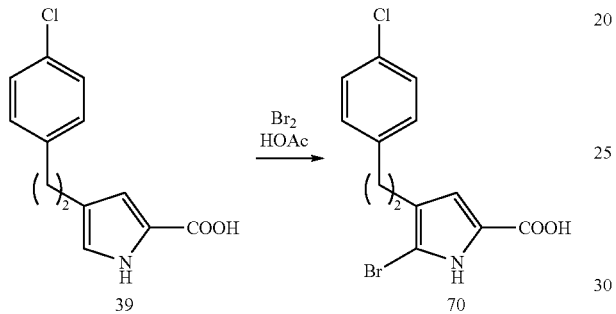

Synthesis of 5-bromo-4-[2-(4-chlorophenyl)-ethyl]-1H-pyrrole-2-carboxylic acid (70)

Bromine (0.049 mL, 0.962 mmol) was added dropwise over 5 minutes to a stirring solution of 39 (0.200 g, 0.802 mmol) in acetic acid (2.5 mL). When the reaction was judged complete by HPLC (30 min), H$_2$O was added, and the solid that precipitated was filtered off and washed with H$_2$O. The light purple solid that was obtained was dissolved in EtOAc, washed with Na$_2$SO$_3$ and H$_2$O, then dried with Na$_2$SO$_4$, filtered, and concentrated. The product was purified by preparative reverse phase HPLC with 40:60 H$_2$O:CH$_3$CN (w/0.05% TFA); 20 mL/min.; λ=214 nM. 0.1520 g (57.7%) of 70 was obtained as a fluffy white solid. $^1$H (CD$_3$OD, 400 MHz): δ 7.22 (2H, d, J=8.8 Hz), 7.12 (2H, d, J=8.8 Hz), 6.65 (1H, s), 2.81 (2H, t, J=7.3 Hz), 2.67 (2H, t, J=7.3 Hz) ppm. Partial $^{13}$C (CD$_3$OD, 100 MHz): δ 163.33, 141.42, 132.54, 131.03, 129.18, 124.73, 117.15, 105.84, 36.72, 29.04 ppm. DEPT (CD$_3$OD, 100 MHz): CH$_2$ carbons: 36.72, 29.04; CH carbons: 131.03, 129.18, 117.15 ppm. HPLC: 10.484 min.

Example 23

Synthesis of 4-[2-(2-bromophenyl)-ethyl]-1H-pyrrole-2-carboxylic acid (73)

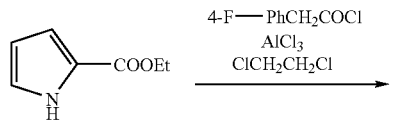

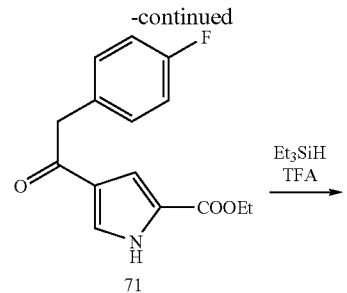

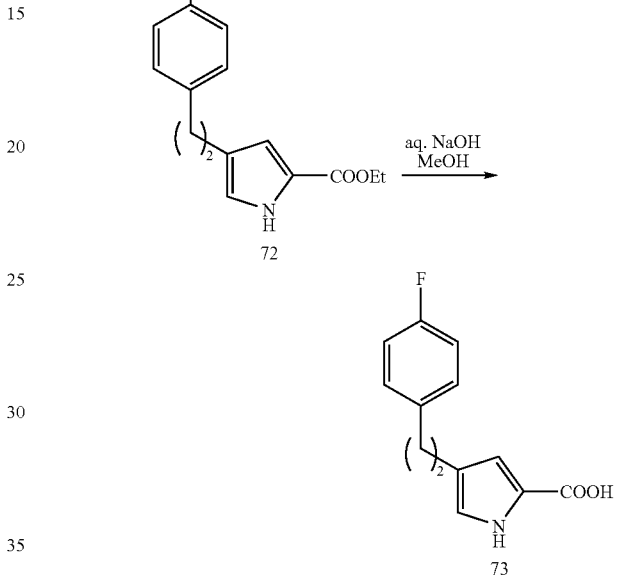

Synthesis of 4-[2-(4-fluorophenyl)-acetyl]-1H-pyrrole-2-carboxylic acid ethyl ester (71)

Ethylpyrrole-2-carboxylate (2.0589 g, 14.80 mmol) in a minimal amount of dichloroethane was added to an ice cooled stirring mixture of aluminum chloride (3.9913 g, 29.93 mmol) and 4-fluorophenylacetyl chloride (5.1338 g, 29.75 mmol) in dichloroethane (22 mL, 0.66 M) under N$_2$. The ice bath was removed, and the reaction was stirred at room temperature for 3.5 h. 20.6195 g (2.6 mMol/g) Polyamine resin HL (200-400 mesh) and dichloroethane (20 mL) were added, and the reaction was stirred for ~60 min. The reaction was then filtered through a glass-fritted funnel directly into ice water. The resin was rinsed with CH$_2$Cl$_2$, then the organic layers were removed, dried with Na$_2$SO$_4$, filtered and concentrated. When 6.5 mL of 80:20 Hexanes:EtOAc were added, the organic liquid turned yellow, leaving behind a tan solid. The solid was removed by filtration, rinsed with 80:20 Hexanes:EtOAc, and dried to obtain pure 71 (2.1838 g, 53.6%). $^1$H (CDCl$_3$, 400 MHz): δ 10.03 (1H, broad s), 7.54 (1H, s), 7.32 (1H, s), 7.23 (2H, dd, J=8.6, 5.3 Hz), 6.99 (2H, t, J=8.6 Hz), 4.35 (2H, q, J=7.1 Hz), 4.04 (2H, s), 1.37 (3H, t, J=7.1 Hz) ppm. $^{13}$C (CDCl$_3$, 100 MHz): δ 192.81, 161.84 (d, J=244 Hz), 160.95, 130.89 (d, J=7.8 Hz), 130.37 (d, J=3.2 Hz), 126.72, 126.36, 124.30, 115.40 (d, J=21.4 Hz), 114.96, 61.02, 45.63, 14.29 ppm. DEPT (CDCl$_3$, 100 MHz): CH$_3$ carbons: 14.29; CH$_2$ carbons: 61.02, 45.63; CH carbons: 130.89 (d, J=7.8 Hz), 126.72, 115.40 (d, J=21.4 Hz), 114.96 ppm. HPLC: 9.689 min.

Synthesis of 4-[2-(4-fluorophenyl)-ethyl]-1H-pyrrole-2-carboxylic acid ethyl ester (72)

Triethylsilane (3.84 mL, 24.1 mmol) was added to a stirring, room temperature solution of 71 (2.1400 g, 7.77 mmol) in trifluoroacetic acid (TFA) (18.5 mL, 0.42 M) under N$_2$. When the reaction was judged complete by HPLC, the TFA was removed under vacuum, and the crude product was taken up in EtOAc, washed with brine, dried with Na$_2$SO$_4$, filtered, concentrated, and purified by preparative reverse phase HPLC with the following conditions: 0 to 12 min, 35:65 H$_2$O:CH$_3$CN; 14-15 min, 35:65 to 0:100 H$_2$O:CH$_3$CN; 20 mL/min.; λ=254 nM; 3.67 g/mL, 0.2 mL/injection. 1.1571 g (57.0%) of 72 was obtained as a fluffy white solid. (Note: An undesired impurity has a retention time of 11.414 min by HPLC.) $^1$H (CDCl$_3$, 400 MHz): δ 9.33 (1H, broad s), 7.13 (2H, dd, J=8.5, 5.6 Hz), 6.96 (2H, t, J=8.8 Hz), 6.79 (1H, s), 6.66 (1H, s), 4.33 (2H, t, J=7.1 Hz), 2.86 (2H, t, J=7.1 Hz), 2.77 (2H, t, J=7.1 Hz), 1.36 (3H, t, J=7.1 Hz) ppm. $^{13}$C (CDCl$_3$, 100 MHz): 6161.31, 161.22 (d, J=242 Hz), 137.46 (d, J=3.2 Hz), 129.71 (d, J=7.7 Hz), 125.22, 122.52, 120.84, 114.89 (d, J=21.9 Hz), 114.79, 60.19, 36.44, 28.73, 14.37 ppm. DEPT (CDCl$_3$, 100 MHz): CH$_3$ carbons: 14.37; CH$_2$ carbons: 60.19, 36.44, 28.73; CH carbons: 129.71 (d, J=7.7 Hz), 120.84, 114.89 (d, J=21.9 Hz), 114.79 ppm. HPLC: 10.797 min.

Synthesis of 4-[2-(4-fluorophenyl)-ethyl]-1H-pyrrole-2-carboxylic acid (73)

Freshly prepared aq. NaOH (10 M in H$_2$O, 22.14 mmol) was added to a stirring, room temperature solution of 72 (1.1571 g, 4.428 mmol) in MeOH (11.1 mL, 0.4 M) under N$_2$. The reaction was heated to reflux until the reaction was judged complete by HPLC (10 min). Upon cooling, the reaction solidified. The product was concentrated and then dissolved in H$_2$O. The product was extracted with EtOAc, then the aqueous layer was made acidic (pH=2) with the dropwise addition of 10% aq. HCl. The product oiled out of solution, so EtOAc was added, and the organic layer was removed, dried with Na$_2$SO$_4$, filter, concentrated to obtain 73 (0.8724 g, 84.4%) as an off-white solid. The product was further purified by repeating the above procedure. The product was dissolved in 10% NaOH, washed with EtOAc, and then acidified with 10% HCl. As before, the product oiled out and was therefore extracted into EtOAc, dried with Na$_2$SO$_4$, filtered, and concentrated. $^1$H (CD$_3$OD, 400 MHz): δ 7.14 (2H, dd, J=8.8, 5.4 Hz), 6.94 (2H, t, J=8.8 Hz), 6.68 (1H, d, J=1.7 Hz), 6.66 (1H, d, J=7.1 Hz), 2.82 (2H, t, J=7.3 Hz), 2.72 (2H, t, J=7.3 Hz) ppm. $^{13}$C (CD$_3$OD, 100 MHz): δ 164.48, 162.69 (d, J=241 Hz), 139.28 (d, J=3.2 Hz), 131.08 (d, J=8.2 Hz), 126.08, 123.47, 122.68, 116.41, 115.68 (d, J=21.0 Hz), 37.77, 29.94 ppm. DEPT (CDCl$_3$, 100 MHz): CH$_2$ carbons: 37.77, 29.94; CH carbons: 131.08 (d, J=8.2 Hz), 122.68, 116.41, 115.68 (d, J=21.0 Hz) ppm. HPLC: 9.575 min.

Example 24

Synthesis of 4-(3-Cyclopentylpropyl)-1H-pyrrole-2-carboxylic acid (76)

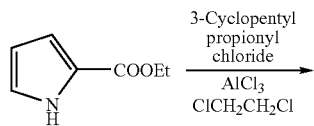

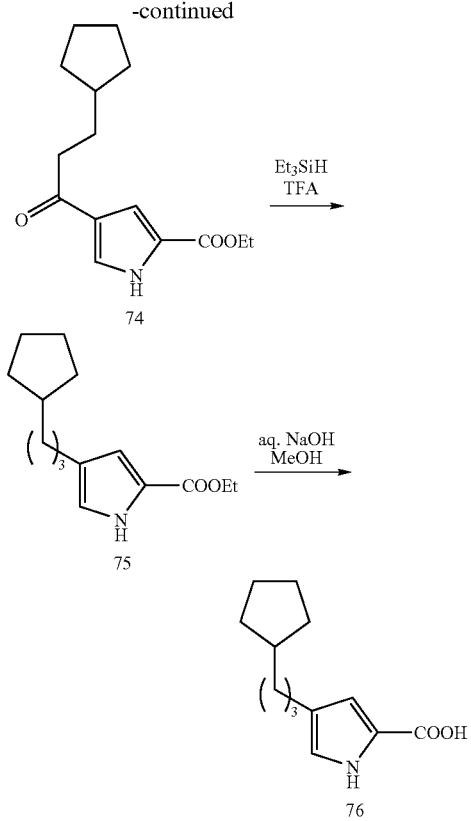

Synthesis of 4-(3-Cyclopentylpropionyl)-1H-pyrrole-2-carboxylic acid ethyl ester (74)

Ethylpyrrole-2-carboxylate (1.8593 g, 13.36 mmol) in a minimal amount of dichloroethane was added to an ice cooled stirring mixture of aluminum chloride (3.5756 g, 26.82 mmol) and 3-cyclopentylpropionyl chloride (4.1 mL, 26.59 mmol) in dichloroethane (20 mL, 0.66 M) under N$_2$. The ice bath was removed, and the reaction was stirred at room temperature for 4 h. 18.18 g (2.6 mMol/g) Polyamine resin HL (200-400 mesh) and dichloroethane (20 mL) were added, and the reaction was stirred for ~60 min. The reaction was then filtered through a glass-fritted funnel directly into ice water. The resin was rinsed with CH$_2$Cl$_2$, then the organic layers were removed, dried with Na$_2$SO$_4$, filtered and concentrated. The crude product was recrystallized from Hexanes/Ethyl acetate. The crude was dissolved in a minimal amount of hot EtOAc, then allowed to slowly cool to room temperature. When no product crystallized, a small amount of hexanes was pipetted down the sides of the flask. Pure crystals of desired product (2.3068 g, 65.6%) were obtained after sitting overnight. $^1$H (CDCl$_3$, 400 MHz): δ 10.04 (1H, broad s), 7.55 (1H, s), 7.29 (1H, s), 4.34 (2H, q, J=7.1 Hz), 2.77 (2H, t, J=7.6 Hz), 1.85-1.67 (5H, m), 1.64-1.46 (4H, m), 1.36 (3H, t, J=7.1 Hz), 1.78-1.06 (2H, m) ppm. $^{13}$C (CDCl$_3$, 100 MHz): 6196.38, 161.09, 127.03, 126.14, 124.05, 114.76, 60.91, 39.82, 39.06, 32.53, 30.82, 25.11, 14.31 ppm. DEPT (CDCl$_3$, 100 MHz): CH$_3$ carbons: 14.31; CH$_2$ carbons: 60.91, 39.06, 32.53, 30.82, 25.11; CH carbons: 126.14, 114.76, 39.82 ppm. HPLC: 10.800 min.

Synthesis of 4-(3-cyclopentylpropyl)-1H-pyrrole-2-carboxylic acid ethyl ester (75)

Triethylsilane (4.28 mL, 26.86 mmol) was added to a stirring, room temperature solution of 74 (2.2816 g, 8.66 mmol) in trifluoroacetic acid (TFA) (20.6 mL, 0.42 M) under $N_2$. When the reaction was judged complete by HPLC, the TFA was removed under vacuum, and the crude product was taken up in EtOAc, washed with brine, dried with $Na_2SO_4$, filtered, concentrated, and purified by preparative reverse phase HPLC with the following conditions: 30:70 $H_2O:CH_3CN$; 20 mL/min.; λ=254 nm. 75 was obtained as a fluffy white solid. $^1$H (CDCl$_3$, 400 MHz): δ 9.43 (1H, broad s), 6.77 (1H, s), 6.74 (1H, s), 4.32 (2H, q, J=7.1 Hz), 2.46 (2H, t, J=7.6 Hz), 1.83-1.71 (3H, m), 1.64-1.46 (6H, m), 1.35 (3H, t, J=7.1 Hz), 1.36-1.31 (2H, m), 1.14-1.02 (2H, m) ppm. $^{13}$C (CDCl$_3$, 100 MHz): δ 161.46, 126.62, 122.33, 120.74, 114.86, 60.10, 40.00, 35.82, 32.65, 30.14, 26.94, 25.13, 14.39 ppm. DEPT (CDCl$_3$, 100 MHz): CH$_3$ carbons: 14.39; CH$_2$ carbons: 60.10, 35.82, 32.65, 30.14, 26.94, 25.13; CH carbons: 120.74, 114.86, 40.00 ppm. HPLC: 12.379 min.

Synthesis of 4-(3-cyclopentylpropyl)1H-pyrrole-2-carboxylic acid (76)

Freshly prepared aq. NaOH (10 M in $H_2O$, 11.23 mmol) was added to a stirring, room temperature solution of 75 (0.56 g, 2.25 mmol) in MeOH (5.6 mL, 0.4 M) under $N_2$. The reaction was heated to reflux until the reaction was judged complete by HPLC (10 min). Upon cooling, the reaction solidified. The product was concentrated and $H_2O$ was added. When the product would not dissolve in $H_2O$, EtOAc was added, followed by 10% HCl to acidify the aqueous layer. The organic was then removed, dried with $Na_2SO_4$, filtered, concentrated, and purified by preparative reverse phase HPLC with the following conditions: 30:70 $H_2O:CH_3CN$; 20 mL/min.; λ=254 nm. 76 was obtained as a fluffy white solid. (Note: An undesired impurity has a retention time of 12.073 min by HPLC). $^1$H (CD$_3$OD, 400 MHz): δ 10.80 (1H, s), 6.72 (1H, s), 6.68 (1H, s), 2.43 (2H, t, J=7.6 Hz), 1.82-1.70 (3H, m), 1.64-1.46 (6H, m), 1.38-1.29 (2H, m), 1.14-1.02 (2H, m) ppm. $^{13}$C (CD$_3$OD, 100 MHz): δ 164.45, 127.29, 122.45, 116.39, 41.31, 37.00, 33.73, 31.43, 27.96, 26.11 ppm. DEPT (CDCl$_3$, 100 MHz): CH$_2$ carbons: 37.00, 33.73, 31.43, 27.96, 26.11; CH carbons: 122.45, 116.39, 41.31 ppm. HPLC: 10.977 min.

Example 25

Synthesis of (S)-5-(2-Phenylpropyl)-1H-pyrazole-3-carboxylic acid (80)

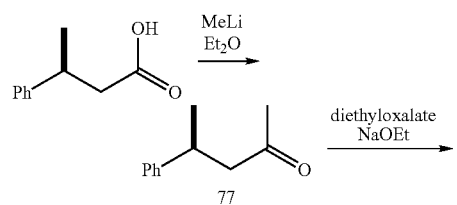

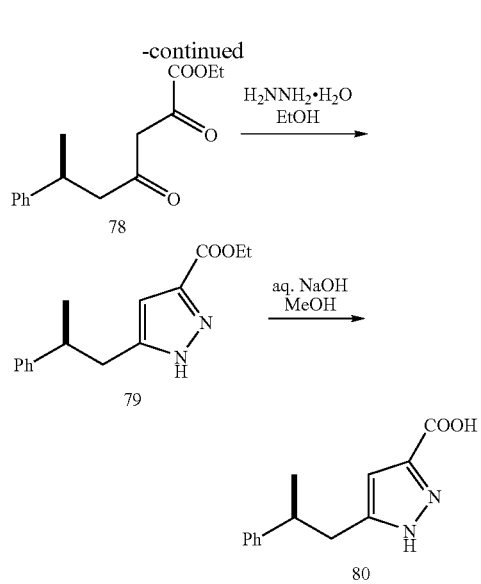

Synthesis of (S)-4-Phenylpentan-2-one (77)

1.6 M Methyl lithium (17.8 mL, 24.9 mmol) was added over 1 hour to a stirring 0° C. solution of (S)-3-Phenylbutyric acid (2.0147 g, 12.18 mmol) in dry Et$_2$O (61 mL, 0.2 M): The ice bath was removed, and the reaction was allowed to stir at room temperature for 1½ additional hours. The reaction was then poured into rapidly stirring ice water containing aq. HCl. The organic layer was removed, washed with NaHCO$_3$ and brine, then dried with Na$_2$SO$_4$, filtered and concentrated to achieve pure 77 (2.0487 g, (2.0487 g, ~100%): HPLC: 10.081 min. (Note: SM has HPLC retention time of 9.127 min.)

Synthesis of (S)-2,4-dioxo-6-phenylheptanoic acid ethyl ester (78)

Sodium hydride (0.3790 g, 15.8 mmol) was added slowly to a NaCl ice bath containing EtOH (4.9 mL, 2.5 M) stirring under $N_2$. (S)-4-Phenylpentan-2-one (78) (2.0487 g, 12.63 mmol) and diethyloxalate (1.67 mL, 12.30 mmol) were mixed together, and then added to the chilled NaOEt solution. After stirring for 5 minutes, the reaction was warmed to room temperature. After 60 min, the reaction was quenched at 0° C. with 1N HCl and extracted 2× with CH$_2$Cl$_2$. The combined organics were washed with H$_2$O, dried with Na$_2$SO$_4$, filtered, concentrated, and purified with 1:1 to 1:3 Hexanes:CH$_2$Cl$_2$ to obtain 78 (0.6895 g, 20.8%): HPLC: 10.940 min.

Synthesis of (S)-5-(2-phenylpropyl)-1H-pyrazole-3-carboxylic acid ethyl ester (79)

Hydrazine hydrate (0.126 mL, 2.59 mmol) was added to a stirring room temperature solution of 78 0.0.6895 g, 2.63 mmol) in EtOH (2.6 mL, 1 M) under $N_2$. The reaction was then heated to reflux until judged complete by HPLC (45 min): The reaction was concentrated and purified with 9:1 to 8:1 Hexanes:(3:1 CH$_2$Cl$_2$:2N NH$_3$ in EtOH) to achieve 0.6153 g (90.6%) of 79. HPLC: 10.001 min.

Synthesis of (S)-5-(2-phenylpropyl-1H-pyrazole-3-carboxylic acid (80)

Freshly prepared aq. NaOH (10 M in H$_2$O, 11.9 mmol) was added to a stirring, room temperature solution of 79 (0.6153 g, 0.2.38 mmol) in MeOH (6 mL, 0.4 M) under N$_2$. The reaction was then heated to reflux until the reaction was judged complete by HPLC (7 min): The reaction was concentrated, redissolved in H₂O, and extracted with EtOAc (1 mL): 10% aq. HCl was added dropwise to the aqueous layer until the pH=2. The white solid that precipitated from the reaction was filtered off and washed with cold H₂O. The solid was dried under vacuum overnight to obtain 0.250 g (45.6%) of 80. $^1$H (CD₃OD, 400 MHz): δ 7.30-7.23 (2H, m), 7.22-7.13 (3H, m), 6.62 (1H, s), 3.14 (1H, app sex, J=7.3 Hz), 3.03 (2H, d, J=7.8 Hz), 1.31 (3H, d, J=6.8 Hz) ppm. $^{13}$C (CD₃OD, 100 MHz): δ 162.00, 149.20, 146.35, 141.76, 129.62, 127.93, 127.64, 109.16, 41.21, 35.22, 22.11 ppm. DEPT (CD₃OD, 100 MHz): CH₃ carbons: 22.11; CH₂ carbons: 35.22; CH carbons: 129.62, 127.93, 127.64, 109.16, 41.21 ppm. HPLC: 8.771 min.

Analytical HPLC conditions: Reverse phase analytical column. At time=0, 95:5 H₂O:CH3CN; ramp up to 60:40 H₂O:CH₃CN by 4 min;

Example 26

In Vitro Measurements of DAAO Activity

Purified pig DAAO, added to a buffered mixture of 50 mM D-Serine produces H₂O₂ in stoichiometric amounts for each D-Serine molecule oxidized. H₂O₂ production can be monitored with a commercially available dye Amplex Red, which in the presence of H₂O₂, is converted to the fluorescent product resorufin. For each described inhibitor, the fluorescence was also measured during additions of 80 μM H₂O₂ in the absence of DAAO, to control for artifactual inhibition of the dye conversion, and to quantify the amount of H₂O₂ produced. In an alternative assay of DAAO activity, the purified pig DAAO is added to buffered mixture of 1 mM phenylglycine in the presence of compounds. The activity of DAAO is monitored spectrophotometrically by its enzymatic conversion of phenylglycine to benzoylformic acid with optical absorption at 252 nm.

Inhibitors of DAAO's enzymatic cycle were serially diluted to reduce the level of inhibition. The parameters of a non-linear equation were adjusted to fit the resulting series of inhibition levels to extrapolate the concentration of compound where 50% inhibition is achieved (IC₅₀). These numbers are averaged for the number (n) of independent measurements (on separate days) of the inhibition. The inhibition is reported in Table 1.

TABLE 1

| Compound No. or Structure | Inhibition of DAAO, IC₅₀ | Compound No. or Structure | Inhibition of DAAO, IC₅₀ |
|---|---|---|---|
| 3 | <10 μM | 45 | <100 μM |
| 6 | <10 μM | 48 | <10 μM |
| 11 + 12 | <10 μM | 51 | <1 μM |
| 15 | <10 μM | 54 | <100 μM |
| 18 | <1 μM | 58 | <1 μM |
| 21 | <1 μM | 62 | <1 μM |
| 24 | <1 μM | 65 | <1 μM |
| 26 | <100 μM | 69 | <1 μM |
| 32 | >100 μM | 70 | <100 μM |
| 36 | <100 μM | 73 | <1 μM |
| 39 | <1 μM | 76 | <10 μM |
| 42 | <1 μM | 80 | <10 μM |
| 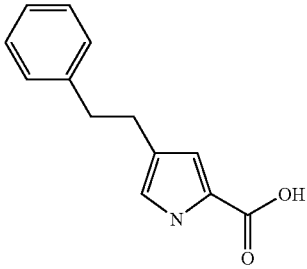 | <1 μM | 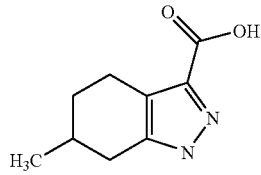 | <100 μM |
| 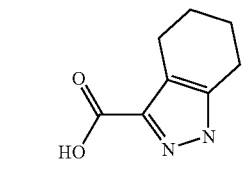 | <1 μM | 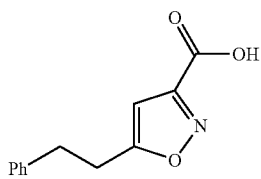 | <100 μM |

TABLE 1-continued

| Compound No. or Structure | Inhibition of DAAO, IC$_{50}$ | Compound No. or Structure | Inhibition of DAAO, IC$_{50}$ |
|---|---|---|---|
| 3-isopropyl-1H-pyrazole-5-carboxylic acid | <1 μM | 4-(2-(4-chlorophenyl)acetyl)-1H-pyrrole-2-carboxylic acid | <100 μM |
| 2,4,5,6-tetrahydrocyclopenta[c]pyrazole-3-carboxylic acid | <1 μM | 5-methylisoxazole-3-carboxylic acid | <100 μM |
| 5-nitro-1H-pyrazole-3-carboxylic acid | <1 μM | 7-cyclohexyl-4,5,6,7-tetrahydro-2H-indazole-3-carboxylic acid | <100 μM |
| 4-nitro-1H-pyrazole-3-carboxylic acid | <1 μM | 1H-pyrazole-3-carboxylic acid | <100 μM |
| 7-methyl-4,5,6,7-tetrahydro-2H-indazole-3-carboxylic acid | <10 μM | 4-dodecanoyl-1H-pyrrole-2-carboxylic acid | <100 μM |
| 2,4,5,6,7,8-hexahydrocycloocta[c]pyrazole-3-carboxylic acid | <10 μM | 5-isopropyl-4,5,6,7-tetrahydro-2H-indazole-3-carboxylic acid | <100 μM |

TABLE 1-continued
| Compound No. or Structure | Inhibition of DAAO, IC$_{50}$ | Compound No. or Structure | Inhibition of DAAO, IC$_{50}$ |
|---|---|---|---|
| 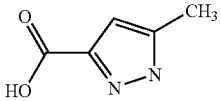 | <10 μM | 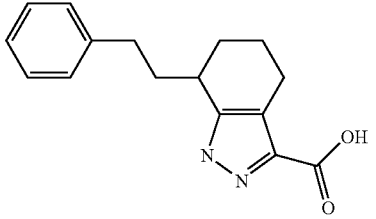 | <100 μM |
| 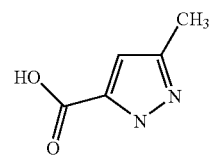 | <10 μM | 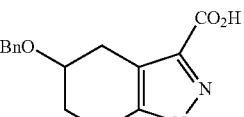 | <100 μM |
| 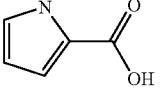 | <10 μM | 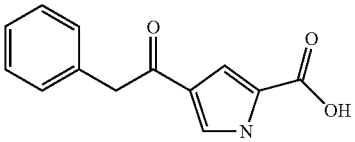 | <100 μM |
| 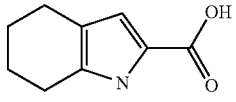 | <10 μM | 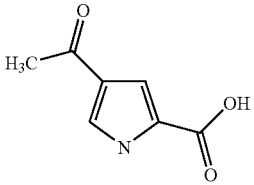 | <100 μM |
| 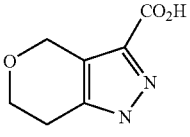 | <10 μM | 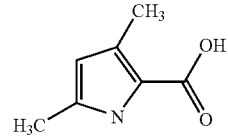 | <100 μM |
| 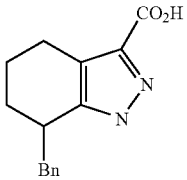 | <10 μM | 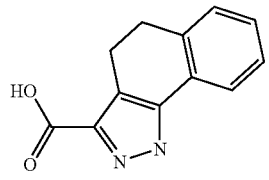 | <100 μM |
| 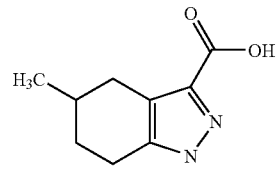 | <10 μM | | |

It can be seen from Table 1 that the $IC_{50}$ values of previously reported DAAO inhibitors are all greater than 1 μM compound for greater than 50% inhibition of DAAO activity. The pyrrole and pyrazole derivatives of the present invention display at least this much inhibitory activity, and several individual examples are 5-fold or greater more active, requiring less than 200 nM of the compounds to inhibit 50% of DAAO activity.

Example 27

Measurements of NMDA Receptor Affinity

To measure the affinity of the compounds reported herein for D-Serine's binding site on the NMDA receptor (also known as the "Glycine site" or the "strychnine-insensitive glycine site"), a radioligand-binding assay was performed with membranes prepared from rat cerebral cortex. The radioactive ligand was [3H]MDL105,519. The amount of radioactivity displaced by the compounds was assessed by scintillation counting. Non-specific binding is accounted for in the presence of 1 mM Glycine. Affinities are calculated from the values of % inhibition of specific [3H]MDL105,519 binding by the test compounds.

Indole-2-carboxylic acid inhibited 77% of specific binding of the radiolabeled compound when tested at 100 μM, while the following compounds, exemplary of substituted pyrroles and pyrazoles, demonstrated no affinity (less than 20% inhibition of [3H]MDL-509,519 specific binding when tested at 100 μM) for the D-Serine binding site of the NMDA receptor:

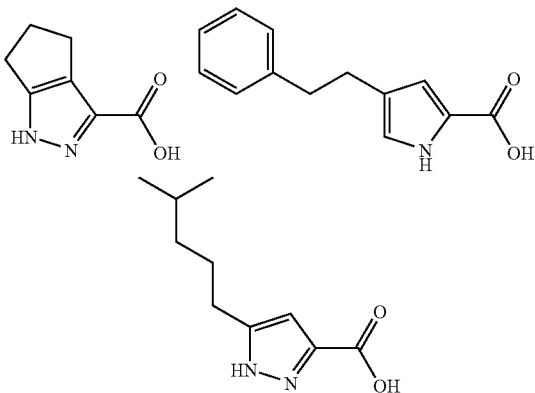

Example 28

Measurements of Rat Brain Uptake

Experiments that evaluate the rat brain penetration of test compounds use a perfusion system where the left carotid artery is cannulated and the branch arteries are tied off. The test compound plus internal controls are perfused for 30 seconds into the left hemisphere in phosphate buffered saline at pH 7.4. The internal controls are atenolol (with low brain uptake) and antipyrine (with high brain uptake). After a 30 second washout with perfusate, the brain is removed surgically. The left hemisphere is homogenized; test compounds (plus internal controls) are extracted from brain homogenate, and analyzed using LC/MS/MS to determine the concentration of test compound and internal controls in the brain. Brain uptake rates for selected compounds, expressed as pmol/g brain/sec±SD for N of 4 rats, are shown in Table 2.

TABLE 2

| Compound No. (from Examples) or Structure | Rat Brain Uptake Rate, pmol/g brain/sec |
|---|---|
| 18 | 17 |
| 21 | 6 |
| 39 | 204 |
| ![structure] | 6 |

Example 29

Measurements of Brain D-Serine Levels

Measurements of d-serine in the brains of mammals indicate that the level of endogenous production is balanced by degradation of d-serine. D-serine is produced from 1-serine by the action of serine racemase, while d-serine is metabolized by the action of DAAO. Exogenously administered d-serine produces short lasting increases in brain d-serine due to the action of DAAO. Likewise, inhibitors of DAAO are shown in this invention to increase several-fold brain levels of d-serine. The clinical utility of exogenously-administered d-serine has been demonstrated in schizophrenics; see Coyle, Joseph J., Ann. N.Y. Acad. Sci., 1003: 318-327 (2003) and U.S. Pat. Nos. 6,227,875; 6,420,351; and 6,667,297. Therefore, measurements of brain d-serine levels in rats are useful for assessing the potential therapeutic action of DAAO inhibitors on increases in d-serine for the treatment of schizophrenia.

In vivo increase in brain D-Serine Compounds were suspended in phosphate buffered saline (pH 7.4 with 2% Tween80) and were administered intraperitoneally into adult male Sprague Daly rats (40-60 days old, Charles River Laboratories, Inc.) weighing 185-225 g at the time of the experiment. After several hours, the rats were killed by decapitation and the cerebellum was rapidly removed and frozen to –80 C for further analysis. The remainder of the brain was likewise removed and frozen. On the day of the analysis, the brain tissue was homogenized in 5 times its volume in ice-cold 5% trichloroacetic acid. The homogenate was centrifuged at 18,000 times gravity for 30 minutes. Pellets were discarded. The supernatant was washed 3 times with water-saturated diethyl ether, discarding the organic layer. After filtration of the aqueous layer through a 0.45 μm pore size filter membrane, the samples were ready for derivatization with o-phthaldialdehyde (OPA) and BOC L-Cys-OH according to the methods of Hashimoto and colleagues (Hashimoto A, et al., J Chromatogr., 582(1-2):41-8 (1992)). Briefly, 50 mg of each derivatization reagent were dissolved in 5 ml of methanol. A 200 μl aliquot of this was added to 100 μl of sample dissolved in 700 μl of borate buffer (0.4 M pH adjusted to 9.0 with sodium hydroxide). D-Serine levels were then detected fluorometrically (344 nm excitation wavelength, 443 nm emission wavelength) by injecting 10 μl aliquots into the high-performance liquid chromatography system.

Compounds exemplary of those in this patent produced robust and significant increases in D-Serine levels in rat brain. In particular, a pyrrole derivative administered in two separate doses (125 mg/kg followed by 75 mg/kg 3 hours later) produced a 4-fold increase in cerebellar D-Serine levels 6 hours after the first dose.

Example 30

Reduction of Neuropathic Pain by DAAO Inhibitors in Animal Model (Spinal Nerve Ligation (SNL) Model)

Animals: Male Sprague-Dawley rats (Hsd:Sprague-Dawley®™SD®™, Harlan, Indianapolis, Ind., U.S.A.) weighing 232±2 g the day of behavioral testing were housed three per cage. Animals had free access to food and water and were maintained on a 12:12 h light/dark schedule for the entire duration of the study. The animal colony was maintained at 21° C. and 60% humidity. All experiments were conducted in accordance with the International Association for the Study of Pain guidelines and had Animal Care and Use Committee approval.

Induction of chronic neuropathic pain: The Spinal Nerve Ligation (SNL) model (Kim and Chung, 1992) was used to induce chronic neuropathic pain. The animals were anesthetized with isoflurane, the left L5 transverse process was removed, and the L5 and L6 spinal nerves were tightly ligated with 6-0 silk suture. The wound was then closed with internal sutures and external staples. Wound clips were removed 10-11 days following surgery.

Mechanical allodynia testing: Baseline, post-injury and post-treatment values for non-noxious mechanical sensitivity were evaluated using 8 Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al., 1994). Animals were placed on a perforated metallic platform and allowed to acclimate to their surroundings for a minimum of 30 minutes before testing. The mean and standard error of the mean (SEM) were determined for each animal in each treatment group. Since this stimulus is normally not considered painful, significant injury-induced increases in responsiveness in this test are interpreted as a measure of mechanical allodynia.

Experimental Groups

Timeline:
4-[2-(4-Chlorophenyl)-ethyl]-1H-pyrrole-2-carboxylic acid (39) and (Vehicle)
(1) von Frey test (baseline)
(2) 0 min: drug administration
(3) 120 min: von Frey test
(4) 240 min: von Frey test
(5) 360 min: von Frey test
(6) 480 min: von Frey test
(7) 495 min: plasma collection Blinding procedure: Drugs were administered by a separate experimenter that was not involved with conducting the behavioral testing. The blind was not broken until the end of the study.

Data analysis: Statistical analyses were conducted using Prism™ 4.01 (GraphPad, San Diego, Calif., USA). Mechanical hypersensitivity of the injured paw was determined by comparing contralateral to ipsilateral paw values within the vehicle group. Data were analyzed using the Mann-Whitney test. Stability of vehicle group injured paw values over time was tested using the Friedman two-way analysis of variance by rank. Drug effect was analyzed at each time point by carrying out a Kruskal-Wallis one-way analysis of variance by rank followed by a Dunn's post hoc test or Mann-Whitney signed rank test.

Results: 4-[2-(4-Chlorophenyl)-ethyl]-1H-pyrrole-2-carboxylic acid induced a substantial decrease in mechanical allodynia that was statistically significant at 240 and 360 min. The maximum effect was observed 360 minutes post dose.

REFERENCES

Chaplan S R, Bach F W, Pogrel J W, Chung J M and Yaksh T L (1994) Quantitative assessment of tactile allodynia in the rat paw. J Neurosci Methods 53:55-63.

Kim S H and Chung J M (1992) An experimental model for peripheral neuropathy produced by segmental spinal nerve ligation in the rat. *Pain* 50:355-63.

Example 31

Dosage Forms

Lactose-Free Tablet Dosage Form

Table 3 provides the ingredients for a lactose-free tablet dosage form of a compound of formula I:

TABLE 3

| Ingredient | Quantity per Tablet (mg) |
|---|---|
| 5-phenethyl-1H-pyrazole-3-carboxylic acid | 75 |
| Microcrystalline cellulose | 125 |
| Talc | 5.0 |

| # | Surgery | Treatment | Dose (mg/kg) | Route | Vehicle | vol. of adm. (ml/kg) | Time course (hours) | n |
|---|---|---|---|---|---|---|---|---|
| 1 | SNL | 4-[2-(4-chlorophenyl)-ethyl]-1H-pyrrole-2-carboxylic acid (39) | 125 | i.p. | PBS | 2 | BL, 2, 4, 6, 8 | 10 |
| 1 | SNL | Gabapentin | 100 | i.p. | saline | 5 | BL, 0.5, 1, 2, 4 | 10 |
| 3 | SNL | saline | — | i.p. | — | 2 | BL, 2, 4, 6, 8 | 9 |

TABLE 3-continued

| Ingredient | Quantity per Tablet (mg) |
|---|---|
| Water (per thousand tablets) | 30.0 mL* |
| Magnesium Stearate | 0.5 |

*The water evaporates during manufacture.

The active ingredient is blended with the cellulose until a uniform blend is formed. The smaller quantity of cornstarch is blended with a suitable quantity of water to form a corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous technique.

Tablet Dosage Form

Another tablet dosage formulation suitable for use with the active ingredients of the invention is provided in Table 4.

TABLE 4

| Ingredient | Quantity per Tablet (mg) | | |
|---|---|---|---|
| | Formula A | Formula B | Formula C |
| 5-phenethyl-1H-pyrazole-3-carboxylic acid | 20 | 40 | 100 |
| Microcrystalline cellulose | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with cellulose, starch and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

Example 32

Synthesis of 4-[2-(4-Chloro-phenyl)-ethyl]-3-methyl-1H-pyrrole-2-carboxylic acid (87)

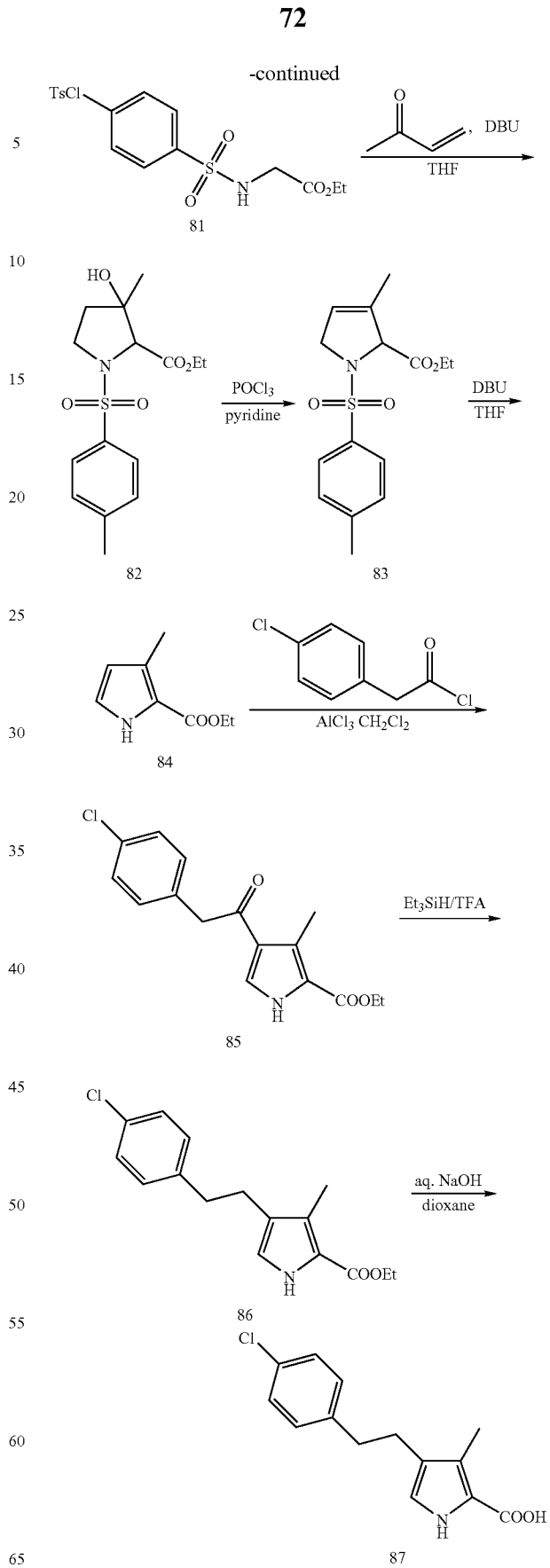

Synthesis of (Toluene-4-sulfonylamino)-acetic acid ethyl ester (81)

Tosyl chloride (14.75 g, 77.37 mmol) was added to a stirring mixture of glycine ethyl ester hydrochloride (9.0 g, 64.48 mmol) and pyridine (11.45 mL, 141.85 mmol) in 100 mL of dichloromethane. After stirring overnight, the mixture was washed with water and dilute NaOH. The combined organics were dried with $Na_2SO_4$, filtered, evaporated under reduced pressure to give 16.0 g (96%) of 81, which was used without purification in the next reaction. $^1$H-NMR (400 MHz, $CDCl_3$): δ 1.18 (t, 3H), 2.42 (s, 3H), 3.76 (d, 2H), 4.08 (q, 2H), 5.22 (m, 1H), 7.30 (d, 2H), 7.75 (d, 2H) ppm. $^{13}$C-NMR (100 MHz, $CDCl_3$): δ 13.99, 21.55, 44.19, 61.89, 127.28, 129.76, 136.20, 143.81, 168.87 ppm. □ DEPT (100 MHz, $CDCl_3$): $CH_3$ carbons: 13.99, 21.55; $CH_2$ carbons: 44.19, 61.89; CH carbons: 127.28, 129.76 ppm. LC/MS: 95%, m/z=257.

Synthesis of 3-Hydroxy-3-methyl-1-(toluene-4-sulfonyl)-pyrrolidine-2-carboxylic acid ethyl ester (82)

1,8-diazabicyclo[5.4.0]-undec-7-ene (DBU) (7 mL, 47.08 mmol) was added to a stirred solution of ethyl vinyl ketone (1.75 mL, 21.4 mmol) and ethyl N-p-toluenesulfonylglycinate 81 (5.5 g, 21.4 mL) in THF (50 mL). The resulting mixture was stirred overnight at room temperature. The mixture was diluted with ether, washed with 5% aq. HCl, 5% sodium bicarbonate solution and water. The combined organics were dried with $Na_2SO_4$, filtered, evaporated under reduced pressure to give crude 82 (5.3 g, 76%) as a yellow oil (diastereoisomers mixture). $^1$H-NMR (400 MHz, $CDCl_3$): δ 1.29 (m, 6H), 1.75 (m, 1H), 2.09 (m, 1H), 2.43 (s, 3H), 3.40 (m, 1H), 3.56 (m, 1H), 4.04 (s, 1H), 4.20 (m, 2H), 7.30 (d, 2H), 7.75 (d, 2H) ppm. $^{13}$C-NMR (100 MHz, $CDCl_3$): δ □14.12, 15.28, 23.04, 25.60, 26.27, 38.20, 38.86, 46.26, 46.46, 61.49, 61.65, 69.10, 71.69, 127.51, 129.70, 134.83, 134.91, 143.58, 143.84, 170.03, 170.45 ppm. DEPT (100 MHz, $CDCl_3$): $CH_3$ carbons: 14.12, 15.28, 23.04, 25.60, 26.27; $CH_2$ carbons: 38.20, 38.86, 46.26, 46.46, 61.49, 61.65; CH carbons: 69.10, 71.69, 127.51, 129.70 ppm. LC/MS: 97.60%, m/z=327.

Synthesis of 3-Methyl-1-(toluene-4-sulfonyl)-2,5-dihydro-1H-pyrrole-2-carboxylic acid ethyl ester (83)

The pyrrolidine oil 82 (10.5 g, 32.11 mmol) was dissolved in pyridine (86 mL). $POCl_3$ (7.48 mL, 80.27 mmol) was added dropwise and the resulting mixture stirred overnight at room temperature. The mixture was poured over ice, extracted with ether and washed with 5% aq. HCl, 5% sodium bicarbonate solution and water. The ether layer was dried over sodium sulfate, filtered and evaporated under reduced pressure to give the crude solid 83 (8.80 g, 88%). $^1$H-NMR (400 MHz, $CDCl_3$): δ 1.28 (t, 3H), 1.69 (m, 3H), 2.43 (s, 3H), 4.10 (m, 1H), 4.20 (q, 2H), 4.21 (m, 1H), 7.31 (d, 2H), 7.75 (d, 2H) ppm. $^{13}$C-NMR (100 MHz, $CDCl_3$): δ 13.58, 14.10, 21.56, 54.64, 61.62, 70.55, 110.02, 122.51, 127.51, 129.73, 169.87 ppm. DEPT (100 MHz, $CDCl_3$): $CH_3$ carbons: 13.58, 14.10, 21.56; $CH_2$ carbons: 54.64, 61.62; CH carbons: 70.55, 122.51, 127.51, 129.73 ppm. LC/MS: 100%, m/z=309.

Synthesis of 3-Methyl-1H-pyrrole-2-carboxylic acid ethyl ester (84)

Pyrroline 83 (8.80 g, 28.48 mmol) was dissolved in THF (70 mL). DBU (9.78 mL, 65.50 mmol) was added dropwise and the resulting solution stirred under reflux overnight. The mixture was cooled to room temperature, diluted with ether and washed with 5% aq. HCl, 5% sodium bicarbonate solution and water. The organic layer was dried over sodium sulfate, filtered and evaporated under reduced pressure to give the crude solid 84 (4.30 g, 98%). $^1$H-NMR (400 MHz, $CDCl_3$): δ 1.37 (t, 3H), 2.35 (s, 3H), 4.31 (q, 2H), 6.08 (d, 1H), 6.81 (d, 1H), 8.90 (s broad, 1H) ppm. $^{13}$C-NMR (100 MHz, $CDCl_3$): δ□ 12.76, 14.53, 59.96, 112.58□, 119.35, 121.53, 127.96, 162.01 ppm. DEPT (100 MHz, $CDCl_3$): $CH_3$ carbons: 12.76, 14.53; $CH_2$ carbons: 59.96; CH carbons: 112.58, 121.53 ppm. LC/MS: 90.74%, m/z=153.

Synthesis of 4-[2-(4-Chloro-phenyl)-acetyl]-3-methyl-1H-pyrrole-2-carboxylic acid ethyl ester (85)

A solution of (4-chlorophenyl)-acetyl chloride (3 mmol) in dichloromethane or 1,2-dichloroethane (4 ml) was added to a solution cooled at −40° C. of 84 (0.229 g, 1.5 mmol) and $AlCl_3$ was added (0.400 g, 3 mmol). The reaction mixture was stirred for 30 minutes at the same temperature. The reaction mixture was poured into ice-water and extracted with ethyl acetate. The organic layer was washed with NaOH (2 M) and brine, dried over $Na_2SO_4$, and evaporated to dryness under vacuum to give crude product 85. Crude yield: 96%

$^1$H-NMR (400 MHz, $CDCl_3$): δ 1.37 (t, 3H), 2.60 (s, 3H), 4.00 (s, 2H), 4.35 (q, 2H), 7.27 (m, 4H), 7.49 (d, 1H), 8.83 (s broad, 1H) ppm. $^{13}$C-NMR (100 MHz, $CDCl_3$): δ 11.81, 14.38, 46.52, 60.94, 121.65, 124.57, 127.46, 128.81, 130.81, 133.54, 162.13, 193.36 ppm. DEPT (100 MHz, $CDCl_3$): $CH_3$ carbons: 11.81, 14.38; $CH_2$ carbons: 46.52, 60.94; CH carbons: 121.65, 128.81, 130.81 ppm. LC/MS: 90.32%, m/z=305.

Synthesis of 4-[2-(4-Chloro-phenyl)-ethyl]-3-methyl-1H-pyrrole-2-carboxylic acid ethyl ester (86)

Triethylsilane (3 equivalents) was added to a solution of 85 in trifluoroacetic acid (2 mL per mmol). The mixture was stirred for 48 h at room temperature. The TFA was removed under vacuum and the crude product was taken up in AcOEt, washed with NaOH (2 M), brine, dried with $Na_2SO_4$, filtered and concentrated to give crude product. The residue was purified by HPLC. Yield: 46% for two steps. $^1$H-NMR (400 MHz, $CDCl_3$): δ 1.35 (t, 3H), 2.26 (s, 3H), 2.69 (m, 2H), 2.78 (m, 2H), 4.31 (q, 2H), 6.55 (d, 1H), 7.08 (d, 2H), 7.22 (d, 2H), 8.86 (s broad, 1H) ppm.

Synthesis of 4-[2-(4-Chloro-phenyl)-ethyl]-3-methyl-1H-pyrrole-2-carboxylic acid (87)

Freshly prepared aq. NaOH (1M in $H_2O$, 10 equivalents) was added at room temperature to a stirred solution of 86 (1 equivalent) in a mixture of 1,4-dioxane and $H_2O$ (v/v 3:1). The reaction was heated to 80° C. until the reaction was judged complete by TLC. The product was extracted with $Et_2O$, then the aqueous layer was made acid (pH=1) with the dropwise addition of 10% aq. HCl. The solid was filtered off and washed with water. The solid was dried under vacuum overnight to obtain 87. Yield: 66%. $^1$H-NMR (400 MHz, $CD_3OD$): δ 2.19 (s, 3H), 2.69 (m, 2H), 2.78 (m, 2H), 6.58 (d, 1H), 7.11 (d, 2H), 7.22 (d, 2H) ppm. LC/MS: 100%, m/z=263. HPLC (200-400 nm): 95.93%

Example 33

Synthesis of 4-[2-(4-Methoxy-phenyl)-ethyl]-3-methyl-1H-pyrrole-2-carboxylic acid (90)

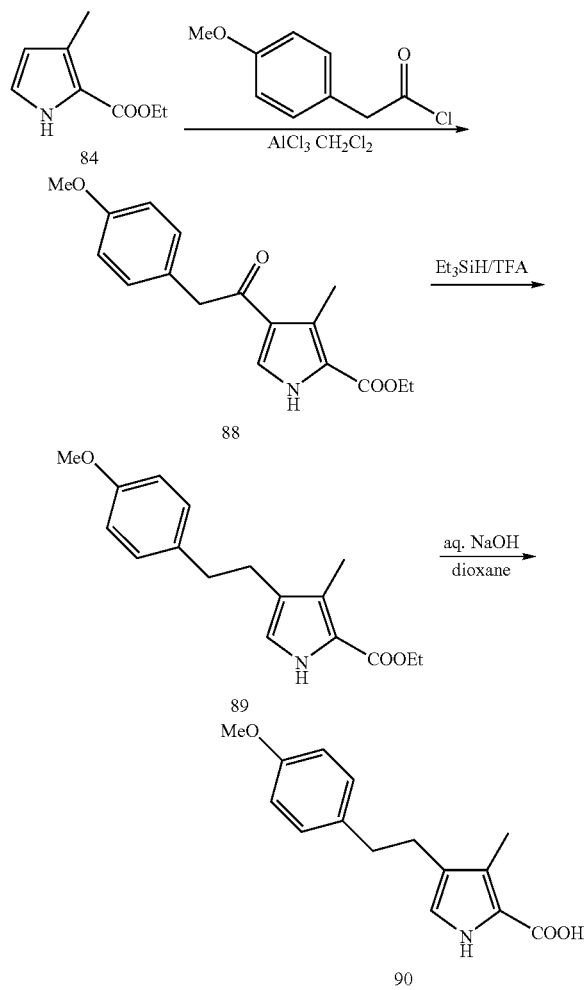

Synthesis of 4-[2-(4-Methoxy-phenyl)-acetyl]-3-methyl-1H-pyrrole-2-carboxylic acid ethyl ester (88)

4-[2-(4-Methoxy-phenyl)-acetyl]-3-methyl-1H-pyrrole-2-carboxylic acid ethyl ester (88) was synthesized from 3-Methyl-1H-pyrrole-2-carboxylic acid ethyl ester (84) following the procedure described in Example 32. Crude yield: 97% $^1$H-NMR (400 MHz, CDCl$_3$): δ 1.36 (t, 3H), 2.61 (s, 3H), 3.79 (s, 3H), 3.97 (s, 2H), 4.33 (q, 2H), 6.50 (d, 2H), 7.16 (d, 2H), 7.46 (d, 1H), 9.27 (s broad, 1H) ppm. $^{13}$C-NMR (100 MHz, CDCl$_3$): δ 11.75, 14.41, 46.60, 55.27, 60.68, 114.07, 127.09, 130.43, 158.45, 194.19 ppm. DEPT (100 MHz, CDCl$_3$): CH$_3$ carbons: 11.75, 14.41, 55.27; CH$_2$ carbons: 46.60, 60.68; CH carbons: 114.07, 127.09, 130.43 ppm. LC/MS: 76.86%, m/z=301.

Synthesis of 4-[2-(4-Methoxy-phenyl)-ethyl]-3-methyl-1H-pyrrole-2-carboxylic acid ethyl ester (89)

4-[2-(4-Methoxy-phenyl)-ethyl]-3-methyl-1H-pyrrole-2-carboxylic acid ethyl ester (89) was synthesized from 4-[2-(4-Methoxy-phenyl)-acetyl]-3-methyl-1H-pyrrole-2-carboxylic acid ethyl ester (88) following the procedure described in Example 32. Yield: 23% $^1$H-NMR (400 MHz, CDCl$_3$): δ 1.36 (t, 3H), 2.27 (s, 3H), 2.69 (m, 2H), 2.76 (m, 2H), 3.79 (s, 3H), 4.31 (q, 2H), 6.59 (d, 1H), 6.82 (m, 2H), 7.08 (m, 2H), 8.70 (s broad, 1H) ppm.
$^{13}$C-NMR (100 MHz, CDCl$_3$): δ 10.23, 14.56, 27.34, 35.78, 55.27, 59.85, 113.70, 119.69, 129.35, 134.14, 157.81 ppm. DEPT (100 MHz, CDCl$_3$): CH$_3$ carbons: 10.23, 14.56, 55.27; CH$_2$ carbons: 27.34, 35.78, 59.85; CH carbons: 113.70, 119.69, 129.35, 134.14 ppm. LC/MS: 100%, m/z=287.

Synthesis of 4-[2-(4-Methoxy-phenyl)-ethyl]-3-methyl-1H-pyrrole-2-carboxylic acid (93)

4-[2-(4-Methoxy-phenyl)-ethyl]-3-methyl-1H-pyrrole-2-carboxylic acid (93) was synthesized from 4-[2-(4-Methoxyphenyl)-ethyl]-3-methyl-1H-pyrrole-2-carboxylic acid ethyl ester (92) following the procedure described in Example 32. Yield: 66%. $^1$H-NMR (400 MHz, CD$_3$OD): δ 2.19 (s, 3H), 2.65 (m, 2H), 2.72 (m, 2H), 3.75 (s, 3H), 6.59 (d, 1H), 6.79 (m, 2H), 7.04 (m, 2H) ppm. $^{13}$C-NMR (100 MHz, CDCl$_3$): δ 10.46, 28.51, 37.32, 55.62, 114.64, 121.89, 125.45, 127.46, 130.44, 135.54, 165.07 ppm. DEPT (100 MHz, CDCl$_3$): CH$_3$ carbons: 10.46, 55.62; CH$_2$ carbons: 28.51, 37.32; CH carbons: 114.64, 121.89, 130.44 ppm. LC/MS: 100%, m/z=259. HPLC (200-400 nm): 94.17%.

Example 34

Synthesis of 4-[2-(3-Methoxyphenyl)-ethyl]-3-methyl-1H-pyrrole-2-carboxylic acid (90)

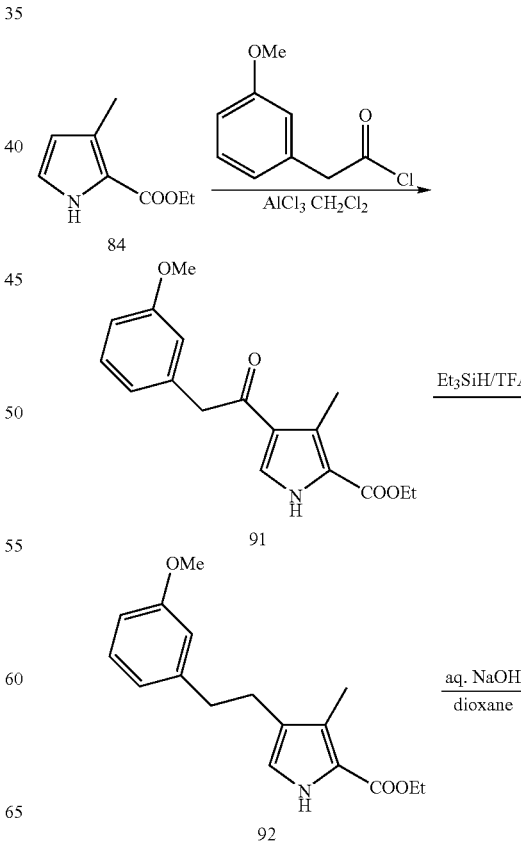

Synthesis of 4-[2-(3-Methoxy-phenyl)-acetyl]-3-methyl-1H-pyrrole-2-carboxylic acid ethyl ester (91)

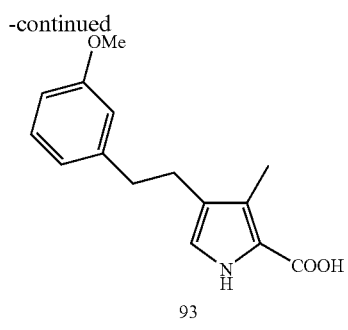

4-[2-(3-Methoxy-phenyl)-acetyl]-3-methyl-1H-pyrrole-2-carboxylic acid ethyl ester (91) was synthesized from 3-methyl-1H-pyrrole-2-carboxylic acid ethyl ester (84) and (3-methoxyphenyl)-acetyl chloride following the procedure described in Example 32. crude yield: 95%. $^1$H-NMR (400 MHz, CDCl$_3$): δ 1.36 (t, 3H), 2.61 (s, 3H), 3.77 (s, 3H), 3.99 (s, 2H), 4.32 (q, 2H), 6.81 (m, 3H), 7.24 (m, 1H), 7.45 (d, 1H), 9.41 (s broad, 1H) ppm. $^{13}$C-NMR (100 MHz, CDCl$_3$): δ □□11.75, 14.40, 47.59, 55.19, 60.66, 112.19, 115.04, 121.71, 127.22, 129.58, 136.75, 159.75, 193.65 ppm. DEPT (100 MHz, CDCl$_3$): CH$_3$ carbons: 11.75, 14.40, 55.19; CH$_2$ carbons: 47.59, 60.66; CH carbons: 112.19, 115.04, 121.71, 127.22, 129.58 ppm. LC/MS: 60.20%, m/z=301

Synthesis of 4-[2-(3-Methoxyphenyl)-ethyl]-3-methyl-1H-pyrrole-2-carboxylic acid ethyl ester (92)

4-[2-(3-Methoxyphenyl)-ethyl]-3-methyl-1H-pyrrole-2-carboxylic acid ethyl ester (92) was synthesized from 4-[2-(3-Methoxyphenyl)-acetyl]-3-methyl-1H-pyrrole-2-carboxylic acid ethyl ester (91) following the procedure described in Example 32. Yield: 18%. $^1$H-NMR (400 MHz, CDCl$_3$): δ 1.36 (t, 3H), 2.28 (s, 3H), 2.72 (m, 2H), 2.79 (m, 2H), 3.79 (s, 3H), 4.31 (q, 2H), 6.61 (d, 1H), 6.67 (m, 3H), 7.20 (m, 1H), 8.72 (s broad, 1H) ppm.

$^{13}$C-NMR (100 MHz, CDCl$_3$): δ □10.24, 14.56, 26.99, 36.73, 55.16, 59.87, 111.11, 114.27, 119.65, 120.89, 129.28, 159.04 ppm. DEPT (100 MHz, CDCl$_3$): CH$_3$ carbons: 10.24, 14.56, 55.16; CH$_2$ carbons: 26.99, 36.73, 59.87; CH carbons: 111.11, 114.27, 119.65, 120.89, 129.28 ppm. LC/MS: 100%, m/z=287.

Synthesis of 4-[2-(3-Methoxy-phenyl)-ethyl]-3-methyl-1H-pyrrole-2-carboxylic acid (93)

4-[2-(3-Methoxy-phenyl)-ethyl]-3-methyl-1H-pyrrole-2-carboxylic acid (93) was synthesized from 4-[2-(3-Methoxyphenyl)-ethyl]-3-methyl-1H-pyrrole-2-carboxylic acid ethyl ester (92) following the procedure described in Example 32. Yield: 57%. $^1$H-NMR (400 MHz, CD$_3$OD): δ 2.20 (s, 3H), 2.70 (m, 2H), 2.76 (m, 2H), 3.73 (s, 3H), 6.61 (d, 1H), 6.72 (m, 3H), 7.13 (m, 1H) ppm. $^{13}$C-NMR (100 MHz, CDCl$_3$): □□□10.48, 28.18, 38.25, 55.51, 112.30, 115.17, 121.95, 125.37, 130.18, 145.05, 161.10 ppm. DEPT (100 MHz, CDCl$_3$): CH$_3$ carbons: 10.48, 55.51; CH$_2$ carbons: 28.18, 38.25; CH carbons: 112.30, 115.17, 121.95, 130.18 ppm. LC/MS: 93.45%, m/z=259. HPLC (200-400 nm): 69.03%.

Example 35

Synthesis of 4-[2-(4-Fluoro-phenyl)-ethyl]-3-methyl-1H-pyrrole-2-carboxylic acid (96)

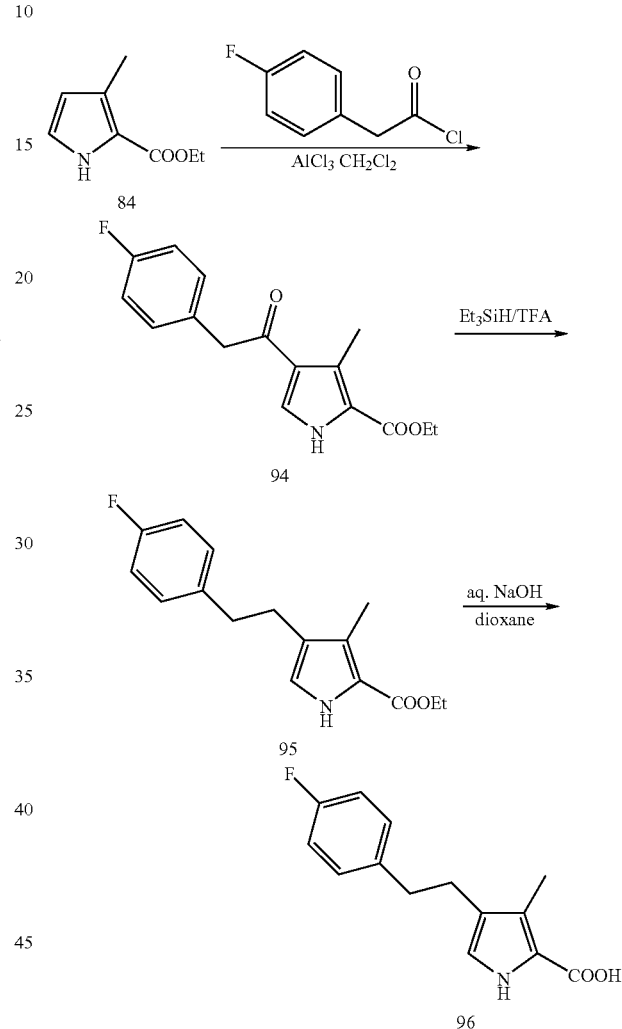

Synthesis of 4-[2-(4-Fluorophenyl)-acetyl]-3-methyl-1H-pyrrole-2-carboxylic acid ethyl ester (94)

4-[2-(4-Fluorophenyl)-acetyl]-3-methyl-1H-pyrrole-2-carboxylic acid ethyl ester (94) was synthesized from 3-methyl-1H-pyrrole-2-carboxylic acid ethyl ester (84) and (4-fluorophenyl)-acetyl chloride following the procedure described in Example 32. Crude yield: 94%. $^1$H-NMR (400 MHz, CDCl$_3$): δ 1.36 (t, 3H), 2.61 (s, 3H), 4.01 (s, 2H), 4.35 (q, 2H), 7.01 (m, 2H), 7.22 (m, 2H), 7.50 (d, 1H), 9.70 (s broad, 1H) ppm. $^{13}$C-NMR (100 MHz, CDCl$_3$): □□□11.79, 14.38, 46.36, 60.89, 115.51, 127.27, 129.93, 130.77, 162.04, 193.62 ppm. DEPT (100 MHz, CDCl$_3$): CH$_3$ carbons: 11.79, 14.38; CH$_2$ carbons: 46.36, 60.89; CH carbons: 115.51, 127.27, 129.93, 130.77 ppm. LC/MS: 77.48%, m/z=289.

Synthesis of 4-[2-(4-fluorophenyl)-ethyl]-3-methyl-1H-pyrrole-2-carboxylic acid ethyl ester (95)

4-[2-(4-Fluorophenyl)-ethyl]-3-methyl-1H-pyrrole-2-carboxylic acid ethyl ester (95) was synthesized from 4-[2-(4-fluorophenyl)-acetyl]-3-methyl-1H-pyrrole-2-carboxylic acid ethyl ester (94) following the procedure described in Example 32. Yield: 23%

$^1$H-NMR (400 MHz, CDCl$_3$): δ 1.36 (t, 3H), 2.26 (s, 3H), 2.69 (m, 2H), 2.78 (m, 2H), 4.31 (q, 2H), 6.57 (d, 1H), 6.95 (m, 2H), 7.10 (m, 2H), 8.70 (s broad, 1H) ppm. $^{13}$C-NMR (100 MHz, CDCl$_3$): δ 10.21, 14.55, 27.20, 35.90, 59.89, 114.89, 115.10, 119.70, 124.60, 129.77, 137.58, 160.00 ppm. DEPT (100 MHz, CDCl$_3$): CH$_3$ carbons: 10.21, 14.55; CH$_2$ carbons: 27.20, 35.90, 59.89; CH carbons: 121.65, 128.81, 130.81 ppm. LC/MS: 100%, m/z=275.

Synthesis of 4-[2-(4-Fluoro-phenyl)-ethyl]-3-methyl-1H-pyrrole-2-carboxylic acid (96)

4-[2-(4-Fluorophenyl)-ethyl]-3-methyl-1H-pyrrole-2-carboxylic acid (96) was synthesized from 4-[2-(4-fluorophenyl)-ethyl]-3-methyl-1H-pyrrole-2-carboxylic acid ethyl ester (95) following the procedure described in Example 32. Yield: 22%. $^1$H-NMR (400 MHz, CDCl$_3$): δ 2.19 (s, 3H), 2.68 (m, 2H), 2.77 (m, 2H), 6.58 (d, 1H), 6.95 (m, 2H), 7.12 (m, 2H) ppm. DEPT (100 MHz, CDCl$_3$): CH$_3$ carbons: 10.43; CH$_2$ carbons: 28.32, 37.31; CH carbons: 115.61, 121.90, 131.11 ppm. LC/MS: 100%, m/z=247. HPLC (200-400 nm): 98.44%.

Example 36

Synthesis of 4-[2-(3-Fluorophenyl)-ethyl]-3-methyl-1H-pyrrole-2-carboxylic acid (99)

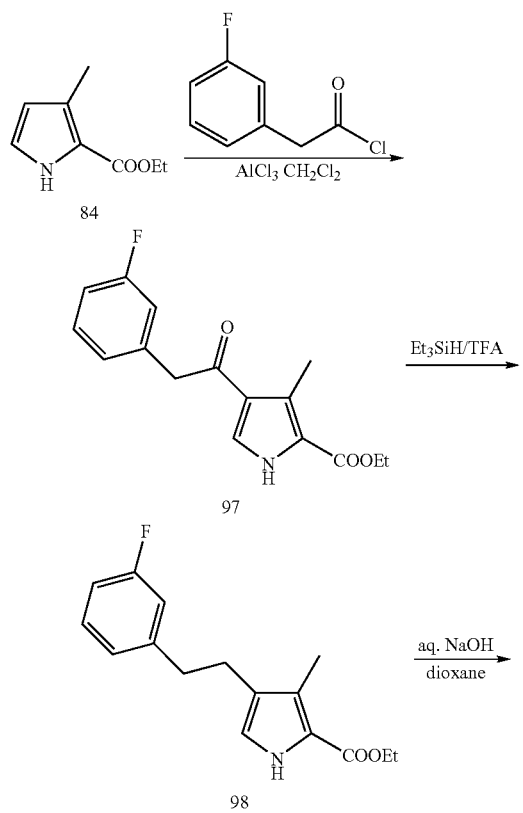

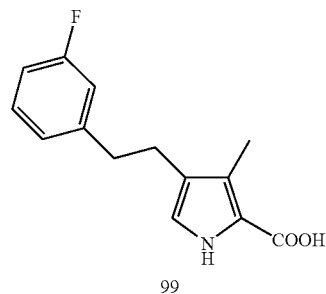

Synthesis of 4-[2-(3-Fluorophenyl)-acetyl]-3-methyl-1H-pyrrole-2-carboxylic acid ethyl ester (97)

4-[2-(3-Fluorophenyl)-acetyl]-3-methyl-1H-pyrrole-2-carboxylic acid ethyl ester was synthesized from 3-methyl-1H-pyrrole-2-carboxylic acid ethyl ester (84) and (3-Fluorophenyl)-acetyl chloride following the procedure described in Example 32. Crude yield: 93%. $^1$H-NMR (400 MHz, CDCl$_3$): δ 1.37 (t, 3H), 2.61 (s, 3H), 4.03 (s, 2H), 4.35 (q, 2H), 7.00 (m, 3H), 7.27 (m, 1H), 7.49 (d, 1H), 9.57 (s broad, 1H) ppm. $^{13}$C-NMR (100 MHz, CDCl$_3$): ☐☐☐11.76, 14.38, 46.93, 60.84, 113.64, 116.30, 125.13, 127.17, 129.94, 137.42, 161.64, 193.02 ppm. DEPT (100 MHz, CDCl$_3$): CH$_3$ carbons: 11.76, 14.38; CH$_2$ carbons: 46.93, 60.84; CH carbons: 116.30, 125.13, 127.17, 129.94 ppm. LC/MS: 91.29%, m/z=289.

Synthesis of 4-[2-(3-Fluoro-phenyl)-ethyl]-3-methyl-1H-pyrrole-2-carboxylic acid ethyl ester (98)

4-[2-(3-Fluoro-phenyl)-ethyl]-3-methyl-1H-pyrrole-2-carboxylic acid ethyl ester (98) was synthesized from 4-[2-(3-Fluorophenyl)-acetyl]-3-methyl-1H-pyrrole-2-carboxylic acid ethyl ester (98) following the procedure described in Example 32. Yield: 27%

$^1$H-NMR (400 MHz, CDCl$_3$): δ 1.36 (t, 3H), 2.27 (s, 3H), 2.72 (m, 2H), 2.81 (m, 2H), 4.31 (q, 2H), 6.59 (d, 1H), 6.88 (m, 3H), 7.22 (m, 1H), 8.79 (s broad, 1H) ppm. $^{13}$C-NMR (100 MHz, CDCl$_3$): δ 10.22, 14.55, 26.80, 36.43, 59.93, 112.64, 115.18, 119.72, 124.16, 129.72, 144.51, 161.65 ppm. DEPT (100 MHz, CDCl$_3$): CH$_3$ carbons: 10.22, 14.55; CH$_2$ carbons: 26.80, 36.43, 59.93; CH carbons: 112.64, 115.18, 119.72, 124.16, 129.72 ppm. LC/MS: 100%, m/z=275.

Synthesis of 4-[2-(3-Fluoro-phenyl)-ethyl]-3-methyl-1H-pyrrole-2-carboxylic acid (99)

4-[2-(3-Fluoro-phenyl)-ethyl]-3-methyl-1H-pyrrole-2-carboxylic acid (99) was synthesized from 4-[2-(3-Fluorophenyl)-ethyl]-3-methyl-1H-pyrrole-2-carboxylic acid ethyl ester (98) following the procedure described in Example 32. Yield: 55%. $^1$H-NMR (400 MHz, CDCl$_3$): δ 2.20 (s, 3H), 2.69 (m, 2H), 2.81 (m, 2H), 6.61 (d, 1H), 6.87 (m, 2H), 6.95 (m, 1H), 7.24 (m, 1H) ppm. DEPT (100 MHz, CDCl$_3$): CH$_3$ carbons: 10.43; CH$_2$ carbons: 27.95, 37.84; CH carbons: 113.53, 116.27, 121.87, 125.48, 130.79 ppm. LC/MS: 100%, m/z=247. HPLC (200-400 nm): 80.81%.

Example 37

Synthesis of 3-Methyl-4-[2-(4-trifluoromethyl-phenyl)-ethyl]-1H-pyrrole-2-carboxylic acid (93)

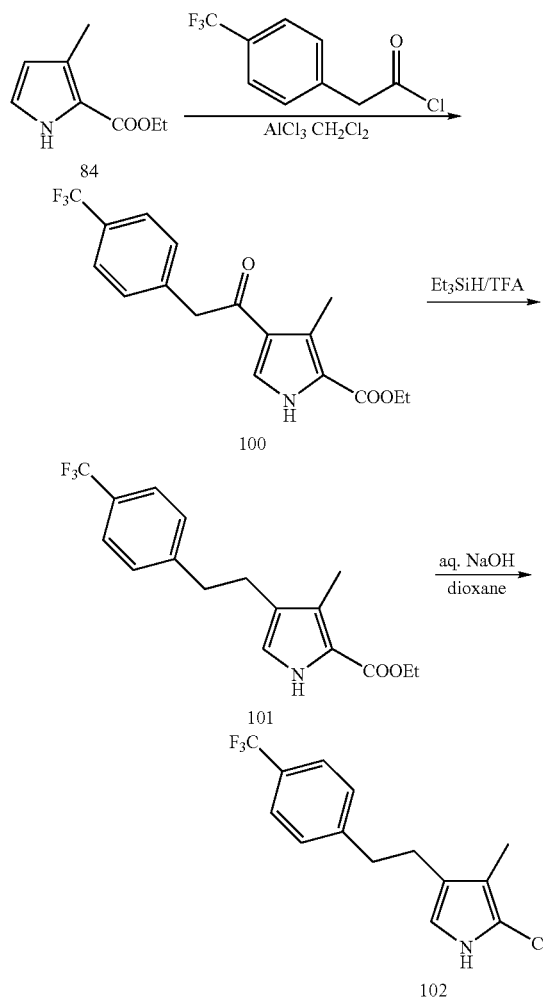

Synthesis of 3-methyl-4-[2-(4-trifluoromethylphenyl)-acetyl]-1H-pyrrole-2-carboxylic acid ethyl ester (100)

3-Methyl-4-[2-(4-trifluoromethylphenyl)acetyl]-1H-pyrrole-2-carboxylic acid ethyl ester (100) was synthesized from 3-methyl-1H-pyrrole-2-carboxylic acid ethyl ester (84) and (4-trifluoromethylphenyl)-acetyl chloride following the procedure described in Example 32. Crude yield: 96%. $^1$H-NMR (400 MHz, CDCl$_3$): δ 1.38 (t, 3H), 2.61 (s, 3H), 4.11 (s, 2H), 4.35 (q, 2H), 7.37 (m, 2H), 7.51 (d, 1H), 7.58 (m, 2H), 9.29 (s broad, 1H) ppm. $^{13}$C-NMR (100 MHz, CDCl$_3$): δ 11.71, 14.41, 46.90, 60.78, 123.70, 124.70, 125.49, 126.75, 129.41, 129.85, 130.00, 161.98, 193.49 ppm. DEPT (100 MHz, CDCl$_3$): CH$_3$ carbons: 11.71, 14.41; CH$_2$ carbons: 46.90, 60.78; CH carbons: 123.70, 124.70, 125.49, 126.75, 129.41, 129.85, 130.00 ppm. LC/MS: 73.23%, m/z=339.

Synthesis of 3-methyl-4-[2-(4-trifluoromethylphenyl)-ethyl]-1H-pyrrole-2-carboxylic acid ethyl ester (101)

3-Methyl-4-[2-(4-trifluoromethylphenyl)-ethyl]-1H-pyrrole-2-carboxylic acid ethyl ester (101) was synthesized from 3-methyl-4-[2-(4-trifluoromethyl-phenyl)-acetyl]-1H-pyrrole-2-carboxylic acid ethyl ester (100) following the procedure described in Example 32. Yield: 22%. $^1$H-NMR (400 MHz, CDCl$_3$): δ 1.36 (t, 3H), 2.27 (s, 3H), 2.73 (m, 2H), 2.87 (m, 2H), 4.31 (q, 2H), 6.56 (d, 1H), 7.26 (m, 2H), 7.52 (m, 2H), 8.72 (s broad, 1H) ppm. $^{13}$C-NMR (100 MHz, CDCl$_3$): δ □10.21, 14.54, 26.78, 36.51, 59.95, 119.70, 124.23, 125.18, 128.81, 161.68 ppm. DEPT (100 MHz, CDCl$_3$): CH$_3$ carbons: 10.21, 14.54; CH$_2$ carbons: 26.78, 36.51, 59.95; CH carbons: 119.70, 124.23, 125.18, 128.81 ppm.

LC/MS: 100%, m/z=325.

Synthesis of 3-methyl-4-[2-(4-trifluoromethylphenyl)-ethyl]-1H-pyrrole-2-carboxylic acid (102)

3-Methyl-4-[2-(4-trifluoromethylphenyl)-ethyl]-1H-pyrrole-2-carboxylic acid (102) was synthesized from 3-methyl-4-[2-(4-trifluoromethylphenyl)ethyl]-1H-pyrrole-2-carboxylic acid ethyl ester (101) following the procedure described in Example 32. Yield: 60%. $^1$H-NMR (400 MHz, CDCl$_3$): δ 2.20 (s, 3H), 2.73 (m, 2H), 2.89 (m, 2H), 6.59 (d, 1H), 7.32 (m, 2H), 7.54 (m, 2H) ppm. $^{13}$C-NMR (100 MHz, CDCl$_3$): δ 10.42, 27.84, 37.90, 120.14, 121.92, 124.74, 126.04, 127.37, 130.26, 148.11, 164.99 ppm. DEPT (100 MHz, CDCl$_3$): CH$_3$ carbons: 10.42; CH$_2$ carbons: 27.84, 37.90; CH carbons: 121.92, 126.04, 130.27 ppm. LC/MS: 100%, m/z=297. HPLC (200-400 nm): 94.63%.

Example 38

Synthesis of 3-Methyl-4-[2-(3-trifluoromethyl-phenyl)-ethyl]-1H-pyrrole-2-carboxylic acid (96)

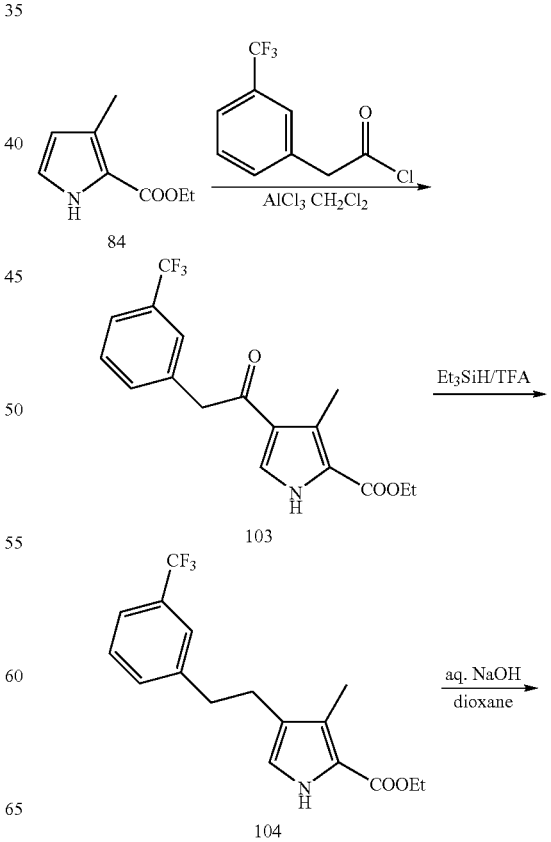

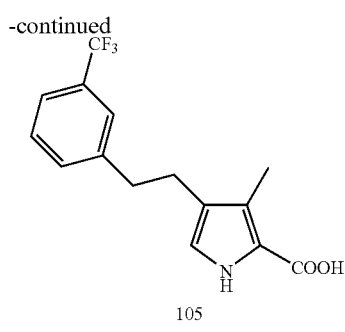

105

Synthesis of 3-Methyl-4-[2-(3-trifluoromethyl-phenyl)-acetyl]-1H-pyrrole-2-carboxylic acid ethyl ester (105)

3-Methyl-4-[2-(3-trifluoromethylphenyl)acetyl]-1H-pyrrole-2-carboxylic acid ethyl ester (103) was synthesized from 3-methyl-1H-pyrrole-2-carboxylic acid ethyl ester (84) and (3-trifluoromethylphenyl)-acetyl chloride following the procedure described in Example 32. Crude yield: 97%. $^1$H-NMR (400 MHz, CDCl$_3$): δ 1.38 (t, 3H), 2.62 (s, 3H), 4.11 (s, 2H), 4.35 (q, 2H), 7.45 (m, 2H), 7.51 (m, 3H), 9.40 (s broad, 1H) ppm. $^{13}$C-NMR (100 MHz, CDCl$_3$): δ 11.73, 14.40, 46.73, 60.78, 123.70, 124.70, 126.82, 128.93, 129.71, 133.01, 135.85, 161.61, 192.58 ppm. DEPT (100 MHz, CDCl$_3$): CH$_3$ carbons: 11.73, 14.40; CH$_2$ carbons: 46.73, 60.78; CH carbons: 123.70, 126.82, 128.93, 129.71, 133.01 ppm. LC/MS: 79.18%, m/z=339.

Synthesis of 3-Methyl-4-[2-(3-trifluoromethylphenyl)-ethyl]-1H-pyrrole-2-carboxylic acid ethyl ester (104)

3-Methyl-4-[2-(3-trifluoromethylphenyl)-ethyl]-1H-pyrrole-2-carboxylic acid ethyl ester (104) was synthesized from 3-methyl-4-[2-(3-trifluoromethylphenyl)-acetyl]-1H-pyrrole-2-carboxylic acid ethyl ester (103) following the procedure described in Example 32. Yield: 16%. $^1$H-NMR (400 MHz, CDCl$_3$): δ 1.36 (t, 3H), 2.26 (s, 3H), 2.74 (m, 2H), 2.87 (m, 2H), 4.31 (q, 2H), 6.58 (d, 1H), 7.38 (m, 4H), 8.72 (s broad, 1H) ppm. $^{13}$C-NMR (100 MHz, CDCl$_3$): δ 10.20, 14.54, 26.87, 35.56, 59.93, 119.67, 122.77, 124.25, 125.16, 128.67, 131.95, 142.77 ppm. DEPT (100 MHz, CDCl$_3$): CH$_3$ carbons: 10.20, 14.54; CH$_2$ carbons: 26.87, 35.56, 59.93; CH carbons: 119.67, 122.77, 125.16, 128.67, 131.95 ppm. LC/MS: 100%, m/z=325.

Synthesis of 3-Methyl-4-[2-(3-trifluoromethyl-phenyl)-ethyl]-1H-pyrrole-2-carboxlic acid 3-Methyl-4-[2-(3-trifluoromethyl-phenyl)-ethyl]-1H-pyrrole-2-carboxylic acid (105) was synthesized from 3-methyl-4-[2-(3-trifluoromethylphenyl)-ethyl]-1H-pyrrole-2-carboxylic acid ethyl ester (104) following the procedure described in Example 32. $^1$H-NMR (400 MHz, CDCl$_3$): □ 2.18 (s, 3H), 2.73 (m, 2H), 2.89 (m, 2H), 6.60 (d, 1H), 7.42 (m, 4H) ppm. $^{13}$C-NMR (100 MHz, CDCl$_3$): δ 10.39, 27.93, 37.87, 121.93, 123.57, 124.69, 126.22, 127.40, 129.94, 133.52, 144.72, 165.01 ppm. DEPT (100 MHz, CDCl$_3$): CH$_3$ carbons: 10.39; CH$_2$ carbons: 27.93, 37.87; CH carbons: 121.93, 123.57, 126.22, 129.94, 133.52 ppm. LC/MS: 100%, m/z=297. HPLC (200-400 nm): 96.89%.

Example 39

4-[2-(4-Chlorophenyl)-ethyl]-5-methyl-1H-pyrrole-2-carboxylic acid (110)

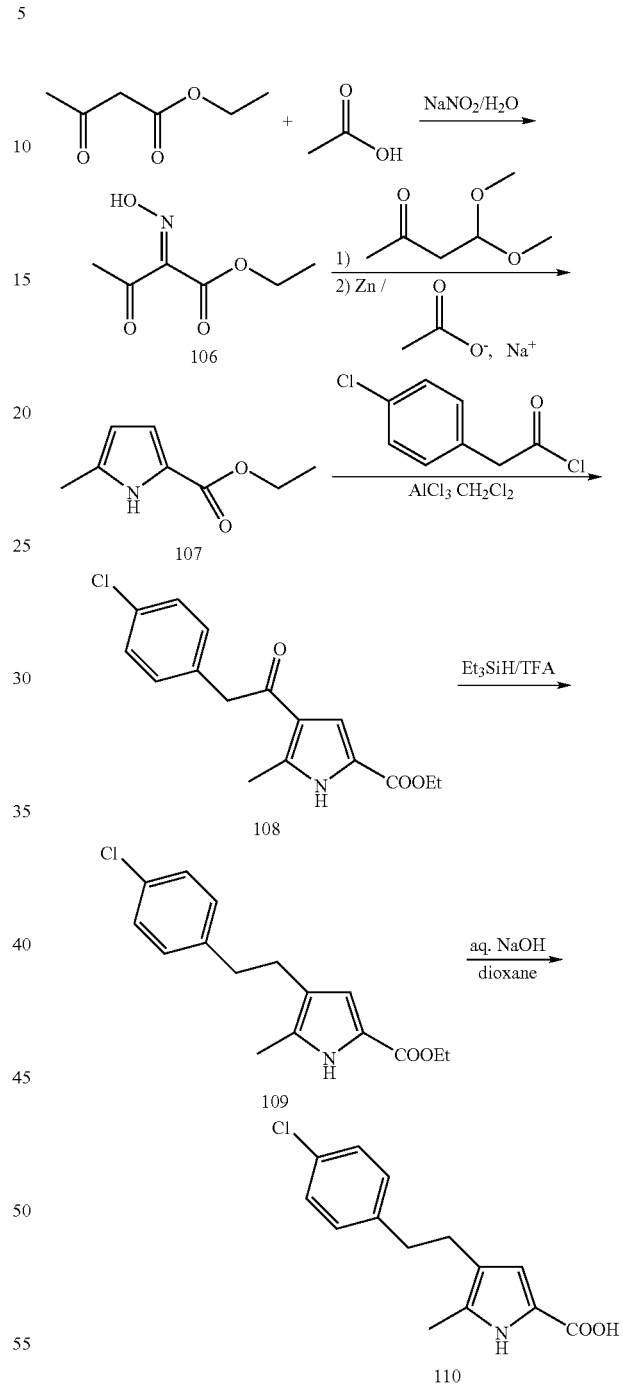

Synthesis of 5-methyl-1H-pyrrole-2-carboxylic acid ethyl ester (107)

Sodium nitrite (11.5 g; 0.160 mol) in water (20 ml) was added dropwise to an ice cooled stirring solution of ethyl acetoacetate (20.7 g; 0.159 mol) in acetic acid (20 ml). The reaction temperature was maintained below 10° C. The mixture was stirred for an additional 1 h at 5° C. and stored overnight at 0° C. to give oxime 97 as an orange-red solution. This solution was added to a mixture of acetoacetaldehyde dimethyl acetal (21 g; 0.159 mol) and glacial acetic acid (35 ml), previously warmed to 60° C., and a mixture of zinc dust (30 g; 0.459 mol) and sodium acetate (30 g; 0.364 mol) was simultaneously and slowly added. After the addition, the mixture was stirred for an additional 2 h. the mixture was poured into ice-water (300 ml) to give a yellow precipitate. Filtration and recrystallization from methanol/water yielded 3.5 g (27%) of 5-methyl-1H-pyrrole-2-carboxylic acid ethyl ester (107), as a cream-colored needles. $^1$H (CDCl$_3$, 400 MHz): δ 9.10 (NH, broad s), 6.82 (1H, d), 5.95 (1H, s), 4.29 (2H, q), 2.31 (3H, s), 1.35 (3H, t) ppm. $^{13}$C (CDCl$_3$, 100 MHz): δ 161.5, 134.1, 121.2, 116.1, 101.8, 60.1, 15.5, 13.1 ppm. LC/MS: 97%.

Synthesis of 4-[2-(4-Chlorophenyl)-acetyl]-5-methyl-1H-pyrrole-2-carboxylic acid ethyl ester (108)

4-[2-(4-Chlorophenyl)-acetyl]-5-methyl-1H-pyrrole-2-carboxylic acid ethyl ester (108) was synthesized from 5-methyl-1H-pyrrole-2-carboxylic acid ethyl ester (107) and (4-chlorophenyl)-acetyl chloride following the procedure described in Example 32. Reaction Conditions: 1,2-dichloroethane/RT. Purification: recrystallization from ether/pentane. Yield: 83%. $^1$H (CDCl$_3$, 400 MHz): δ 9.65 (NH, broad s), 7.28 (3H, m), 7.2 (2H, d), 4.35 (2H, q), 4.04 (2H, s), 2.57 (3H, s), 1.38 (3H, t) ppm. $^{13}$C (CDCl$_3$, 100 MHz): δ 193.7, 161.5, 141.0, 133.5, 132.6, 130.9, 130.7, 128.9, 128.6, 121.4, 120.5, 116.9, 61.0, 46.1, 14.4, 14.0 ppm. LC/MS: 100%

Synthesis of 4-[2-(4-Chlorophenyl)-ethyl]-5-methyl-1H-pyrrole-2-carboxylic acid ethyl ester (109)

4-[2-(4-Chlorophenyl)-ethyl]-5-methyl-1H-pyrrole-2-carboxylic acid ethyl ester (109) was synthesized from 4-[2-(4-chlorophenyl)-acetyl]-5-methyl-1H-pyrrole-2-carboxylic acid ethyl ester (108) following the procedure described in Example 32. Purification: Recrystallization from ether/pentane. Yield: 82%. $^1$H (CDCl$_3$, 400 MHz): δ 9.65 (NH, broad s), 7.20 (2H, d), 7.04 (2H, d), 6.72 (1H, s), 4.29 (2H, q), 2.78 (2H, dd), 2.64 (2H, dd), 2.04 (3H, s), 1.35 (3H, t) ppm. $^{13}$C (CDCl$_3$, 100 MHz): δ 161.6, 140.4, 131.5, 131.2, 129.9, 128.3, 121.3, 119.8, 115.7, 60.1, 36.7, 27.8 14.5, 11.0 ppm. LC/MS: 96%.

Synthesis of 4-[2-(4-Chlorophenyl)-ethyl]-5-methyl-1H-pyrrole-2-carboxylic acid (110)

To a solution of 4-[2-(4-Chlorophenyl)-ethyl]-5-methyl-1H-pyrrole-2-carboxylic acid ethyl ester (109) in dioxane, 10 equiv of NaOH aq (1.5 M) was added then the mixture was heated at 80° C. for 3 hours. When the reaction is judged complete, the solvent is removed under vacuum, H$_2$O was added and an equal volume of Et$_2$O was added. The organic layer was removed then the aqueous layer was made acidic with HCl (1M). If the product precipitates out at this point, it was filtered off, washed with H$_2$O, and dried to obtain pure desired product. If the product didn't crash out when the aqueous layer is made acidic, Et$_2$O was added, and the organic layer was removed (2×). The organic layer was dried with Na$_2$SO$_4$, filtered, and concentrated to obtain desired product. Purification: precipitation. Amount: 20.6 mg. $^1$H (MeOD 400 MHz): δ 7.2 (2H, dd), 7.08 (2H, dd), 6.59 (1H, s), 2.76 (2H, dd), 2.63 (2H, dd), 1.97 (3H, s) ppm. DEPT (CD$_3$OD, 100 MHz): CH$_3$: δ 10.8, CH$_2$: □□ 28.9, 38.0, CH: 116.4, 129.1, 131.3 ppm. HPLC (20 min): 97.8%. LC/MS: 100%.

Example 40

Synthesis of 4-[2-(4-Fluoro-phenyl)-ethyl]-5-methyl-1H-pyrrole-2-carboxylic acid (113)

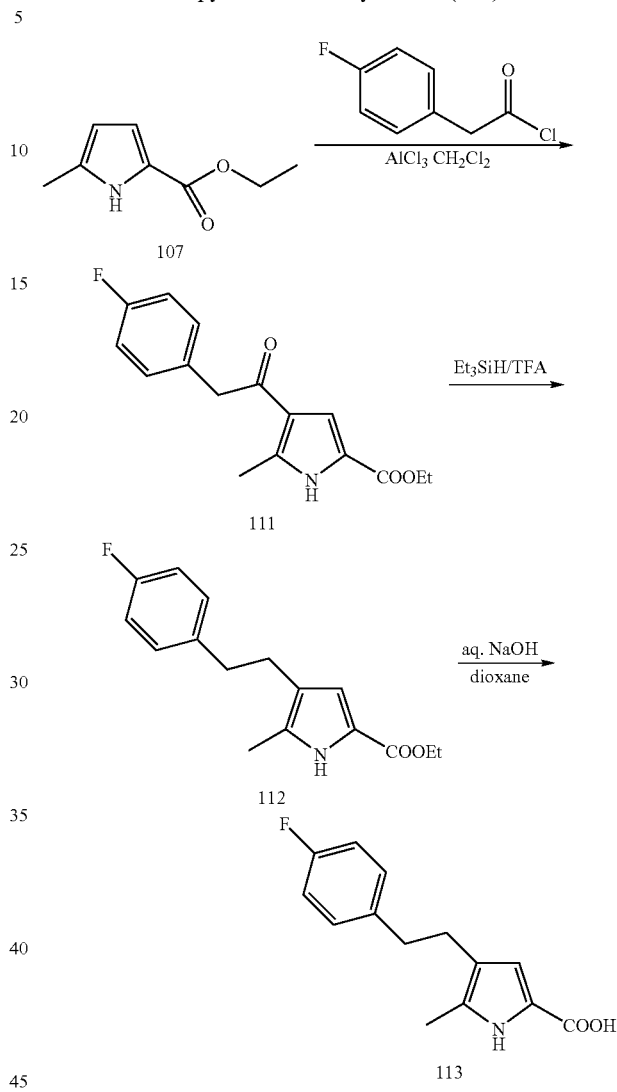

Synthesis of 4-[2-(4-Fluorophenyl)-acetyl]-5-methyl-1H-pyrrole-2-carboxylic acid ethyl ester (111)

4-[2-(4-Fluorophenyl)-acetyl]-5-methyl-1H-pyrrole-2-carboxylic acid ethyl ester (111) was synthesized from 5-methyl-1H-pyrrole-2-carboxylic acid ethyl ester (107) and (4-Fluorophenyl)-acetyl chloride following the procedure described in Example 32. Reaction Conditions: 1,2-dichloroethane/RT. Purification: recrystallization from ether/pentane. Yield: 76%. $^1$H (CDCl$_3$, 400 MHz): δ 10.5 (NH, broad s), 7.31 (1H, s), 7.22 (2H, dd), 6.99 (2H, dd), 4.36 (2H, q), 4.06 (2H, s), 2.58 (3H, s), 1.39 (3H, t) ppm. $^{13}$C (CDCl$_3$, 100 MHz): δ 194.1, 163.0, 161.5, 160.6, 141.0, 131.1, 130.7, 121.5, 120.5, 116.9, 115.4, 115.2, 61.0, 45.9, 14.4, 14.0 ppm. LC/MS: 100%.

Synthesis of 4-[2-(4-Fluoro-phenyl)-ethyl]-5-methyl-1H-pyrrole-2-carboxylic acid ethyl ester (112)

4-[2-(4-Fluorophenyl)-ethyl]-5-methyl-1H-pyrrole-2-carboxylic acid ethyl ester (112) was synthesized from 4-[2-(4-

Fluoro-phenyl)-acetyl]-5-methyl-1H-pyrrole-2-carboxylic acid ethyl ester (111) following the procedure described in Example 32. Purification: Recrystallization from ether/pentane. Yield: 86%. $^1$H (CDCl$_3$, 400 MHz): δ 9.45 (NH, broad s), 7.06 (2H, m), 6.94 (2H, m), 6.72 (1H, s), 4.29 (2H, q), 2.78 (2H, dd), 2.64 (2H, dd), 2.03 (3H, s), 1.34 (3H, t) ppm. $^{13}$C (CDCl$_3$, 100 MHz): δ 162.5, 160.1, 137.6, 131.1, 129.9, 121.4, 119.8, 115.7, 115.0, 60.0, 36.5, 28.0 14.5, 11.0 ppm. LC/MS: 100%.

Synthesis of 4-[2-(4-Fluorophenyl)-ethyl]-5-methyl-1H-pyrrole-2-carboxylic acid (113)

4-[2-(4-Fluorophenyl)-ethyl]-5-methyl-1H-pyrrole-2-carboxylic acid (113) was synthesized from 4-[2-(4-Fluoro-phenyl)-ethyl]-5-methyl-1H-pyrrole-2-carboxylic acid ethyl ester (112) following the procedure described in Example 39. Purification: precipitation. Amount: 21.5 mg. $^1$H (CD$_3$OD, 400 MHz): δ 7.10 (2H, dd), 6.94 (2H, dd), 6.60 (1H, s), 2.77 (2H, dd), 2.64 (2H, dd), 1.97 (3H, s) ppm. $^{13}$C (CD$_3$OD, 100 MHz): δ 166.0, 161.5, 139.4, 131.5, 131.3, 131.2, 122.5, 121.9, 116.6, 115.8, 115.5, 37.8, 29.1, 10.8 ppm. HPLC (20 min): 96.6%. LC/MS: 100%.

Example 41

Synthesis of 4-[2-(3-Fluoro-phenyl)-ethyl]-5-methyl-1H-pyrrole-2-carboxylic acid (116)

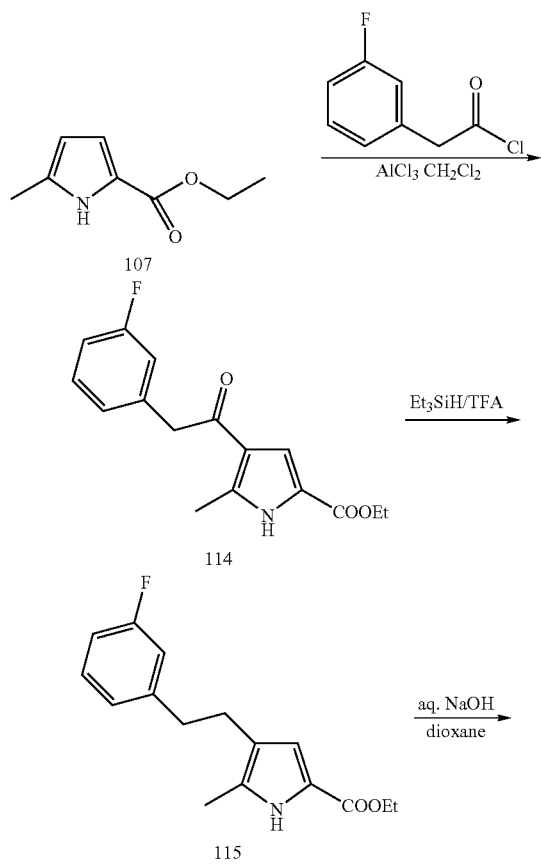

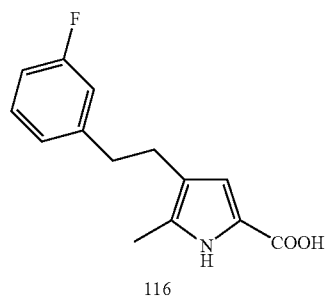

Synthesis of 4-[2-(3-Fluoro-phenyl)-acetyl]-5-methyl-1H-pyrrole-2-carboxylic acid ethyl ester (114)

4-[2-(3-Fluorophenyl)-acetyl]-5-methyl-1H-pyrrole-2-carboxylic acid ethyl ester (114) was synthesized from 5-methyl-1H-pyrrole-2-carboxylic acid ethyl ester (107) and (3-fluorophenyl)-acetyl chloride following the procedure described in Example 32. Reaction Conditions: 1,2-dichloroethane/RT. Purification: recrystallization from ether/pentane. Yield: 78%. $^1$H (CDCl$_3$, 400 MHz): δ 10.6 (NH, broad s), 7.30 (1H, s), 7.26 (1H, dd), 7.04 (1H, d), 6.99 (1H, d), 6.92 (1H, dd), 4.37 (2H, q), 4.07 (2H, s), 2.58 (3H, s), 1.39 (3H, t) ppm. $^{13}$C (CDCl$_3$, 100 MHz): δ 193.5, 164.0, 161.6, 141.0, 137.4, 130.0, 125.3, 121.5, 120.5, 116.9, 116.4, 113.7, 61.0, 46.4, 14.4, 14.0 ppm. LC/MS: 98%.

Synthesis of 4-[2-(3-Fluorophenyl)-ethyl]-5-methyl-1H-pyrrole-2-carboxylic acid ethyl ester (115)

4-[2-(3-Fluorophenyl)-ethyl]-5-methyl-1H-pyrrole-2-carboxylic acid ethyl ester (115) was synthesized from 4-[2-(3-Fluoro-phenyl)-acetyl]-5-methyl-1H-pyrrole-2-carboxylic acid ethyl ester (114) following the procedure described in Example 32. Purification: Recrystallization from ether/pentane. Yield: 79%. $^1$H (CDCl$_3$, 400 MHz): δ 9.55 (NH, broad s), 7.19 (1H, m), 6.86 (3H, m), 6.72 (1H, s), 4.29 (2H, q), 2.80 (2H, dd), 2.66 (2H, dd), 2.07 (3H, s), 1.34 (3H, t) ppm. $^{13}$C (CDCl$_3$, 100 MHz): δ 164.1, 161.6, 144.6, 131.1, 129.7, 124.2, 121.3, 119.8, 115.6, 115.2, 112.6, 60.1, 37.1, 27.6, 14.5, 11.0 ppm. LC/MS: 93%

Synthesis of 4-[2-(3-Fluorophenyl)-ethyl]-5-methyl-1H-pyrrole-2-carboxylic acid (116)

4-[2-(3-Fluorophenyl)-ethyl]-5-methyl-1H-pyrrole-2-carboxylic acid (117) was synthesized from 4-[2-(3-Fluorophenyl)-ethyl]-5-methyl-1H-pyrrole-2-carboxylic acid ethyl ester (116) following the procedure described in Example 39. Purification: Extraction. Amount: 10 mg. $^1$H (MeOD, 400 MHz): δ 7.23 (1H, m), 6.94 (1H, d), 6.84 (2H, m), 6.65 (1H, s), 2.79 (2H, dd), 2.66 (2H, dd), 2.0 (3H, s) ppm. DEPT (MeOD, 100 MHz): CH$_3$: □ 10.8, CH$_2$: δ28.7, 38.3, CH: 113.3, 116.3, 117.4, 125.5, 130.7 ppm. HPLC (20 nm): 96.4%. LC/MS: 94%.

Example 42

Synthesis of 5-Methyl-4-[2-(4-trifluoromethyl-phenyl)-ethyl]-1H-pyrrole-2-carboxylic acid (119)

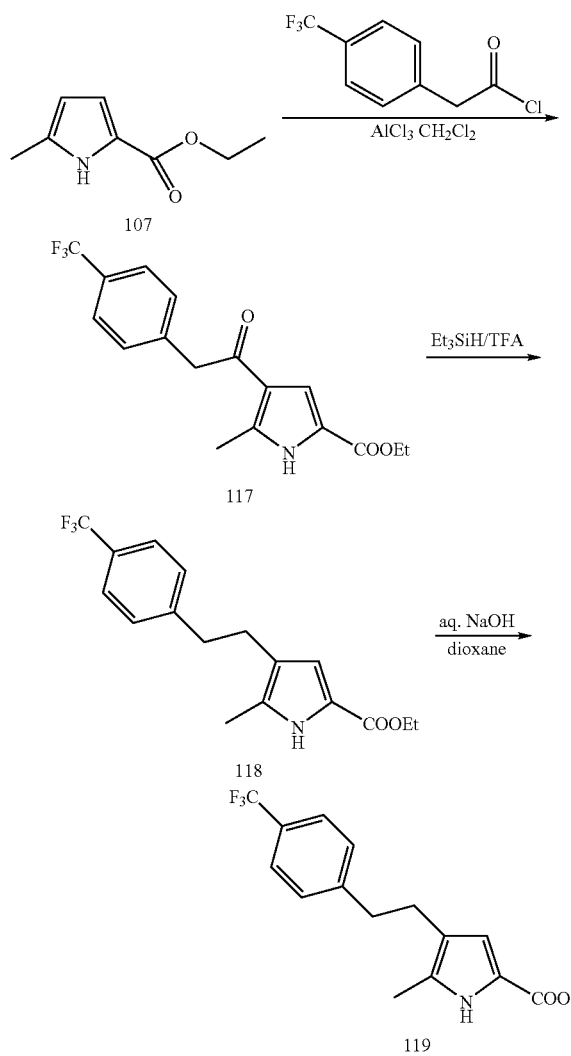

Synthesis of 5-Methyl-4-[2-(4-trifluoromethylphenyl)-acetyl]-1H-pyrrole-2-carboxylic acid ethyl ester (117)

5-Methyl-4-[2-(4-trifluoromethyl-phenyl)-acetyl]-1H-pyrrole-2-carboxylic acid ethyl ester (117) was synthesized from 5-methyl-1H-pyrrole-2-carboxylic acid ethyl ester (107) and (4-trifluoromethylphenyl)-acetyl chloride following the procedure described in Example 32. Reaction Conditions: 1,2-dichloroethane/−40° C. Purification: prep/HPLC. Yield: 33%. $^1$H (CDCl$_3$, 400 MHz): δ 10.5 (NH, broad s), 7.56 (2H, d), 7.34 (2H, d), 7.32 (1H, s), 4.37 (2H, q), 4.15 (2H, s), 2.59 (3H, s), 1.38 (3H, t) ppm. $^{13}$C (CDCl$_3$, 100 MHz): δ 193.3, 161.5, 141.0, 139.0, 130.9, 125.5, 128.6, 121.4, 120.6, 114.0 61.0, 46.5, 14.5, 14.0 ppm. LC/MS: 98%.

Synthesis of 5-Methyl-4-[2-(4-trifluoromethylphenyl)-ethyl]-1H-pyrrole-2-carboxylic acid ethyl ester (118)

5-Methyl-4-[2-(4-trifluoromethylphenyl)-ethyl]-1H-pyrrole-2-carboxylic acid ethyl ester (118) was synthesized from 5-methyl-4-[2-(4-trifluoromethyl-phenyl)-acetyl]-1H-pyrrole-2-carboxylic acid ethyl ester (117) following the procedure described in Example 32. Purification: prep/HPLC. Yield: 50%. $^1$H (CDCl$_3$, 400 MHz): δ 9.35 (NH, broad s), 7.50 (2H, d7.23 (2H, d), 6.72 (1H, s), 4.29 (2H, q), 2.85 (2H, dd), 2.66 (2H, dd), 2.03 (3H, s), 1.34 (3H, t) ppm. HPLC: 100%.

Synthesis of 5-Methyl-4-[2-(4-trifluoromethylphenyl)-ethyl]-1H-pyrrole-2-carboxylic acid (119)

5-Methyl-4-[2-(4-trifluoromethyl-phenyl)-ethyl]-1H-pyrrole-2-carboxylic acid (119) was synthesized from 5-methyl-4-[2-(4-trifluoromethyl-phenyl)-ethyl]-1H-pyrrole-2-carboxylic acid ethyl ester (118) following the procedure described in Example 39. Purification: Extraction. Amount: 11.6 mg. $^1$H (CDCl$_3$, 400 MHz): δ 9.15 (NH, ☐☐broad s), 7.50 (2H, d), 7.24 (2H, d), 6.86 (1H, s), 2.89 (2H, dd), 2.68 (2H, dd), 2.04 (3H, s) ppm. $^{13}$C (CDCl$_3$, 100 MHz): δ 165.7, 145.9, 132.5, 128.4, 128.13, 125.2, 122.0, 118.8, 117.9, 37.0, 27.5, 11.2 ppm. HPLC (20 min): 94.5%. LC/MS: 97%.

Example 43

Synthesis of 5-Methyl-4-[2-(3-trifluoromethyl-phenyl)-ethyl]-1H-pyrrole-2-carboxylic acid (122)

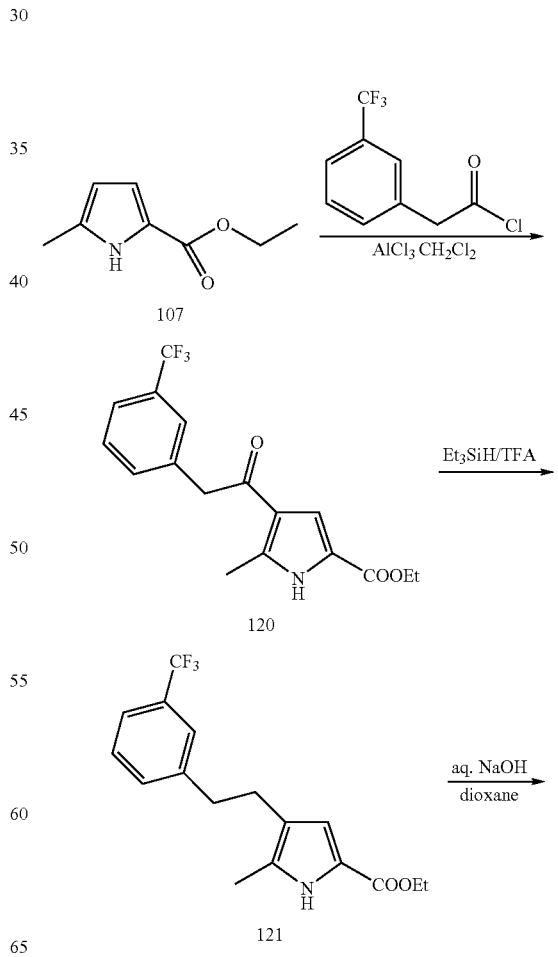

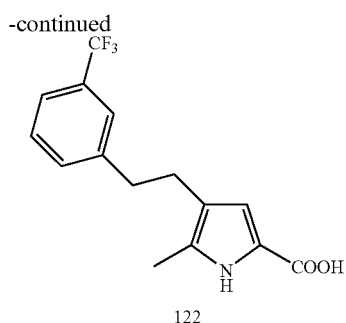

122

Synthesis of 5-Methyl-4-[2-(3-trifluoromethyl-phenyl)-acetyl]-1H-pyrrole-2-carboxylic acid ethyl ester (120)

5-Methyl-4-[2-(3-trifluoromethyl-phenyl)-acetyl]-1H-pyrrole-2-carboxylic acid ethyl ester (120) was synthesized from 5-methyl-1H-pyrrole-2-carboxylic acid ethyl ester (107) and (3-trifluoromethylphenyl)-acetyl chloride following the procedure described in Example 32. Reaction Conditions: 1,2-dichloroethane/−40° C. Purification: prep/HPLC. Yield: 16%. $^1$H (CDCl$_3$, 400 MHz): δ 10.7 (NH, broad s), 7.48 (4H, m), 7.34 (1H, s), 4.37 (2H, q), 4.15 (2H, s), 2.59 (3H, s), 1.39 (3H, t) ppm. $^{13}$C (CDCl$_3$, 100 MHz): δ 193.3, 161.6, 141.2, 136.0, 133.2, 131.2, 128.8, 128.2, 126.4, 123.6, 121.4, 120.6, 116.9, 61.0, 46.3, 14.3, 13.9 ppm. LC/MS: 100%.

Synthesis of 5-Methyl-4-[2-(3-trifluoromethyl-phenyl)-ethyl]-1H-pyrrole-2-carboxylic acid ethyl ester (121)

5-Methyl-4-[2-(3-trifluoromethyl-phenyl)-ethyl]-1H-pyrrole-2-carboxylic acid ethyl ester (121) was synthesized from 5-Methyl-4-[2-(3-trifluoromethyl-phenyl)-acetyl]-1H-pyrrole-2-carboxylic acid ethyl ester (120) following the procedure described in Example 32. Purification: prep/HPLC. $^1$H (CDC$_3$, 400 MHz): δ 9.25 (NH, broad s), 7.4 (4H, m), 6.72 (1H, s), 4.30 (2H, q), 2.87 (2H, dd), 2.68 (2H, dd), 2.03 (3H, s), 1.35 (3H, t) ppm. $^{13}$C (CDCl$_3$, 100 MHz): δ 161.5, 142.8, 132.0, 130.9, 130.7, 130.4, 128.7, 125.2, 122.7, 121.0, 120.0, 115.6, 60.1, 37.2, 27.7, 14.5, 11.0 ppm. LC/MS: 94%.

Synthesis of 5-Methyl-4-[2-(3-trifluoromethyl-phenyl)-ethyl]-1H-pyrrole-2-carboxylic acid 5-Methyl-4-[2-(3-trifluoromethyl-phenyl)-ethyl]-1H-pyrrole-2-carboxylic acid (122) was synthesized from 5-Methyl-4-[2-(3-trifluoromethyl-phenyl)-ethyl]-1H-pyrrole-2-carboxylic acid ethyl ester (121) following the procedure described in Example 39. Purification: Extraction. Amount: 9.5 mg. $^1$H (CD$_3$OD, 400 MHz): δ 7.4 (4H, m), 6.65 (1H, s), 2.87 (2H, dd), 2.69 (2H, dd), 1.95 (3H, s) ppm. $^{13}$C (CD$_3$OD, 100 MHz): δ 164.5, 144.7, 133.6, 132.6, 131.3, 129.9, 126.3, 123.6, 121.8, 121.0, 117.4, 38.3, 28.7, 10.7 ppm. HPLC (20 min): 95.6%. LC/MS: 100%.

Example 44

Synthesis of 4-[2-(4-Methoxy-phenyl)-ethyl]-5-methyl-1H-pyrrole-2-carboxylic acid (125)

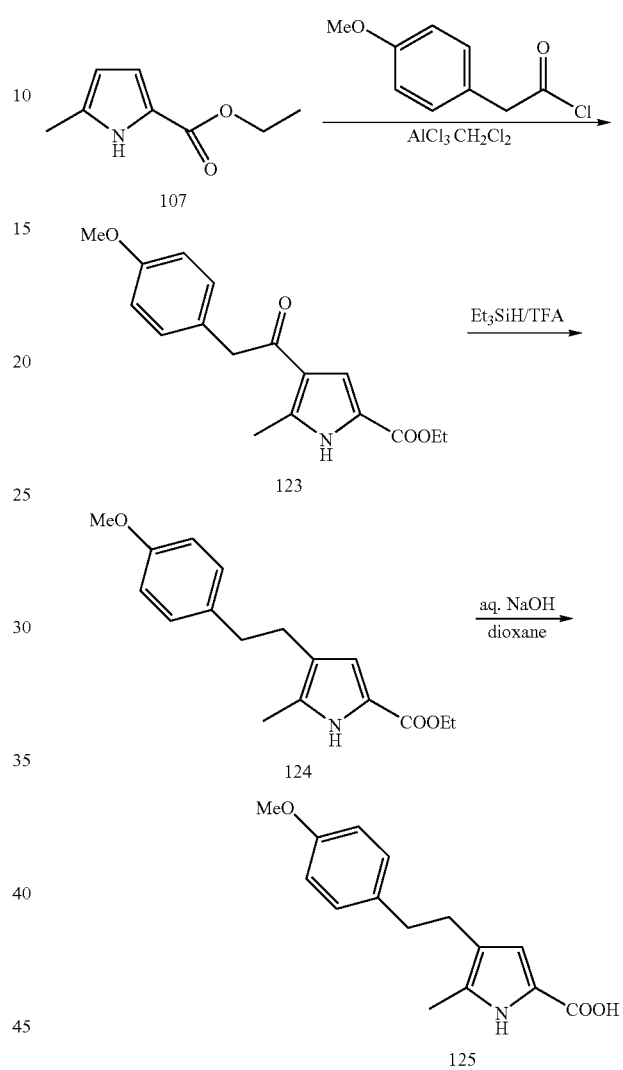

Synthesis of 4-[2-(4-Methoxy-phenyl)-acetyl]-5-methyl-1H-pyrrole-2-carboxylic acid ethyl ester (123)

4-[2-(4-Methoxy-phenyl)-acetyl]-5-methyl-1H-pyrrole-2-carboxylic acid ethyl ester (123) was synthesized from 5-methyl-1H-pyrrole-2-carboxylic acid ethyl ester (107) and (4-Methoxyphenyl)-acetyl chloride following the procedure described in Example 32. Reaction Conditions: 1,2-dichloroethane/−40° C. Purification: prep/HPLC. Yield: 72%. $^1$H (CDCl$_3$, 400 MHz): δ 10.45 (NH, broad s), 7.31 (1H, s), 7.18 (2H, d), 6.84 (2H, d), 4.37 (2H, q), 4.01 (2H, s), 3.74 (3H, s), 2.57 (3H, s), 1.38 (3H, t) ppm. $^{13}$C (CDCl$_3$, 100 MHz): δ 194.7, 161.5, 158.4, 140.8, 130.5, 127.1, 121.6, 120.4, 117.1, 114.0, 60.8, 55.2, 46.0, 14.4, 14.0 ppm. LC/MS: 100%.

Synthesis of 4-[2-(4-Methoxy-phenyl)-ethyl]-5-methyl-1H-pyrrole-2-carboxylic acid ethyl ester (124)

4-[2-(4-Methoxy-phenyl)-ethyl]-5-methyl-1H-pyrrole-2-carboxylic acid ethyl ester (124) was synthesized from 4-[2-(4-Methoxy-phenyl)-acetyl]-5-methyl-1H-pyrrole-2-carboxylic acid ethyl ester (123) following the procedure described in Example 32. Purification: Recrystallization from ether/pentane. Yield: 75%. $^1$H (CDCl$_3$, 400 MHz): δ 9.0 (NH, broad s), 7.05 (2H, d), 6.82 (2H, d), 6.74 (1H, s), 4.29 (2H, q), 3.78 (3H, s), 2.75 (2H, dd), 2.64 (2H, dd), 2.05 (3H, s), 1.34 (3H, t) ppm. $^{13}$C (CDCl$_3$, 100 MHz): δ 158.8, 135.2, 131.7, 130.4, 122.9, 120.8, 116.6, 114.7, 63.0, 61.0 56.3, 37.4, 29.2, 15.5, 12.2 ppm.

Synthesis of 4-[2-(4-Methoxy-phenyl)-ethyl]-5-methyl-1H-pyrrole-2-carboxylic acid (125)

4-[2-(4-Methoxy-phenyl)-ethyl]-5-methyl-1H-pyrrole-2-carboxylic acid (125) was synthesized from 4-[2-(4-Methoxy-phenyl)-ethyl]-5-methyl-1H-pyrrole-2-carboxylic acid ethyl ester (124) following the procedure described in Example 39. Purification: precipitation. Amount: 27.4 mg. $^1$H (CD$_3$OD, 400 MHz): δ 7.01 (2H, dd), 6.78 (2H, dd), 6.64 (1H, s), 3.30 (3H, s), 2.71 (2H, dd), 2.62 (2H, dd), 1.98 (3H, s) ppm. $^{13}$C (CD$_3$OD, 100 MHz): δ 159.3, 135.5, 132.7, 130.5, 122.7, 120.7, 117.5, 114.6, 55.6, 37.8, 29.3, 10.8 ppm. HPLC (20 min): 95.6%. LC/MS: 100%.

Example 45

Synthesis of 4-[2-(3-Methoxy-phenyl)-ethyl]-5-methyl-1H-pyrrole-2-carboxylic acid (128)

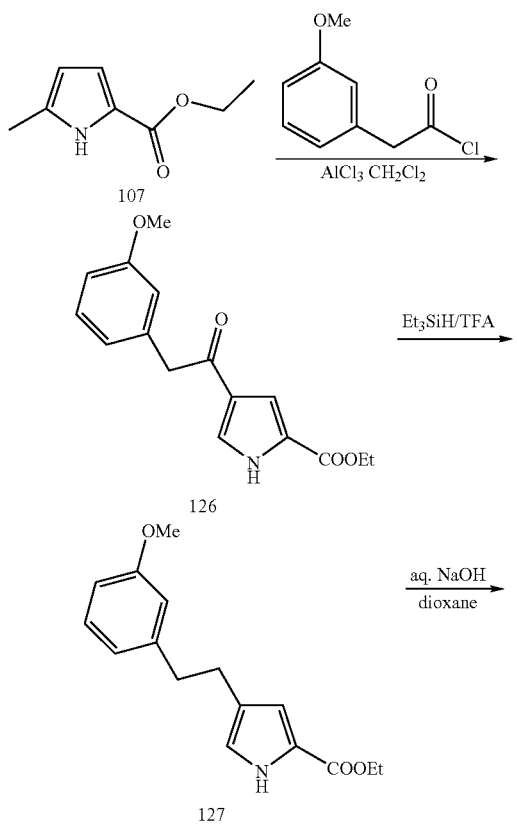

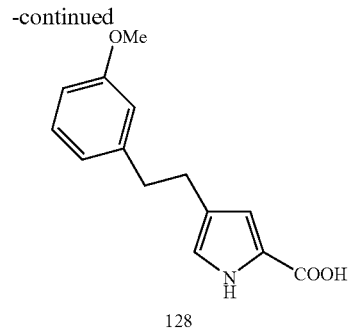

Synthesis of 4-[2-(3-Methoxy-phenyl)-acetyl]-5-methyl-1H-pyrrole-2-carboxylic acid ethyl ester (126)

4-[2-(3-Methoxy-phenyl)-acetyl]-5-methyl-1H-pyrrole-2-carboxylic acid ethyl ester (126) was synthesized from 5-methyl-1H-pyrrole-2-carboxylic acid ethyl ester (107) and (3-methoxyphenyl)-acetyl chloride following the procedure described in Example 32. Reaction Conditions: 1,2-dichloroethane/−40° C. Purification: Recrystallization from ether/pentane. Yield: 50%. $^1$H (CDCl$_3$, 400 MHz): δ 10.80 (NH, broad s), 7.32 (1H, s), 7.18 (1H, dd), 6.85 (1H, d), 6.83 (1H, s), 6.75 (1H, d), 4.33 (2H, q), 4.04 (2H, s), 3.74 (3H, s), 2.55 (3H, s), 1.36 (3H, t) ppm. $^{13}$C (CDCl$_3$, 100 MHz): δ 194.3, 161.5, 159.7, 141.1, 136.7, 129.4, 121.9, 121.6, 120.4, 117.2, 115.2, 112.1, 60.8, 55.1, 47.0, 14.4, 13.9 ppm. LC/MS: 100%.

Synthesis of 4-[2-(3-Methoxy-phenyl)-ethyl]-5-methyl-1H-pyrrole-2-carboxylic acid ethyl ester (127)

4-[2-(3-Methoxy-phenyl)-ethyl]-5-methyl-1H-pyrrole-2-carboxylic acid ethyl ester (127) was synthesized from 4-[2-(3-Methoxy-phenyl)-acetyl]-5-methyl-1H-pyrrole-2-carboxylic acid ethyl ester (126) following the procedure described in Example 32. Purification: Recrystallization from ether/pentane. Yield: 82%. $^1$H (CDCl$_3$, 400 MHz): δ 9.40☐ (NH,☐broad s), 6.74 (4H, m), 4.30 (2H, q), 3.77 (3H, s), 2.78 (2H, dd), 2.67 (2H, dd), 2.08 (3H, s), 1.34 (3H, t) ppm. $^{13}$C (CDCl$_3$, 100 MHz): δ 161.5, 159.6, 143.7, 131.0, 129.3, 121.8, 121.0, 119.8, 115.7, 114.3, 111.2, 60.0, 55.2, 37.4, 27.9, 14.5, 11.1 ppm. LC/MS: 93%.

Synthesis of 4-[2-(3-Methoxyphenyl)-ethyl]-5-methyl-1H-pyrrole-2-carboxylic acid (128)

To a solution of 4-[2-(3-methoxy-phenyl)-ethyl]-5-methyl-1H-pyrrole-2-carboxylic acid ethyl ester (127) in EtOH, 3 equiv of NaOH aq (3 M) was added then the mixture was heated at 80° C. for 1 hour. When the reaction is judged complete, the solvent was removed under vacuum, H$_2$O was added and an equal volume of Et$_2$O was added. The organic layer was removed then the aqueous layer was made acidic with HCl (1M). If the product precipitated out at this point, it was filtered off, washed with H$_2$O, and dried to obtain pure desired product. If the product didn't crash out when the aqueous layer is made acidic, Et$_2$O was added, and the organic layer was removed (2×). The organic layer was dried with Na$_2$SO$_4$, filtered, and concentrated to obtain desired product. Purification: Extraction. Amount: 37 mg. $^1$H (CDCl$_3$, 400 MHz): δ 8.90 (NH, broad s), 7.19 (1H, dd), 6.88 (1H, s), 6.75 (2H, m), 6.94 (1H, s), 3.78 (3H, s), 2.80 (2H, dd), 2.68 (2H, dd), 2.08 (3H, s) ppm. $^{13}$C (CDCl$_3$, 100 MHz): δ 165.5, 159.6, 143.5, 132.3, 129.3, 122.6, 121.0, 118.7, 117.8, 114.2, 111.2, 55.2, 37.3, 27.8, 11.3 ppm. HPLC (20 min): 91.6%. LC/MS: 97%.

Example 46

Synthesis of 5-Methyl-4-(2-naphthalen-1-yl-ethyl)-1H-pyrrole-2-carboxylic acid (131)

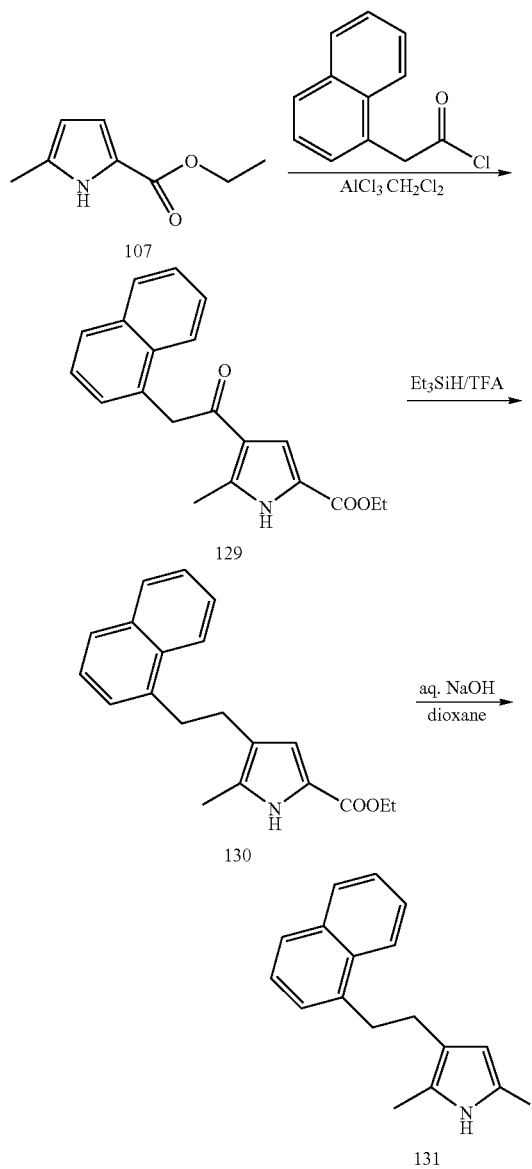

Synthesis of 5-Methyl-4-(2-naphthalen-1-yl-acetyl)-1H-pyrrole-2-carboxylic acid ethyl ester (129)

5-Methyl-4-(2-naphthalen-1-yl-acetyl)-1H-pyrrole-2-carboxylic acid ethyl ester (129) was synthesized from 5-methyl-1H-pyrrole-2-carboxylic acid ethyl ester (107) and following the procedure described in Example 32. Reaction conditions: 1,2-dichloroethane/−40° C. Purification: prep/HPLC. Yield: 52%. LC/MS: 62%.

Synthesis of 5-Methyl-4-(2-naphthalen-1-yl-ethyl)-1H-pyrrole-2-carboxylic acid ethyl ester (130)

5-Methyl-4-(2-naphthalen-1-yl-ethyl)-1H-pyrrole-2-carboxylic acid ethyl ester (130) was synthesized from 5-Methyl-4-(2-naphthalen-1-yl-acetyl)-1H-pyrrole-2-carboxylic acid ethyl ester (129) following the procedure described in Example 32. Purification: no purification.

Synthesis of 5-Methyl-4-(2-naphthalen-1-yl-ethyl)-1H-pyrrole-2-carboxylic acid (131)

5-Methyl-4-(2-naphthalen-1-yl-ethyl)-1H-pyrrole-2-carboxylic acid (131) was synthesized from 5-methyl-4-(2-naphthalen-1-yl-ethyl)-1H-pyrrole-2-carboxylic acid ethyl ester (130) following the procedure described in Example 45. Purification: prep HPLC. Amount: 5.2 mg. $^1$H (CD$_3$OD, 400 MHz): δ 8.06 (1H, d), 7.82 (1H, d), 7.67 (1H, d), 7.45 (2H, m), 7.31 (1H, dd), 7.18 (1H, d), 6.72 (1H, s), 3.24 (2H, dd), 2.76 (2H, dd), 1.84 (3H, s) ppm. DEPT (CD$_3$OD, 100 MHz): CH$_3$: δ 10.8, CH$_2$: δ 28.4, 35.9, CH: 116.8, 124.8, 126.4, 126.5, 126.7, 127.4, 127.6, 129.8 ppm. HPLC (20 min): 98.6%. LC/MS: 100%.

Example 47

Synthesis of 5-Methyl-4-(3-naphthalen-2-yl-propyl)-1H-pyrrole-2-carboxylic acid (134)

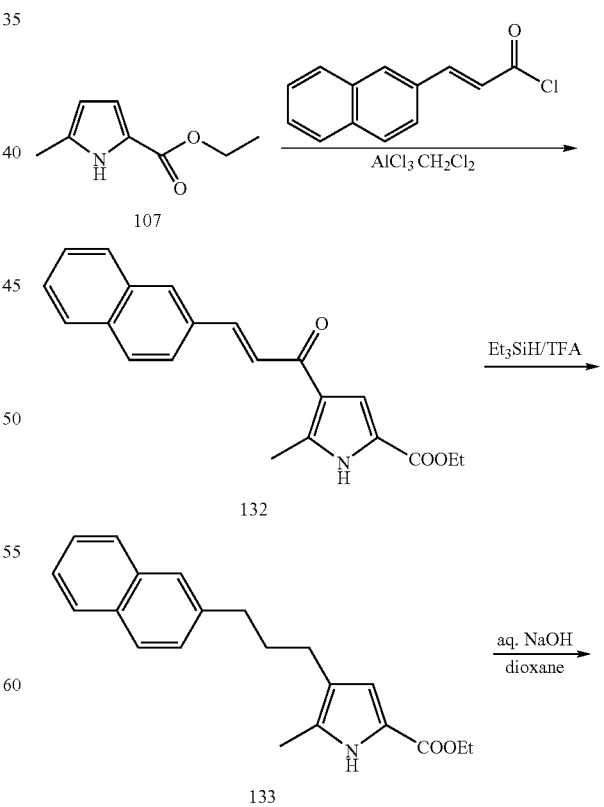

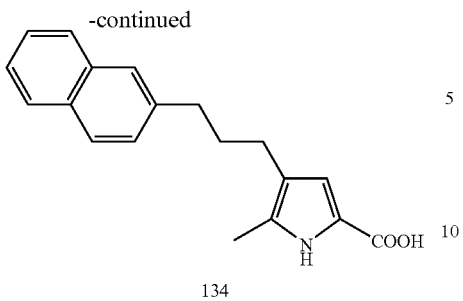

134

Synthesis of 5-Methyl-4-(3-naphthalen-2-yl-acryloyl)-1H-pyrrole-2-carboxylic acid ethyl ester (132)

5-Methyl-4-(3-naphthalen-2-yl-acryloyl)-1H-pyrrole-2-carboxylic acid ethyl ester (132) was synthesized from 5-methyl-1H-pyrrole-2-carboxylic acid ethyl ester (107) and 3-naphthalen-2-yl-acryloyl chloride following the procedure described in Example 32. Reaction conditions: 1,2-dichloromethane/−40° C.→RT. Purification: no purification. LC/MS: 40%.

Synthesis of 5-Methyl-4-(3-naphthalen-2-yl-propyl)-1H-pyrrole-2-carboxylic acid ethyl ester (133)

5-Methyl-4-(3-naphthalen-2-yl-propyl)-1H-pyrrole-2-carboxylic acid ethyl ester (133) was synthesized from 5-methyl-4-(3-naphthalen-2-yl-acryloyl)-1H-pyrrole-2-carboxylic acid ethyl ester (132) following the procedure described in Example 32. Reduction of 132 gave both the reduction of the carbonyl and of the double bond. Purification: no purification. Yield: 100% by LC/MS.

Synthesis of 5-Methyl-4-(3-naphthalen-2-yl-propyl)-1H-pyrrole-2-carboxylic acid (134)

5-Methyl-4-(3-naphthalen-2-yl-propyl)-1H-pyrrole-2-carboxylic acid (134) was synthesized from 5-methyl-4-(3-naphthalen-2-yl-propyl)-1H-pyrrole-2-carboxylic acid ethyl ester (133) following the procedure described in Example 45. Purification: Extraction and prep HPLC. Amount: 20 mg. $^1$H (CDCl$_3$, 400 MHz): δ 8.95 (NH, broad s), 7.77 (3H, m), 7.60 (1H, s), 7.42 (2H, m), 7.32 (1H, d), 6.89 (1H, s), 2.80 (2H, m), 2.46 (2H, m), 2.18 (3H, s), 1.96 (2H, m) ppm. DEPT (CDCl$_3$, 100 MHz): CH$_3$: δ 11.6, CH$_2$: δ 25.2, 32.0, 35.5, CH: 117.9, 125.0, 125.9, 126.4, 127.4, 127.6, 127.7, 127.8 ppm. HPLC (20 min): 88.4%. LC/MS: 94%.

Example 48

Synthesis of 5-Methyl-4-(2-naphthalen-2-yl-ethyl)-1H-pyrrole-2-carboxylic acid (137)

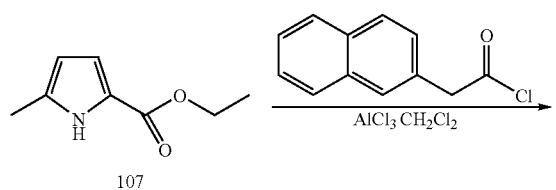

107

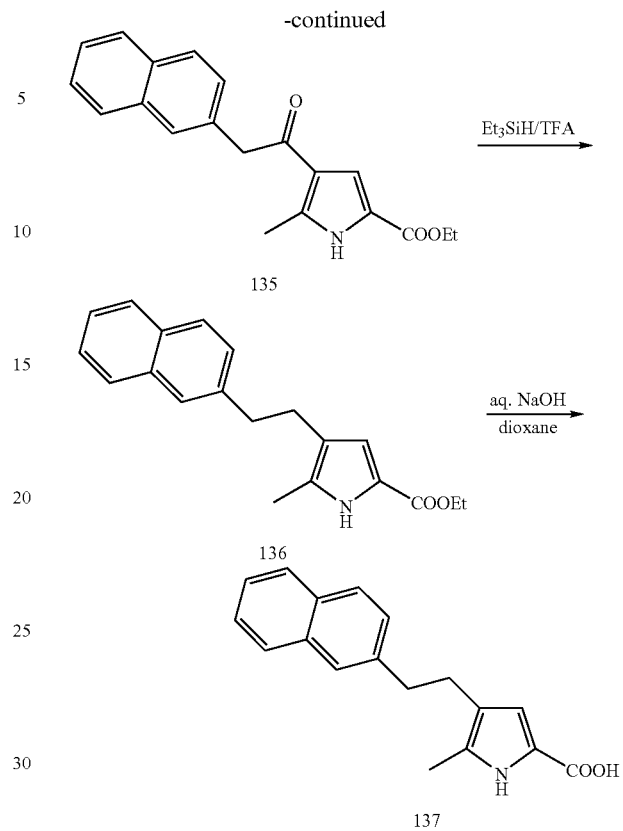

Synthesis of 5-Methyl-4-(2-naphthalen-2-yl-acetyl)-1H-pyrrole-2-carboxylic acid ethyl ester (135)

5-Methyl-4-(2-naphthalen-2-yl-acetyl)-1H-pyrrole-2-carboxylic acid ethyl ester (135) was synthesized from 5-methyl-1H-pyrrole-2-carboxylic acid ethyl ester (107) and naphthalen-2-yl-acetyl chloride following the procedure described in Example 32. Reaction Conditions: 1,2-dichloromethane/−40° C.→RT. Purification: no purification. LC/MS: 80%.

Synthesis of 5-Methyl-4-(2-naphthalen-2-yl-ethyl)-1H-pyrrole-2-carboxylic acid ethyl ester (136)

5-Methyl-4-(2-naphthalen-2-yl-ethyl)-1H-pyrrole-2-carboxylic acid ethyl ester (136) was synthesized from 5-Methyl-4-(2-naphthalen-2-yl-acetyl)-1H-pyrrole-2-carboxylic acid ethyl ester (135) following the procedure described in Example 32. Purification: no purification.

Synthesis of 5-Methyl-4-(2-naphthalen-2-yl-ethyl)-1H-pyrrole-2-carboxylic acid (137)

5-Methyl-4-(2-naphthalen-2-yl-ethyl)-1H-pyrrole-2-carboxylic acid (137) was synthesized from 5-Methyl-4-(2-naphthalen-2-yl-ethyl)-1H-pyrrole-2-carboxylic acid ethyl ester (136) following the procedure described in Example 45. Purification: prep HPLC. Amount: 12.6 mg. $^1$H (CD$_3$OD, 400 MHz): δ □07.77 (1H, d), 7.73 (2H, m), 7.54 (1H, s), 7.38 (2H, m), 7.28 (1H, dd), 6.68 (1H, s), 2.95 (2H, dd), 2.74 (2H, dd) ppm. $^{13}$C (CD$_3$OD, 100 MHz): δ 165.8, 141.04, 135.15, 133.6, 131.9, 128.7, 128.6, 128.5, 128.4, 127.6, 126.7, 126.1, 122.3, 122.0, 116.9, 38.8, 29.0, 10.9 ppm. HPLC (20 min): 99.0%. LC/MS: 100%.

Example 49

Synthesis of 5-Methyl-4-(2-phenyl-propyl)-1H-pyrrole-2-carboxylic acid (140)

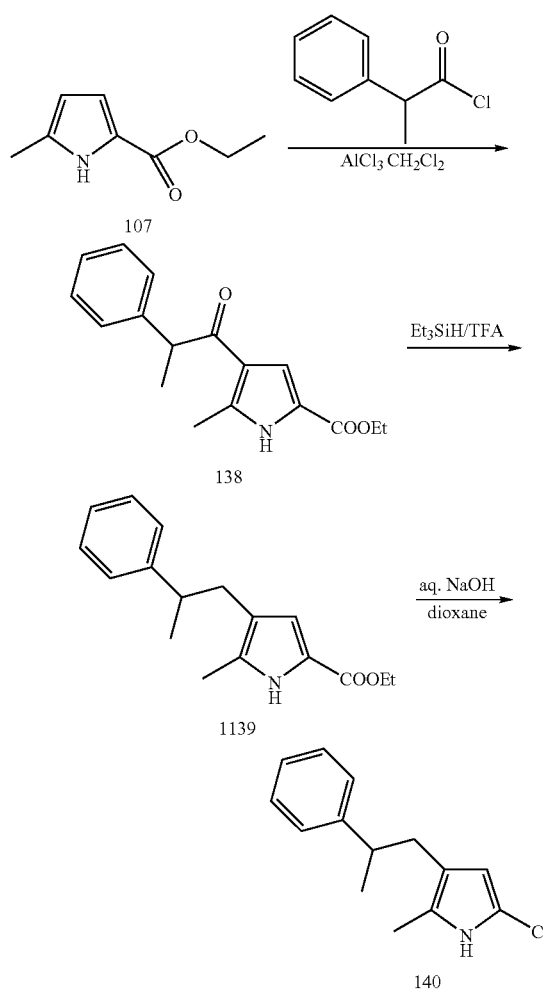

Synthesis of 5-Methyl-4-(2-phenyl-propionyl)-1H-pyrrole-2-carboxylic acid ethyl ester (138)

5-Methyl-4-(2-phenyl-propionyl)-1H-pyrrole-2-carboxylic acid ethyl ester (138) was synthesized from 5-methyl-1H-pyrrole-2-carboxylic acid ethyl ester (107) and 2-phenyl-propionyl chloride following the procedure described in Example 32. Reaction conditions: 1,2-dichloromethane/−40° C.→RT. Purification: no purification. LC/MS: 86%.

Synthesis of 5-Methyl-4-(2-phenyl-propyl)-1H-pyrrole-2-carboxylic acid ethyl ester (139)

5-Methyl-4-(2-phenyl-propyl)-1H-pyrrole-2-carboxylic acid ethyl ester (139) was synthesized from 5-Methyl-4-(2-phenyl-propionyl)-1H-pyrrole-2-carboxylic acid ethyl ester (138) following the procedure described in Example 32. Purification: no purification.

Synthesis of 5-Methyl-4-(2-phenyl-propyl)-1H-pyrrole-2-carboxylic acid (140)

5-Methyl-4-(2-phenyl-propyl)-1H-pyrrole-2-carboxylic acid (140) was synthesized from 5-Methyl-4-(2-phenyl-propyl)-1H-pyrrole-2-carboxylic acid ethyl ester (139) following the procedure described in Example 45. Purification: prep HPLC. Amount: 13 mg. $^1$H (CDCl$_3$, 400 MHz): δ 8.7 (NH, broad s), 7.27 (3H, m), 7.18 (2H, m), 6.77 (1H, s), 2.90 (1H, m), 2.62 (2H, m), 1.97 (3H, s), 1.27 (3H, d) ppm. DEPT (CDCl$_3$, 100 MHz): CH$_3$, δ 11.3, 20.9 CH$_2$: δ 35.0, CH: 41.4, 118.6, 126.0, 127.1, 128.3 ppm. HPLC (20 min): 93.1%. LC/MS: 96%.

Example 50

Synthesis of 4-(2-Naphthalen-2-yl-ethyl)-1H-pyrrole-2-carboxylic acid (128)

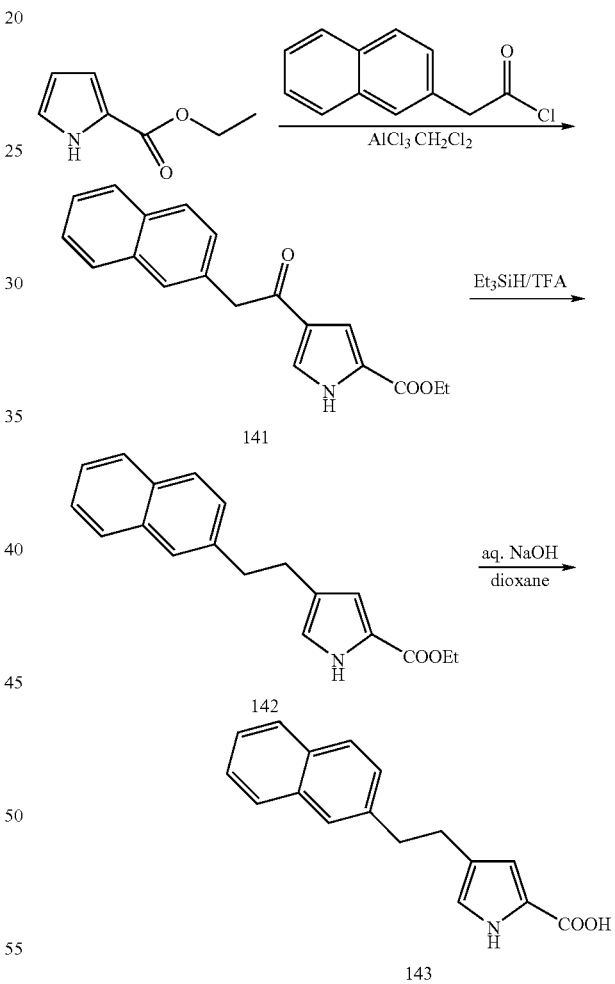

Synthesis of 4-(2-Naphthalen-2-yl-acetyl)-1H-pyrrole-2-carboxylic acid ethyl ester (141)

4-(2-Naphthalen-2-yl-acetyl)-1H-pyrrole-2-carboxylic acid ethyl ester (141) was synthesized from 1H-pyrrole-2-carboxylic acid ethyl ester and naphthalen-2-yl-acetyl chloride following the procedure described in Example 32. Reaction Conditions: 1,2-dichloromethane/−40° C.→RT. Purification: no purification. LC/MS: 78%.

Synthesis of 4-(2-Naphthalen-2-yl-ethyl)-1H-pyrrole-2-carboxylic acid ethyl ester (142)

4-(2-Naphthalen-2-yl-ethyl)-1H-pyrrole-2-carboxylic acid ethyl ester (142) was synthesized from 4-(2-Naphthalen-2-yl-acetyl)-1H-pyrrole-2-carboxylic acid ethyl ester (141) following the procedure described in Example 32. Purification: no purification.

Synthesis of 4-(2-naphthalen-2-yl-ethyl)-1H-pyrrole-2-carboxylic acid (143)

4-(2-Naphthalen-2-yl-ethyl)-1H-pyrrole-2-carboxylic acid (143) was synthesized from 4-(2-Naphthalen-2-yl-ethyl)-1H-pyrrole-2-carboxylic acid ethyl ester (142) following the procedure described in Example 45. Purification: silica gel chromatography (eluent: $CH_2Cl_2 \to AcOEt$). $^1H$ (MeOD, 400 MHz): δ 7.77 (3H, m), 7.61 (1H, s), 7.54 (1H, s), 7.38 (3H, m), 7.34 (1H, s), 6.68 (1H, s), 3.01 (2H, dd), 2.86 (2H, dd) ppm. DEPT (MeOD, 100 MHz): $CH_2$: δ 29.8, 38.9, CH: 116.4, 122.7, 126.1, 126.8, 127.5, 128.4, 128.5, 128.6, 128.7 ppm. HPLC (20 nm): 96.9% LC/MS: 100%

Example 51

Synthesis of 4-(2-[4-bromophenyl]-ethyl)-1H-pyrrole-2-carboxylic acid (146)

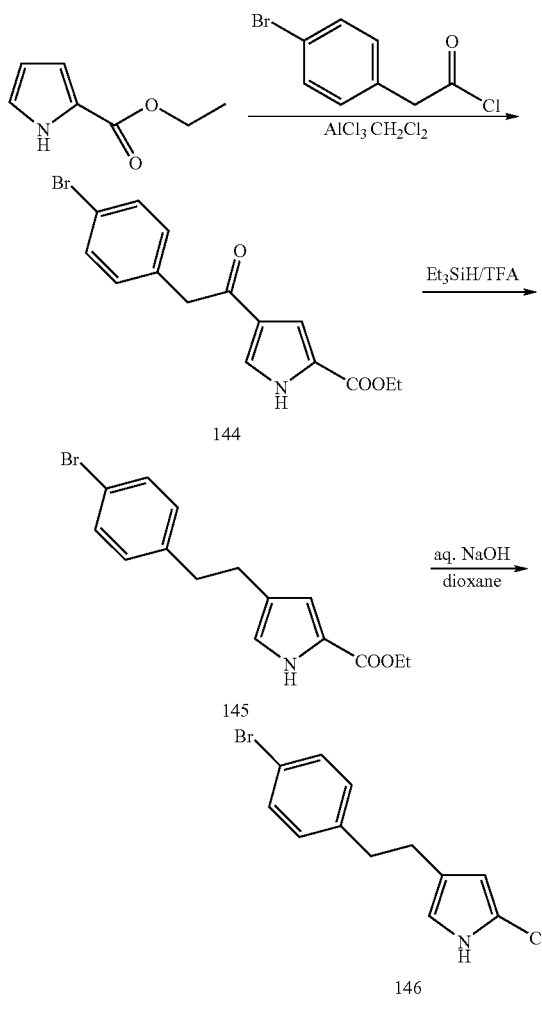

Synthesis of 4-(2-[4-bromophenyl]-2-yl-acetyl)-1H-pyrrole-2-carboxylic acid ethyl ester (144)

4-(2-[4-Bromophenyl]-2-yl-acetyl)-1H-pyrrole-2-carboxylic acid ethyl ester (144) was synthesized from 1H-pyrrole-2-carboxylic acid ethyl ester and 4-bromophenyl-2-yl-acetyl chloride following the procedure described in Example 32. Reaction Conditions: 1,2-dichloromethane/−40° C.→RT. Purification: no purification.

Synthesis of 4-(2-[4-bromophenyl]-2-yl-ethyl)-1H-pyrrole-2-carboxylic acid ethyl ester (145)

4-(2-[4-Bromophenyl]-2-yl-ethyl)-1H-pyrrole-2-carboxylic acid ethyl ester (145) was synthesized from 4-(2-[4-bromophenyl]-2-yl-acetyl)-1H-pyrrole-2-carboxylic acid ethyl ester (144) following the procedure described in Example 32. Purification: no purification.

Synthesis of 4-(2-[4-bromophenyl]-ethyl)-1H-pyrrole-2-carboxylic acid (146)

4-(2-[4-Bromophenyl]-ethyl)-1H-pyrrole-2-carboxylic acid (146) was synthesized from 4-(2-[4-bromophenyl]-2-yl-ethyl)-1H-pyrrole-2-carboxylic acid ethyl ester (145) following the procedure described in Example 45. Purification: Crystallization from water. $^1H$ NMR ($CD_3OD$, 400 MHz): δ 7.36 (2H, d), 7.07 (2H, d), 6.69 (1H, s); 6.67 (1H, s); 2.81 (2H, m); 2.72 (2H, m) ppm. $^{13}C$ NMR ($CD_3OD$, 100 MHz): 164.5, 142.7, 132.26, 131.6, 125.9, 123.5, 122.8, 120.4, 116.4, 38.0, 29.7 ppm. HPLC (20 nm): 92.75% yield 91%.

Example 52

Synthesis of 4-(2-[2-fluorophenyl]-ethyl)-1H-pyrrole-2-carboxylic acid (149)

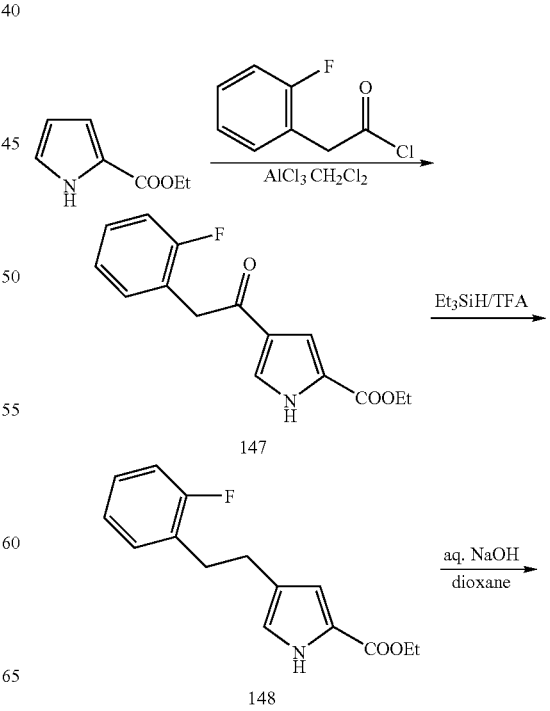

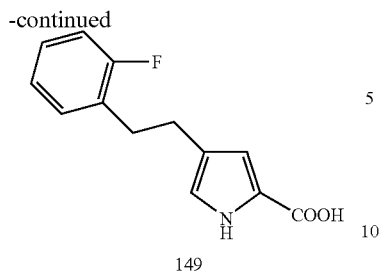

149

Synthesis of 4-(2-[4-fluorophenyl]-2-yl-acetyl)-1H-pyrrole-2-carboxylic acid ethyl ester (147)

4-(2-[4-Fluorophenyl]-2-yl-acetyl)-1H-pyrrole-2-carboxylic acid ethyl ester (147) was synthesized from 1H-pyrrole-2-carboxylic acid ethyl ester and (4-fluorophenyl)-2-yl-acetyl chloride following the procedure described in Example 32. Reaction Conditions: 1,2-dichloromethane/−40° C.→RT. Purification: no purification.

Synthesis of 4-(2-[4-fluorophenyl]-2-yl-ethyl)-1H-pyrrole-2-carboxylic acid ethyl ester (148)

4-(2-[4-Fluorophenyl]-2-yl-ethyl)-1H-pyrrole-2-carboxylic acid ethyl ester (1481) was synthesized from 4-(2-[4-fluorophenyl]-2-yl-acetyl)-1H-pyrrole-2-carboxylic acid ethyl ester (147) following the procedure described in Example 32. Purification: no purification.

Synthesis of 4-(2-[4-fluorophenyl]-ethyl)-1H-pyrrole-2-carboxlic acid (149)

4-(2-[4-Fluorophenyl]-ethyl)-1H-pyrrole-2-carboxylic acid (149) was synthesized from 4-(2-[4-fluorophenyl]-2-yl-ethyl)-1H-pyrrole-2-carboxylic acid ethyl ester (148) following the procedure described in Example 45. Purification: Crystallization from water. $^1$H NMR (CDC$_3$, 400 MHz): δ 7.16 (2H, m), 7.03 (2H, m), 6.70 (2H, m); 2.87 (2H, m), 2.73 (2H, m) ppm. $^{13}$C NMR (CD$_3$OD, 100 MHz): 164.4, 161.4, 132.0, 130.0, 128.8, 126.0, 125.0, 123.5, 122.8, 116.4, 115.8, 31.8, 28.5 ppm. Yield 71%. HPLC 20 min: 97.76%.

Example 53

Synthesis of 4-(2-[4-methylphenyl]-ethyl)-1H-pyrrole-2-carboxylic acid (152)

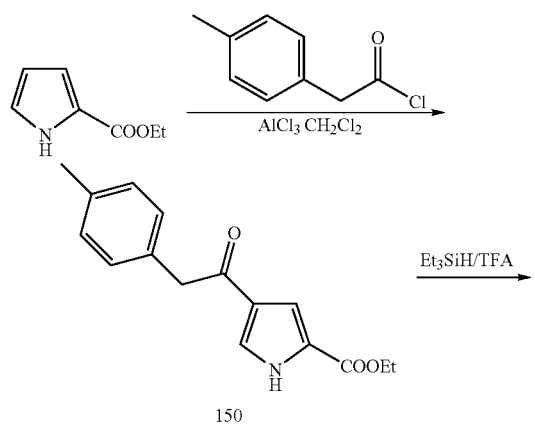

150

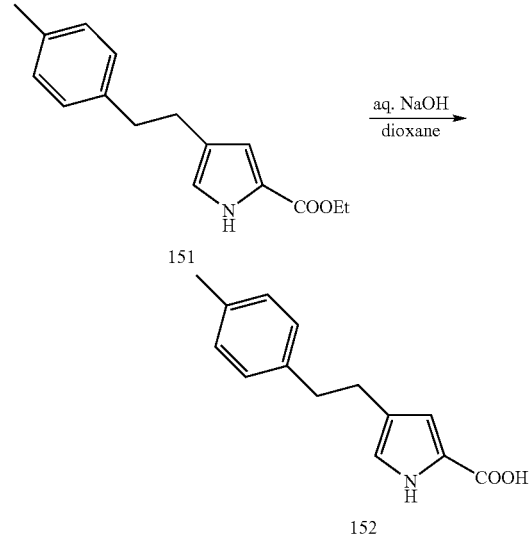

151

152

Synthesis of 4-(2-[4-methylphenyl]-2-yl-acetyl)-1H-pyrrole-2-carboxylic acid ethyl ester (150)

4-(2-[4-Methylphenyl]-2-yl-acetyl)-1H-pyrrole-2-carboxylic acid ethyl ester (150) was synthesized from 1H-pyrrole-2-carboxylic acid ethyl ester and p-tolyl-2-yl-acetyl chloride following the procedure described in Example 32. Reaction Conditions: 1,2-dichloromethane/−40° C.→RT. Purification: no purification.

Synthesis of 4-(2-[4-methylphenyl]-2-yl-ethyl)-1H-pyrrole-2-carboxylic acid ethyl ester (151)

4-(2-[4-Methylphenyl]-2-yl-ethyl)-1H-pyrrole-2-carboxylic acid ethyl ester (151) was synthesized from 4-(2-[4-methylphenyl]-2-yl-acetyl)-1H-pyrrole-2-carboxylic acid ethyl ester (150) following the procedure described in Example 32. Purification: no purification.

Synthesis of 4-(2-[4-methylphenyl]-ethyl)-1H-pyrrole-2-carboxylic acid (152)

4-(2-[4-Methylphenyl]-ethyl)-1H-pyrrole-2-carboxylic acid (152) was synthesized from 4-(2-[4-methylphenyl]-2-yl-ethyl)-1H-pyrrole-2-carboxylic acid ethyl ester (151) following the procedure described in Example 45. Purification: Crystallization from water. $^1$H NMR (CDCl$_3$, 400 MHz): δ 7.04 (4H, m), 6.68 (1H, s); 6.67 (1H, s); 2.78 (2H, m), 2.72 (2H, m), 2.27 (3H, s) ppm. $^{13}$C NMR (CD$_3$OD, 100 MHz): 164.5, 140.3, 136.2, 129.9, 129.4, 126.5, 123.3, 122.7, 116.5, 38.3, 30.1, 21.1 ppm. Yield 55%. HPLC 20 nm: 96.23%

Example 54

Synthesis of 4-(2-[2-methylphenyl]-ethyl)-1H-pyrrole-2-carboxylic acid (155)

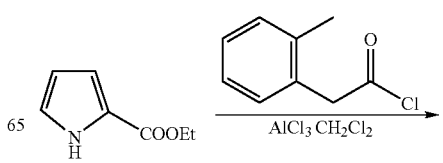

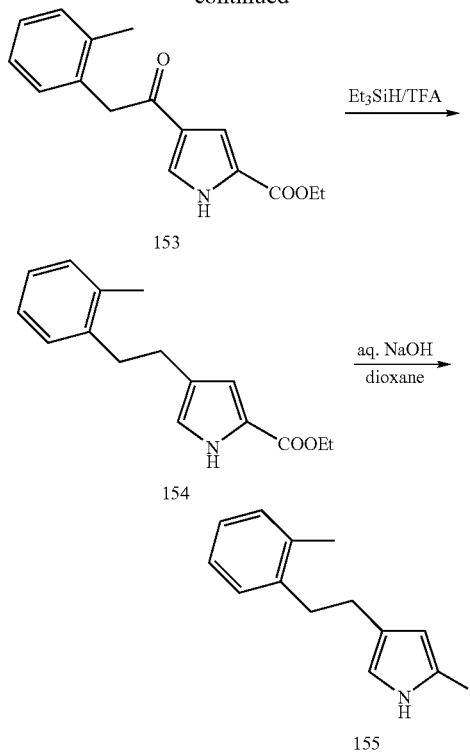

Synthesis of 4-(2-[2-methylphenyl]-2-yl-acetyl)-1H-pyrrole-2-carboxylic acid ethyl ester (153)

4-(2-[2-Methylphenyl]-2-yl-acetyl)-1H-pyrrole-2-carboxylic acid ethyl ester (153) was synthesized from 1H-pyrrole-2-carboxylic acid ethyl ester and o-tolyl-2-yl-acetyl chloride following the procedure described in Example 32. Reaction Conditions: 1,2-dichloromethane/−40° C.→RT. Purification: no purification.

Synthesis of 4-(2-[2-methylphenyl]-2-yl-ethyl)-1H-pyrrole-2-carboxylic acid ethyl ester (154)

4-(2-[2-Methylphenyl]-2-yl-ethyl)-1H-pyrrole-2-carboxylic acid ethyl ester (154) was synthesized from 4-(2-[2-methylphenyl]-2-yl-acetyl)-1H-pyrrole-2-carboxylic acid ethyl ester (153) following the procedure described in Example 32. Purification: no purification.

Synthesis of 4-(2-[2-methylphenyl]-ethyl)-1H-pyrrole-2-carboxylic acid (155)

4-(2-[2-Methylphenyl]-ethyl)-1H-pyrrole-2-carboxylic acid (155) was synthesized from 4-(2-[2-methylphenyl]-2-yl-ethyl)-1H-pyrrole-2-carboxylic acid ethyl ester (153) following the procedure described in Example 45. Purification: Crystallization from water. $^1$H NMR (CDCl$_3$, 400 MHz): δ 7.08 (4H, m), 6.71 (1H, s); 6.69 (1H, s); 2.83 (2H, m), 2.69 (2H, m), 2.27 (3H, s) ppm. $^{13}$C NMR (CD$_3$OD, 100 MHz): 164.5, 141.5, 136.9, 131.0, 130.0, 127.0, 126.9, 126.58, 123.4, 122.6, 116.4, 63.1, 28.9, 19.4 ppm. Yield 73% HPLC 20 nm: 96.95%

Example 55

Synthesis of 4-(2-[3-methylphenyl]-ethyl)-1H-pyrrole-2-carboxylic acid (158)

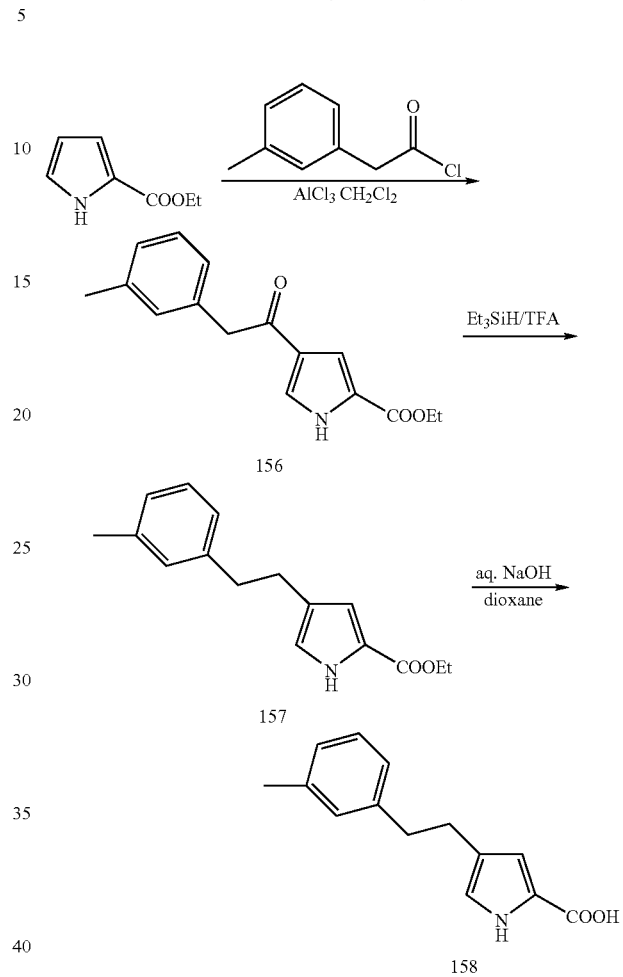

Synthesis of 4-(2-[3-methylphenyl]-2-yl-acetyl)-1H-pyrrole-2-carboxylic acid ethyl ester (156)

4-(2-[3-Methylphenyl]-2-yl-acetyl)-1H-pyrrole-2-carboxylic acid ethyl ester (156) was synthesized from 1H-pyrrole-2-carboxylic acid ethyl ester and m-tolyl-2-yl-acetyl chloride following the procedure described in Example 32. Reaction Conditions: 1,2-dichloromethane/−40° C.→RT. Purification: no purification.

Synthesis of 4-(2-[3-methylphenyl]-2-yl-ethyl)-1H-pyrrole-2-carboxylic acid ethyl ester (157)

4-(2-[3-Methylphenyl]-2-yl-ethyl)-1H-pyrrole-2-carboxylic acid ethyl ester (157) was synthesized from 4-(2-[3-methylphenyl]-2-yl-acetyl)-1H-pyrrole-2-carboxylic acid ethyl ester (156) following the procedure described in Example 32. Purification: no purification.

Synthesis of 4-(2-[3-methylphenyl]-ethyl)-1H-pyrrole-2-carboxylic acid (158)

4-(2-[3-Methylphenyl]-ethyl)-1H-pyrrole-2-carboxylic acid (158) was synthesized from 4-(2-[3-methylphenyl]-2-ylethyl)-1H-pyrrole-2-carboxylic acid ethyl ester (157) following the procedure described in Example 45. Purification: Crystallization from water. $^1$H NMR (CDCl$_3$, 400 MHz): δ 9.00 (1H, broad s), 7.18 (1H, m), 7.00 (3H, m), 6.91 (1H, s), 6.75 (1H, s), 2.82 (4H, m), 2.38 (3H, s) ppm. LC/MS: 100%, m/z=229 g/mol. Yield=72%.

Example 56

Synthesis of 4-(2-[2-chloro-4-fluorophenyl]-ethyl)-1H-pyrrole-2-carboxylic acid (161)

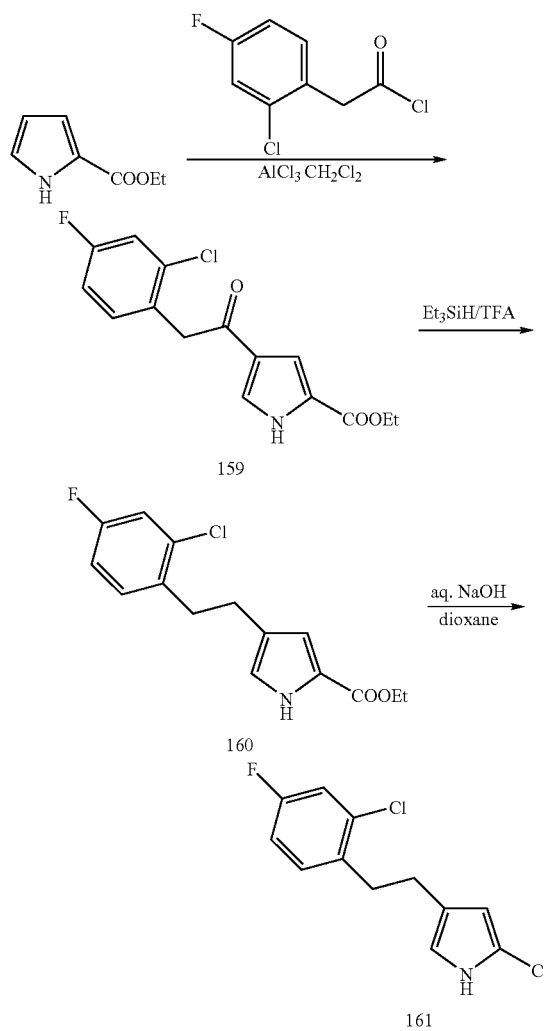

Synthesis of 4-(2-[2-chloro-4-fluorophenyl]-2-yl-acetyl)-1H-pyrrole-2-carboxylic acid ethyl ester (159)

4-(2-[2-chloro-4-fluorophenyl]-2-yl-acetyl)-1H-pyrrole-2-carboxylic acid ethyl ester (159) was synthesized from 1H-pyrrole-2-carboxylic acid ethyl ester and (2-chloro-4-fluorophenyl)-2-yl-acetyl chloride following the procedure described in Example 32. Reaction Conditions: 1,2-dichloromethane/−40° C.→RT. Purification: no purification.

Synthesis of 4-(2-[2-chloro-4-fluorophenyl]-2-yl-ethyl)-1H-pyrrole-2-carboxylic acid ethyl ester (160)

4-(2-[2-chloro-4-fluorophenyl]-2-yl-ethyl)-1H-pyrrole-2-carboxylic acid ethyl ester (160) was synthesized from 4-(2-[2-chloro-4-fluorophenyl]-2-yl-acetyl)-1H-pyrrole-2-carboxylic acid ethyl ester (159) following the procedure described in Example 32. Purification: no purification.

Synthesis of 4-(2-[2-chloro-4-fluorophenyl]-ethyl)-1H-pyrrole-2-carboxylic acid (161)

4-(2-[2-chloro-4-fluorophenyl]-ethyl)-1H-pyrrole-2-carboxylic acid (161) was synthesized from 4-(2-[2-chloro-4-fluorophenyl]-2-yl-ethyl)-1H-pyrrole-2-carboxylic acid ethyl ester (160) following the procedure described in Example 45. Purification: precipitation from water. $^1$H NMR (CDCl$_3$, 400 MHz): δ 7.19 (2H, m), 6.96 (1H, m); 6.70 (2H, m); 2.95 (2H, m), 2.73 (2H, m) ppm. $^{13}$C NMR (CD$_3$OD 100 MHz): 164.4, 161.2, 136.9, 135.4, 132.9, 125.7, 123.6, 122.7, 117.4, 116.4, 114.7, 35.7, 28.0 ppm. Yield 51%. HPLC 20 nm: 98.85%

Example 57

Synthesis of 4-(2-[2,4-dichlorophenyl]-ethyl)-1H-pyrrole-2-carboxylic acid (164)

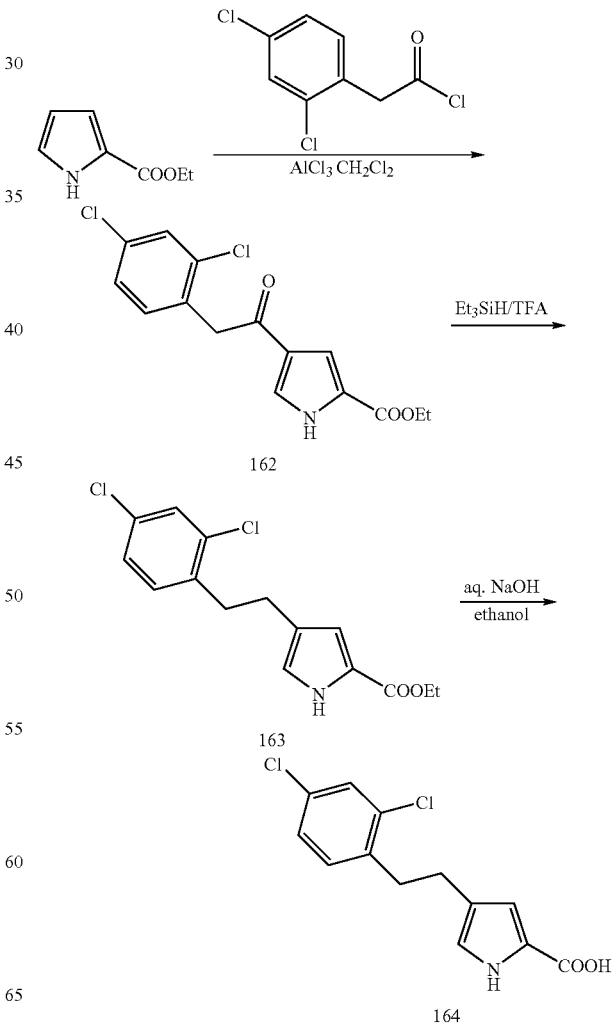

Synthesis of 4-(2-[2,4-dichlorophenyl]-2-yl-acetyl)-1H-pyrrole-2-carboxylic acid ethyl ester (162)

4-(2-[2,4-dichlorophenyl]-2-yl-acetyl)-1H-pyrrole-2-carboxylic acid ethyl ester (162) was synthesized from 1H-pyrrole-2-carboxylic acid ethyl ester and o,p-dichlorophenyl-2-yl-acetyl chloride following the procedure described in Example 32. Reaction Conditions: 1,2-dichloromethane/–40° C.→RT. Purification: no purification.

Synthesis of 4-(2-[2,4-dichlorophenyl]-2-yl-ethyl)-1H-pyrrole-2-carboxylic acid ethyl ester (163)

4-(2-[2,4-dichlorophenyl]-2-yl-ethyl)-1H-pyrrole-2-carboxylic acid ethyl ester (163) was synthesized from 4-(2-[2,4-dichlorophenyl]-2-yl-acetyl)-1H-pyrrole-2-carboxylic acid ethyl ester (162) following the procedure described in Example 32. Purification: no purification.

Synthesis of 4-(2-[2,4-dichlorophenyl]-ethyl)-1H-pyrrole-2-carboxylic acid (164)

4-(2-[2,4-dichlorophenyl]-ethyl)-1H-pyrrole-2-carboxylic acid (164) was synthesized from 4-(2-[2,4-dichlorophenyl]-2-yl-ethyl)-1H-pyrrole-2-carboxylic acid ethyl ester (163) following the procedure described in Example 45 (Note: reaction solvent changed to ethanol). Purification: precipitation from water. $^1$H NMR (CD$_3$OD, 400 MHz): δ 7.43 (1H, s), 7.20 (2H, m), 6.69 (2H, s), 2.96 (2H, t), 2.78 (2H, t) ppm. Yield=46%.

Example 58

Synthesis of 4-(2-[3,4-dichlorophenyl]-ethyl)-1H-pyrrole-2-carboxylic acid (167)

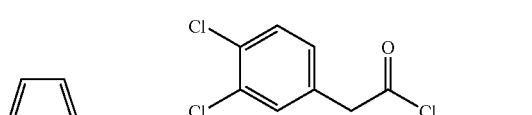

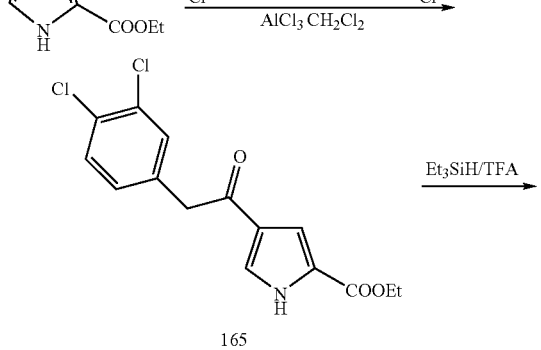

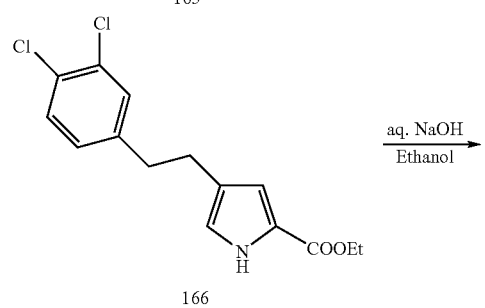

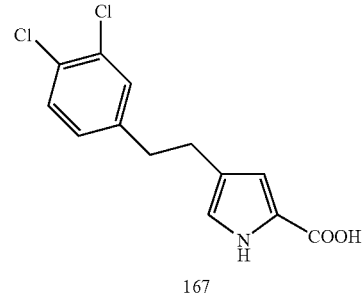

Synthesis of 4-(2-[3,4-dichlorophenyl]-2-yl-acetyl)-1H-pyrrole-2-carboxylic acid ethyl ester (165)

4-(2-[3,4-dichlorophenyl]-2-yl-acetyl)-1H-pyrrole-2-carboxylic acid ethyl ester (165) was synthesized from 1H-pyrrole-2-carboxylic acid ethyl ester and m,p-dichlorophenyl-2-yl-acetyl chloride following the procedure described in Example 32. Reaction Conditions: 1,2-dichloromethane/–40° C.→RT. Purification: no purification.

Synthesis of 4-(2-[3,4-dichlorophenyl]-2-yl-ethyl)-1H-pyrrole-2-carboxylic acid ethyl ester (166)

4-(2-[3,4-dichlorophenyl]-2-yl-ethyl)-1H-pyrrole-2-carboxylic acid ethyl ester (166) was synthesized from 4-(2-[3,4-dichlorophenyl]-2-yl-acetyl)-1H-pyrrole-2-carboxylic acid ethyl ester (165) following the procedure described in Example 32. Purification: no purification.

Synthesis of 4-(2-[3,4-dichlorophenyl]-ethyl)-1H-pyrrole-2-carboxylic acid (167)

4-(2-[3,4-dichlorophenyl]-ethyl)-1H-pyrrole-2-carboxylic acid (167) was synthesized from 4-(2-[3,4-dichlorophenyl]-2-yl-ethyl)-1H-pyrrole-2-carboxylic acid ethyl ester (166) following the procedure described in Example 45 (Note: reaction solvent changed to ethanol). Purification: precipitation from water. $^1$H NMR (CD$_3$OD 400 MHz): δ 7.36 (2H, m), 7.08 (1H, m), 6.68 (2H, m), 2.83 (4H, m) ppm. Yield=87%.

Example 59

Synthesis of 4-(2-[2,4-difluorophenyl]-ethyl)-1H-pyrrole-2-carboxylic acid (170)

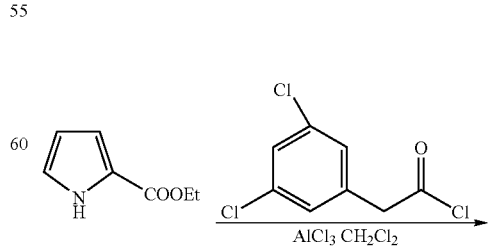

125.6, 123.6, 122.7, 116.3, 112.4, 112.2, 101.9, 38.3, 29.2 ppm. Yield 70%. HPLC 20 nm: 99.05%

Example 60

Synthesis of 4,5,6,7-tetrahydro-2H-isoindole-1-carboxylic acid (172)

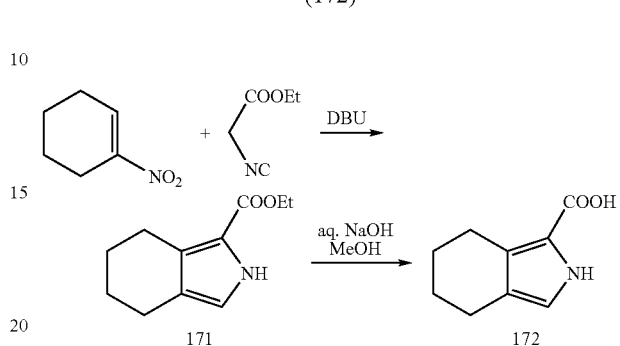

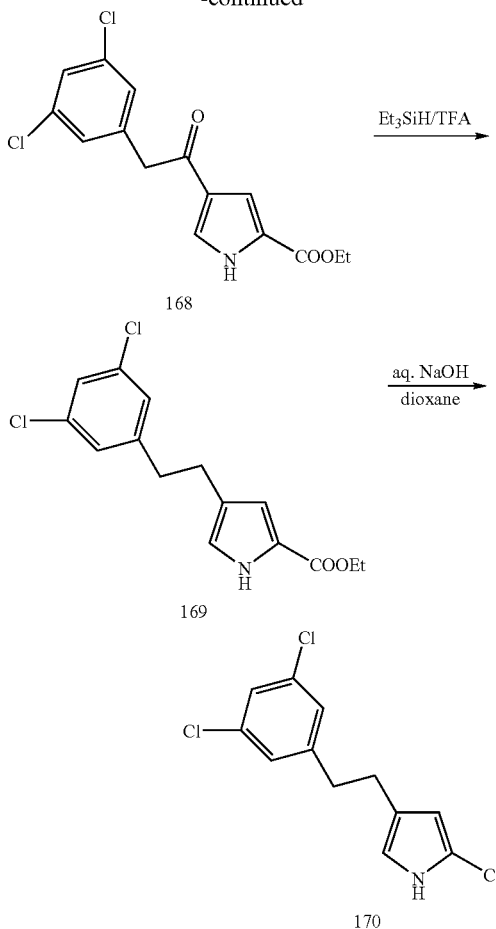

Synthesis of 4-(2-[2,4-difluorophenyl]-2-yl-acetyl)-1H-pyrrole-2-carboxylic acid ethyl ester (168)

4-(2-[2,4-Difluorophenyl]-2-yl-acetyl)-1H-pyrrole-2-carboxylic acid ethyl ester (168) was synthesized from 1H-pyrrole-2-carboxylic acid ethyl ester and o,p-difluorophenyl-2-yl-acetyl chloride following the procedure described in Example 32. Reaction Conditions: 1,2-dichloromethane/−40° C.→RT. Purification: no purification.

Synthesis of 4-(2-[2,4-difluorophenyl]-2-yl-ethyl)-1H-pyrrole-2-carboxylic acid ethyl ester (169)

4-(2-[2,4-difluorophenyl]-2-yl-ethyl)-1H-pyrrole-2-carboxylic acid ethyl ester (169) was synthesized from 4-(2-[2,4-difluorophenyl]-2-yl-acetyl)-1H-pyrrole-2-carboxylic acid ethyl ester (168) following the procedure described in Example 32. Purification: no purification.

Synthesis of 4-(2-[2,4-difluorophenyl]-ethyl)-1H-pyrrole-2-carboxylic acid (170)

4-(2-[2,4-difluorophenyl]-ethyl)-1H-pyrrole-2-carboxylic acid (170) was synthesized from 4-(2-[2,4-difluorophenyl]-2-yl-ethyl)-1H-pyrrole-2-carboxylic acid ethyl ester (169) following the procedure described in Example 45. Purification: precipitation from water. $^1$H NMR (CDC$_3$, 400 MHz): δ 6.76 (2H, m), 6.70 (3H, m); 2.87 (2H, m), 2.75 (2H, m) ppm. $^{13}$C NMR (CD$_3$OD, 100 MHz): 165.6, 164.5, 163.2, 148.0,

Synthesis of 4,5,6,7-tetrahydro-2H-isoindole-1-carboxylic acid ethyl ester (171)

1,8-Diazabicyclo[5.4.0]-undec-7-ene (6.2 mL, 41.5 mmol) in 2-propanol (45 mL) was added by addition funnel over ~25 minutes to a stirring solution of 1-nitrocyclohexene (5.0441 g, 39.67 mmol) and ethylisocyanoacetate (4.3340 g, 37.16 mmol) in THF (45 mL). The reaction was judged complete after stirring overnight at room temperature. 2N HCl (~100 mL) and EtOAc (~50 mL) were added. The organic layer was removed, then washed with H$_2$O, 5% NaHCO$_3$, and H$_2$O. The crude product was dried with Na$_2$SO$_4$, filtered, concentrated, and purified by silica gel chromatography (Combiflash column, 100% CH$_2$Cl$_2$) to obtain 171 contaminated with a minor impurity. Attempts to recrystallize from hexanes were unsuccessful at removing the impurity, so the product was carried on to the next step with no further purification. $^1$H (CDCl$_3$, 400 MHz): δ 9.01 (1H, broad s), 6.64 (1H, s), 4.31 (3H, q, J=7.2 Hz), 2.82 (2H, t, J=5.6 Hz), 2.55 (2H, t, J=5.6 Hz), 1.80-1.68 (4H, m), 1.36 (3H, t, J=7.2 Hz) ppm. $^{13}$C (CD$_3$OD, 100 MHz): 6161.71, 128.06 and 127.84, 121.98 and 121.96, 118.74 and 118.55, 118.03 and 117.71, 59.62, 23.41 and 23.39, 23.36 and 23.33, 23.16 and 23.13, 21.88 and 21.86, 14.48 ppm. DEPT (CD$_3$OD, 100 MHz): CH$_3$ carbons: 14.48; CH$_2$ carbons: 59.62, 23.41 and 23.39, 23.36 and 23.33, 23.16 and 23.13, 21.88 and 21.86; CH carbons: 118.74 and 118.55 ppm. HPLC: 10.689 min.

Synthesis of 4,5,6,7-tetrahydro-2H-isoindole-1-carboxylic acid (172)

Freshly prepared aq. NaOH (10 M in H$_2$O, 10.3 mmol) was added to a stirring, room temperature solution of 171 (0.3966 g, 2.05 mmol) in MeOH (5.1 mL, 0.4 M) under N$_2$. The reaction was then heated to reflux for 20 minutes. A small amount of starting material remained. A large amount of undesired product along with only a small amount of desired product was observed by HPLC. The reaction was concentrated, redissolved in H$_2$O, and extracted with EtOAc (1 mL). 10% aq. HCl was added dropwise to the aqueous layer until the pH=2. The white solid that precipitated from the reaction was filtered off and washed with cold H$_2$O. The solid was dried under vacuum overnight to obtain 0.0076 g (11.6%) of 172. $^1$H (CD$_3$OD, 400 MHz): δ 5.62 (1H, s), 2.77 (2H, t, J=5.6

Hz), 2.52 (2H, t, J=5.4 Hz), 1.78-1.66 (4H, m) ppm. $^{13}$C (CD$_3$OD, 100 MHz): δ 164.87, 129.69, 122.48, 120.57, 118.42, 24.74, 24.69, 24.35, 22.94 ppm. DEPT (CD$_3$OD, 100 MHz): CH$_2$ carbons: 24.74, 24.69, 24.35, 22.94; CH carbons: 120.57 ppm. HPLC: 8.896 min.

Example 61

Synthesis of 5-bromo-4-[2-(2-bromophenyl)-ethyl]-1H-pyrrole-2-carboxylic acid (173)

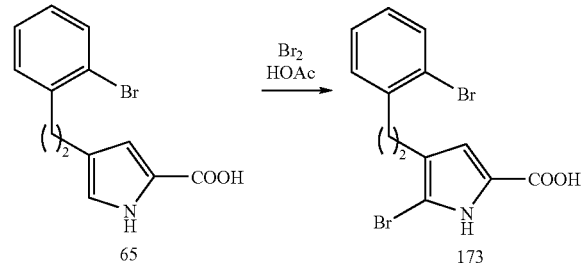

Synthesis of 5-bromo-4-[2-(2-bromophenyl)-ethyl]-1H-pyrrole-2-carboxylic acid (173)

Bromine (0.021 mL, 0.414 mmol) was added dropwise over 5 minutes to a stirring solution of 65 (0.1014 g, 0.345 mmol) in acetic acid (1.1 mL). When the reaction was judged complete by HPLC (20 min), H$_2$O was added, and the solid that precipitated was filtered off and washed with H$_2$O. The light purple solid that was obtained was dissolved in EtOAc, washed with Na$_2$SO$_3$ and H$_2$O, then dried with Na$_2$SO$_4$, filtered, and concentrated. The product was purified by preparative reverse phase HPLC with 40:60 H$_2$O:CH$_3$CN (w/0.05% TFA); 20 mL/min.; λ=214 nM. 0.0574 g (44.6%) of 173 was obtained as a fluffy pale pink solid. $^1$H (CD$_3$OD, 400 MHz): δ 7.50 (1H, d, J=7.8 Hz), 7.24-7.00 (3H, m), 6.68 (1H, s), 2.92 (2H, t, J=7.8 Hz), 2.67 (2H, t, J=-7.8 Hz) ppm. Partial $^{13}$C (CD$_3$OD, 100 MHz): δ 163.25, 141.86, 133.73, 131.85, 128.89, 128.54, 125.26, 124.68, 117.16, 105.89, 37.91, 27.62 ppm. DEPT (CD$_3$OD, 100 MHz): CH$_2$ carbons: 37.91, 27.62; CH carbons: 133.73, 131.85, 128.89, 128.54, 117.16 ppm. HPLC: 10.473 min.

Example 62

Synthesis of 5-bromo-4-[2-(4-chlorophenyl)-ethyl]-1H-pyrrole-2-carboxylic acid (174)

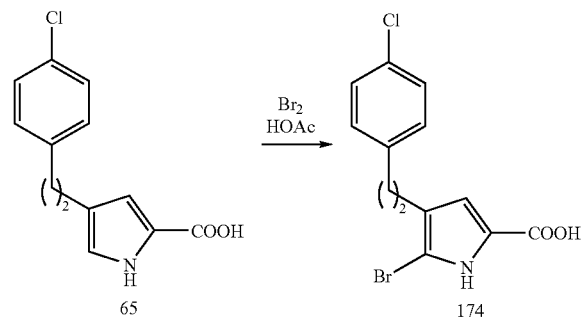

Synthesis of 5-bromo-4-[2-(4-chlorophenyl)-ethyl]-1H-pyrrole-2-carboxylic acid (174)

5-Bromo-4-[2-(4-chlorophenyl)-ethyl]-1H-pyrrole-2-carboxylic acid was made using the procedure in Example 61. $^1$H (CD$_3$OD, 400 MHz): δ 7.22 (2H, d, J=8.8 Hz), 7.12 (2H, d, J=8.8 Hz), 6.65 (1H, s), 2.81 (2H, t, J=7.3 Hz), 2.67 (2H, t, J=7.3 Hz) ppm. $^{13}$C (CD$_3$OD, 100 MHz): δ 163.33, 141.42, 132.54, 131.03, 129.18, 124.73, 117.46, 105.84, 36.72, 29.04 ppm.

Example 63

Synthesis of 5-(3-phenylpropyl)-1H-pyrrole-2-carboxylic acid (177)

Synthesis of 5-(3-phenylpropionyl)1H-pyrrole-2-carboxylic acid ethyl ester (175) and 4-(3-phenylpropionyl)-1H-pyrrole-2-carboxylic acid ethyl ester (43)

Ethylpyrrole-2-carboxylate (2.0211 g, 14.5 mmol) in a minimal amount of dichloroethane (2 mL) was added to an ice cooled stirring mixture of zinc chloride (4.0151 g, 29.5 mmol) and hydrocinnamoyl chloride (5.0348 g, 29.9 mmol) in dichloroethane (20 mL, 0.66 M) under N$_2$. After stirring 10 min, the ice bath was removed, and the reaction was allowed to warm to room temperature until it was judged complete by HPLC (2 h 45 min). PS-Trisamine™ resin (13.44 g) was added, and the reaction was stirred at room temperature for about 1.5 h. The reaction was filtered through a frit into a flask containing ice water. The frit was washed with $CH_2Cl_2$, then the combined organics were washed with $H_2O$, dried with $Na_2SO_4$, filtered, concentrated, and purified by silica gel chromatography (Combiflash column, 25:75 Hexanes:$CH_2Cl_2$) to obtain 0.5374 g (14%) of 175 (lower Rf). No attempt was made to isolate 43 (higher Rf). HPLC: 10.58 min. (Starting material: 8.90 min.)

Synthesis of
5-(3-phenylpropyl)-1H-pyrrole-2-carboxylic acid
ethyl ester (176)

Triethylsilane (0.977 mL, 6.14 mmol) was added to a stirring, room temperature solution of 5-(3-phenylpropionyl) 1H-pyrrole-2-carboxylic acid ethyl ester (175) (0.5374 g, 1.98 mmol) in trifluoroacetic acid (TFA) (4.72 mL, 0.42 M) under $N_2$. The reaction was judged complete by HPLC after stirring at room temperature overnight. The TFA was removed under vacuum, and the crude product was purified by preparative reverse phase HPLC with the following conditions: 35:65 $H_2O:CH_3CN$; 20 mL/min.; λ=254 nM. HPLC: 11.12 min.

Synthesis of
5-(3-phenylpropyl)-1H-pyrrole-2-carboxylic acid
(177)

Freshly prepared aq. NaOH (10 M in $H_2O$, 1.22 mmol) was added to a stirring, room temperature solution of 5-(3-phenylpropyl)-1H-pyrrole-2-carboxylic acid ethyl ester (85) (0.0629 g, 0.244 mmol) in MeOH (0.61 mL, 0.4 M) under $N_2$. The reaction was heated to reflux until the reaction was judged complete by HPLC. The product was concentrated and then 2 mL of diethyl ether and 2 mL of $H_2O$ were added. The organic layer was removed and discarded, then 2 mL of diethyl ether was added, and 10% aq. HCl was added dropwise until the pH=2. The diethyl ether later was removed, and the aqueous was extracted with another portion of diethyl ether. The combined organics were dried, and concentrated to provide the desired product. (Note: An undesired impurity has a retention time of 10.85 min by HPLC. HPLC: 9.91 min.

Example 64

Conversion of 4-[2-(4-chlorophenyl)-ethyl]-1H-pyrrole-2-carboxylic acid to the sodium salt (178)

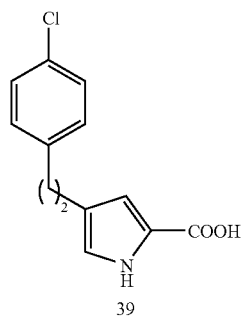

-continued

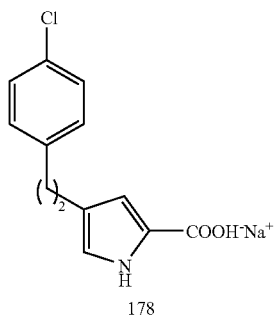

Formation of the Sodium Salt of 4-[2-(4-chlorophenyl)-ethyl]-1H-pyrrole-2-carboxylic acid (178)

4-[2-(4-Chlorophenyl)-ethyl]-1H-pyrrole-2-carboxylic acid (39) (4.2668 g, 17.09 mmol) was dissolved in 60 mL (0.17 M) of MeOH. The solution was cooled in a 0° C. ice bath, then an aqueous solution of sodium hydroxide (0.6872 g, 17.09 mmol NaOH, 2.7 M) slowly with stirring. A white solid oiled out of solution. The methanol was removed on the rotovap, then 32 mL of $H_2O$ was added, and flask was mixed well to dissolve at room temperature. The slight pink discoloration observed when the starting acid was dissolved in methanol was removed when the solution was filtered through filter paper. Lyophilization of the colorless solution provided 4.5345 g (97.7%) of a fluffy white solid.

Example 65

Synthesis of
4-Methyl-2-phenethyl-1H-pyrrole-2-carboxylic acid
ethyl ester (182)

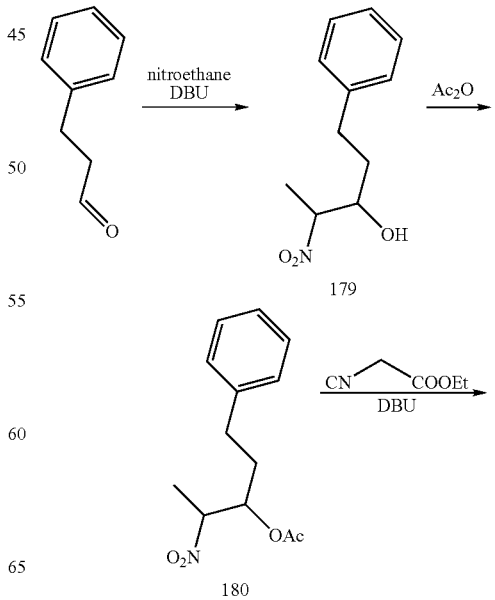

117

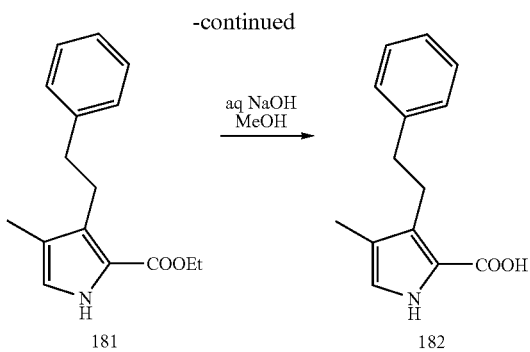

Synthesis of 4-Nitro-1-phenyl-pentan-3-ol (179)

Following the procedure of One et al, *J. Heterocyclic Chem.*, 1994, 31, 707-710, which is incorporated by reference, nitroethane (10 mL, 139.2 mmol, 96%) and 3-phenylpropionaldehyde (18.49 mL, 139.9 mmol) were dissolved in THF (70 mL, 2 M). After cooling to −10° C. in a brine bath, 1,8-diazabicyclo[5.4.0]-undec-7-ene (DBU) (1.46 mL, 9.74 mmol) was added, and allowed to stir until complete by HPLC (75 min). The reaction was diluted with diethyl ether and H$_2$O, and then the organic was removed and washed with saturated aqueous NaHCO$_3$ and brine. The aqueous layers were back-extracted with diethyl ether, and the combined organics were dried with Na$_2$SO$_4$, filtered, and concentrated to provide 179, which was used without further purification in the next step. HPLC: 9.68 min. (Note: The retention time for the starting materials follow: nitroethane: 6.49 min.; 3-phenylpropionaldehyde: 9.45 min).

Synthesis of Acetic acid 2-nitro-1-phenethylpropyl ester (180)

Crude 4-Nitro-1-phenyl-pentan-3-ol (179) from above was dissolved in CH$_2$Cl$_2$ (60 mL) and cooled in an ice bath under nitrogen. Concentrated sulfuric acid (0.76 mL, 14.2 mmol) then acetic anhydride (13.83 mL, 146.2 mmol) were added slowly, and the reaction was allowed to warm to room temperature, and was stirred until judged complete by HPLC (3 h, 40 min). (Note: The reaction turned black soon after the addition of the acetic anhydride.) The reaction was quenched by pouring slowly into water, then the organic layer was removed, washed with aq. NaHCO$_3$, dried, filtered, and concentrated. The crude product was purified by purified by silica gel chromatography (Combiflash column, 95:5 Hexanes:EtOAc) to achieve pure 180 (21.4447 g, 65.5%, 2 steps). HPLC: 10.45 min.

Synthesis of 4-Methyl-2-phenethyl-1H-pyrrole-2-carboxylic acid ethyl ester (181)

Acetic acid 2-nitro-1-phenethylpropyl ester (180) (10.4302 g, 44.2 mmol) and ethyl isocyanoacetate (4.957 g, 44.2 mmol) were weighed out into a 250 mL round bottom flask. The flask was sealed with a septum, purged with nitrogen, then dissolved in a solution of THF and iso-propyl alcohol (1.6:1, 44 mL, 1M). The reaction was cooled in an ice bath, then DBU (13.6 mL, 2.05 mmol) was added. The reaction was allowed to warm to room temperature, and was allowed to stir at room temperature until judged complete by HPLC (2 h, 25 min.). The reaction was diluted with H$_2$O and diethyl ether, and the organic layer was removed, extracted with 2N HCl, H$_2$O, and NaHCO$_3$. The combined organics were dried with Na$_2$SO$_4$, filtered, and concentrated. The crude product was purified by purified by silica gel chromatography (Combiflash column, 95:5 Hexanes:EtOAc). The product crystallized from the combined Combiflash fractions to obtain a batch of 3.3224 g (29%) of pure 181 and 3.7709 g of 181 containing a small amount of impure material. HPLC: 11.27 min.

Synthesis of 4-Methyl-2-phenethyl-1H-pyrrole-2-carboxylic acid (182)

4-Methyl-2-phenethyl-1H-pyrrole-2-carboxylic acid ethyl ester (181) was hydrolyzed as described above to obtain pure desired product. $^1$H (CD$_3$OD, 400 MHz): δ 10.60 (1H, br s), 7.24-7.00 (5H, m), 6.62 (1H, s), 2.99 (2H, dd, J=9.6, 7.3 Hz), 2.67 (2H, dd, J=9.6, 7.8 Hz), 1.83 (3H, s) ppm. $^{13}$C (CD$_3$OD, 100 MHz): δ 164.75, 143.86, 132.12, 129.58, 129.10, 126.61, 122.27, 122.10, 120.68, 38.32, 28.61, 9.80 ppm. DEPT (CD$_3$OD, 100 MHz): CH$_2$ carbons: 38.32, 28.61; CH carbons: 129.58, 129.10, 126.61, 122.27 ppm. HPLC: 9.947 min.

Example 66

Synthesis of 4-[2-(4-chlorophenyl)-ethyl]-1H-pyrrole-2-carboxylic acid ethyl ester (38)

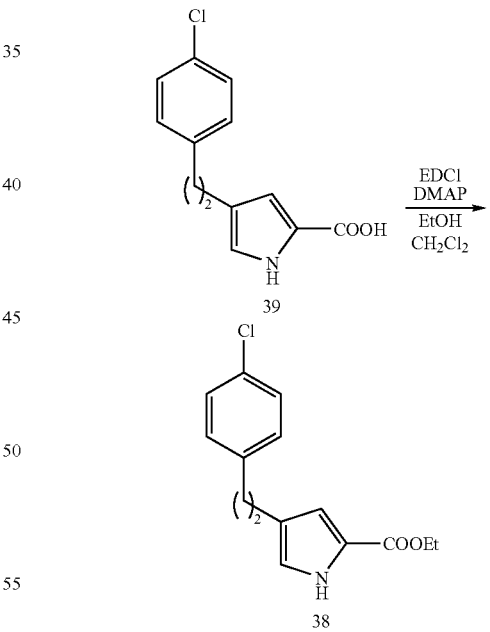

Synthesis of 4-[2-(4-chlorophenyl)-ethyl]-1H-pyrrole-2-carboxylic acid amide (38)

To a solution of 39 (0.5026 g, 2.01 mmol) in CH$_2$Cl$_2$ (8.4 mL, 0.24 M) was added 1-[3-(dimethylamine)propyl]-3-ethylcarbodiimidehydrochloride (EDCI, 0.4700 g, 2.42 mmol), 4-(dimethylamino)pyridine (DMAP, 0.0270 g, 0.20 mmol), and EtOH (0.352 mL, 6.04 mmol), and the reaction was stirred at room temperature overnight. The solid by-product was filtered off and rinsed with $CH_2Cl_2$, then the combined organics were washed with 5% aq. $NaHCO_3$, 5% aq. HCl, and $H_2O$. The combined organics were dried with $Na_2SO_4$, filtered, and concentrated. The product was purified by silica gel chromatography (Combiflash column, 90:10 Hexanes: EtOAc) to obtain 0.2974 g (53.2%) of 38. The analytical data for 38 matched that when synthesized before by a different method. HPLC: 11.261 min. (Note: HPLC of starting material=10.028 min.)

Example 67

Synthesis of 4-Phenylaminomethyl-1H-pyrrole-2-carboxylic acid (184)

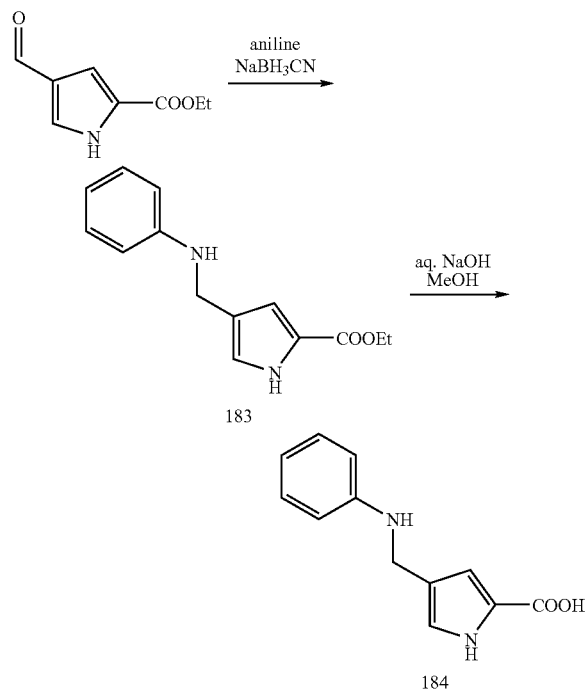

Synthesis of 4-Phenylaminomethyl-1H-pyrrole-2-carboxylic acid ethyl ester (183)

0.2012 g (1.20 mmol) of 4-formyl-1H-pyrrole-2-carboxylic acid ethyl ester was dissolved in 4.8 mL (0.25 M) of 5% acetic acid in methanol. Aniline (0.13 mL g, 1.44 mmol) was added, and the reaction was stirred at room temperature under nitrogen for 45 minutes, then sodium cyanoborohydride (0.1244 g, 1.98 mmol) was added slowly and the reaction was allowed to stir at room temperature overnight. About 2 mL of saturated $K_2CO_3$ were added, and the reaction was extracted twice with ethyl acetate. The combined organics were washed with saturated $NaHCO_3$ (~3 mL) and brine (~3 mL), then the combined organics were dried with $Na_2SO_4$, filtered and concentrated en vacuo. The crude product was purified by silica gel chromatography (Combiflash column, 85:15 Hexanes: Ethyl acetate) to obtain 0.2663 g (91%) of 4-phenylaminomethyl]-1H-pyrrole-2-carboxylic acid ethyl ester (183) as a colorless viscous oil. Note: Starting material 4-formyl-1H-pyrrole-2-carboxylic acid ethyl ester has an HPLC retention time=7.337 min. $^1H$ ($CDCl_3$, 400 MHz): 89.49 (1H, broad s), 7.19 (2H, dd, J=8.6, 7.3 Hz), 6.73 (1H, tt, J=7.3, 1.1 Hz), 6.66 (2H, dd, J=8.6, 1.1 Hz), 6.91 (1H, d, J=2.0 Hz), 6.90 (1H, d, J=2.0 Hz), 4.33 (2H, q, J=7.2 Hz), 4.19 (2H, s), 3.90 (1H, broad s), 1.36 (3H, t, J=7.2 Hz) ppm. HPLC: 6.936 min.

Synthesis of 4-Phenylaminomethyl-1H-pyrrole-2-carboxylic acid (184)

4-phenylaminomethyl]-1H-pyrrole-2-carboxylic acid ethyl ester (183) (0.0773 g, 0.316 mmol) was weighed out into a round bottom flask. A stir bar, condenser, and septum are added, and the flask was purged with $N_2$. The ester was dissolved in EtOH (0.70 mL, 0.45 M), and then freshly prepared aqueous NaOH (0.0354 g, 0.283 mL $H_2O$) was added with stirring to the ester solution. The reaction flask was immediately immersed in an oil bath preheated to 85° C., and the reaction was heated and stirred under $N_2$ until judged complete by HPLC (15 min). The solvent was removed on the rotovap, and 0.8 mL $H_2O$ was added. The aqueous layer was slowly and carefully made acidic with 10% aqueous HCl. The product was purified by reverse phase preparative HPLC (45: 55 $H_2O$ with 0.05% TFA: $CH_3CN$ with 0.05% TFA) to obtain pure 4-phenylaminomethyl-1H-pyrrole-2-carboxylic acid. $^1H$ ($CD_3OD$, 400 MHz): δ 7.51-7.40 (5H, m), 6.99 (1H, d, J=1.5 Hz), 6.86 (1H, d, J=1.5 Hz), 4.46 (2H, s) ppm. $^{13}C$ ($CD_3OD$, 100 MHz): 8163.92, 137.17, 131.10, 129.97, 125.95, 125.07, 123.71, 117.37, 115.77, 49.38 ppm. DEPT ($CD_3OD$, 100 MHz): $CH_2$ carbons: 49.38; CH carbons: 131.10, 129.97, 125.94, 123.71, 117.37 ppm. HPLC: 5.724 min.

Example 68

Synthesis of 4-[(Acetylphenylamino)-methyl]-1H-pyrrole-2-carboxylic acid (186)

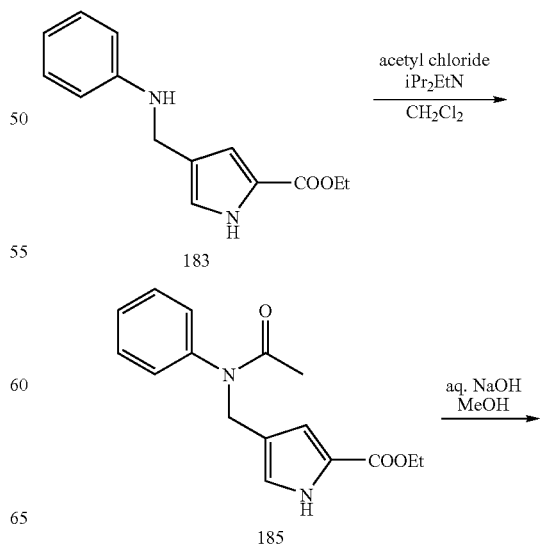

-continued

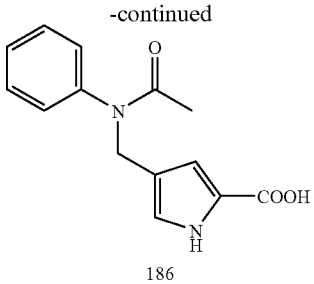

186

Synthesis of 4-[(Acetylphenylamino)-methyl]-1H-pyrrole-2-carboxylic acid ethyl ester (185)

4-Phenylaminomethyl-1H-pyrrole-2-carboxylic acid ethyl ester (183) (0.1523 g, 0.623 mmol) was weighed out into a 10 mL flask. A stir bar and septum were added, and the flask was purged with nitrogen. The amine was dissolved in methylene chloride (1.6 mL, 0.4 M) and then the flask was cooled to 0° C. N,N-diisopropyl ethyl amine (0.1194 mL, 0.686 mmol) was added, then acetyl chloride (0.0488 mL, 0.686 mmol) was added slowly by syringe to the stirring 0° C. solution. The reaction was then allowed to warm to room temperature. When the reaction was judged complete by HPLC (35 min) the reaction was diluted with methylene chloride and quenched with water. The organic phase was removed, washed with brine, dried with $Na_2SO_4$, filtered and concentrated en vacuo. The crude product was sufficiently pure by HPLC and NMR analysis that it was used in the next step without further purification (0.1625 g, 91%, white crystalline solid). $^1$H ($CD_3OD$, 400 MHz): δ 11.22 (1H, broad s), 7.43-7.31 (3H, m), 7.08 (2H, dd, J=7.0, 1.5 Hz), 6.75 (1H, d, J=1.5 Hz), 6.68 (1H, d, J=1.5 Hz), 4.70 (2H, s), 4.24 (2H, q, J=7.0 Hz), 1.81 (3H, s), 1.31 (3H, t, J=7.0 Hz) ppm. $^{13}$C ($CD_3OD$, 100 MHz): δ 172.47, 162.64, 143.86, 130.68, 129.34, 129.27, 124.50, 124.33, 122.19, 116.72, 61.16, 46.60, 22.64, 14.75 ppm. DEPT ($CD_3OD$, 100 MHz): $CH_3$ carbons: 22.64, 14.75; $CH_2$ carbons: 61.16, 46.60; CH carbons: 130.68, 129.34, 129.27, 124.33, 116.72 ppm. HPLC: 8.738 min.

Synthesis of 4-[(Acetylphenylamino)-methyl]-1H-pyrrole-2-carboxlic acid (186)

4-[(Acetylphenylamino)-methyl]-1H-pyrrole-2-carboxylic acid ethyl ester (185) (0.1353 g, 0.473 mmol) was weighed out into a round bottom flask. A stir bar, condenser, and septum are added, and the flask was purged with $N_2$. The ester was dissolved in EtOH (1.05 mL, 0.45 M), and then freshly prepared aqueous NaOH (0.0529 g, 0.42 mL $H_2O$) was added with stirring to the ester solution. The reaction flask was immediately immersed in an oil bath preheated to 85° C., and the reaction was heated and stirred under $N_2$ until judged complete by HPLC (45 min). The solvent was removed on the rotovap, and 1.0 mL $CH_2Cl_2$ and 1.0 mL $H_2O$ were added. The aqueous layer was slowly and carefully made acidic with 10% aqueous HCl. Although the aqueous got cloudy, no precipitate crashed out. The product was extracted from the aqueous layer with three portions of $CH_2Cl_2$, dried with $Na_2SO_4$, filtered, and concentrated en vacuo to obtain pure 4-[(Acetylphenylamino)-methyl]-1H-pyrrole-2-carboxylic acid (186, 0.0968 mg, 79%). $^1$H ($CD_3OD$, 400 MHz): δ 11.11 (1H, broad s), 7.46-7.31 (3H, m), 7.09 (2H, dd, J=7.0, 1.5 Hz), 6.74 (1H, s), 6.68 (1H, s), 4.71 (2H, s), 1.82 (3H, s) ppm. $^{13}$C ($CD_3OD$, 100 MHz): δ 172.49, 164.19, 143.87, 130.69, 129.37, 129.28, 124.41, 124.24, 122.14, 116.88, 46.64, 22.64 ppm. DEPT ($CD_3OD$, 100 MHz): $CH_3$ carbons: 22.64; $CH_2$ carbons: 46.64; CH carbons: 130.69, 129.37, 129.28, 124.24, 116.88 ppm. HPLC: 7.518 min.

Example 69

Synthesis of 4-[(4-chlorophenylamino)-methyl]-1H-pyrrole-2-carboxylic acid (188)

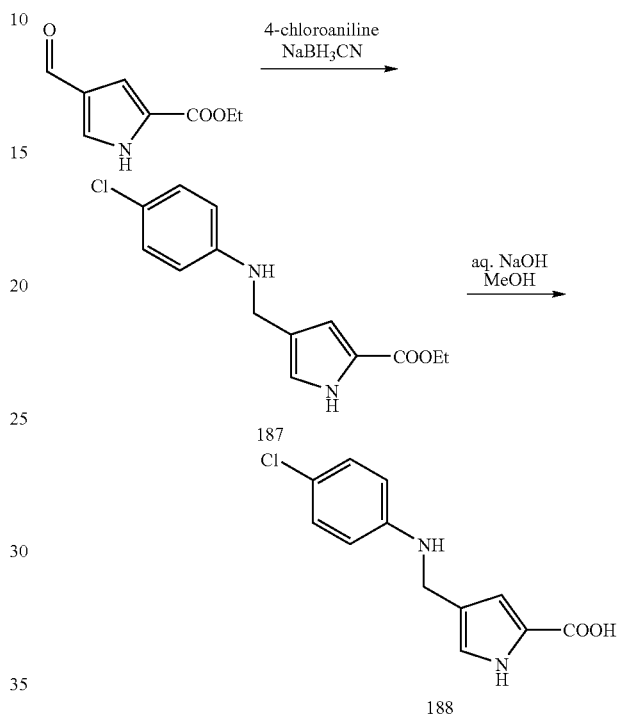

Synthesis of 4-[(4-chlorophenylamino)-methyl]-1H-pyrrole-2-carboxylic acid ethyl ester (187)

0.5052 g (3.02 mmol) of 4-formyl-1H-pyrrole-2-carboxylic acid ethyl ester was dissolved in 12.0 mL (0.25 M) of 5% acetic acid in methanol. 4-chloroaniline (0.4633 g, 3.63 mmol) was added, and the reaction was stirred at room temperature under nitrogen for 30 minutes, then sodium cyanoborohydride (0.3013 g, 4.79 mmol) was added slowly and the reaction was allowed to stir at room temperature overnight. About 5 mL of saturated $K_2CO_3$ were added, and the reaction was extracted twice with ethyl acetate. The combined organics were washed with saturated $NaHCO_3$ (~6 mL) and brine (~6 mL), then the combined organics were dried with $Na_2SO_4$, filtered and concentrated en vacuo. The crude product was purified by silica gel chromatography (Combiflash column, 85:15 Hexanes:Ethyl acetate) to obtain 0.5806 g (69%) of 4-[(4-chlorophenylamino)methyl]-1H-pyrrole-2-carboxylic acid ethyl ester (187) as a light tan solid. Note: Starting material 4-formyl-1H-pyrrole-2-carboxylic acid ethyl ester has an HPLC retention time=7.337 min. HPLC: 8.543 min.

Synthesis of 4-[(4-chlorophenylamino)-methyl]-1H-pyrrole-2-carboxylic acid (188)

4-[(4-chlorophenylamino)-methyl]-1H-pyrrole-2-carboxylic acid ethyl ester (187) (0.1070 g, 0.384 mmol) was weighed out into a round bottom flask. A stir bar, condenser, and septum are added, and the flask was purged with $N_2$. The ester was dissolved in EtOH (0.85 mL, 0.45 M), and then freshly prepared aqueous NaOH (0.0432 g, 0.123 mL H$_2$O) was added with stirring to the ester solution. The reaction flask was immediately immersed in an oil bath preheated to 85° C., and the reaction was heated and stirred under N$_2$ until judged complete by HPLC (30 min). The solvent was removed on the rotovap, and 0.8 mL H$_2$O was added. The aqueous layer was slowly and carefully made acidic with 10% aqueous HCl. The product was purified by reverse phase preparative HPLC (45:55 H$_2$O with 0.05% TFA: CH$_3$CN with 0.05% TFA) to obtain pure 4-[(4-chlorophenylamino)-methyl]-1H-pyrrole-2-carboxylic acid (188). $^1$H (CD$_3$OD, 400 MHz): δ 7.12 (2H, d, J=8.4 Hz), 6.92 (1H, s), 6.85 (1H, s), 6.95 (2H, d, J=8.4 Hz), 4.16 (2H, s) ppm. $^{13}$C (CD$_3$OD, 100 MHz): δ 164.24, 146.44, 129.96, 124.87, 124.15, 123.56, 122.98, 117.22, 116.24, 43.18 ppm. DEPT (CD$_3$OD, 100 MHz): CH$_2$ carbons: 43.18; CH carbons: 129.96, 123.56, 117.22, 116.24 ppm. HPLC: 7.137 min.

Example 70

Synthesis of 4-[(Acetyl-(4-chlorophenyl)-amino)-methyl]-1H-pyrrole-2-carboxylic acid (190)

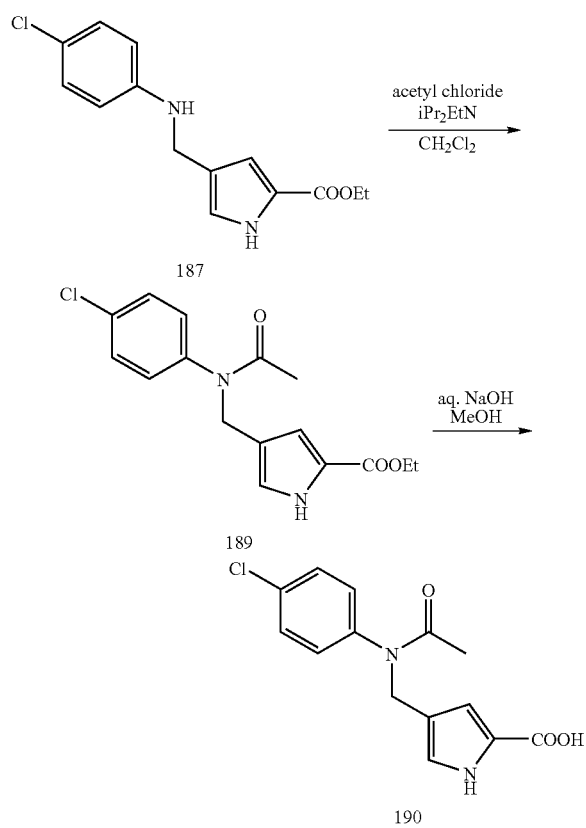

Synthesis of 4-[(Acetyl-(4-chlorophenyl)-amino)-methyl]-1H-pyrrole-2-carboxylic acid ethyl ester (189)

4-[(4-chlorophenylamino)-methyl]-1H-pyrrole-2-carboxylic acid ethyl ester (187) (0.2868 g, 1.03 mmol) was weighed out into a 10 mL flask. A stir bar and septum were added, and the flask was purged with nitrogen. The amine was dissolved in methylene chloride (2.6 mL, 0.4 M) and then the flask was cooled to 0° C. N,N-diisopropyl ethyl amine (0.1971 mL, 1.13 mmol) was added, then acetyl chloride (0.0805 mL, 1.13 mmol) was added slowly by syringe to the stirring 0° C. solution. The reaction was then allowed to warm to room temperature. When the reaction was judged complete by HPLC (90 min) the reaction was diluted with methylene chloride and quenched with water. The organic phase was removed, washed with brine, dried with Na$_2$SO$_4$, filtered and concentrated en vacuo. The crude product was purified by silica gel chromatography (Combiflash column, 2:1 Hexanes: Ethyl acetate) to obtain pure 4-[(acetyl-(4-chlorophenyl)-amino)-methyl]-1H-pyrrole-2-carboxylic acid ethyl ester (189, 0.2701 g, 82%) as a sticky white solid. $^1$H (CD$_3$OD, 400 MHz): δ 11.25 (1H, broad s), 7.35 (2H, d, J=8.4 Hz), 7.05 (2H, d, J=8.4 Hz), 6.76 (1H, s), 6.69 (1H, s), 4.68 (2H, s), 4.22 (2H, q, J=7.1 Hz), 1.81 (3H, s), 1.29 (3H, t, J=7.1 Hz) ppm. $^{13}$C (CD$_3$OD, 100 MHz): δ 172.17, 162.50, 142.39, 134.87, 130.94, 130.70, 124.46 & 124.30, 123.94, 121.91 & 121.88, 116.64, 61.13, 46.43, 22.70, 14.75 ppm. DEPT (CD$_3$OD, 100 MHz): CH$_3$ carbons: 22.70, 14.75; CH$_2$ carbons: 61.13, 46.43; CH carbons: 130.94, 130.70, 124.46 & 124.30, 116.64 ppm. HPLC: 9.247 min.

Synthesis of 4-[(Acetyl-(4-chlorophenyl)-amino)-methyl]-1H-pyrrole-2-carboxylic acid (190)

4-[(acetyl-(4-chlorophenyl)-amino)-methyl]-1H-pyrrole-2-carboxylic acid ethyl ester (0.2701 g, 0.842 mmol) was weighed out into a round bottom flask. A stir bar, condenser, and septum are added, and the flask was purged with N$_2$. The ester was dissolved in EtOH (1.87 mL, 0.45 M), and then freshly prepared aqueous NaOH (0.0943 g, 0.75 mL H$_2$O) was added with stirring to the ester solution. The reaction flask was immediately immersed in an oil bath preheated to 85° C., and the reaction was heated and stirred under N$_2$ until judged complete by HPLC (11 min). The solvent was removed on the rotovap, and 1.6 mL CH$_2$Cl$_2$ and 1.6 mL H$_2$O were added. The aqueous layer was slowly and carefully made acidic with 10% aqueous HCl. The product oiled out. The product was extracted from the aqueous layer with three portions of CH$_2$Cl$_2$, dried with Na$_2$SO$_4$, filtered, and concentrated en vacuo to obtain pure 4-[(Acetyl-(4-chlorophenyl)-amino)-methyl]-1H-pyrrole-2-carboxylic acid (190, 0.2242 mg, 91%). $^1$H (CD$_3$OD, 400 MHz): δ 11.14 (1H, broad s), 7.38 (2H, d, J=8.4 Hz), 7.07 (2H, d, J=8.4 Hz), 6.75 (1H, s), 6.69 (1H, s), 4.69 (2H, s), 1.82 (3H, s) ppm. $^{13}$C (CD$_3$OD, 100 MHz): δ 172.32, 164.16 & 164.13, 142.41, 134.98, 131.02, 130.74, 124.43, 124.27, 121.90 & 121.86, 116.85 & 116.81, 46.49, 22.67 ppm. DEPT (CD$_3$OD, 100 MHz): CH$_3$ carbons: 22.67; CH$_2$ carbons: 46.49; CH carbons: 131.02, 130.74, 124.27 & 124.09, 116.85 & 116.81 ppm. HPLC: 8.077 min.

Example 71

Synthesis of 4-{[(4-chlorophenyl)-methylamino] methyl]-1H-pyrrole-2-carboxylic acid (192)

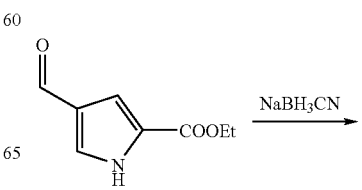

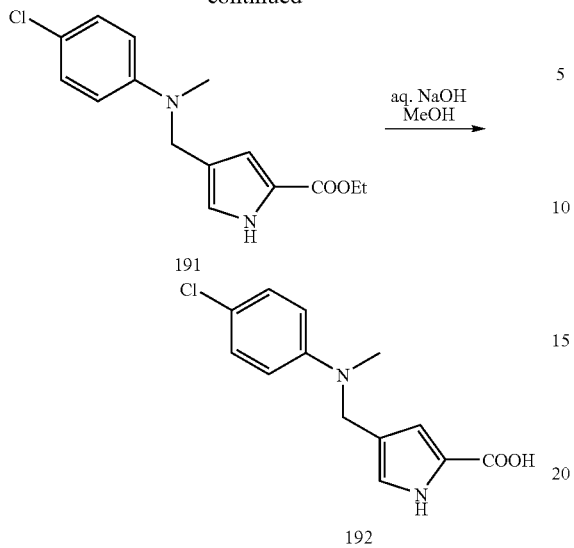

Synthesis of 4-[[(4-chlorophenyl)-methylamino]methyl]-1H-pyrrole-2-carboxylic acid ethyl ester (191)

4-chloro-N-methylaniline (0.225 mL, 1.86 mmol) was added to a stirring, room temperature solution of 4-formyl-1H-pyrrole-2-carboxylic acid ethyl ester (0.2585 g, 1.55 mmol) in 5% acetic acid in methanol under $N_2$. After stirring at room temperature for 30 minutes, sodium cyanoborohydride (0.1585 g, 2.52 mmol) was added, and the reaction was stirred at room temperature overnight. About 3 mL of saturated $K_2CO_3$ were added, and the reaction was extracted twice with ethyl acetate. The combined organics were washed with saturated $NaHCO_3$ (~4 mL) and brine (~4 mL), then the combined organics were dried with $Na_2SO_4$, filtered and concentrated en vacuo. The crude product was purified by silica gel chromatography (Combiflash column, 85:15 Hexanes: Ethyl acetate) to obtain 0.3419 g (76%) of 4-{[(4-chlorophenyl)-methylamino]methyl]-1H-pyrrole-2-carboxylic acid ethyl ester (191) as a light tan solid. Note: Starting material 4-formyl-1H-pyrrole-2-carboxylic acid ethyl ester has an HPLC retention time=7.337 min. HPLC: 8.478 min.

Synthesis of 4-{[(4-chlorophenyl)-methylamino]methyl]-1H-pyrrole-2-carboxylic acid (192)

4-{[(4-Chlorophenyl)-methylamino]methyl]-1H-pyrrole-2-carboxylic acid ethyl ester (191) (0.3419 g, 1.17 mmol) was weighed out into a round bottom flask. A stir bar, condenser, and septum are added, and the flask was purged with $N_2$. The ester was dissolved in EtOH (2.6 mL, 0.45 M), and then freshly prepared aqueous NaOH (0.1336 g, 1.0 mL $H_2O$) was added with stirring to the ester solution. The reaction flask was immediately immersed in an oil bath preheated to 85° C., and the reaction was heated and stirred under $N_2$ until judged complete by HPLC (15 min). The solvent was removed on the rotovap and the crude product was immediately purified by reverse phase preparative HPLC (45:55 $H_2O$ with 0.05% TFA: $CH_3CN$ with 0.05% TFA) to obtain pure 4-{[(4-chlorophenyl)-methylamino]methyl]-1H-pyrrole-2-carboxylic acid (192).

$^1$H (CD$_3$OD, 400 MHz): δ 7.22 (2H, d, J=9.2 Hz), 6.95 (2H, d, J=9.2 Hz), 6.81 (1H, d, J=1.5 Hz), 6.70 (1H, d, J=1.5 Hz), 4.43 (2H, s), 3.00 (3H, s) ppm. Partial $^{13}$C (CD$_3$OD, 100 MHz): δ 130.12, 124.02, 117.99, 116.47, 52.37, 39.91 ppm. DEPT (CD$_3$OD, 100 MHz): CH$_3$ carbons: 14.48; CH$_2$ carbons: 59.62, 23.41 and 23.39, 23.36 and 23.33, 23.16 and 23.13, 21.88 and 21.86; CH carbons: 118.74 and 118.55 ppm.

Example 72

Synthesis of 4-Benzyl-4,5,6,7-tetrahydro-1H-indole-2-carboxylic acid (198)

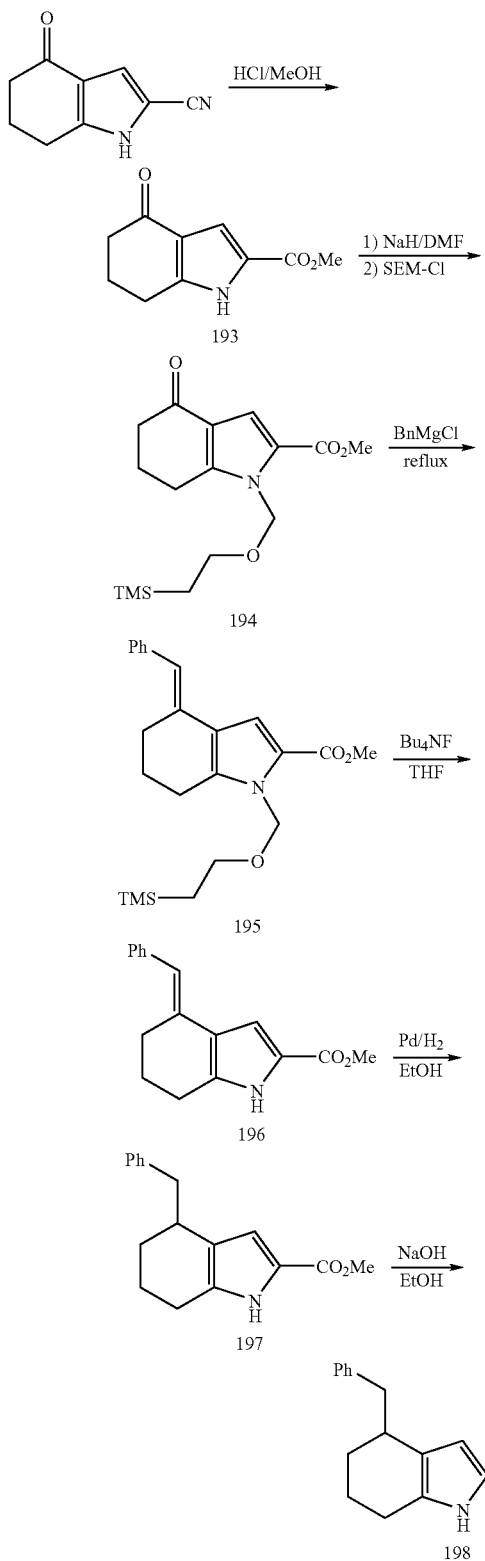

Synthesis of 4-Oxo-4,5,6,7-tetrahydro-1H-indole-2-carboxylic acid methyl ester (193)

A solution of 4-oxo-4,5,6,7-tetrahydro-1H-indole-2-carbonitrile (4.5 g, 28.1 mmol, prepared as described in *Synth. Comm.* 1995, 25, 507-514) in HCl gas saturated methanol (200 ml) was refluxed for 6 days. The solvent was removed under vacuum. The resulting product (3.5 g) was a 65/35 mixture of expected ester and starting material as shown by NMR analysis. This mixture was used in the next step without any further purification.

Synthesis of 4-Oxo-1-(2-trimethylsilyl-ethoxymethyl)-4,5,6,7-tetrahydro-1H-indole-2-carboxylic acid methyl ester (194)

A DMF (3 ml) solution of ester (500 mg, 2.6 mmol) was added to a cooled (0° C.) suspension of sodium hydride (114 mg, 60% in oil, 2.8 mmol) in DMF (2 ml). After 10 minutes, SEM-Cl (550 µl, 3.1 mmol) was added. The mixture was then stirred at room temperature for 2 h, then poured into ice-water and extracted with ethyl acetate. After concentration, the expected compound was obtained as a crude oil (930 mg).
$^1$H NMR (CDC$_3$, 400 MHz): δ 7.27 (1H, s), 5.78 (2H, s), 3.61 (2H, m), 2.94 (2H, m), 2.50 (2H, m), 2.18 (2H, m), 0.92 (2H, m) ppm. LC/MS: 60%

Synthesis of 4-Benzylidene-1-(2-trimethylsilyl-ethoxymethyl)-4,5,6,7-tetrahydro-1H-indole-2-carboxylic acid methyl ester (195)

A dry THF solution (7 ml) of protected ester (900 mg, 2.78 mmol) was added to a solution of benzylmagnesium chloride (3.4 ml, 2M in THF, 6.8 mmol) in THF (10 ml). After 2 h at room temperature, some more benzylmagnesium chloride (1.7 ml, 2M in THF, 3.4 mmol) was added. The mixture was then refluxed for 1 night. Water was then added and the reaction mixture was extracted with ethyl acetate. The organic layer was washed with brine, dried over Na$_2$SO$_4$ and concentrated under reduced pressure to give the above titled compound (900 mg). LC/MS: 50%, m/z=397 g/mol.

Synthesis of 4-Benzylidene-4,5,6,7-tetrahydro-1H-indole-2-carboxmlic acid methyl ester (196)

Tetrabutylammonium fluoride (23 ml, 1M in THF, 23 mmol) was added over 5 min to a solution of ester (900 mg, 2.26 mmol) in cooled THF (0° C.). The reaction mixture was then heated for 4 h at 80° C. After 48 h at room temperature, the reaction mixture was partitioned between ether and water. The organic layer was dried over MgSO4 and concentrated under reduced pressure to give the crude above titled compound. Silica gel chromatography (eluent cyclohexane/AcOEt: 80/20) afforded the pure starting material (100 mg) and the corresponding deprotected nitrile (80 mg). The still protected pure ester (100 mg, 0.25 mmol) was mixed with TBAF (750 µl, 0.75 mmol). The THF was removed under vacuum. After concentration, the reaction mixture was heated with ethylenediamine (0.25 ml) in DMF (1 ml) for 16 h. After concentration the above titled compound was obtained as an oil (80 mg). LC/MS 76%, m/z=267 g/mol.

Synthesis of 4-Benzyl-4,5,6,7-tetrahydro-1H-indole-2-carboxylic acid methyl ester (197)

The saturated ester derivative was hydrogenated at normal pressure over Pd in EtOH for 3 h. The catalyst was removed by filtration and the solvent evaporated under reduced pressure to give the above titled compound, which was purified by silica gel chromatography (eluent cyclohexane/CH$_2$Cl$_2$: 50/50). Yield: 20 mg. LC/MS: 60%, m/z=269 g/mol.

Synthesis of 4-Benzyl-4,5,6,7-tetrahydro-1H-indole-2-carboxylic acid (198)

Freshly prepared aq. NaOH (1M in H$_2$O, 0.8 ml, 0.8 mmol) was added at room temperature to a stirred solution of ester (20 mg, 0.08 mmol) in EtOH (5 ml). The reaction was heated to 80° C. until the reaction was judged complete by TLC. The product was extracted with Et$_2$O, then the aqueous layer was made acid (pH=1) with the dropwise addition of 10% aq. HCl. The solid was filtered off and washed with water. The solid was dried under vacuum overnight to give the above titled compound (19 mg). $^1$H NMR (CDCl$_3$, 400 MHz): δ☐☐ 8.8 (1H, br s), 7.3-7.33 (2H, m), 7.2-7.26 (3H, m), 6.81 (1H, s), 3.09 (1H, dd), 2.9 (1H, m), 2.55-2.65 (3H, m), 1.9-2.0 (1H, m), 1.6-1.8 (2H, m), 1.3-1.4 (1H, m). LC/MS: 89%, m/z=255 g/mol.

The invention claimed is:

1. A method for treating schizophrenia, the method comprising administering to a subject in need thereof a therapeutically effective amount of a compound of formula IA, or a pharmaceutically acceptable salt thereof:

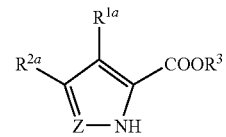

IA wherein $R^{1a}$ is hydrogen;

$R^{2a}$ is $XYR^5$;

X and Y are independently selected from O, S, NH, and $(CR^6R^7)_n$;

$R^3$ is hydrogen;

Z is CH;

$R^5$ is selected from aryl, substituted aryl, heteroaryl and substituted heteroaryl;

$R^6$ and $R^7$ are independently selected from hydrogen and alkyl;

n is an integer from 1 to 6;

at least one of $R^{1a}$ and $R^{2a}$ is $XYR^5$; and at least one of X and Y is $(CR^6R^7)_n$.

2. A method according claim 1, wherein X and Y are $CR^6R^7$.

3. A method according to claim 1, wherein $R^5$ is substituted aryl.

4. A method according to claim 2, wherein $R^6$ and $R^7$ are hydrogen.

5. A method according to claim 1, wherein Z is C, $R^{1a}$ is hydrogen $R^{2a}$ is $XYR^5$, X and Y are $CR^6R^7$, $R^5$ is substituted aryl and $R^6$ and $R^7$ are hydrogen.

6. A method according to claim 5, wherein the compound of formula IA is chosen from:

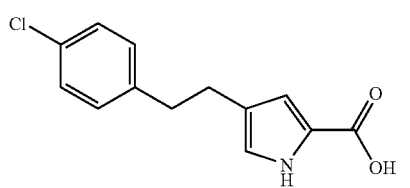
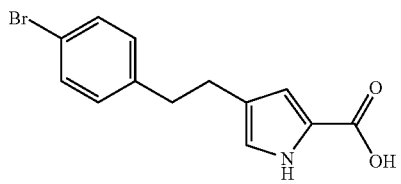
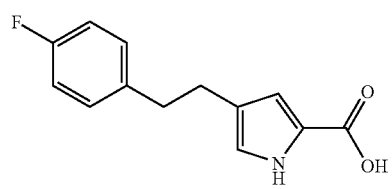
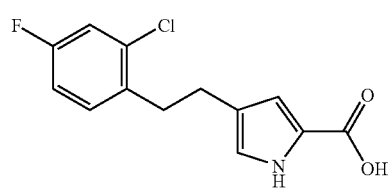
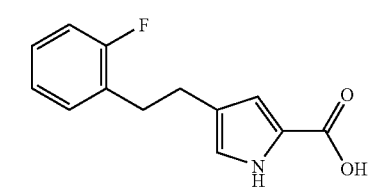
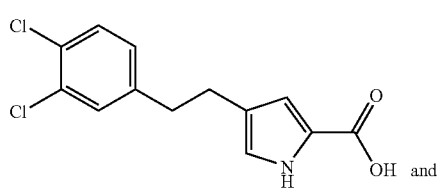 and
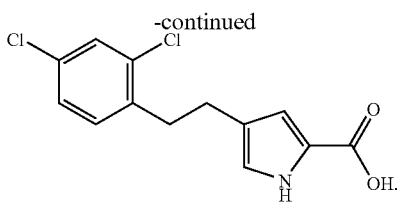
7. A method for treating schizophrenia, the method comprising administering to a subject in need thereof a therapeutically effective amount of a compound selected from
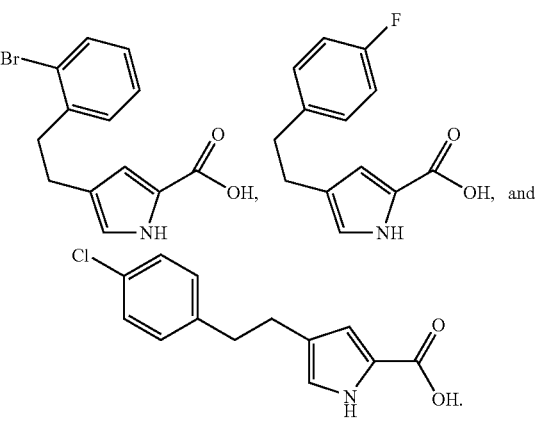
8. A method according to claim 7, wherein the compound is
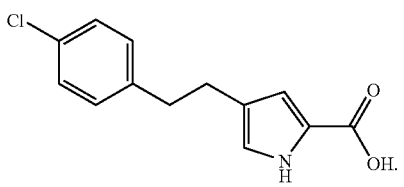
* * * * *